(12) United States Patent
Mintier et al.

(10) Patent No.: US 7,572,618 B2
(45) Date of Patent: Aug. 11, 2009

(54) POLYNUCLEOTIDES ENCODING NOVEL PCSK9 VARIANTS

(75) Inventors: Gabriel A. Mintier, Hightstown, NJ (US); Jian Chen, Princeton, NJ (US); Bowman Miao, Churchville, PA (US); Rex Arnold Parker, Titusville, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 11/824,461

(22) Filed: Jun. 28, 2007

(65) Prior Publication Data

US 2008/0008697 A1  Jan. 10, 2008

Related U.S. Application Data

(60) Provisional application No. 60/818,234, filed on Jun. 30, 2006.

(51) Int. Cl.
C12N 9/50 (2006.01)
C12N 9/00 (2006.01)
C12N 1/20 (2006.01)
C12N 15/00 (2006.01)
C07H 21/02 (2006.01)
C07H 21/04 (2006.01)

(52) U.S. Cl. .................... 435/219; 435/183; 435/252.3; 435/320.1; 536/23.1; 536/23.2

(58) Field of Classification Search ........................ None
See application file for complete search history.

(56) References Cited

U.S. PATENT DOCUMENTS

| | | | |
|---|---|---|---|
| 7,129,338 | B1 | 10/2006 | Ota et al. |
| 7,300,754 | B2 | 11/2007 | Abi Fadel et al. |
| 2003/0119038 | A1 | 6/2003 | Bingham et al. |
| 2004/0023243 | A1 | 2/2004 | Henry et al. |
| 2004/0038242 | A1 | 2/2004 | Edmonds et al. |
| 2004/0248177 | A1 | 12/2004 | Fadel et al. |
| 2005/0101529 | A1 | 5/2005 | Yue et al. |
| 2006/0068428 | A1 | 3/2006 | Vance et al. |
| 2006/0147945 | A1 | 7/2006 | Edmonds et al. |
| 2006/0223088 | A1 | 10/2006 | Rosen et al. |
| 2006/0223090 | A1 | 10/2006 | Rosen et al. |
| 2007/0015696 | A1 | 1/2007 | Rosen et al. |
| 2007/0037206 | A1 | 2/2007 | Rosen et al. |

FOREIGN PATENT DOCUMENTS

| | | |
|---|---|---|
| EP | 1 403 282 A1 | 3/2004 |
| JP | 2002017376 | 1/2002 |
| JP | 2002017376 A | 1/2002 |
| JP | 2003512840 T | 4/2003 |
| JP | 2005130764 A | 5/2005 |
| WO | WO01/31007 A2 | 5/2001 |
| WO | WO01/57081 A2 | 8/2001 |
| WO | WO01/98468 A2 | 12/2001 |
| WO | WO02/46383 A2 | 6/2002 |
| WO | WO02/090526 A2 | 11/2002 |
| WO | WO02/012993 A2 | 12/2002 |
| WO | WO02/012994 A2 | 12/2002 |
| WO | WO2004/097047 A1 | 11/2004 |
| WO | WO2007030937 A2 | 3/2007 |
| WO | WO2007128121 A1 | 11/2007 |

OTHER PUBLICATIONS

Seidah et al. Int J Biochem Cell Biol. 2008;40(6-7):1111-25. Epub Feb. 8, 2008.*

Allard, D. et al., "Novel Mutations of the PCSK9 Gene Cause Variable Phenotype of Autosomal Dominant Hypercholesterolemia", Human Mutation, Mutation in Brief#854 (2005) Online.

Benjannet, S. et al., "The Proprotein Convertase (PC) PCSK9 Is Inactivated by Furin and/or PC5/6A", The Journal of Biological Chemistry, vol. 281(41), pp. 30561-30571 (2006).

Cameron, J. et al., "Effect of mutations in the *PCSK9* gene on the cell surface LDL receptors", Human Molecular Genetics, vol. 15(9), pp. 1551-1558 (2006).

Cohen, Ph.D., J. et al., "Sequence Variations in *PCSK9*, Low LDL, and Protection against Coronary Heart Disease", The New England Journal of Medicine, vol. 354(12), pp. 1264-1272 (2006).

Costet, P. et al., "Hepatic PCSK9 Expression is Regulated by Nutritional Status via Insulin and Sterol Regulatory Element-binding Protein 1c", The Journal of Biological Chemistry, vol. 281(10), pp. 6211-6218 (2006).

Evans, D. et al., "The E670G SNP in the *PCSK9* gene is associated with polygenic hypercholesterolemia in men but not in women", MNC Medical Genetics, vol. 7(66), pp. 1-5 (2006).

Holla, Ø. et al., "Degradation of the LDL receptors by PCSK9 is not mediated by a secreted protein acted upon by PCSK9 extracellularly", BMC Cell Biology, vol. 8(9), pp. 1-12 (2007).

Kotowski, I. et al., "A Spectrum of *PCSK9* Alleles Contributes to Plasma Levels of Low-Density Lipoprotein Cholesterol", The American Journal of Human Genetics, vol. 78, pp. 410-422 (2006).

Leren, TP., "Mutations in the PCSK9 gene in Norwegian subjects with autosomal dominant hypercholesterolemia", Clin Genet, vol. 65, pp. 419-422 (2004).

(Continued)

*Primary Examiner*—Christian L Fronda
(74) *Attorney, Agent, or Firm*—Stephen C. D'Amico

(57) ABSTRACT

The present invention provides novel polynucleotides encoding PCSK9b and PCSK9c polypeptides, fragments and homologues thereof. Also provided are vectors, host cells, antibodies, and recombinant and synthetic methods for producing said polypeptides. The invention further relates to diagnostic and therapeutic methods for applying these novel PCSK9b and PCSK9c polypeptides to the diagnosis, treatment, and/or prevention of various diseases and/or disorders related to these polypeptides. The invention further relates to screening methods for identifying agonists and antagonists of the polynucleotides and polypeptides of the present invention.

22 Claims, 18 Drawing Sheets

OTHER PUBLICATIONS

Figure 5:
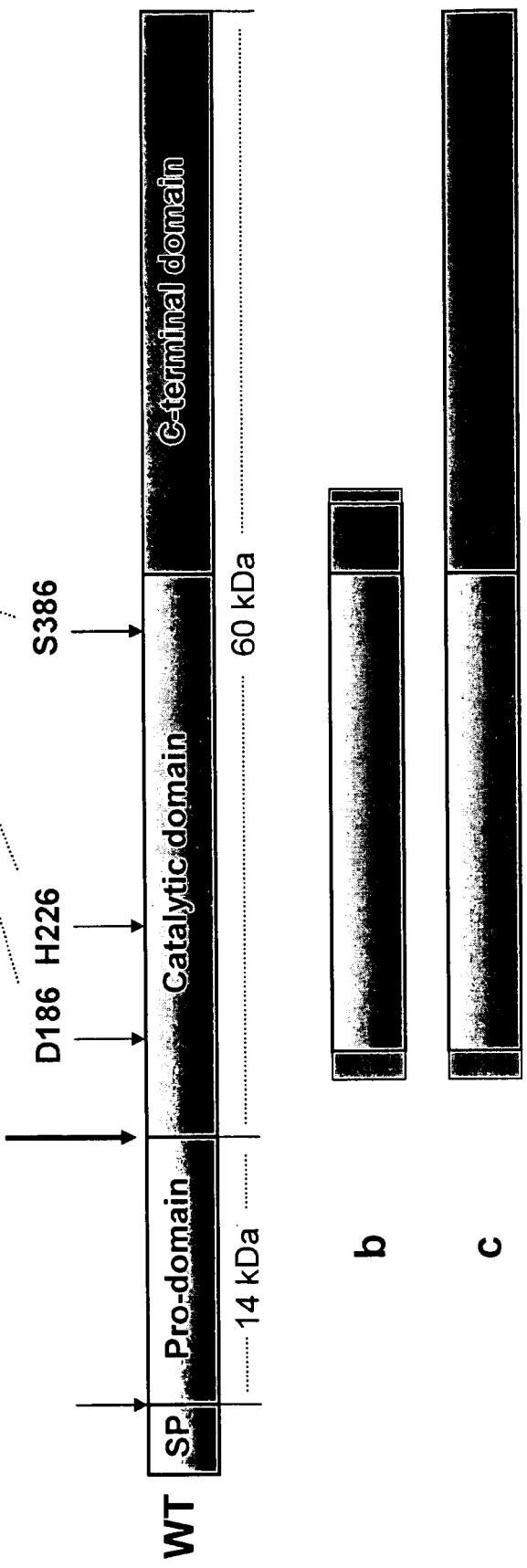

Naoumova, R. et al., "Severe Hypercholesterolemia in Four British Families with the D374Y Mutation in the PCSK9 Gene Long-Term Follow-Up and Treatment response", Arterioscler Thromb Basc Biol., vol. 25, pp. 2654-2660 (2005).

Ouguerram, K. et al., "Apolipoprotein B100 Metabolism in Autosomal-Dominant Hypercholesterolemia Related to Mutations in *PCSK9*", Arterioscler Throm Basc Biol., vol. 24, pp. 1448-1453 (2004).

Pisciotta, L. et al., "Additive effect of mutations in LDLR and PCSK9 genes on the phenotype of familial hypercholesterolemia", Atherosclerosis, vol. 186, pp. 433-440 (2006).

Shibata, N. et al., "No genetic association between PCSK9 polymorphisms and Alzheimer's disease and plasma cholesterol level in Japanese patients", Psychiatric Genetics, vol. 15 p. 239 (2005).

Yue, P. et al., "The c.43_44insCTG Variation in *PCSK9* is Associated with Low Plasma LDL-Cholesterol in a Caucasian Population", Human Mutation, vol. 27(5), pp. 460-466, (2006).

Abifadel, M. et al., "PCSK9, du gène à la proteéine, Un Nouvel Acteur dans l'homéostasie du cholestérol", Medicine Sciences, vol. 22, pp. 916-918 (2006).

Abifadel, et al., "Mutations in PCSK9 cause autosomal dominant hypercholesterolemia", Nature Genetics, vol. 34(2), pp. 154-156 (2003).

Attie, Alan, D., "The Mystery of PCSK9", Arterioscler. Thromb. Vasc. Biol., vol. 24, pp. 1337-1339 (2004).

Austin, et al., "Risk Factors For Coronary Heart Disease In Adult Female Twins", Amer. J. Epidemiology, vol. 125(2), pp. 308-318 (1987).

Benjannet, et al., "NARC-1/PCSK9 and Its Natural Mutants", J. Biol. Chem., vol. 279(47), pp. 48865-48875 (2004).

Berge, et al., "Missense Mutations in the PCSK9 Gene Are Associated With Hypocholesterolemia and Possibly Increased Response to Statin Therapy", Arterioscler. Thromb. Vasc. Biol., vol. 26, pp. 1094-1100 (2006).

Brown, et al., "A proteolytic pathway that controls the cholesterol content of membranes, cells, and blood", PNAS, vol. 96, pp. 11041-11048 (1999).

Cohen, et al., "Low LDL cholesterol in individuals of African descent resulting from frequent nonsense mutations in PCSK9", Nature Genetics, vol. 37(2), pp. 161-165 (2005).

Desai, et al., "Nell1-deficient mice have reduced expression of extracellular matrix proteins causing cranial and vertebral defects", Human. Molec. Genetics, vol. 15(8), pp. 1329-1341 (2006).

Dubuc, et al., "Statins Upregulate PCSK9, the Gene Encoding the Proprotein Convertase Neural Apoptosis-Regulated Convertase-1 Implicated in Familial Hypercholesterolemia", Arterioscler. Thromb. Vasc. Biol., vol. 24, pp. 1454-1459 (2004).

Fredrickson, et al., "Fat Transport in Lipoproteins—An Integrated Approach To Mechanisms And Disorders (Concluded)", New Eng. J. Medicine, vol. 276(5), pp. 273-281 (1967).

Goldstein, et al., "Familial Hypercholesterolemia: Pathogenesis of a Receptor Disease", Johns Hopkins Med. J., vol. 143, pp. 8-16 (1978).

Graham, et al., "Antisense inhibition of proprotein convertase subtilisin/kexin type 9 reduces serum LDL in hyperlipidemic mice", J. Lipid Res., vol. 48, pp. 763-767 (2007).

Hallman, et al., Relation of PCSK9 Mutations to Serum Low-Density Lipoprotein Cholesterol in Childhood and Adulthood (from the Bogalusa Heart Study), Am. J. Cardiol., vol. 100, pp. 69-72 (2007).

Horton, et al., "Molecular biology of PCSK9: its role in LDL metabolism", TIBS, vol. 32(2), vol. 32(2), pp. 71-77 (2007).

Houghten, et al., "Generation and use of synthetic peptide combinatorial libraries for basic research and drug discovery", Nature, vol. 354, pp. 84-86 (1991).

Hunt, et al., "Genetic Localization to Chromosome 1p32 of the Third Locus for Familial Hypercholesterolemia in a Utah Kindred", Arterioscler. Thromb. Vasc. Biol., vol. 20, pp. 1089-1093 (2000).

Innerarity, et al., "Familial defective apolipoprotein B-100: Low density lipoproteins with abnormal receptor binding", PNAS, vol. 84, pp. 6919-6923 (1987).

Khachadurian, Avedis, K., "The Inheritance of Essential Familial Hypercholesterolemia", American J. Med., vol. 37, pp. 402-407 (1964).

Lagace, et al., "Secreted PCSK9 decreases the number of LDL receptors in hepatocytes and in livers of parabiotic mice", J. Clin. Invest., vol. 116(11), pp. 2995-3005 (2006).

Lalanne, et al., "Wild-type PCSK9 inhibits LDL clearance but does not affect apoB-containing lipoprotein production in mouse and cultured cells", J. Lipid Res., vol. 46, pp. 1312-1319 (2005).

Lam, et al., "A new type of synthetic peptide library for identifying ligand-binding activity", Nature, vol. 354, pp. 82-84 (1991).

Lambert, Gilles, "Unravelling the functional significance of PCSK9", Curr. Opin. Lipidol., vol. 18, pp. 304-309 (2007).

Lambert, et al., "Fasting Induces Hyperlipidemia in Mice Overexpressing Proprotein Convertase Subtilisin Kexin Type 9: Lack of Modulation of Very-Low-Density Lipoprotein Hepatic Output by the Low-Density Lipoprotein Receptor", Endocrinology, vol. 147(10), pp. 4985-4995 (2006).

Lusis, Aldons, J., "Atherosclerosis", Nature, 407(6801), pp. 233-241 (2000).

Maxwell, et al., "Adenoviral-mediated expression of Pcsk9 in mice results in a low-density lipoprotein receptor knockout phenotype", PNAS, vol. 101(18), pp. 7100-7105 (2004).

Maxwell, et al., "Overexpression of PCSK9 accelerates the degradation of the LDLR in a post-endoplasmic reticulum compartment", PNAS, vol. 102(6), pp. 2069-2074 (2005).

Maxwell, et al., "Novel putative SREBP and LXR target genes identified by microarray analysis in liver of cholesterol-fed mice", J. Lipid Res., vol. 44, pp. 2109-2119 (2003).

Mayne, et al., "Plasma PCSK9 levels correlate with cholesterol in men but not in women", Biochem. Biophysical Res. Comm., vol. 361, pp. 451-456 (2007).

McNutt, et al., "Catalytic Activity is not Required for Secreted PCSK9 to Reduce Low Density Lipoprotein Receptors in HepG2 Cells", J. Biol. Chem., vol. 282(29), pp. 20799-20803 (2007).

Morganroth, et al., "Pseudohomozygous type II hyperlipoproteinemia", J. Pediatrics, vol. 85(5), pp. 639-643 (1974).

Naureckiene, et al., "Functional characterization of Narc 1, a novel proteinase related to proteinase K", Biochem. Biophysics, vol. 420, pp. 55-67 (2003).

Park, et al., "Post-transcriptional Regulation of Low Density Lipoprotein Receptor Protein by Proprotein Convertase Subtilisin/Kexin Type 9a in Mouse Liver", J. Biol. Chem., vol. 279(48), pp. 50630-50638 (2004).

Perusse, et al., "Genetic and Environmental Determinants of Serum Lipids and Lipoproteins in French Canadian Families", Arteriosclerosis, vol. 9, pp. 308-318 (1989).

Piper, et al., "The Crystal Structure of PCSK9: A Regulator of Plasma LDL-Cholesterol", Structure, vol. 15, pp. 545-552 (2007).

Poirier, et al., "Implication of the proprotein convertase NARC-1/PCSK9 in the development of the nervous system", J. Neurochem., vol. 98, pp. 838-850 (2006).

Rashid, et al., "Decreased plasma cholesterol and hypersensitivity to statins in mice lacking Pcsk9", PNAS, vol. 102(15), pp. 5374-5379 (2005).

Repa, et al., "Regulation of mouse sterol regulatory element-binding protein-1c gene (SREBP-1c) by oxysterol receptors, LXRα and LXRβ", Genes Develop., vol. 14, pp. 2819-2830 (2000).

Rice, et al., "Familial Aggregation of Lipids and Lipoproteins in Families Ascertained through Random and Nonrandom Probands in the Minnesota Lipid Research Clinic Family Study", Human Biol., vol. 63(4), pp. 419-439 (1991).

Seidah, et al., "The secretory proprotein convertase neural apoptosis-regulated convertase 1 (NARC-1): Liver regeneration and neuronal differentiation", PNAS, vol. 100(3), pp. 928-933 (2003).

Shimomura, et al., "Insulin selectively increases SREBP-1c mRNA in the livers of rats with streptozotocin-induced diabetes", PNAS, vol. 96(24), pp. 13656-13661 (1999).

Songyang, et al., "SH2 Domains Recognize Specific Phosphopeptide Sequences", Cell. vol. 72, pp. 767-778 (1993).

Sun, et al., "Evidence for effect of mutant PCSK9 on apolipoprotein B secretion as the cause of unusually severe dominant hypercholesterolaemia", Human Molec. Genetics, vol. 14(9), pp. 1161-1169 (2005).

Timms, et al., "A mutation in PCSK9 causing autosomal-dominant hypercholesterolemia in a Utah pedigree", Hum. Genet., vol. 114, pp. 349-353 (2004).

Varret, et al., "A Third Major Locus for Autosomonal Dominant Hypercholesterolemia Maps to 1p34.1-p32", Am. J. Hum. Genet., vol. 64, pp. 1378-1387 (1999).

Zhao, et al., "Molecular Characterization of Loss-of-Function Mutations in PCSK9 and Identification of a Compound Heterozygote", Amer. J. Hum. Genet., vol. 79, pp. 514-523 (2006).

NCBI Entrez Accession No. AAV67948 (gi:55925154), Rieder, et al., Nov. 27, 2004.

NCBI Entrez Accession No. AK124635 (gi:34530476), Ninomiya, et al., Sep. 14, 2006.

NCBI Entrez Accession No. AL158848 (gi:9930836), Mclay, K., Jul. 10, 2001.

NCBI Entrez Accession No. EAX06660 (gi:119627065), Venter, et al., Dec. 18, 2006.

NCBI Entrez Accession No. NM_153565 (gi:23956351), Graham, et al., Sep. 3, 2007.

NCBI Entrez Accession No. NM_174936 (gi:31317306), McNutt, et al., Sep. 24, 2007.

NCBI Entrez Accession No. NP_777596 (gi:31317307), McNutt, et al., Sep. 24, 2007.

NCBI Entrez Accession No. XP_173014 (gi:27480028), International Human Genome Sequencing Consortium, Jan. 3, 2003.

* cited by examiner

FIG. 1A

```
  1 GATGACTTGGGTCCTTCTTGGCAGTAGCATTGCCAGCTGATGGCCTTGGACAGTTACCTG 60

61 CCCTCTCTAGGCCTCCCTTTCCTTGTCTATGAAATACATTATAGAATAGGATGTAGTGTG 120

121 TGAGGATTTTTTGGAGGTTAAACGAGTGAATATATTTAAGGCGCTTTCACCAGTGCCTGG 180

181 GATGTGCTCTGTAGTTTCTGTGTGTTAACTATAAGGTTGACTTTATGCTCATTCCCTCCT 240

241 CTCCCACAAATGTCGCCTTGGAAAGACGGAGGCAGCCTGGTGGAGGTGTATCTCCTAGAC 300
  1          M  S  P  W  K  D  G  G  S  L  V  E  V  Y  L  L  D   17

301 ACCAGCATACAGAGTGACCACCGGGAAATCGAGGGCAGGGTCATGGTCACCGACTTCGAG 360
 18  T  S  I  Q  S  D  H  R  E  I  E  G  R  V  M  V  T  D  F  E   37

361 AATGTGCCCGAGGAGGACGGGACCCGCTTCCACAGACAGGCCAGCAAGTGTGACAGTCAT 420
 38  N  V  P  E  E  D  G  T  R  F  H  R  Q  A  S  K  C  D  S  H   57

421 GGCACCCACCTGGCAGGAGTGGTCAGCGGCCGGGATGCCGGCGTGGCCAAGGGTGCCAGC 480
 58  G  T  H  L  A  G  V  V  S  G  R  D  A  G  V  A  K  G  A  S   77

481 ATGCGCAGCCTGCGCGTGCTCAACTGCCAAGGGAAGGGCACGGTTAGCGGCACCCTCATA 540
 78  M  R  S  L  R  V  L  N  C  Q  G  K  G  T  V  S  G  T  L  I   97

541 GGCCTGGAGTTTATTCGGAAAAGCCAGCTGGTCCAGCCTGTGGGGCCACTGGTGGTGCTG 600
 98  G  L  E  F  I  R  K  S  Q  L  V  Q  P  V  G  P  L  V  V  L  117

601 CTGCCCCTGGCGGGTGGGTACAGCCGCGTCCTCAACGCCGCCTGCCAGCGCCTGGCGAGG 660
118  L  P  L  A  G  G  Y  S  R  V  L  N  A  A  C  Q  R  L  A  R  137

661 GCTGGGGTCGTGCTGGTCACCGCTGCCGGCAACTTCCGGGACGATGCCTGCCTCTACTCC 720
138  A  G  V  V  L  V  T  A  A  G  N  F  R  D  D  A  C  L  Y  S  157

721 CCAGCCTCAGCTCCCGAGGTCATCACAGTTGGGGCCACCAATGCCCAGGACCAGCCGGTG 780
158  P  A  S  A  P  E  V  I  T  V  G  A  T  N  A  Q  D  Q  P  V  177
                       *     *

781 ACCCTGGGGACTTTGGGGACCAACTTTGGCCGCTGTGTGGACCTCTTTGCCCCAGGGGAG 840
178  T  L  G  T  L  G  T  N  F  G  R  C  V  D  L  F  A  P  G  E  197
                                       *

841 GACATCATTGGTGCCTCCAGCGACTGCAGCACCTGCTTTGTGTCACAGAGTGGGACATCA 900
198  D  I  I  G  A  S  S  D  C  S  T  C  F  V  S  Q  S  G  T  S  217

901 CAGGCTGCTGCCCACGTGGCTGGCATTGCAGCCATGATGCTGTCTGCCGAGCCGGAGCTC 960
218  Q  A  A  A  H  V  A  G  I  A  A  M  M  L  S  A  E  P  E  L  237
```

FIG. 1B

```
 961 ACCCTGGCCGAGTTGAGGCAGAGACTGATCCACTTCTCTGCCAAAGATGTCATCAATGAG 1020
 238  T   L   A   E   L   R   Q   R   L   I   H   F   S   A   K   D   V   I   N   E   257

1021 GCCTGGTTCCCTGAGGACCAGCGGGTACTGACCCCCAACCTGGTGGCCGCCCTGCCCCCC 1080
 258  A   W   F   P   E   D   Q   R   V   L   T   P   N   L   V   A   A   L   P   P   277

1081 AGCACCCATGGGGCAGGCCCTTTTTGCAGGTTGGCAGCTGTTTTGCAGGACTGTGTGGTC 1140
 278  S   T   H   G   A   G   P   F   C   R   L   A   A   V   L   Q   D   C   V   V   297

1141 AGCACACTCGGGGCCTACACGGATGGCCACAGCCATCGCCCGCTGCGCCCCAGATGAGGA 1200
 298  S   T   L   G   A   Y   T   D   G   H   S   H   R   P   L   R   P   *       315

1201 GCTGCTGAGCTGCTCCAGTTTCTCCAGGAGTGGGAAGCGGCGGGGCGAGCGCATGGAGGC 1260

1261 CCAAGGGGGCAAGCTGGTCTGCCGGGCCCACAACGCTTTTGGGGGTGAGGGTGTCTACGC 1320

1321 CATTGCCAGGTGCTGCCTGCTACCCCAGGCCAACTGCAGCGTCCACACAGCTCCACCAGC 1380

1381 TGAGGCCAGCATGGGGACCCGTGTCCACTGCCACCAACAGGGCCACGTCCTCACAGGCTG 1440

1441 CAGCTCCCACTGGGAGGTGGAGGACCTTGGCACCCACAAGCCGCCTGTGCTGAGGCCACG 1500

1501 AGGTCAGCCCAACCAGTGCGTGGGCCACAGGGAGGCCAGCATCCACGCTTCCTGCTGCCA 1560

1561 TGCCCCAGGTCTGGAATGCAAAGTCAAGGAGCATGGAATCCCGGCCCCTCAGGAGCAGGT 1620

1621 GACCGTGGCCTGCGAGGAGGGCTGGACCCTGACTGGCTGCAGTGCCCTCCCTGGGACCTC 1680

1681 CCACGTCCTGGGGGCCTACGCCGTAGACAACACGTGTGTAGTCAGGAGCCGGGACGTCAG 1740

1741 CACTACAGGCAGCACCAGCGAAGAGGCCGTGACAGCCGTTGCCATCTGCTGCCGGAGCCG 1800

1801 GCACCTGGCGCAGGCCTCCCAGGAGCTCCAGTGACAGCCCCATCCCAGGATGGGTGTCTG 1860

1861 GGGAGGGTCAAGGGCTGGGGCTGAGCTTTAAAATGGTTCCGACTTGTCCCTCTCTCAGCC 1920

1921 CTCCATGGCCTGGCACGAGGGGATGGGGATGCTTCCGCCTTTCCGGGGCTGCTGGCCTGG 1980

1981 CCCTTGAGTGGGGCAGCCTCCTTGCCTGGAACTCACTCACTCTGGGTGCCTCCTCCCCAG 2040

2041 GTGGAGGTGCCAGGAAGCTCCCTCCCTCACTGTGGGGCATTTCACCATTCAAACAGGTCG 2100
```

FIG. 1C

```
2101 AGCTGTGCTCGGGTGCTGCCAGCTGCTCCCAATGTGCCGATGTCCGTGGGCAGAATGACT 2160

2161 TTTATTGAGCTCTTGTTCCGTGCCAGGCATTCAATCCTCAGGTCTCCACCAAGGAGGCAG 2220

2221 GATTCTTCCCATGGATAGGGGAGGGGGCGGTAGGGGCTGCAGGGACAAACATCGTTGGGG 2280

2281 GGTGAGTGTGAAAGGTGCTGATGGCCCTCATCTCCAGCTAACTGTGGAGAAGCCCCTGGG 2340

2341 GGCTCCCTGATTAATGGAGGCTTAGCTTTCTGGATGGCATCTAGCCAGAGGCTGGAGACA 2400

2401 GGTGTGCCCCTGGTGGTCACAGGCTGTGCCTTGGTTTCCTGAGCCACCTTTACTCTGCTC 2460

2461 TATGCCAGGCTGTGCTAGCAACACCCAAAGGTGGCCTGCGGGGAGCCATCACCTAGGACT 2520

2521 GACTCGGCAGTGTGCAGTGGTGCATGCACTGTCTCAGCCAACCCGCTCCACTACCCGGCA 2580

2581 GGGTACACATTCGCACCCCTACTTCACAGAGGAAGAAACCTGGAACCAGAGGGGGCGTGC 2640

2641 CTGCCAAGCTCACACAGCAGGAACTGAGCCAGAAACGCAGATTGGGCTGGCTCTGAAGCC 2700

2701 AAGCCTCTTCTTACTTCACCCGGCTGGGCTCCTCATTTTTACGGGTAACAGTGAGGCTGG 2760

2761 GAAGGGGAACACAGACCAGGAAGCTCGGTGAGTGATGGCAGAACGATGCCTGCAGGCATG 2820

2821 GAACTTTTTCCGTTATCACCCAGGCCTGATTCACTGGCCTGGCGGAGATGCTTCTAAGGC 2880

2881 ATGGTCGGGGGAGAGGGCCAACAACTGTCCCTCCTTGAGCACCAGCCCCACCCAAGCAAG 2940

2941 CAGACATTTATCTTTTGGGTCTGTCCTCTCTGTTGCCTTTTACAGCCAACTTTTCTAGA 3000

3001 CCTGTTTTGCTTTTGTAACTTGAAGATATTTATTCTGGGTTTTGTAGCATTTTTATTAAT 3060

3061 ATGGTGACTTTTTAAAATAAAAACAAACAAACGTTGTCCTAAAAAAAAAAAAAAAAAAAA 3120

3121 AAAAAAAAAAAAAAAAAAAAAAAAAAAAAAAAAAAAAAAAAAAAAAAAAAAAAA 3175
```

FIG. 2A

```
  1 TGCTAGCAGCAACCTGCCTGAAGTCTTCCTTTGGCCTGGCTGAGAGTTTCTGAGACCTGC  60

61 GCTGGAGCGGAGGTGCTTCCTTCCTTGCTTCCTTTCTTCCTCTCTCCCTTCTCCATCCAG 120

121 CAGGCTGGACCTGCCTGGCATCTGTGAGCTCTCCCTACTTTCTCCTATACCCTAACCTTT 180

181 GTCCTGCATGGGCGACTCCCCCAGTGAGTCTCTTGCAGCTTTTACCCCAGTGCCTGCTTC 240

241 TTGGAGAATCCAAACTGATCCAGTTAGGGATGATAAAGTGTAGGGTAGGCGCTCGGTGAC 300

301 TGTTTTCTCTGAGGTTGTGACTCGTGTGAGGCAGAAGCAGTCCCCGTGAGCCCTCCTGGT 360

361 ATCTTGTGGAGTGGAGAACGCTTGGACCTGGAGCCAGGAGGCCCAGACATACATCCTGTC 420

421 CGAGCTGCAGCTTCCTGTCTCTAAAATGAGCCGGCCAGCGCAGGTGGCCAGACATCACTG 480

481 TTATTCTCCTTTGAGTCTTTAAATCTTGTTGTCTTTCTTGCAGACTCGGTGAGCTGTGAA 540

541 AGGCTATAATAGGGGCTTTATTTTACACTTTGATACTATTTTTTGAACATTCATATTATT 600

601 GTTAGATATTGATATTCATATGAAGGAGCAGGATGACTTGGGTCCTTCTTGGCAGTAGCA 660

661 TTGCCAGCTGATGGCCTTGGACAGTTACCTGCCCTCTCTAGGCCTCCCTTTCCTTGTCTA 720

721 TGAAATACATTATAGAATAGGATGTAGTGTGTGAGGATTTTTGGAGGTTAAACGAGTGA 780

781 ATATATTTAAGGCGCTTTCACCAGTGCCTGGGATGTGCTCTGTAGTTTCTGTGTGTTAAC 840

841 TATAAGGTTGACTTTATGCTCATTCCCTCCTCTCCCACAAATGTCGCCTTGGAAAGACGG 900
  1                                             M  S  P  W  K  D  G   7

901 AGGCAGCCTGGTGGAGGTGTATCTCCTAGACACCAGCATACAGAGTGACCACCGGGAAAT 960
  8  G  S  L  V  E  V  Y  L  L  D̲  T  S  I  Q  S  D  H  R  E  I  27

961 CGAGGGCAGGGTCATGGTCACCGACTTCGAGAATGTGCCCGAGGAGGACGGGACCCGCTT 1020
 28  E  G  R  V  M  V  T  D  F  E  N  V  P  E  E  D  G  T  R  F  47

1021 CCACAGACAGGCCAGCAAGTGTGACAGTCATGGCACCCACCTGGCAGGGGTGGTCAGCGG 1080
 48  H  R  Q  A  S  K  C  D  S  H̲  G  T  H  L  A  G  V  V  S  G  67
```

FIG. 2B

```
1081 CCGGGATGCCGGCGTGGCCAAGGGTGCCAGCATGCGCAGCCTGCGCGTGCTCAACTGCCA 1140
  68  R   D   A   G   V   A   K   G   A   S   M   R   S   L   R   V   L   N   C   Q   87

1141 AGGGAAGGGCACGGTTAGCGGCACCCTCATAGGCCTGGAGTTTATTCGGAAAAGCCAGCT 1200
  88  G   K   G   T   V   S   G   T   L   I   G   L   E   F   I   R   K   S   Q   L   107

1201 GGTCCAGCCTGTGGGGCCACTGGTGGTGCTGCTGCCCCTGGCGGGTGGGTACAGCCGCGT 1260
 108  V   Q   P   V   G   P   L   V   V   L   L   P   L   A   G   G   Y   S   R   V   127

1261 CCTCAACGCCGCCTGCCAGCGCCTGGCGAGGGCTGGGGTCGTGCTGGTCACCGCTGCCGG 1320
 128  L   N   A   A   C   Q   R   L   A   R   A   G   V   V   L   V   T   A   A   G   147

1321 CAACTTCCGGGACGATGCCTGCCTCTACTCCCCAGCCTCAGCTCCCGAGGTCATCACAGT 1380
 148  N   F   R   D   D   A   C   L   Y   S   P   A   S   A   P   E   V   I   T   V   167
                                              *       *

1381 TGGGGCCACCAATGCCCAGGACCAGCCGGTGACCCTGGGGACTTTGGGGACCAACTTTGG 1440
 168  G   A   T   N   A   Q   D   Q   P   V   T   L   G   T   L   G   T   N   F   G   187

1441 CCGCTGTGTGGACCTCTTTGCCCCAGGGGAGGACATCATTGGTGCCTCCAGCGACTGCAG 1500
 188  R   C   V   D   L   F   A   P   G   E   D   I   I   G   A   S   S   D   C   S   207
              *

1501 CACCTGCTTTGTGTCACAGAGTGGGACATCACAGGCTGCTGCCCACGTGGCTGGCATTGC 1560
 208  T   C   F   V   S   Q   S   G   T   S   Q   A   A   A   H   V   A   G   I   A   227

1561 AGCCATGATGCTGTCTGCCGAGCCGGAGCTCACCCTGGCCGAGTTGAGGCAGAGACTGAT 1620
 228  A   M   M   L   S   A   E   P   E   L   T   L   A   E   L   R   Q   R   L   I   247

1621 CCACTTCTCTGCCAAAGATGTCATCAATGAGGCCTGGTTCCCTGAGGACCAGCGGGTACT 1680
 248  H   F   S   A   K   D   V   I   N   E   A   W   F   P   E   D   Q   R   V   L   267

1681 GACCCCCAACCTGGTGGCCGCCCTGCCCCCCAGCACCCATGGGGCAGGTTGGCAGCTGTT 1740
 268  T   P   N   L   V   A   A   L   P   P   S   T   H   G   A   G   W   Q   L   F   287

1741 TTGCAGGACTGTGTGGTCAGCACACTCGGGGCCTACACGGATGGCCACAGCCATCGCCCG 1800
 288  C   R   T   V   W   S   A   H   S   G   P   T   R   M   A   T   A   I   A   R   307

1801 CTGCGCCCCAGATGAGGAGCTGCTGAGCTGCTCCAGTTTCTCCAGGAGTGGGAAGCGGCG 1860
 308  C   A   P   D   E   E   L   L   S   C   S   S   F   S   R   S   G   K   R   R   327

1861 GGGCGAGCGCATGGAGGCCCAAGGGGGCAAGCTGGTCTGCCGGGCCCACAACGCTTTTGG 1920
 328  G   E   R   M   E   A   Q   G   G   K   L   V   C   R   A   H   N   A   F   G   347

1921 GGGTGAGGGTGTCTACGCCATTGCCAGGTGCTGCCTGCTACCCCAGGCCAACTGCAGCGT 1980
 348  G   E   G   V   Y   A   I   A   R   C   C   L   L   P   Q   A   N   C   S   V   367
```

FIG. 2C

```
1981 CCACACAGCTCCACCAGCTGAGGCCAGCATGGGGACCCGTGTCCACTGCCACCAACAGGG 2040
 368  H  T  A  P  P  A  E  A  S  M  G  T  R  V  H  C  H  Q  Q  G  387

2041 CCACGTCCTCACAGGCTGCAGCTCCCACTGGGAGGTGGAGGACCTTGGCACCCACAAGCC 2100
 388  H  V  L  T  G  C  S  S  H  W  E  V  E  D  L  G  T  H  K  P  407

2101 GCCTGTGCTGAGGCCACGAGGTCAGCCCAACCAGTGCGTGGGCCACAGGGAGGCCAGCAT 2160
 408  P  V  L  R  P  R  G  Q  P  N  Q  C  V  G  H  R  E  A  S  I  427

2161 CCACGCTTCCTGCTGCCATGCCCCAGGTCTGGAATGCAAAGTCAAGGAGCATGGAATCCC 2220
 428  H  A  S  C  C  H  A  P  G  L  E  C  K  V  K  E  H  G  I  P  447

2221 GGCCCCTCAGGAGCAGGTGACCGTGGCCTGCGAGGAGGGCTGGACCCTGACTGGCTGCAG 2280
 448  A  P  Q  E  Q  V  T  V  A  C  E  E  G  W  T  L  T  G  C  S  467

2281 TGCCCTCCCTGGGACCTCCCACGTCCTGGGGGCCTACGCCGTAGACAACACGTGTGTAGT 2340
 468  A  L  P  G  T  S  H  V  L  G  A  Y  A  V  D  N  T  C  V  V  487

2341 CAGGAGCCGGGACGTCAGCACTACAGGCAGCACCAGCGAAGGGGCCGTGACAGCCGTTGC 2400
 488  R  S  R  D  V  S  T  T  G  S  T  S  E  G  A  V  T  A  V  A  507

2401 CATCTGCTGCCGGAGCCGGCACCTGGCGCAGGCCTCCCAGGAGCTCCAGTGACAGCCCCA 2460
 508  I  C  C  R  S  R  H  L  A  Q  A  S  Q  E  L  Q  *           523

2461 TCCCAGGATGGGTGTCTGGGGAGGGTCAAGGGCTGGGGCTGAGCTTTAAAATGGTTCCGA 2520

2521 CTTGTCCCTCTCTCAGCCCTCCATGGCCTGGCACGAGGGGATGGGGATGCTTCCGCCTTT 2580

2581 CCGGGGCTGCTGGCCTGGCCCTTGAGTGGGGCAGCCTCCTTGCCTGGAACTCACTCACTC 2640

2641 TGGGTGCCTCCTCCCCAGGTGGAGGTGCCAGGAAGCTCCCTCCCTCACTGTGGGCATTT 2700

2701 CACCATTCAAACAGGTCGAGCTGTGCTCGGGTGCTGCCAGCTGCTCCCAATGTGCCGATG 2760

2761 TCCGTGGGCAGAATGACTTTTATTGAGCTCTTGTTCCGTGCCAGGCATTCAATCCTCAGG 2820

2821 TCTCCACCAAGGAGGCAGGATTCTTCCCATGGATAGGGGAGGGGGCGGTAGGGGCTGCAG 2880

2881 GGACAAACATCGTTGGGGGGTGAGTGTGAAAGGTGCTGATGGCCCTCATCTCCAGCTAAC 2940

2941 TGTGGAGAAGCCCCTGGGGGCTCCCTGATTAATGGAGGCTTAGCTTTCTGGATGGCATCT 3000
```

FIG. 2D

```
3001 AGCCAGAGGCTGGAGACAGGTGCGCCCCTGGTGGTCACAGGCTGTGCCTTGGTTTCCTGA 3060

3061 GCCACCTTTACTCTGCTCTATGCCAGGCTGTGCTAGCAACACCCAAAGGTGGCCTGCGGG 3120

3121 GAGCCATCACCTAGGACTGACTCGGCAGTGTGCAGTGGTGCATGCACTGTCTCAGCCAAC 3180

3181 CCGCTCCACTACCCGGCAGGGTACACATTCGCACCCCTACTTCACAGAGGAAGAAACCTG 3240

3241 GAACCAGAGGGGGCGTGCCTGCCAAGCTCACACAGCAGGAACTGAGCCAGAAACGCAGAT 3300

3301 TGGGCTGGCTCTGAAGCCAAGCCTCTTCTTACTTCACCCGGCTGGGCTCCTCATTTTTAC 3360

3361 GGGTAACAGTGAGGCTGGGAAGGGGAACACAGACCAGGAAGCTCGGTGAGTGATGGCAGA 3420

3421 ACGATGCCTGCAGGCATGGAACTTTTTCCGTTATCACCCAGGCCTGATTCACTGGCCTGG 3480

3481 CGGAGATGCTTCTAAGGCATGGTCGGGGGAGAGGGCCAACAACTGTCCCTCCTTGAGCAC 3540

3541 CAGCCCCACCCAAGCAAGCAGACATTTATCTTTTGGGTCTGTCCTCTCTGTTGCCTTTTT 3600

3601 ACAGCCAACTTTTCTAGACCTGTTTTGCTTTTGTAACTTGAAGATATTTATTCTGGGTTT 3660

3661 TGTAGCATTTTTATTAATATGGTGACTTTTTAAAATAAAAACAAACAAACGTTGTCCTAA 3720

3721 AAAAAAAAAAAAAAAAAAAAAAAAAAAAAAAAAAAA 3756
```

FIG. 3A

```
                              1                                                      50
PCSK9           (1)    MGTVSSRRSWWPLPLLLLLLLGPAGARAQEDEDGDYEELVLALRSEED
PCSK9 variant   (1)    ------------------------------------------------
PCSK9b          (1)    ------------------------------------------------
PCSK9c          (1)    ------------------------------------------------

51                                                    100
PCSK9          (51)    GLAEAPEHGTTATFHRCAKDPWRLPGTYVVVLKEETHLSQSERTARRLQA
PCSK9 variant   (1)    ------------------------------------------------
PCSK9b          (1)    ------------------------------------------------
PCSK9c          (1)    ------------------------------------------------

101                                                   150
PCSK9         (101)    QAARRGYLTKILHVFHGLLPGFLVKMSGDLLELALKLPHVDYIEEDSSVF
PCSK9 variant   (1)    ------------------------------------------------
PCSK9b          (1)    ------------------------------------------------
PCSK9c          (1)    ------------------------------------------------

151                                                   200
PCSK9         (151)    AQSIPWNLERITPPRYRADEYQPPDGGSLVEVYLLDTSIQSDHREIEGRV
PCSK9 variant   (1)    -----------------------MSPWKDGGSLVEVYLLDTSIQSDHREIEGRV
PCSK9b          (1)    -----------------------MSPWKDGGSLVEVYLLDTSIQSDHREIEGRV
PCSK9c          (1)    -----------------------MSPWKDGGSLVEVYLLDTSIQSDHREIEGRV
                                                     *

201                                                   250
PCSK9         (201)    MVTDFENVPEEDGTRFHRQASKCDSHGTHLAGVVSGRDAGVAKGASMRSL
PCSK9 variant  (32)    MVTDFENVPEEDGTRFHRQASKCDSHGTHLAGVVSGRDAGVAKGASMRSL
PCSK9b         (32)    MVTDFENVPEEDGTRFHRQASKCDSHGTHLAGVVSGRDAGVAKGASMRSL
PCSK9c         (32)    MVTDFENVPEEDGTRFHRQASKCDSHGTHLAGVVSGRDAGVAKGASMRSL
                                                     *
```

FIG. 3B

| | | |
|---|---|---|
| PCSK9 | (251) | RVLNCQGKGTVSGTLIGLEFIRKSQLVQPVGPLVVLLPLAGGYSRVLNAA |
| PCSK9 variant | (82) | RVLNCQGKGTVSGTLIGLEFIRKSQLVQPVGPLVVLLPLAGGYSRVLNAA |
| PCSK9b | (82) | RVLNCQGKGTVSGTLIGLEFIRKSQLVQPVGPLVVLLPLAGGYSRVLNAA |
| PCSK9c | (82) | RVLNCQGKGTVSGTLIGLEFIRKSQLVQPVGPLVVLLPLAGGYSRVLNAA |
| PCSK9 | (301) | CQRLARAGVVLVTAAGNFRDDACLYSPASAPEVITVGATNAQDQPVTLGT |
| PCSK9 variant | (132) | CQRLARAGVVLVTAAGNFRDDACLYSPASAPEGRTSLMPPATAAPALCHR |
| PCSK9b | (132) | CQRLARAGVVLVTAAGNFRDDACLYSPASAPEVITVGATNAQDQPVTLGT |
| PCSK9c | (132) | CQRLARAGVVLVTAAGNFRDDACLYSPASAPEVITVGATNAQDQPVTLGT |
| PCSK9 | (351) | LGTNFGRCVDLFAPGEDIIGASSDCSTCFVSQSGTSQAAAHVAGIAAMML |
| PCSK9 variant | (182) | VGHHRLLPHWLALQP--------------------------------- |
| PCSK9b | (182) | LGTNFGRCVDLFAPGEDIIGASSDCSTCFVSQSGTSQAAAHVAGIAAMML |
| PCSK9c | (182) | LGTNFGRCVDLFAPGEDIIGASSDCSTCFVSQSGTSQAAAHVAGIAAMML |
| PCSK9 | (401) | SAEPELTLAELRQRLIHFSAKDVINEAWFPEDQRVLTPNLVAALPPSTHG |
| PCSK9 variant | (197) | ------------------------------------------------ |
| PCSK9b | (232) | SAEPELTLAELRQRLIHFSAKDVINEAWFPEDQRVLTPNLVAALPPSTHG |
| PCSK9c | (232) | SAEPELTLAELRQRLIHFSAKDVINEAWFPEDQRVLTPNLVAALPPSTHG |
| PCSK9 | (451) | AGWQLFCRTVWSAHSGPTRMATAVARCAPDEELLSCSSFSRSGKRRGERM |
| PCSK9 variant | (197) | ------------------------------------------------ |
| PCSK9b | (282) | AGPFCRLAAVLQDCVVSTLGAYTDGHSHRPLRPR--------------- |
| PCSK9c | (282) | AGWQLFCRTVWSAHSGPTRMATAIARCAPDEELLSCSSFSRSGKRRGERM |

FIG. 3C

```
                        501                                                    550
PCSK9          (501)    EAQGGKLVCRAHNAFGGEGVYAIARCCLLPQANCSVHTAPPAEASMGTRV
PCSK9 variant  (197)    --------------------------------------------------
PCSK9b         (316)    --------------------------------------------------
PCSK9c         (332)    EAQGGKLVCRAHNAFGGEGVYAIARCCLLPQANCSVHTAPPAEASMGTRV 551                                                    600
PCSK9          (551)    HCHQQGHVLTGCSSHWEVEDLGTHKPPVLRPRGQPNQCVGHREASIHASC
PCSK9 variant  (197)    --------------------------------------------------
PCSK9b         (316)    --------------------------------------------------
PCSK9c         (382)    HCHQQGHVLTGCSSHWEVEDLGTHKPPVLRPRGQPNQCVGHREASIHASC 601                                                    650
PCSK9          (601)    CHAPGLECKVKEHGIPAPQEQVTVACEEGWTLTGCSALPGTSHVLGAYAV
PCSK9 variant  (197)    --------------------------------------------------
PCSK9b         (316)    --------------------------------------------------
PCSK9c         (432)    CHAPGLECKVKEHGIPAPQEQVTVACEEGWTLTGCSALPGTSHVLGAYAV 651                                          692
PCSK9          (651)    DNTCVVRSRDVSTTGSTSEGAVTAVAICCRSRHLAQASQELQ
PCSK9 variant  (197)    -----------------------------------------
PCSK9b         (316)    -----------------------------------------
PCSK9c         (482)    DNTCVVRSRDVSTTGSTSEGAVTAVAICCRSRHLAQASQELQ
```

FIG. 4

PCSK9b

| Protein | Genbank Accession | Identity | Similarity |
|---|---|---|---|
| Human PCSK9 | gi|NM_174936 | 40.8% | 40.6% |
| Human PCSK9 variant | gi|AK124635 | 53.7% | 53.3% |
| Human PCSK9 – Catalytic Domain | gi|NM_174936 | 100.0% | 100.0% |
| Human PCSK9 variant – Catalytic Domain | gi|AK124635 | 100.0% | 100.0% |

PCSK9c

| Protein | Genbank Accession | Identity | Similarity |
|---|---|---|---|
| Human PCSK9 | gi|NM_174936 | 74.9% | 74.7% |
| Human PCSK9 variant | gi|AK124635 | 32.3% | 32.1% |
| Human PCSK9 – Catalytic Domain | gi|NM_174936 | 100.0% | 100.0% |
| Human PCSK9 variant – Catalytic Domain | gi|AK124635 | 100.0% | 100.0% |

FIG. 7
A.
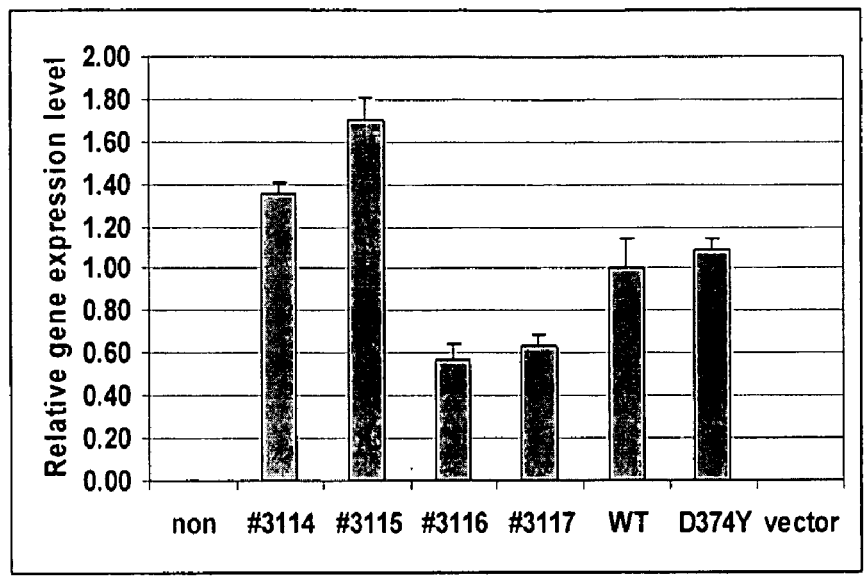
B.
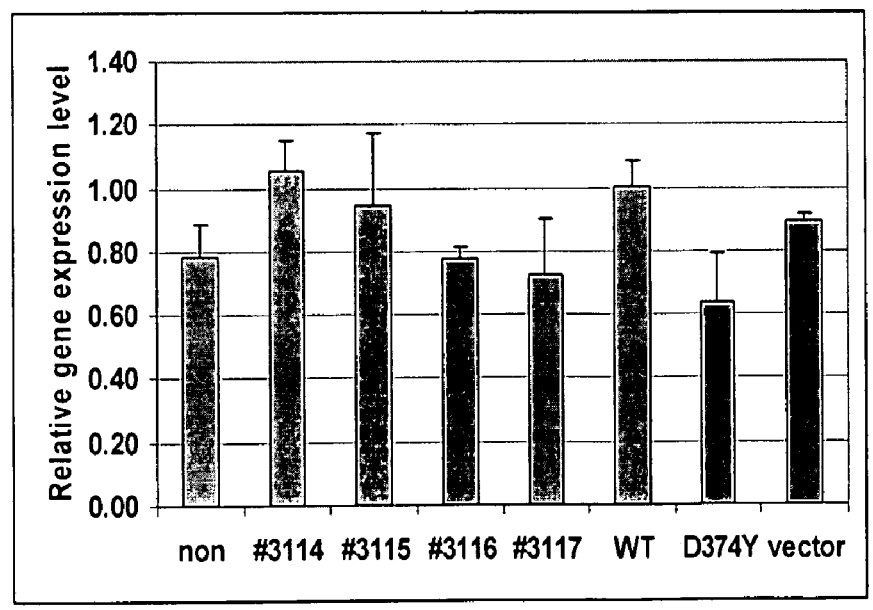

POLYNUCLEOTIDES ENCODING NOVEL PCSK9 VARIANTS

This application claims benefit to provisional application U.S. Ser. No. 60/818,234 filed Jun. 30, 2006, under 35 U.S.C. 119(e). The entire teachings of the referenced application are incorporated herein by reference.

FIELD OF THE INVENTION

The present invention provides novel polynucleotides encoding PCSK9b and PCSK9c polypeptides, fragments and homologues thereof. Also provided are vectors, host cells, antibodies, and recombinant and synthetic methods for producing said polypeptides. The invention further relates to diagnostic and therapeutic methods for applying these novel PCSK9b and PCSK9c polypeptides to the diagnosis, treatment, and/or prevention of various diseases and/or disorders related to these polypeptides. The invention further relates to screening methods for identifying agonists and antagonists of the polynucleotides and polypeptides of the present invention.

BACKGROUND OF THE INVENTION

Atherosclerosis is a disease of the arteries responsible for coronary heart disease (CVD) that underlies most deaths in industrialized countries (Lusis, 2000). Several risk factors for CHD have now been well established: dyslipidemias, hypertension, diabetes, smoking, poor diet, inactivity and stress. The most clinically relevant and common dyslipidemias are characterized by an increase in beta-lipoproteins (VLDL and LDL particles) with hypercholesterolemia in the absence or presence of hypertriglyceridemia (Fredrickson et al, 1967). An isolated elevation of LDL cholesterol is one of the most common risk factors for CVD. Twin studies (Austin et al, 1987) and family data (Perusse, 1989; Rice et al, 1991) have shown the importance of genetic factors in the development of the disease, particularly when its complications occur early in life. Mendelian forms of hypercholesterolemia have been identified: at first the autosomal dominant form (ADH) (Khachadurian, 1964) and later the autosomal recessive form (ARH), initially described as "pseudohomozygous type II hyperlipoproteinemia" (Morganroth et al, 1967).

ADH is a heterogeneous genetic disorder. Its most frequent and archetypal form is Familial Hypercholesterolemia (FH) with a frequency of 1 in 500 for heterozygotes and 1 per million for homozygotes (Goldstein et al, 1973). The disease is co-dominant with homozygotes being affected earlier and more severely than heterozygotes. FH is caused by mutations in the gene that encodes the LDL receptor (Goldstein & Brown, 1978) (LDLR at 19p13.1-p13.3) (MIN 143890). It is characterized by a selective increase of LDL cholesterol levels in plasma giving rise to tendon and skin xanthomas, arcus corneae and cardiovascular deposits leading to progressive and premature atherosclerosis, CHD and mortality (occurring before 55 years). The second form of ADH is Familial Defective apo B-100 (FDB) caused by mutations in the apolipoprotein B gene (APOB at 2p23-p24), encoding the ligand of the LDL receptor (Inneraty et al, 1987) (MIN 144010). The existence of a greater level of genetic heterogeneity in ADH (Saint-Jore et al, 2000) has been reported and the implication of a third locus named HCHOLA3 (formerly FH3) has been detected and mapped at 1p34.1-p32 in a French family (Varret et al, 1999) (MIM 603776). These results were confirmed by Hunt et al. in a large Utah kindred (Hunt et al, 2000).

PCSK9, for Proprotein Convertase Subtilisin/Kexin type 9 (also referred to as HCHOLA3, NARC-1, or FH3) is a protease belonging to the proteinase K subfamily of the secretory subtilase family (Naureckiene et al., Arch. of Biochem. And Biophy., 420:55-57 (2003)). PCSK9 has been shown to play a role in cholesterol homeostasis by regulating apolipoprotein receptor secretion. It may also have a role in the differentiation of brain cortical neurons (Seidah et al., PNAS 100(3): 928-933 (2003)).

The wild type PCSK9 gene contains 12 exons. The translated protein contains a signal peptide in the NH2-terminus, and in cells and tissues an about 74 kDa zymogen (precursor) form of the full-length protein is found in the endoplasmic reticulum. During initial processing in the cell, the about 14 kDa prodomain peptide is autocatalytically cleaved to yield a mature about 60 kDa protein containing the catalytic domain and a C-terminal domain often referred to as the cysteine-histidine rich domain (CHRD) (FIG. 1). This about 60 kDa form of PCSK9 is secreted from liver cells. The secreted form of PCSK9 appears to be the physiologically active species, although an intracellular functional role of the about 60 kDa form has not been ruled out.

Several mutant forms of PCSK9 are known, including S127R, N157K, F216L, R218S, and D374Y, with S127R, F216L, and D374Y being linked to autosomal dominant hypercholesterolemia (ADH). Benjannet et al. (J. Biol. Chem., 279(47):48865-48875 (2004)) demonstrated that the S127R and D374Y mutations result in a significant decrease in the level of pro-PCSK9 processed in the ER to form the active secreted zymogen. As a consequence it is believed that wild-type PCSK9 increases the turnover rate of the LDL receptor causing inhibition of LDL clearance (Maxwell et al., PNAS, 102(6):2069-2074 (2005); Benjannet et al., and Lalanne et al), while PCSK9 autosomal dominant mutations result in increased levels of LDLR, increased clearance of circulating LDL, and a corresponding decrease in plasma cholesterol levels (Rashid et al., PNAS, 102(15):5374-5379 (2005).

Lalanne et al. demonstrated that LDL catabolism was impaired and apolipoprotein B-containing lipoprotein synthesis was enhanced in two patients harboring S127R mutations in PCSK9 (J. Lipid Research, 46:1312-1319 (2005)). Sun et al. also provided evidence that mutant forms of PCSK9 are also the cause of unusually severe dominant hypercholesterolaemia as a consequence of its affect of increasing apolipoprotein B secretion (Sun et al, Hum. Mol. Genet., 14(9): 1161-1169 (2005)). These results were consistent with earlier results which demonstrated adenovirus-mediated overexpression of PCSK9 in mice results in severe hypercholesteromia due to durastic decreases in the amount of LDL receptor Dubuc et al., Thromb. Vasc. Biol., 24:1454-1459 (2004), in addition to results demonstrating mutant forms of PCSK9 also reduce the level of LDL receptor (Park et al., J. Biol. Chem., 279:50630-50638 (2004). The overexpression of PCSK9 in cell lines, including liver-derived cells, and in livers of mice in vivo, results in a pronounced reduction in LDLR protein levels and LDLR functional activity without changes in LDLR mRNA level (Maxwell K. N., Breslow J. L., Proc. Nat. Amer. Sci., 101:7100-7105 (2004); Benjannet S. et al., J. Bio. Chem. 279: 48865-48875 (2004)).

Using the above examples, it is clear the availability of novel forms of PCSK9 provide an opportunity for the identification of PCSK9 agonists, as well as, in the identification of PCSK9 inhibitors. All of which might be therapeutically useful under different circumstances.

The present invention also relates to recombinant vectors, which include the isolated nucleic acid molecules of the present invention, and to host cells containing the recombinant vectors, as well as to methods of making such vectors and host cells, in addition to their use in the production of PCSK9b and PCSK9c polypeptides or peptides using recombinant techniques. Synthetic methods for producing the polypeptides and polynucleotides of the present invention are provided. Also provided are diagnostic methods for detecting diseases, disorders, and/or conditions related to the PCSK9b and PCSK9c polypeptides and polynucleotides, and therapeutic methods for treating such diseases, disorders, and/or conditions. The invention further relates to screening methods for identifying binding partners of the polypeptides.

BRIEF SUMMARY OF THE INVENTION

The present invention provides isolated nucleic acid molecules, that comprise, or alternatively consist of, a polynucleotide encoding the PCSK9b protein having the amino acid sequence shown in FIGS. 1A-C (SEQ ID NO:2), respectively, or the amino acid sequence encoded by the cDNA clone, PCSK9b (also referred to as PCSK9-b), deposited as ATCC® Deposit Number PTA-7622 on May 10, 2006.

The present invention provides isolated nucleic acid molecules, that comprise, or alternatively consist of, a polynucleotide encoding the PCSK9c protein having the amino acid sequence shown in FIGS. 1A-D (SEQ ID NO:4), respectively, or the amino acid sequence encoded by the cDNA clone, PCSK9c (also referred to as PCSK9-c), deposited as ATCC® Deposit Number PTA-7622 on May 10, 2006.

The present invention also relates to recombinant vectors, which include the isolated nucleic acid molecules of the present invention, and to host cells containing the recombinant vectors, as well as to methods of making such vectors and host cells, in addition to their use in the production of PCSK9b or PCSK9c polypeptides or peptides using recombinant techniques. Synthetic methods for producing the polypeptides and polynucleotides of the present invention are provided. Also provided are diagnostic methods for detecting diseases, disorders, and/or conditions related to the PCSK9b or PCSK9c polypeptides and polynucleotides, and therapeutic methods for treating such diseases, disorders, and/or conditions. The invention further relates to screening methods for identifying binding partners of the polypeptides.

The invention further provides an isolated PCSK9b or PCSK9c polypeptide having an amino acid sequence encoded by a polynucleotide described herein.

The invention further relates to a polynucleotide encoding a polypeptide fragment of SEQ ID NO:2 or SEQ ID NO:4, or a polypeptide fragment encoded by the cDNA sequence included in the deposited clone, which is hybridizable to SEQ ID NO:1 or SEQ ID NO:3.

The invention further relates to a polynucleotide encoding a polypeptide domain of SEQ ID NO:2 or SEQ ID NO:4 or a polypeptide domain encoded by the cDNA sequence included in the deposited clone, which is hybridizable to SEQ ID NO:1 or SEQ ID NO:3.

The invention further relates to a polynucleotide encoding a polypeptide epitope of SEQ ID NO:2 or SEQ ID NO:4 or a polypeptide epitope encoded by the cDNA sequence included in the deposited clone, which is hybridizable to SEQ ID NO:1 or SEQ ID NO:3.

The invention further relates to a polynucleotide encoding a polypeptide of SEQ ID NO:2 or SEQ ID NO:4 or the cDNA sequence included in the deposited clone, which is hybridizable to SEQ ID NO:1 or SEQ ID NO:3, having biological activity.

The invention further relates to a polynucleotide which is a variant of SEQ ID NO:1 or SEQ ID NO:3.

The invention further relates to a polynucleotide which is an allelic variant of SEQ ID NO:1 or SEQ ID NO:3.

The invention further relates to a polynucleotide which encodes a species homologue of the SEQ ID NO:2 or SEQ ID NO:4.

The invention further relates to a polynucleotide which represents the complimentary sequence (antisense) of SEQ ID NO:1 or SEQ ID NO:4.

The invention further relates to a polynucleotide capable of hybridizing under stringent conditions to any one of the polynucleotides specified herein, wherein said polynucleotide does not hybridize under stringent conditions to a nucleic acid molecule having a nucleotide sequence of only A residues or of only T residues.

The invention further relates to an isolated nucleic acid molecule of SEQ ID NO:2 or SEQ ID NO:4, wherein the polynucleotide fragment comprises a nucleotide sequence encoding a subtilisin protease K proteinase.

The invention further relates to an isolated nucleic acid molecule of SEQ ID NO:1 or SEQ ID NO:3, wherein the polynucleotide fragment comprises a nucleotide sequence encoding the sequence identified as SEQ ID NO:2 or SEQ ID NO:4 or the polypeptide encoded by the cDNA sequence included in the deposited clone, which is hybridizable to SEQ ID NO:1 or SEQ ID NO:3.

The invention further relates to an isolated nucleic acid molecule of SEQ ID NO:1 or SEQ ID NO:3, wherein the polynucleotide fragment comprises the entire nucleotide sequence of SEQ ID NO:1 or SEQ ID NO:3 or the cDNA sequence included in the deposited clone, which is hybridizable to SEQ ID NO:1 or SEQ ID NO:3.

The invention further relates to an isolated nucleic acid molecule of SEQ ID NO:1 or SEQ ID NO:3, wherein the nucleotide sequence comprises sequential nucleotide deletions from either the C-terminus or the N-terminus.

The invention further relates to an isolated polypeptide comprising an amino acid sequence that comprises a polypeptide fragment of SEQ ID NO:2 or SEQ ID NO:4 or the encoded sequence included in the deposited clone.

The invention further relates to a polypeptide fragment of SEQ ID NO:2 or SEQ ID NO:4 or the encoded sequence included in the deposited clone, having biological activity.

The invention further relates to a polypeptide domain of SEQ ID NO:2 or SEQ ID NO:4 or the encoded sequence included in the deposited clone.

The invention further relates to a polypeptide epitope of SEQ ID NO:2 or SEQ ID NO:4 or the encoded sequence included in the deposited clone.

The invention further relates to a full length protein of SEQ ID NO:2 or SEQ ID NO:4 or the encoded sequence included in the deposited clone.

The invention further relates to a variant of SEQ ID NO:2 or SEQ ID NO:4.

The invention further relates to an allelic variant of SEQ ID NO:2 or SEQ ID NO:4.

The invention further relates to a species homologue of SEQ ID NO:2 or SEQ ID NO:4.

The invention further relates to the isolated polypeptide of SEQ ID NO:2 or SEQ ID NO:4, wherein the full length protein comprises sequential amino acid deletions from either the C-terminus or the N-terminus.

The invention further relates to an isolated antibody that binds specifically to the isolated polypeptide of SEQ ID NO:2 or SEQ ID NO:4.

The invention further relates to a method for preventing, treating, or ameliorating a medical condition, comprising administering to a mammalian subject a therapeutically effective amount of the polypeptide of SEQ ID NO:2 or SEQ ID NO:4 or the polynucleotide of SEQ ID NO:1 or SEQ ID NO:3.

The invention further relates to a method of diagnosing a pathological condition or a susceptibility to a pathological condition in a subject comprising the steps of: (a) determining the presence or absence of a mutation in the polynucleotide of SEQ ID NO:1 or SEQ ID NO:3; and (b) diagnosing a pathological condition or a susceptibility to a pathological condition based on the presence or absence of said mutation.

The invention further relates to a method of diagnosing a pathological condition or a susceptibility to a pathological condition in a subject comprising the steps of: (a) determining the presence or amount of expression of the polypeptide of SEQ ID NO:2 or SEQ ID NO:4 in a biological sample; and (b) diagnosing a pathological condition or a susceptibility to a pathological condition based on the presence or amount of expression of the polypeptide.

The invention further relates to a method for identifying a binding partner to the polypeptide of SEQ ID NO:2 or SEQ ID NO:4 comprising the steps of: (a) contacting the polypeptide of SEQ ID NO:2 or SEQ ID NO:4 with a binding partner; and (b) determining whether the binding partner effects an activity of the polypeptide.

The invention further relates to a gene corresponding to the cDNA sequence of SEQ ID NO:1 or SEQ ID NO:3.

The invention further relates to a method of identifying an activity in a biological assay, wherein the method comprises the steps of: (a) expressing SEQ ID NO:1 or SEQ ID NO:3 in a cell; (b) isolating the supernatant; (c) detecting an activity in a biological assay; and (d) identifying the protein in the supernatant having the activity.

The invention further relates to a process for making polynucleotide sequences encoding gene products having altered activity selected from the group consisting of SEQ ID NO:2 or SEQ ID NO:4 activity comprising the steps of: (a) shuffling a nucleotide sequence of SEQ ID NO:1 or SEQ ID NO:3; (b) expressing the resulting shuffled nucleotide sequences; and (c) selecting for altered activity selected from the group consisting of SEQ ID NO:2 or SEQ ID NO:4 activity as compared to the activity selected from the group consisting of SEQ ID NO:2 or SEQ ID NO:4 activity of the gene product of said unmodified nucleotide sequence.

The invention further relates to a shuffled polynucleotide sequence produced by a shuffling process, wherein said shuffled DNA molecule encodes a gene product having enhanced tolerance to an inhibitor of any one of the activities selected from the group consisting of SEQ ID NO:2 or SEQ ID NO:4 activity.

The invention further relates to a method for preventing, treating, or ameliorating a medical condition with the polypeptide provided as SEQ ID NO:2 or SEQ ID NO:4, in addition to, its encoding nucleic acid, wherein the medical condition is a reproductive disorder.

The invention further relates to a method for preventing, treating, or ameliorating a medical condition with the polypeptide provided as SEQ ID NO:2 or SEQ ID NO:4, in addition to, its encoding nucleic acid, wherein the medical condition is a disorder related to aberrant PCSK9 signaling and/or activity.

The invention further relates to a method for preventing, treating, or ameliorating a medical condition with the polypeptide provided as SEQ ID NO:2 or SEQ ID NO:4, in addition to, its encoding nucleic acid, wherein the medical condition is a cardiovascular disorder, hypercholesterolemia, autosomal dominant hypercholesterolemia; disorders associated with aberrant LDL receptor function; disorders associated with apolipoprotein B; disorders associated with autosomal recessive hypercholesterolemia; disorders associated with elevated cholesterol; disorders associated with elevated LDL; disorders associated with reduced clearance rate of LDL in the liver; disorders associated with elevated LDL apoB production; familial hypercholesterolemia; lipid metabolism disorders; elevated LDL; cholesterol depositions; tendon xanthomas; atheroma; premature arteriosclerosis, coronary heart disease; famialial defective apolipoprotein B; statin hypersensitivity; disorders associated with accelerated LDLR degradation, neural differentiation disorders.

The invention further relates to a method for preventing, treating, or ameliorating a medical condition with the polypeptide provided as SEQ ID NO:2 or SEQ ID NO:4, in addition to, its encoding nucleic acid, wherein the medical condition is a metabolic disorder.

The invention further relates to a method for preventing, treating, or ameliorating a medical condition with the polypeptide provided as SEQ ID NO:2 or SEQ ID NO:4, in addition to, its encoding nucleic acid, wherein the medical condition is a metabolic disorder selected from the group consisting of: dyslipidemia, diabetic dyslipidemia, mixed dyslipidemia, hypercholesteremia, hypertriglyceridemia, type II diabetes mellitus, type I diabetes, insulin resistance, hyperlipidemia, obesity, anorexia nervosa.

The invention further relates to a method of identifying a compound that modulates the biological activity of PCSK9b and/or PCSK9c, comprising the steps of: (a) combining a candidate modulator compound with PCSK9b and/or PCSK9c having the sequence set forth in SEQ ID NO:2 or SEQ ID NO:4; and (b) measuring an effect of the candidate modulator compound on the activity of PCSK9b and/or PCSK9c.

The invention further relates to a method of identifying a compound that modulates the biological activity of PCSK9b and/or PCSK9c, comprising the steps of: (a) combining a candidate modulator compound with PCSK9b and/or PCSK9c having the sequence set forth in SEQ ID NO:2 or SEQ ID NO:4; and (b) measuring an effect of the candidate modulator compound on the activity of PCSK9b and/or PCSK9c, wherein said method optionally includes the addition of a suitable PCSK9 substrate either before, during, or after addition of said candidate modulator compound.

The invention further relates to a method of identifying an antagonist compound that modulates the biological activity of PCSK9b and/or PCSK9c, comprising the steps of: (a) combining a candidate modulator compound with PCSK9b and/or PCSK9c having the sequence set forth in SEQ ID NO:2 or SEQ ID NO:4 in the presence of a suitable PCSK9 substrate; and (b) identifying antagonist compounds by measuring an effect of the candidate modulator compound on the activity of PCSK9b and/or PCSK9c, wherein said identified antagonist compound decreases proteinase activity of PCSK9b and/or PCSK9c.

The invention further relates to a method of identifying an agonist compound that modulates the biological activity of PCSK9b and/or PCSK9c, comprising the steps of: (a) combining a candidate modulator compound with PCSK9b and/or PCSK9c having the sequence set forth in SEQ ID NO:2 or SEQ ID NO:4 in the presence of a suitable PCSK9 substrate; and (b) identifying agonist compounds by measuring an effect of the candidate modulator compound on the activity of PCSK9b and/or PCSK9c, wherein said identified agonist compound increases proteinase activity of PCSK9b and/or PCSK9c.

The invention further relates to a method of identifying a compound that modulates the biological activity of PCSK9b and/or PCSK9c, comprising the steps of: (a) combining a candidate modulator compound with a host cell expressing PCSK9b and/or PCSK9c having the sequence as set forth in SEQ ID NO:2 or SEQ ID NO:4; and (b) measuring an effect of the candidate modulator compound on the activity of the expressed PCSK9b and/or PCSK9c.

The invention further relates to a method of identifying an antagonist compound that modulates the biological activity of wild-type PCSK9, comprising the steps of: (a) combining a candidate modulator compound with PCSK9b and/or PCSK9c having the sequence set forth in SEQ ID NO:2 or SEQ ID NO:4 in the presence of a suitable PCSK9 substrate; and (b) identifying antagonist compounds by measuring an effect of the candidate modulator compound on the activity of PCSK9, wherein said identified antagonist compound decreases proteinase activity of PCSK9.

The invention further relates to a method of identifying an agonist compound that modulates the biological activity of PCSK9, comprising the steps of: (a) combining a candidate modulator compound with PCSK9b and/or PCSK9c having the sequence set forth in SEQ ID NO:2 or SEQ ID NO:4 in the presence of a suitable PCSK9 substrate; and (b) identifying agonist compounds by measuring an effect of the candidate modulator compound on the activity of PCSK9, wherein said identified agonist compound increases proteinase activity of PCSK9.

The invention further relates to a method of identifying a compound that modulates the biological activity of PCSK9, comprising the steps of: (a) combining a candidate modulator compound with a host cell expressing PCSK9b and/or PCSK9c having the sequence as set forth in SEQ ID NO:2 or SEQ ID NO:4; and (b) measuring an effect of the candidate modulator compound on the activity of the expressed PCSK9b and/or PCSK9c.

The invention further relates to a method of screening for a compound that is capable of modulating the biological activity of PCSK9b and/or PCSK9c, comprising the steps of: (a) providing a host cell described herein; (b) determining the biological activity of PCSK9b and/or PCSK9c in the absence of a modulator compound; (c) contacting the cell with the modulator compound; and (d) determining the biological activity of PCSK9b and/or PCSK9c in the presence of the modulator compound; wherein a difference between the activity of PCSK9b and/or PCSK9c in the presence of the modulator compound and in the absence of the modulator compound indicates a modulating effect of the compound.

The invention further relates to a method of screening for a compound that is capable of modulating the biological activity of PCSK9, comprising the steps of: (a) providing a host cell comprising PCSK9b and/or PCSK9c; (b) determining the biological activity of PCSK9 in the absence of a modulator compound; (c) contacting the cell with the modulator compound; and (d) determining the biological activity of PCSK9 in the presence of the modulator compound; wherein a difference between the activity of PCSK9 in the presence of the modulator compound and in the absence of the modulator compound indicates a modulating effect of the compound.

The invention further relates to an N-terminal truncation of PCSK9 (SEQ ID NO:5), wherein said N-terminal truncation results in the deletion of anywhere between about 1 to about 218 amino acids from the N-terminus of SEQ ID NO:5, and wherein said N-terminal truncation results in elevated PCSK9 biological activity, including, but not limited to decreased LDLR protein levels, and/or decreased LDL uptake by LDLR.

The invention further relates to an N-terminal truncation of PCSK9 (SEQ ID NO:5), wherein said N-terminal truncation results in the deletion of anywhere between about 1 to about 218 amino acids from the N-terminus of SEQ ID NO:5, including, but not limited to decreased LDLR protein levels, and/or decreased LDL uptake by LDLR, and wherein said elevated PCSK9 biological activity is at least about 5%, 10%, 15%, 20%, 25%, 30%, 35%, 40%, 45%, 50%, 55%, 60%, 65%, 70%, 75%, 80%, 85%, 90%, 100%, or more than wild-type elevated PCSK9 biological activity. In this context, the term "about" shall be construed to mean anywhere between 1, 2, 3, 4, or 5 percent more or less than the cited amount. Alternatively, said elevated PCSK9 biological activity may be at least about 1×, 2×, 3×, 4×, 5×, 6×,7×, 8×, 9×, or 10× more than wildtype PCSK9 biological activity. In this context, the term "about" shall be construed to mean anywhere between 0.1×, 0.2×, 0.3×, 0.4×, 0.5×, 0.6×, 0.7×, 0.8×, or 0.9× more or less than the cited amount.

As used herein the terms "modulate" or "modulates" refer to an increase or decrease in the amount, quality or effect of a particular activity, DNA, RNA, or protein of PCSK9b and/or PCSK9c.

BRIEF DESCRIPTION OF THE FIGURES/DRAWINGS

The file of this patent contains at least one Figure executed in color. Copies of this patent with color Figure(s) will be provided by the Patent and Trademark Office upon request and payment of the necessary fee.

FIGS. 1A-C show the polynucleotide sequence (SEQ ID NO:1) and deduced amino acid sequence (SEQ ID NO:2) of the novel PCSK9 varient, PCSK9b of the present invention. The standard one-letter abbreviation for amino acids is used to illustrate the deduced amino acid sequence. The polynucleotide sequence contains a sequence of 3175 nucleotides (SEQ ID NO:1), encoding a polypeptide of 315 amino acids (SEQ ID NO:2). An analysis of the PCSK9b polypeptide determined that it comprised the following features: a catalytic domain located from about amino acid 10 to about amino acid 256 of SEQ ID NO:2 denoted in italics, with the canonical catalytic triad residing at amino acids D17, H57, and S217 of SEQ ID NO:2 denoted by double underlining; and six conserved cysteine residues located at amino acids C54, C86, C132, C154, C189, and C206 of SEQ ID NO:2 denoted in bold, with disulfite bonds predicted to form between the following cysteine pairs: C54 and C86, and C154 and C189; and a predicted $Ca^{2+}$ ion binding domain predicted to form between residues D191, P162, and V164 of SEQ ID NO:2, denoted by an asterisk (*) below the amino acid residue.

FIGS. 2A-D show the polynucleotide sequence (SEQ ID NO:3) and deduced amino acid sequence (SEQ ID NO:4) of the novel PCSK9 varient, PCSK9c of the present invention. The standard one-letter abbreviation for amino acids is used to illustrate the deduced amino acid sequence. The polynucleotide sequence contains a sequence of 3756 nucleotides (SEQ ID NO:3), encoding a polypeptide of 523 amino acids (SEQ ID NO:4). An analysis of the PCSK9c polypeptide determined that it comprised the following features: a catalytic domain located from about amino acid 10 to about amino acid 256 of SEQ ID NO:4 denoted in italics, with the canonical catalytic triad residing at amino acids D17, H57, and S217 of SEQ ID NO:4 denoted by double underlining; and six conserved cysteine residues located at amino acids C54, C86, C132, C154, C189, and C206 of SEQ ID NO:4 denoted in bold, with disulfide bonds predicted to form between the following cysteine pairs: C54 and C86, and C154 and C189; and a predicted $Ca^{2+}$ ion binding domain predicted to form between residues D191, P162, and V164 of SEQ ID NO:4, denoted by an asterisk (*) below the amino acid residue.

FIGS. 3A-C show the regions of identity and similarity between the sequences of the encoded PCSK9b and PCSK9c polypeptides of the present invention with the sequence of the human wild type PCSK9 protein (PCSK9; GENBANK® Accession No: gi|NM_174936; SEQ ID NO:5); as well as the sequence of a known variant of the wild type PCSK9 polypeptide (PCSK9 variant; GENBANK® Accession No: gi|AK124635; SEQ ID NO:6). The alignment was performed using the CLUSTALW algorithm using default parameters as described herein (VECTOR NTI® suite of programs). The darkly shaded amino acids represent regions of matching identity. The lightly shaded amino acids represent regions of matching similarity. Dots ("•") between residues indicate gapped regions of non-identity for the aligned polypeptides. The location of the conserved catalytic triad amino acids are denoted by an asterisk (*).

FIG. 4 shows a table illustrating the percent identity and percent similarity between the PCSK9b and PCSK9c polypeptides of the present invention with PCSK9 and its variant. As shown, the catalytic domain of both PCSK9b and PCSK9c shares 100% identity with the catalytic domain of PCSK9. The percent identity and percent similarity values were determined using the CLUSTALW algorithm using default parameters as described herein (VECTOR NTI® suite of programs).

FIG. 5 provides a schematic diagram of the PCSK9b and PCSK9c variants in comparison to the wild type PCSK9. As shown, both PCSK9b and PCSK9c variants start from original intron 3. PCSK9b has a novel splicing site in exon 9 which causes a frame shift and early truncation of the C-terminal domain as a consequence of an in-frame stop codon.

Figure 6:
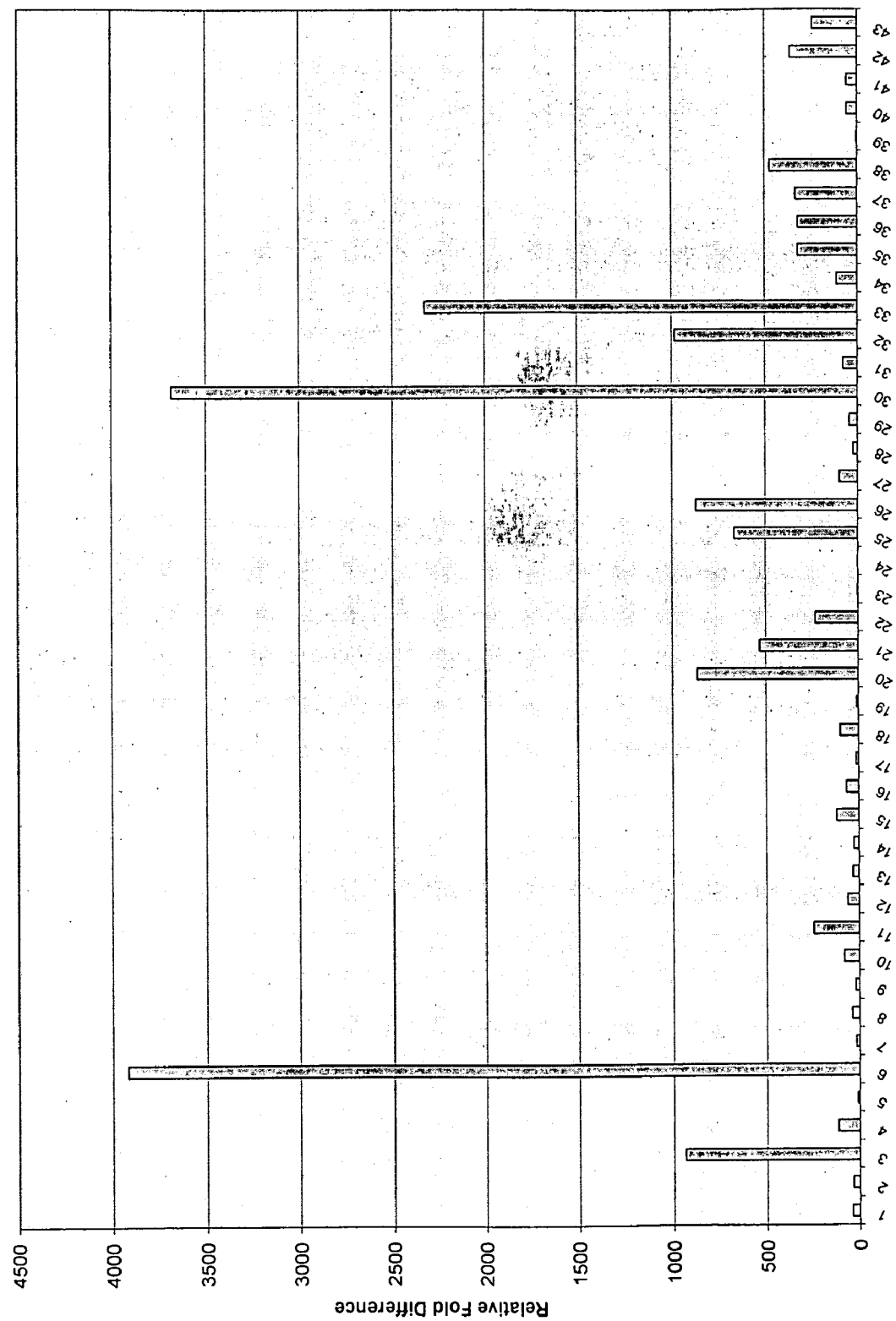

FIG. 6 shows an expression profile of the human PCSK9b and PCSK9c polypeptides. The figure illustrates the relative expression level of PCSK9b and PCSK9c amongst various mRNA tissue sources. The identity of each tissue is provided in Table IV in Example 3. As shown, the PCSK9b and PCSK9c polypeptides were expressed predominately in cerebellum of the brain and liver, at levels approximately 3500 fold higher than the lowest expressed tissue. Significant expression was observed in the lung, in pulmonary blood vessels, and tissues of the GI tract. Expression data was obtained by measuring the steady state PCSK9b and PCSK9c mRNA levels by quantitative PCR using the PCR primer pair provided as SEQ ID NO:10 and 11, and TAQMAN® probe (SEQ ID NO:12) as described in Example 3 herein.

FIG. 7 shows the results of overexpression of PCSK9b and PCSK9c variants in HEK and CHO cells. Panel "A" shows the observed expression level of PCSK9, while Panel "B" shows the observed expression level of LDLR, after HEK cells were transiently transfected with wild type PCSK9 (WT), PCSK9 mutant D374Y, and PCSK9b and PCSK9c plasmids. PCSK9b variant plasmids are represented as "#3114", "#3115", while the PCSK9c variant plasmids are represented as "#3116" and "#3117"). Expression data was obtained by measuring the steady state PCSK9b and PCSK9c mRNA levels by quantitative PCR as described in Example 4 herein.

FIG. 8 shows the results of western blot analysis of both cell lysates and conditioned media of HEK and CHO cells transiently transfected with PCSK9b and PCSK9c variants using PCSK9 specific antibody. Panel "A" shows the Western blot of PCSK9 in cell lysates from PCSK9 transfected HEK cells using PCSK9 antibody, while Panel "B" shows the Western blot of PCSK9 of conditioned media from CHO cells transiently transfected with PCSK9 variants. PCSK9b variant plasmids are represented as "#3114", "#3115", while the PCSK9c variant plasmids are represented as "#3116" and "#3117"). Wildtype PCSK9 is represented as "WT", while the PCSK9 mutant D374Y is represented as "D374Y". As shown, both PCSK9b and PCSK9c variant proteins were secreted by the transfected cells as evidenced by their detection in conditioned media despite both variants lacking a signal peptide. Western blots were performed according to the method described in Example 4 herein.

FIG. 9 shows the results of designed to assess whether PCSK9b and PCSK9c variant are able to decrease LDL binding to the LDLR. Panel A shows the results of DiI-LDL uptake in HepG2 cells transfected with PCSK9b and PCSK9c, while Panel B. shows the results of Western blot on cell lysates from CHO cells transfected with PCSK9b or PCSK9c. Both PCSK9 and LDLR antibodies were used for the Western Blots. PCSK9b variant plasmids are represented as "3114", "3115"; the PCSK9c variant plasmids are represented as "3116" and "3117"); wildtype PCSK9 is represented as "WT"; the PCSK9 mutant D374Y is represented as "D3"; vector only is represented as "vec", and cells incubated in 10% FBS containing medium is represented as "FBS", while cells inbutated in 5% lipoprotein deficient serum growth medium is represented as "LPDS". As shown in panel "A", transient transfection of HepG2 cells with both PCSK9b and PCSK9c variant proteins resulted in a decreased level of DiI-LDL uptake that exceeded the level observed for wild-type PCSK9. As shown in panel "B", transient transfection of CHO cells with the PCSK9c variant resulted in decreased LDLR protein level, while transient transfection of variant b did not appear to affect LDLR protein level under these conditions. DiI-LDL uptake assays and Western blots were performed according to the methods described in Example 4 herein.

DETAILED DESCRIPTION OF THE INVENTION

The present invention may be understood more readily by reference to the following detailed description of the preferred embodiments of the invention and the Examples included herein.

The invention provides novel human sequences that encode variants of PCSK9 thereof, PCSK9b and PCSK9c, in addition to N-terminal truncated forms of PCSK9. PCSK9 has been implicated in the incidence of a variety of diseases and/or disorders, including hypercholesterolemia, its related cardiovascular disorders, in addition to other disorders known in the art or described herein.

In the present invention, "isolated" refers to material removed from its original environment (e.g., the natural environment if it is naturally occurring), and thus is altered "by the hand of man" from its natural state. For example, an isolated polynucleotide could be part of a vector or a composition of matter, or could be contained within a cell, and still be "isolated" because that vector, composition of matter, or particular cell is not the original environment of the polynucleotide. The term "isolated" does not refer to genomic or cDNA libraries, whole cell total or mRNA preparations, genomic DNA preparations (including those separated by electrophoresis and transferred onto blots), sheared whole cell genomic DNA preparations or other compositions where the art demonstrates no distinguishing features of the polynucleotide/sequences of the present invention.

In specific embodiments, the polynucleotides of the invention are about at least 15, at least 30, at least 50, at least 100, at least 125, at least 500, at least 837, at least 903, at least 1000, or at least 1554 continuous nucleotides but are less than or equal to 300 kb, 200 kb, 100 kb, 50 kb, 15 kb, 10 kb, 7.5 kb, 5 kb, 2.5 kb, 2.0 kb, or 1 kb, in length. In this context, about means 1, 2, 3, 4, 5, 6, 7, 8, 9, or 10 nucleotides longer or shorter at either the 5' or 3' end, or both. In a further embodiment, polynucleotides of the invention comprise a portion of the coding sequences, as disclosed herein, but do not comprise all or a portion of any intron. In another embodiment, the polynucleotides comprising coding sequences do not contain coding sequences of a genomic flanking gene (i.e., 5' or 3' to the gene of interest in the genome). In other embodiments, the polynucleotides of the invention do not contain the coding sequence of more than 1000, 500, 250, 100, 50, 25, 20, 15, 10, 5, 4, 3, 2, or 1 genomic flanking gene(s).

As used herein, a "polynucleotide" refers to a molecule having a nucleic acid sequence contained in SEQ ID NO:1 or SEQ ID NO:3, or the cDNA contained within the clone deposited with the ATCC®. For example, the polynucleotide can contain the nucleotide sequence of the full length cDNA sequence, including the 5' and 3' untranslated sequences, the coding region, with or without a signal sequence, the secreted protein coding region, as well as fragments, epitopes, domains, and variants of the nucleic acid sequence. Moreover, as used herein, a "polypeptide" refers to a molecule having the translated amino acid sequence generated from the polynucleotide as broadly defined.

In the present invention, the full length sequence identified as SEQ ID NO:1 or SEQ ID NO:3 was generated by overlapping sequences contained in one or more clones (contig analysis). Representative clones containing all of the sequence for SEQ ID NO:1 and SEQ ID NO:3 was deposited with the American Type Culture Collection ("ATCC®"). As shown in Table I, each clone is identified by a cDNA Clone ID (Identifier) and the ATCC® Deposit Number. The ATCC® is located at 10801 University Boulevard, Manassas, Va. 20110-2209, USA. The ATCC® deposit was made pursuant to the terms of the Budapest Treaty on the international recognition of the deposit of microorganisms for purposes of patent procedure. The deposited clone for PCSK9b is inserted in the pSport2 vector (Invitrogen). The deposited clone for PCSK9c is inserted in the pSport1 vector (Invitrogen).

Unless otherwise indicated, all nucleotide sequences determined by sequencing a DNA molecule herein were determined using an automated DNA sequencer (such as the Model 373, preferably a Model 3700, from Applied Biosystems, Inc.), and all amino acid sequences of polypeptides encoded by DNA molecules determined herein were predicted by translation of a DNA sequence determined above. Therefore, as is known in the art for any DNA sequence determined by this automated approach, any nucleotide sequence determined herein may contain some errors. Nucleotide sequences determined by automation are typically at least about 90% identical, more typically at least about 95% to at least about 99.9% identical to the actual nucleotide sequence of the sequenced DNA molecule. The actual sequence can be more precisely determined by other approaches including manual DNA sequencing methods well known in the art. As is also known in the art, a single insertion or deletion in a determined nucleotide sequence compared to the actual sequence will cause a frame shift in translation of the nucleotide sequence such that the predicted amino acid sequence encoded by a determined nucleotide sequence will be completely different from the amino acid sequence actually encoded by the sequenced DNA molecule, beginning at the point of such an insertion or deletion.

Using the information provided herein, such as the nucleotide sequence in FIGS. 1A-C (SEQ ID NO:1), a nucleic acid molecule of the present invention encoding the PCSK9b polypeptide may be obtained using standard cloning and screening procedures, such as those for cloning cDNAs using mRNA as starting material.

Using the information provided herein, such as the nucleotide sequence in FIGS. 2A-D (SEQ ID NO:3), a nucleic acid molecule of the present invention encoding the PCSK9c polypeptide may be obtained using standard cloning and screening procedures, such as those for cloning cDNAs using mRNA as starting material.

A "polynucleotide" of the present invention also includes those polynucleotides capable of hybridizing, under stringent hybridization conditions, to sequences contained in SEQ ID NO:1, the complement thereof, or the cDNA within the clone deposited with the ATCC®. "Stringent hybridization conditions" refers to an overnight incubation at 42 degree C. in a solution comprising 50% formamide, 5×SSC (750 mM NaCl, 75 mM trisodium citrate), 50 mM sodium phosphate (pH 7.6), 5× Denhardt's solution, 10% dextran sulfate, and 20 µg/ml denatured, sheared salmon sperm DNA, followed by washing the filters in 0.1×SSC at about 65 degree C.

Also contemplated are nucleic acid molecules that hybridize to the polynucleotides of the present invention at lower stringency hybridization conditions. Changes in the stringency of hybridization and signal detection are primarily accomplished through the manipulation of formamide concentration (lower percentages of formamide result in lowered stringency); salt conditions, or temperature. For example, lower stringency conditions include an overnight incubation at 37 degree C. in a solution comprising 6×SSPE (20× SSPE=3M NaCl; 0.2M NaH2PO4; 0.02M EDTA, pH 7.4), 0.5% SDS, 30% formamide, 100 ug/ml salmon sperm blocking DNA; followed by washes at 50 degree C. with 1×SSPE, 0.1% SDS. In addition, to achieve even lower stringency, washes performed following stringent hybridization can be done at higher salt concentrations (e.g. 5×SSC).

Note that variations in the above conditions may be accomplished through the inclusion and/or substitution of alternate blocking reagents used to suppress background in hybridization experiments. Typical blocking reagents include Denhardt's reagent, BLOTTO, heparin, denatured salmon sperm DNA, and commercially available proprietary formulations. The inclusion of specific blocking reagents may require modification of the hybridization conditions described above, due to problems with compatibility.

Of course, a polynucleotide which hybridizes only to polyA+ sequences (such as any 3' terminal polyA+ tract of a cDNA shown in the sequence listing), or to a complementary stretch of T (or U) residues, would not be included in the definition of "polynucleotide" since such a polynucleotide would hybridize to any nucleic acid molecule containing a poly (A) stretch or the complement thereof (e.g., practically any double-stranded cDNA clone generated using oligo dT as a primer).

The polynucleotide of the present invention can be composed of any polyribonucleotide or polydeoxyribonucleotide, which may be unmodified RNA or DNA or modified RNA or DNA. For example, polynucleotides can be composed of single- and double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions. In addition, the polynucleotide can be composed of triple-stranded regions comprising RNA or DNA or both RNA and DNA. A polynucleotide may also contain one or more modified bases or DNA or RNA backbones modified for stability or for other reasons. "Modified" bases include, for example, tritylated bases and unusual bases such as inosine. A variety of modifications can be made to DNA and RNA; thus, "polynucleotide" embraces chemically, enzymatically, or metabolically modified forms.

The polypeptide of the present invention can be composed of amino acids joined to each other by peptide bonds or modified peptide bonds, i.e., peptide isosteres, and may contain amino acids other than the 20 gene-encoded amino acids. The polypeptides may be modified by either natural processes, such as posttranslational processing, or by chemical modification techniques which are well known in the art. Such modifications are well described in basic texts and in more detailed monographs, as well as in a voluminous research literature. Modifications can occur anywhere in a polypeptide, including the peptide backbone, the amino acid side-chains and the amino or carboxyl termini. It will be appreciated that the same type of modification may be present in the same or varying degrees at several sites in a given polypeptide. Also, a given polypeptide may contain many types of modifications. Polypeptides may be branched, for example, as a result of ubiquitination, and they may be cyclic, with or without branching. Cyclic, branched, and branched cyclic polypeptides may result from posttranslation natural processes or may be made by synthetic methods. Modifications include acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cysteine, formation of pyroglutamate, formylation, gamma-carboxylation, glycosylation, GPI anchor formation, hydroxylation, iodination, methylation, myristoylation, oxidation, pegylation, proteolytic processing, phosphorylation, prenylation, racemization, selenoylation, sulfation, transfer-RNA mediated addition of amino acids to proteins such as arginylation, and ubiquitination. (See, for instance, Proteins—Structure and Molecular Properties, 2nd Ed., T. E. Creighton, W. H. Freeman and Company, New York (1993); Posttranslational Covalent Modification of Proteins, B. C. Johnson, Ed., Academic Press, New York, pgs. 1-12 (1983); Seifter et al., Meth Enzymol 182:626-646 (1990); Rattan et al., Ann NY Acad Sci 663:48-62 (1992).)

"SEQ ID NO:X" refers to a polynucleotide sequence while "SEQ ID NO:Y" refers to a polypeptide sequence, both sequences are identified by an integer specified in Table I.

"A polypeptide having biological activity" refers to polypeptides exhibiting activity similar, but not necessarily identical to, an activity of a polypeptide of the present invention, including mature forms, as measured in a particular biological assay, with or without dose dependency. In the case where dose dependency does exist, it need not be identical to that of the polypeptide, but rather substantially similar to the dose-dependence in a given activity as compared to the polypeptide of the present invention (i.e., the candidate polypeptide will exhibit greater activity or not more than about 25-fold less and, preferably, not more than about ten-fold less activity, and most preferably, not more than about three-fold less activity relative to the polypeptide of the present invention.)

The term "organism" as referred to herein is meant to encompass any organism referenced herein, though preferably to eukaryotic organisms, more preferably to mammals, and most preferably to humans.

The present invention encompasses the identification of proteins, nucleic acids, or other molecules, that bind to polypeptides and polynucleotides of the present invention (for example, in a receptor-ligand interaction). The polynucleotides of the present invention can also be used in interaction trap assays (such as, for example, that described by Ozenberger and Young (Mol Endocrinol., 9(10):1321-9, (1995); and Ann. N.Y. Acad. Sci., 7; 766:279-81, (1995)).

The polynucleotide and polypeptides of the present invention are useful as probes for the identification and isolation of full-length cDNAs and/or genomic DNA which correspond to the polynucleotides of the present invention, as probes to hybridize and discover novel, related DNA sequences, as probes for positional cloning of this or a related sequence, as probe to "subtract-out" known sequences in the process of discovering other novel polynucleotides, as probes to quantify gene expression, and as probes for microarrays.

In addition, polynucleotides and polypeptides of the present invention may comprise one, two, three, four, five, six, seven, eight, or more membrane domains.

Also, in preferred embodiments the present invention provides methods for further refining the biological function of the polynucleotides and/or polypeptides of the present invention.

Specifically, the invention provides methods for using the polynucleotides and polypeptides of the invention to identify orthologs, homologs, paralogs, variants, and/or allelic variants of the invention. Also provided are methods of using the polynucleotides and polypeptides of the invention to identify the entire coding region of the invention, non-coding regions of the invention, regulatory sequences of the invention, and secreted, mature, pro-, prepro-, forms of the invention (as applicable).

In preferred embodiments, the invention provides methods for identifying the glycosylation sites inherent in the polynucleotides and polypeptides of the invention, and the subsequent alteration, deletion, and/or addition of said sites for a number of desirable characteristics which include, but are not limited to, augmentation of protein folding, inhibition of protein aggregation, regulation of intracellular trafficking to organelles, increasing resistance to proteolysis, modulation of protein antigenicity, and mediation of intercellular adhesion.

In further preferred embodiments, methods are provided for evolving the polynucleotides and polypeptides of the present invention using molecular evolution techniques in an effort to create and identify novel variants with desired structural, functional, and/or physical characteristics.

The present invention further provides for other experimental methods and procedures currently available to derive functional assignments. These procedures include but are not limited to spotting of clones on arrays, micro-array technology, PCR based methods (e.g., quantitative PCR), anti-sense methodology, gene knockout experiments, and other procedures that could use sequence information from clones to build a primer or a hybrid partner.

Polynucleotides and Polypeptides of the Invention
Features of the Polypeptide Encoded by
Polynucleotide No:1

The polypeptide of this polynucleotide provided as SEQ ID NO:2 (FIGS. 1A-C), encoded by the polynucleotide sequence according to SEQ ID NO:1 (FIGS. 1A-C), and/or encoded by the polynucleotide contained within the deposited clone, PCSK9b (also referred to as PCSK9-b), is a variant of the human PCSK9 polypeptide (PCSK9; GENBANK® Accession No: gi|NM_174936; SEQ ID NO:5). An alignment of the PCSK9b polypeptide with PCSK9 in addition to a known PCSK9 variant (PCSK9 variant; GENBANK® Accession No: gi|AK124635; SEQ ID NO:6) is provided in FIGS. 3A-C. The percent identity and similarity values between the PCSK9b polypeptide to these polypeptides is provided in FIG. 4.

The determined nucleotide sequence of the PCSK9b cDNA in FIGS. 1A-C (SEQ ID NO:1) contains an open reading frame encoding a protein of about 315 amino acid residues, with a deduced molecular weight of about 33.2 kDa. The amino acid sequence of the predicted PCSK9b polypeptide is shown in FIGS. 1A-C (SEQ ID NO:2).

The PCSK9b polypeptide was predicted to comprise a catalytic domain located from about amino acid 10 to about amino acid 256 of SEQ ID NO:2, with the canonical catalytic triad residing at amino acids D17, H57, and S217 of SEQ ID NO:2; and six conserved cysteine residues located at amino acids C54, C86, C132, C154, C189, and C206 of SEQ ID NO:2, with disulfite bonds predicted to form between the following cysteine pairs: C54 and C86, and C154 and C189; and a predicted $Ca^{2+}$ ion binding domain predicted to form between residues D191, P162, and V164 of SEQ ID NO:2. In this context, the term "about" may be construed to mean 1, 2, 3, 4, 5, 6, 7, 8, 9, or 10 amino acids beyond the N-terminal and/or C-terminal boundaries of the above referenced amino acid locations.

Since the PCSK9b polypeptide retains the catalytic triad of the wild-type PCSK9 polypeptide, in addition to its conserved cysteines, it is expected that the PCSK9b polypeptide retains at least some PCSK9 biological activity, including but not limited to proteinase activity, convertase activity, subtilisin-kexin isozyme-1/site 1 protease activity, autocatalytic activity cleaving the PCSK9, PCSK9b, PCSK9c, or other variants of PCSK9 between amino acids corresponding to amino acids Gln-151 and Ser-152; sterol-dependent gene expression regulatory activity (Maxwell et al., *J Lipid Res.* 2003; 44: 2109-2119), insulin-dependent gene expression regulatory activity (Shimomura et al., *Proc Natl Acad Sci USA*. 1999; 96: 13656-13661), LXR transcription factor-dependent gene expression regulatory activity (Repa et al., *Genes Dev.* 2000; 14: 2819-2830); LDL receptor protein regulatory activity (Maxwell et al., *Proc Natl Acad Sci USA*. 2004; 101: 7100-7105); statin-dependent upregulation activity (Dubuc et al., *Arterioscler Thromb Vasc Biol.* 2004; 24: 1454-1459).

In confirmation of PCSK9b retaining PCSK9 biological activity, DiI-LDL uptake assays were performed and PCSK9b was shown to have PCSK9 activity. Surprisingly, PCSK9b was found to have greater activity than wildtype PCSK9. The DiI-LDL uptake assay is a standardized functional assay for the LDLR receptor, and wildtype PCSK9 activity acts to reduce LDLR activity. Therefore DiI-LDL uptake by cells can be used as a surrogate functional assay for measuring PCSK9 activity. Transient expression of PCSK9b acted to decrease the uptake of DiI-LDL in HepG2 cells, compared to vector control, indicating that PCSK9b is competent to express PCSK9 functional activity on LDLR (FIG. 9). In this assay, PCSK9b showed greater activity than wildtype PCSK9, though not as great as PCSK9c. Accordingly, PCSK9b retains the ability of wildtype PCSK9 to modulate the functional activity on LDLR.

Figure 9A:
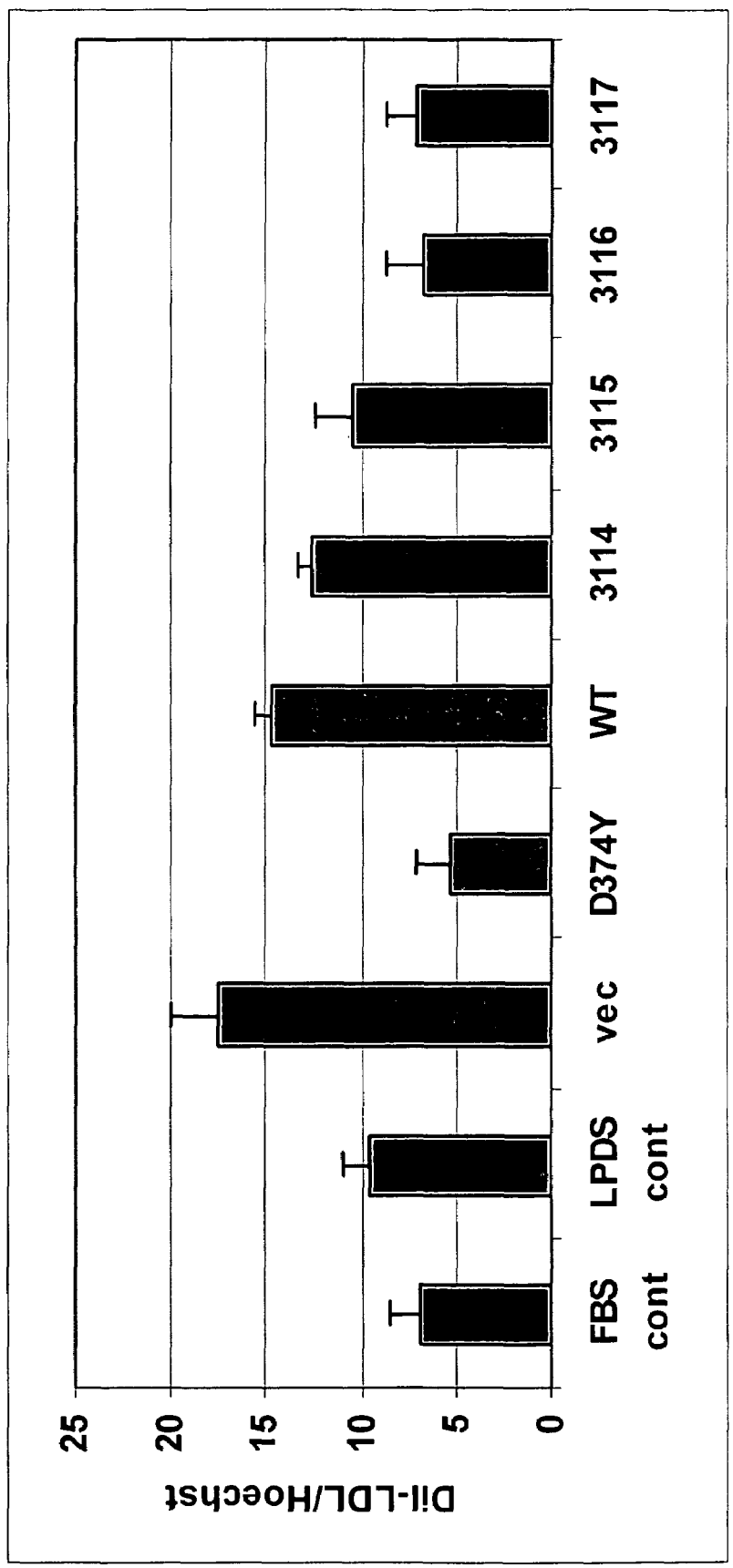

PCSK9b was shown to have about 25% more function than wildtype PCSK9 as demonstrated in the LDL uptake assay (see FIG. 9A). Accordingly, the invention further relates to an N-terminal truncation of PCSK9, such as PCSK9c for example (SEQ ID NO:2), wherein said N-terminal truncation results in an elevation of PCSK9 biological activity, including, but not limited to decreased LDLR protein levels and/or decreased LDL uptake by LDLR, and wherein said elevated PCSK9 biological activity is at least about 5%, 10%, 15%, 20%, 25%, 30%, 35%, 40%, 45%, 50%, 55%, 60%, 65%, 70%, 75%, 80%, 85%, 90%, 100%, or more than wildtype elevated PCSK9 biological activity. In this context, the term "about" shall be construed to mean anywhere between 1, 2, 3, 4, or 5 percent more or less than the cited amount. Alternatively, said elevated PCSK9 biological activity may be at least about 1×, 2×, 3×, 4×, 5×, 6×, 7×, 8×, 9×, or 10× more than wildtype PCSK9 biological activity. In this context, the term "about" shall be construed to mean anywhere between 0.1×, 0.2×, 0.3×, 0.4×, 0.5×, 0.6×, 0.7×, 0.8×, or 0.9× more or less than the cited amount.

In preferred embodiments, the present invention also encompasses a polynucleotide that comprises a polypeptide that encodes at least about 279 contiguous amino acids of SEQ ID NO:2. The present invention also encompasses a polynucleotide that comprises at least about 837 contiguous nucleotides of SEQ ID NO:1. In this context, the term "about" shall be construe to mean 0, 1, 2, 3, 4, 5, 6, 7, 8, 9, 10, 11, 12, 13, 14, 15, 16, 17, 18, 19, or 20 more or less amino acids at either the N- or C-terminus, or both, or 0, 1, 2, 3, 4, 5, 6, 7, 8, 9, 10, 11, 12, 13, 14, 15, 16, 17, 18, 19, or 20 nucleotides at either the 5 prime or 3 prime end, or both. Preferably, the polypeptides and/or polypeptides encoded by said polynucleotides retain biological activity.

In preferred embodiments, the present invention encompasses a polynucleotide lacking the initiating start codon, in addition to, the methinone of the resulting encoded polypeptide of PCSK9b. Specifically, the present invention encompasses the polynucleotide corresponding to nucleotides 253 thru 1194 of SEQ ID NO:1, and the polypeptide corresponding to amino acids 2 thru 315 of SEQ ID NO:2'. Also encompassed are recombinant vectors comprising said encoding sequence, and host cells comprising said vector.

As described herein, misense mutations of the wild-type PCSK9 at amino acid locations S127R, F216L, and D374Y have been shown to result in aberrant function of the PCSK9 protein resulting in the incidence of hypercholesterolemia (Attie, A. D., *Art. Thromb. and Vasc. Biol,* 2004; 24:1337). According, the same mutations at the corresponding amino acid positions of the PCSK9b polypeptide of the present invention would be useful in methods of diagnosing patients susceptible to the incidence of hypercholesterolemia. It should be noted that PCSK9b lacks a corresponding amino acid for the S127R mutation on account of alternative splicing (see alignment provided in FIGS. 3A-C).

In preferred embodiments, the present invention also encompasses a polynucleotide of SEQ ID NO:2 wherein the serine at amino acid position 47 is substituted with a leucine. The present invention also encompasses a polypeptide of SEQ ID NO:2 lacking the initiating start codon, in addition to, the methionine of the resulting encoded polypeptide of PCSK9b, wherein serine at amino acid position 47 is substituted with a leucine. Polynucleotides encoding these polypeptides are also provided. Also encompassed are recombinant vectors comprising said encoding sequence, and host cells comprising said vector.

In preferred embodiments, the present invention also encompasses a polynucleotide of SEQ ID NO:2 wherein the aspartic acid at amino acid position 205 is substituted with a tyrosine. The present invention also encompasses a polypeptide of SEQ ID NO:2 lacking the initiating start codon, in addition to, the methionine of the resulting encoded polypeptide of PCSK9b, wherein the aspartic acid at amino acid position 205 is substituted with a tyrosine. Polynucleotides encoding these polypeptides are also provided. Also encompassed are recombinant vectors comprising said encoding sequence, and host cells comprising said vector.

Since the PCSK9b polypeptide represents a variant form of the wild-type PCSK9 polypeptide (PCSK9; GENBANK® Accession No: gi|NM_174936; SEQ ID NO:5), it is expected that the expression pattern of the PCSK9b variant is the same or similar to the PCSK9 polypeptide.

The wild-type PCSK9 polypeptide was determined to be predominantly expressed in liver and neuronal tissue, and to a lesser extent in kidney mesenchymal cells and intestinal epithelia (Seidah et al., PNAS 100(3):928-933 (2003)).

Expression profiling designed to measure the steady state mRNA levels encoding the PCSK9b and PCSK9c polypeptides confirmed that they shared the predominate liver and neuronal expression pattern of wild-type PCSK9. Specifically, PCSK9b and PCSK9c were predominately expressed in liver and cerebellum at levels that were over 3500 times that of the tissue with the lowest expression (the heart). PCSK9b and PCSK9c were also expressed relatively highly in the lung and its associated vasculature. PCSK9b and PCSK9c were also expressed throughout the gastrointestinal tract (See FIG. 6). The PCSK9b and PCSK9c expression in the cerebellum indicates that PCSK9b and PCSK9c may function in neuronal differentiation.

The PCSK9b polynucleotides and polypeptides of the present invention, including modulators and/or fragments thereof, have uses that include detecting, prognosing, treating, preventing, and/or ameliorating the following diseases and/or disorders: autosomal dominant hypercholesterolemia; disorders associated with aberrant LDL receptor function; disorders associated with apolipoprotein B; disorders associated with autosomal recessive hypercholesterolemia; disorders associated with elevated cholesterol; disorders associated with elevated LDL; disorders associated with reduced clearance rate of LDL in the liver; disorders associated with elevated LDL apoB production; familial hypercholesterolemia; lipid metabolism disorders; elevated LDL; cholesterol depositions; tendon xanthomas; atheroma; premature arteriosclerosis, coronary heart disease; famialial defective apolipoprotein B; statin hypersensitivity; disorders associated with accelerated LDLR degradation.

The PCSK9b polynucleotides and polypeptides of the present invention, including modulators and/or fragments thereof, have uses that include detecting, prognosing, treating, preventing, and/or ameliorating the following diseases and/or disorders: neural differentiation disorders.

The PCSK9b polynucleotides and polypeptides of the present invention, including modulators and/or fragments thereof, have uses that include detecting, prognosing, treating, preventing, and/or ameliorating the following cardiovascular diseases and/or disorders: myocardio infarction, congestive heart failure, arrthymias, cardiomyopathy, atherosclerosis, arterialsclerosis, microvascular disease, embolism, thrombosis, pulmonary edema, palpitation, dyspnea, angina, hypotension, syncope, heart murmur, aberrant ECG, hypertrophic cardiomyopathy, the Marfan syndrome, sudden death, prolonged QT syndrome, congenital defects, cardiac viral infections, valvular heart disease, hypertension, among others disclosed herein, particularly in the "Cardiovascular Disorders" section and below.

Similarly, PCSK9b polynucleotides and polypeptides may be useful for ameliorating cardiovascular diseases and symptoms which result indirectly from various non-cardiovascular effects, which include, but are not limited to, the following, obesity, smoking, Down syndrome (associated with endocardial cushion defect); bony abnormalities of the upper extremities (associated with atrial septal defect in the Holt-Oram syndrome); muscular dystrophies (associated with cardiomyopathy); hemochromatosis and glycogen storage disease (associated with myocardial infiltration and restrictive cardiomyopathy); congenital deafness (associated with prolonged QT interval and serious cardiac arrhythmias); Raynaud's disease (associated with primary pulmonary hypertension and coronary vasospasm); connective tissue disorders, i.e., the Marfan syndrome, Ehlers-Danlos and Hurler syndromes, and related disorders of mucopolysaccharide metabolism (aortic dilatation, prolapsed mitral valve, a variety of arterial abnormalities); acromegaly (hypertension, accelerated coronary atherosclerosis, conduction defects, cardiomyopathy); hyperthyroidism (heart failure, atrial fibrillation); hypothyroidism (pericardial effusion, coronary artery disease); rheumatoid arthritis (pericarditis, aortic valve disease); scleroderma (cor pulmonale, myocardial fibrosis, pericarditis); systemic lupus erythematosus (valvulitis, myocarditis, pericarditis); sarcoidosis (arrhythmias, cardiomyopathy); postmenopausal effects, Chlamydial infections, polycystic ovary disease, thyroid disease, alcoholism, diet, and exfoliative dermatitis (high-output heart failure), for example.

Moreover, polynucleotides and polypeptides, including fragments and/or antagonists thereof, have uses which include, directly or indirectly, treating, preventing, diagnosing, and/or prognosing the following, non-limiting, cardiovascular infections: blood stream invasion, bacteremia, sepsis, *Streptococcus pneumoniae* infection, group a streptococci infection, group b streptococci infection, *Enterococcus* infection, nonenterococcal group D streptococci infection, nonenterococcal group C streptococci infection, nonenterococcal group G streptococci infection, *Streptoccus viridans* infection, *Staphylococcus aureus* infection, coagulase-negative staphylococci infection, gram-negative Bacilli infection, Enterobacteriaceae infection, *Pseudomonas* spp. Infection, *Acinobacter* spp. Infection, *Flavobacterium meningosepticum* infection, *Aeromonas* spp. Infection, *Stenotrophomonas maltophilia* infection, gram-negative coccobacilli infection, *Haemophilus influenza* infection, *Branhamella catarrhalis* infection, anaerobe infection, *Bacteriodes fragilis* infection, *Clostridium* infection, fungal infection, *Candida* spp. Infection, non-albicans *Candida* spp. Infection, *Hansenula anomala* infection, *Malassezia furfur* infection, nontuberculous *Mycobacteria* infection, *Mycobacterium avium* infection, *Mycobacterium chelonae* infection, *Mycobacterium fortuitum* infection, spirochetal infection, *Borrelia burgdorferi* infection, in addition to any other cardiovascular disease and/or disorder (e.g., non-sepsis) implicated by the causative agents listed above or elsewhere herein.

The PCSK9b polynucleotides and polypeptides of the present invention, including modulators and/or fragments thereof, have uses that include detecting, prognosing, treating, preventing, and/or ameliorating the following metabolic diseases and/or disorders: dyslipidemia, diabetic dyslipidemia, mixed dyslipidemia, hypercholesteremia, hypertriglyceridemia, type II diabetes mellitus, type I diabetes, insulin resistance, hyperlipidemia, obesity, and/or anorexia nervosa.

The present invention also encompasses therapeutic combinations of a modulator of PCSK9b with a statin for the treatment, prevention and/or amelioration of a disease or disorder referenced herein, particularly dyslipidemia. Representative statins include, but are not limited to, the following: pravastatin, lovastatin, cerivastatin, simvastatin, pitivastatin, atorvastatin or rousuvastatin.

The PCSK9b polynucleotides and polypeptides of the present invention, including modulators and/or fragments thereof, have uses that include modulating signal transduction activity, in various cells, tissues, and organisms, and particularly in liver, brain, mammalian adipose, omentum, spleen, inflammatory tissues, macrophages, neutrophils, synovial histiomonocytes, neutrophils, and epithelioid histiocytes.

The PCSK9b polynucleotides and polypeptides of the present invention, including modulators and/or fragments thereof, have uses that include detecting, prognosing, treating, preventing, and/or ameliorating the following hepatic disorders: hepatoblastoma, jaundice, hepatitis, liver metabolic, diseases and conditions that are attributable to the differentiation of hepatocyte progenitor cells, cirrhosis, hepatic cysts, pyrogenic abscess, amebic abcess, hydatid cyst, cystadenocarcinoma, adenoma, focal nodular hyperplasia, hemangioma, hepatocellulae carcinoma, cholangiocarcinoma, and angiosarcoma, granulomatous liver disease, liver transplantation, hyperbilirubinemia, jaundice, parenchymal liver disease, portal hypertension, hepatobiliary disease, hepatic parenchyma, hepatic fibrosis, anemia, gallstones, cholestasis, carbon tetrachloride toxicity, beryllium toxicity, vinyl chloride toxicity, choledocholithiasis, hepatocellular necrosis, aberrant metabolism of amino acids, aberrant metabolism of carbohydrates, aberrant synthesis proteins, aberrant synthesis of glycoproteins, aberrant degradation of proteins, aberrant degradation of glycoproteins, aberrant metabolism of drugs, aberrant metabolism of hormones, aberrant degradation of drugs, aberrant degradation of drugs, aberrant regulation of lipid metabolism, aberrant regulation of cholesterol metabolism, aberrant glycogenesis, aberrant glycogenolysis, aberrant glycolysis, aberrant gluconeogenesis, hyperglycemia, glucose intolerance, hyperglycemia, decreased hepatic glucose uptake, decreased hepatic glycogen synthesis, hepatic resistance to insulin, portal-systemic glucose shunting, peripheral insulin resistance, hormonal abnormalities, increased levels of systemic glucagon, decreased levels of systemic cortisol, increased levels of systemic insulin, hypoglycemia, decreased gluconeogenesis, decreased hepatic glycogen content, hepatic resistance to glucagon, elevated levels of systemic aromatic amino acids, decreased levels of systemic branched-chain amino acids, hepatic encephalopathy, aberrant hepatic amino acid transamination, aberrant hepatic amino acid oxidative deamination, aberrant ammonia synthesis, aberrant albumin secretion, hypoalbuminemia, aberrant cytochromes b5 function, aberrant P450 function, aberrant glutathione S-acyltransferase function, aberrant cholesterol synthesis, and aberrant bile acid synthesis.

Moreover, polynucleotides and polypeptides, including fragments and/or antagonists thereof, have uses which include, directly or indirectly, treating, preventing, diagnosing, and/or prognosing the following, non-limiting, hepatic infections: liver disease caused by sepsis infection, liver disease caused by bacteremia, liver disease caused by Pneomococcal pneumonia infection, liver disease caused by Toxic shock syndrome, liver disease caused by Listeriosis, liver disease caused by Legionnaries' disease, liver disease caused by Brucellosis infection, liver disease caused by *Neisseria gonorrhoeae* infection, liver disease caused by *Yersinia* infection, liver disease caused by Salmonellosis, liver disease caused by Nocardiosis, liver disease caused by *Spirochete* infection, liver disease caused by *Treponema pallidum* infection, liver disease caused by *Brrelia burgdorferi* infection, liver disease caused by Leptospirosis, liver disease caused by *Coxiella burnetii* infection, liver disease caused by *Rickettsia richettsii* infection, liver disease caused by *Chlamydia trachomatis* infection, liver disease caused by *Chlamydia psittaci* infection, liver disease caused by hepatitis virus infection, liver disease caused by Epstein-Barr virus infection in addition to any other hepatic disease and/or disorder implicated by the causative agents listed above or elsewhere herein.

The PCSK9b polynucleotides and polypeptides, including fragments and/or antagonsists thereof, may have uses which include identification of modulators of PCSK9b function including antibodies (for detection or neutralization), naturally-occurring modulators and small molecule modulators. Antibodies to domains of the PCSK9b protein could be used as diagnostic agents of lipid metabolic disorders, including hypercholesterolemia, among others.

The expression level of PCSK9b also may be useful as a biomarker for predicting which patients may be at risk of developing hypercholesterolemia, and/or those patients which may be at risk of being overly sensitive to statin therapy.

PCSK9b polypeptides and polynucleotides have additional uses which include diagnosing diseases related to the over and/or under expression of PCSK9b by identifying mutations in the PCSK9b gene by using PCSK9b sequences as probes or by determining PCSK9b protein or mRNA expression levels. PCSK9b polypeptides may be useful for screening compounds that affect the activity of the protein. PCSK9b peptides can also be used for the generation of specific antibodies and as bait in yeast two hybrid screens to find proteins the specifically interact with PCSK9b (described elsewhere herein).

In preferred embodiments, the present invention is also directed to polynucleotides comprising, or alternatively consisting of, a sequence encoding the following N-terminal PCSK9b deletion polypeptides: M1-R315, S2-R315, P3-R315, W4-R315, K5-R315, D6-R315, G7-R315, G8-R315, S9-R315, L10-R315, V11-R315, E12-R315, V13-R315, Y14-R315, L15-R315, L16-R315, D17-R315, T18-R315, S19-R315, I20-R315, Q21-R315, S22-R315, D23-R315, H24-R315, R25-R315, E26-R315, I27-R315, E28-R315, G29-R315, R30-R315, V31-R315, M32-R315, V33-R315, T34-R315, D35-R315, F36-R315, E37-R315, N38-R315, V39-R315, P40-R315, E41-R315, E42-R315, D43-R315, G44-R315, T45-R315, R46-R315, F47-R315, H48-R315, R49-R315, Q50-R315, A51-R315, S52-R315, K53-R315, C54-R315, D55-R315, S56-R315, H57-R315, G58-R315, T59-R315, H60-R315, L61-R315, A62-R315, G63-R315, V64-R315, V65-R315, S66-R315, G67-R315, R68-R315, D69-R315, A70-R315, G71-R315, V72-R315, A73-R315, K74-R315, G75-R315, A76-R315, S77-R315, M78-R315, R79-R315, S80-R315, L81-R315, R82-R315, V83-R315, L84-R315, N85-R315, C86-R315, Q87-R315, G88-R315, K89-R315, G90-R315, T91-R315, V92-R315, S93-R315, G94-R315, T95-R315, L96-R315, I97-R315, G98-R315, L99-R315, E100-R315, F101-R315, I102-R315, R103-R315, K104-R315, S105-R315, Q106-R315, L107-R315, V108-R315, Q109-R315, P110-R315, V111-R315, G112-R315, P113-R315, L114-R315, V115-R315, V116-R315, L117-R315, L118-R315, P119-R315, L120-R315, A121-R315, G122-R315, G123-R315, Y124-R315, S125-R315, R126-R315, V127-R315, L128-R315, N129-R315, A130-R315, A131-R315, C132-R315, Q133-R315, R134-R315, L135-R315, A136-R315, R137-R315, A138-R315, G139-R315, V140-R315, V141-R315, L142-R315, V143-R315, T144-R315, A145-R315, A146-R315, G147-R315, N148-R315, F149-R315, R150-R315, D151-R315, D152-R315, A153-R315, C154-R315, L155-R315, Y156-R315, S157-R315, P158-R315, A159-R315, S160-R315, A161-R315, P162-R315, E163-R315, V164-R315, I165-R315, T166-R315, V167-R315, G168-R315, A169-R315, T170-R315, N171-R315, A172-R315, Q173-R315, D174-R315, Q175-R315, P176-R315, V177-R315, T178-R315, L179-R315, G180-R315, T181-R315, L182-R315, G183-R315, T184-R315, N185-R315, F186-R315, G187-R315, R188-R315, C189-R315, V190-R315, D191-R315, L192-R315, F193-R315, A194-R315, P195-R315, G196-R315, E197-R315, D198-R315, I199-R315, I200-R315, G201-R315, A202-R315, S203-R315, S204-R315, D205-R315, C206-R315, S207-R315, T208-R315, C209-R315, F210-R315, V211-R315, S212-R315, Q213-R315, S214-R315, G215-R315, T216-R315, S217-R315, Q218-R315, A219-R315, A220-R315, A221-R315, H222-R315, V223-R315, A224-R315, G225-R315, I226-R315, A227-R315, A228-R315, M229-R315, M230-R315, L231-R315, S232-R315, A233-R315, E234-R315, P235-R315, E236-R315, L237-R315, T238-R315, L239-R315, A240-R315, E241-R315, L242-R315, R243-R315, Q244-R315, R245-R315, L246-R315, I247-R315, H248-R315, F249-R315, S250-R315, A251-R315, K252-R315, D253-R315, V254-R315, I255-R315, N256-R315, E257-R315, A258-R315, W259-R315, F260-R315, P261-R315, E262-R315, D263-R315, Q264-R315, R265-R315, V266-R315, L267-R315, T268-R315, P269-R315, N270-R315, L271-R315, V272-R315, A273-R315, A274-R315, L275-R315, P276-R315, P277-R315, S278-R315, T279-R315, H280-R315, G281-R315, A282-R315, G283-R315, P284-R315, F285-R315, C286-R315, R287-R315, L288-R315, A289-R315, A290-R315, V291-R315, L292-R315, Q293-R315, D294-R315, C295-R315, V296-R315, V297-R315, S298-R315, T299-R315, L300-R315, G301-R315, A302-R315, Y303-R315, T304-R315, D305-R315, G306-R315, H307-R315, S308-R315, and/or H309-R315 of SEQ ID NO:2. Polypeptide sequences encoded by these polynucleotides are also provided. In addition, the invention also encompasses polynucleotides encoding a polypeptide that is at least as long as any one of the aforementioned polypeptides. The present invention also encompasses the use of these N-terminal PCSK9b deletion polypeptides as immunogenic and/or antigenic epitopes as described elsewhere herein.

In preferred embodiments, the present invention is also directed to polynucleotides comprising, or alternatively consisting of, a sequence encoding the following C-terminal PCSK9b deletion polypeptides: M1-R315, M1-P314, M1-R313, M1-L312, M1-P311, M1-R310, M1-H309, M1-S308, M1-H307, M1-G306, M1-D305, M1-T304, M1-Y303, M1-A302, M1-G301, M1-L300, M1-T299, M1-S298, M1-V297, M1-V296, M1-C295, M1-D294, M1-Q293, M1-L292, M1-V291, M1-A290, M1-A289, M1-L288, M1-R287, M1-C286, M1-F285, M1-P284, M1-G283, M1-A282, M1-G281, M1-H280, M1-T279, M1-S278, M1-P277, M1-P276, M1-L275, M1-A274, M1-A273, M1-V272, M1-L271, M1-N270, M1-P269, M1-T268, M1-L267, M1-V266, M1-R265, M1-Q264, M1-D263, M1-E262, M1-P261, M1-F260, M1-W259, M1-A258, M1-E257, M1-N256, M1-I255, M1-V254, M1-D253, M1-K252, M1-A251, M1-S250, M1-F249, M1-H248, M1-I247, M1-L246, M1-R245, M1-Q244, M1-R243, M1-L242, M1-E241, M1-A240, M1-L239, M1-T238, M1-L237, M1-E236, M1-P235, M1-E234, M1-A233, M1-S232, M1-L231, M1-M230, M1-M229, M1-A228, M1-A227, M1-I226, M1-G225, M1-A224, M1-V223, M1-H222, M1-A221, M1-A220, M1-A219, M1-Q218, M1-S217, M1-T216, M1-G215, M1-S214, M1-Q213, M1-S212, M1-V211, M1-F210, M1-C209, M1-T208, M1-S207, M1-C206, M1-D205, M1-S204, M1-S203, M1-A202, M1-G201, M1-I200, M1-I199, M1-D198, M1-E197, M1-G196, M1-P195, M1-A194, M1-F193, M1-L192, M1-D191, M1-V190, M1-C189, M1-R188, M1-G187, M1-F186, M1-N185, M1-T184, M1-G183, M1-L182, M1-T181, M1-G180, M1-L179, M1-T178, M1-V177, M1-P176, M1-Q175, M1-D174, M1-Q173, M1-A172, M1-N171, M1-T170, M1-A169, M1-G168, M1-V167, M1-T166, M1-I165, M1-V164, M1-E163, M1-P162, M1-A161, M1-S160, M1-A159, M1-P158, M1-S157, M1-Y156, M1-L155, M1-C154, M1-A153, M1-D152, M1-D151, M1-R150, M1-F149, M1-N148, M1-G147, M1-A146, M1-A145, M1-T144, M1-V143, M1-L142, M1-V141, M1-V140, M1-G139, M1-A138, M1-R137, M1-A136, M1-L135, M1-R134, M1-Q133, M1-C132, M1-A131, M1-A130, M1-N129, M1-L128, M1-V127, M1-R126, M1-S125, M1-Y124, M1-G123, M1-G122, M1-A121, M1-L120, M1-P119, M1-L118, M1-L117, M1-V116, M1-V115, M1-L114, M1-P113, M1-G112, M1-V111, M1-P110, M1-Q109, M1-V108, M1-L107, M1-Q106, M1-S105, M1-K104, M1-R103, M1-I102, M1-F100, M1-E100, M1-L99, M1-G98, M1-I97, M1-L96, M1-T95, M1-G94, M1-S93, M1-V92, M1-T91, M1-G90, M1-K89, M1-G88, M1-Q87, M1-C86, M1-N85, M1-L84, M1-V83, M1-R82, M1-L81, M1-S80, M1-R79, M1-M78, M1-S77, M1-A76, M1-G75, M1-K74, M1-A73, M1-V72, M1-G71, M1-A70, M1-D69, M1-R68, M1-G67, M1-S66, M1-V65, M1-V64, M1-G63, M1-A62, M1-L61, M1-H60, M1-T59, M1-G58, M1-H57, M1-S56, M1-D55, M1-C54, M1-K53, M1-S52, M1-A51, M1-Q50, M1-R49, M1-H48, M1-F47, M1-R46, M1-T45, M1-G44, M1-D43, M1-E42, M1-E41, M1-P40, M1-V39, M1-N38, M1-E37, M1-F36, M1-D35, M1-T34, M1-V33, M1-M32, M1-V31, M1-R30, M1-G29, M1-E28, M1-I27, M1-E26, M1-R25, M1-H24, M1-D23, M1-S22, M1-Q21, M1-I20, M1-S19, M1-T18, M1-D17, M1-L16, M1-L15, M1-Y14, M1-V13, M1-E12, M1-V11, M1-L10, M1-S9, M1-G8, and/or M1-G7 of SEQ ID NO:2. Polypeptide sequences encoded by these polynucleotides are also provided. In addition, the invention also encompasses polynucleotides encoding a polypeptide that is at least as long as any one of the aforementioned polypeptides. The present invention also encompasses the use of these C-terminal PCSK9b deletion polypeptides as immunogenic and/or antigenic epitopes as described elsewhere herein.

Alternatively, preferred polypeptides of the present invention may comprise polypeptide sequences corresponding to, for example, internal regions of the PCSK9b polypeptide (e.g., any combination of both N- and C-terminal PCSK9b polypeptide deletions) of SEQ ID NO:2. For example, internal regions could be defined by the equation: amino acid NX to amino acid CX, wherein NX refers to any N-terminal deletion polypeptide amino acid of PCSK9b (SEQ ID NO:2), and where CX refers to any C-terminal deletion polypeptide amino acid of PCSK9b (SEQ ID NO:2). Polynucleotides encoding these polypeptides are also provided. The present invention also encompasses the use of these polypeptides as an immunogenic and/or antigenic epitope as described elsewhere herein.

The present invention also encompasses immunogenic and/or antigenic epitopes of the PCSK9b polypeptide.

Many polynucleotide sequences, such as EST sequences, are publicly available and accessible through sequence databases. Some of these sequences are related to SEQ ID NO:1 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides consisting of a nucleotide sequence described by the general formula of a-b, where a is any integer between 1 to 3161 of SEQ ID NO:1, b is an integer between 15 to 3175, where both a and b correspond to the positions of nucleotide residues shown in SEQ ID NO:1, and where b is greater than or equal to a+14.

Features of the Polypeptide Encoded by Polynucleotide No:2

The polypeptide of this polynucleotide provided as SEQ ID NO:4 (FIGS. 2A-D), encoded by the polynucleotide sequence according to SEQ ID NO:3 (FIGS. 2A-D), and/or encoded by the polynucleotide contained within the deposited clone, PCSK9c (also referred to as PCSK9-c), is a variant of the human PCSK9 polypeptide (PCSK9; GENBANK® Accession No: gi|NM_174936; SEQ ID NO:5). An alignment of the PCSK9c polypeptide with PCSK9 in addition to a known PCSK9 variant (PCSK9 variant; GENBANK® Accession No: gi|AK124635; SEQ ID NO:6) is provided in FIGS. 3A-C. The percent identity and similarity values between the PCSK9c polypeptide to these polypeptides is provided in FIG. 4.

The determined nucleotide sequence of the PCSK9c cDNA in FIGS. 2A-D (SEQ ID NO:3) contains an open reading frame encoding a protein of about 523 amino acid residues, with a deduced molecular weight of about 55.2 kDa. The amino acid sequence of the predicted PCSK9c polypeptide is shown in FIGS. 2A-D (SEQ ID NO:4).

The PCSK9c polypeptide was predicted to comprise a catalytic domain located from about amino acid 10 to about amino acid 256 of SEQ ID NO:4, with the canonical catalytic triad residing at amino acids D17, H57, and S217 of SEQ ID NO:4; and six conserved cysteine residues located at amino acids C54, C86, C132, C154, C189, and C206 of SEQ ID NO:4, with disulfite bonds predicted to form between the following cysteine pairs: C54 and C86, and C154 and C189; and a predicted $Ca^{2+}$ ion binding domain predicted to form between residues D191, P162, and V164 of SEQ ID NO:4. In this context, the term "about" may be construed to mean 1, 2, 3, 4, 5, 6, 7, 8, 9, or 10 amino acids beyond the N-terminal and/or C-terminal boundaries of the above referenced amino acid locations.

Since the PCSK9c polypeptide retains the catalytic triad of the wild-type PCSK9 polypeptide, in addition to its conserved cysteines, it is expected that the PCSK9c polypeptide retains PCSK9 biological activity, including but not limited to proteinase activity, convertase activity, subtilisin-kexin isozyme-1/site 1 protease activity, autocatalytic activity cleaving the PCSK9, PCSK9b, PCSK9c, or other variants of PCSK9 between amino acids corresponding to amino acids Gln-151 and Ser-152; sterol-dependent gene expression regulatory activity (Maxwell et al., *J Lipid Res.* 2003; 44: 2109-2119), insulin-dependent gene expression regulatory activity (Shimomura et al., *Proc Natl Acad Sci USA*. 1999; 96: 13656-13661), LXR transcription factor-dependent gene expression regulatory activity (Repa et al., *Genes Dev.* 2000; 14: 2819-2830); LDL receptor protein regulatory activity (Maxwell et al., *Proc Natl Acad Sci USA*. 2004; 101: 7100-7105); statin-dependent upregulation activity (Dubuc et al.; *Arterioscler Thromb Vasc Biol.* 2004; 24: 1454-1459).

In confirmation of PCSK9c retaining PCSK9 biological activity, DiI-LDL uptake assays were performed and PCSK9c was shown to have PCSK9 activity. Surprisingly, PCSK9c was found to have greater activity than wildtype PCSK9. The DiI-LDL uptake assay is a standardized functional assay for the LDLR receptor, and wildtype PCSK9 activity acts to reduce LDLR activity. Therefore DiI-LDL uptake by cells can be used as a surrogate functional assay for measuring PCSK9 activity. Transient expression of PCSK9c acted to decrease the uptake of DiI-LDL in HepG2 cells, compared to vector control, indicating that PCSK9c is competent to express PCSK9 functional activity on LDLR (FIG. 9). In this assay, PCSK9c showed greater activity than both wild-type PCSK9 and PCSK9b. Accordingly, PCSK9c retains the ability of wildtype PCSK9 to modulate the functional activity on LDLR.

PCSK9c was shown to have about 50% more function than wildtype PCSK9 as demonstrated in the LDL uptake assay (see FIG. 9A). Accordingly, the invention further relates to an N-terminal truncation of PCSK9, such as PCSK9c for example (SEQ ID NO:4), wherein said N-terminal truncation results in an elevation of PCSK9 biological activity, including, but not limited to decreased LDLR protein levels and/or decreased LDL uptake by LDLR, and wherein said elevated PCSK9 biological activity is at least about 5%, 10%, 15%, 20%, 25%, 30%, 35%, 40%, 45%, 50%, 55%, 60%, 65%, 70%, 75%, 80%, 85%, 90%, 100%, or more than wildtype elevated PCSK9 biological activity. In this context, the term "about" shall be construed to mean anywhere between 1, 2, 3, 4, or 5 percent more or less than the cited amount. Alternatively, said elevated PCSK9 biological activity may be at least about 1×, 2×, 3×, 4×, 5×, 6×,7×, 8×, 9×, or 10× more than wildtype PCSK9 biological activity. In this context, the term "about" shall be construed to mean anywhere between 0.1×, 0.2×, 0.3×, 0.4×, 0.5×, 0.6×, 0.7×, 0.8×, or 0.9× more or less than the cited amount.

In preferred embodiments, the present invention also encompasses a polynucleotide that comprises a polypeptide that encodes at least about 301 contiguous amino acids of SEQ ID NO:4. The present invention also encompasses a polypeptide that comprises at least about 496 amino acids of SEQ ID NO:4. The present invention also encompasses a polypeptide that comprises at least about 518 amino acids of SEQ ID NO:4. The present invention also encompasses a polynucleotide that comprises at least about 903 contiguous nucleotides of SEQ ID NO:3. The present invention also encompasses a polynucleotide that comprises at least about 1488 contiguous nucleotides of SEQ ID NO:3. The present invention also encompasses a polynucleotide that comprises at least about 1554 contiguous nucleotides of SEQ ID NO:3. In this context, the term "about" shall be construe to mean 0, 1, 2, 3, 4, 5, 6, 7, 8, 9, 10, 11, 12, 13, 14, 15, 16, 17, 18, 19, or 20 more or less amino acids at either the N- or C-terminus, or both, or 0, 1, 2, 3, 4, 5, 6, 7, 8, 9, 10, 11, 12, 13, 14, 15, 16, 17, 18, 19, or 20 nucleotides at either the 5 prime or 3 prime end, or both. Preferably, the polypeptides and/or polypeptides encoded by said polynucleotides retain biological activity.

In preferred embodiments, the present invention encompasses a polynucleotide lacking the initiating start codon, in addition to the methionine of the resulting encoded polypeptide of PCSK9c. Specifically, the present invention encompasses the polynucleotide corresponding to nucleotides 884 thru 2049 of SEQ ID NO:3, and the polypeptide corresponding to amino acids 2 thru 523 of SEQ ID NO:4. Also encompassed are recombinant vectors comprising said encoding sequence, and host cells comprising said vector.

Since the PCSK9c polypeptide represents a variant form of the wild-type PCSK9 polypeptide (PCSK9; GENBANK® Accession No: gi|NM_174936; SEQ ID NO:5), it is expected that the expression pattern of the PCSK9c variant is the same or similar to the PCSK9 polypeptide.

As described herein, misense mutations of the wild-type PCSK9 at amino acid locations S127R, F216L, and D374Y have been shown to result in aberrant function of the PCSK9 protein resulting in the incidence of hypercholesterolemia (Attie, A. D., *Art. Thromb. and Vasc. Biol,* 2004; 24:1337). According, the same mutations at the corresponding amino acid positions of the PCSK9c polypeptide of the present invention would be useful in methods of diagnosing patients susceptible to the incidence of hypercholesterolemia. It should be noted that PCSK9c lacks a corresponding amino acid for the S127R mutation on account of alternative splicing (see alignment provided in FIGS. 3A-C).

In preferred embodiments, the present invention also encompasses a polynucleotide of SEQ ID NO:4 wherein the serine at amino acid position 47 is substituted with a leucine. The present invention also encompasses a polypeptide of SEQ ID NO:4 lacking the initiating start codon, in addition to, the methionine of the resulting encoded polypeptide of PCSK9c, wherein serine at amino acid position 47 is substituted with a leucine. Polynucleotides encoding these polypeptides are also provided. Also encompassed are recombinant vectors comprising said encoding sequence, and host cells comprising said vector.

In preferred embodiments, the present invention also encompasses a polynucleotide of SEQ ID NO:4 wherein the aspartic acid at amino acid position 205 is substituted with a tyrosine. The present invention also encompasses a polypeptide of SEQ ID NO:4 lacking the initiating start codon, in addition to, the methionine of the resulting encoded polypeptide of PCSK9c, wherein aspartic acid at amino acid position 205 is substituted with a tyrosine. Polynucleotides encoding these polypeptides are also provided. Also encompassed are recombinant vectors comprising said encoding sequence, and host cells comprising said vector.

The wild-type PCSK9 polypeptide was determined to be predominantly expressed in liver and neuronal tissue, and to a lesser extent in kidney mesenchymal cells and intestinal epithelia (Seidah et al., PNAS 100(3):928-933 (2003)).

Expression profiling designed to measure the steady state mRNA levels encoding the PCSK9b and PCSK9c polypeptides confirmed that they shared the predominate liver and neuronal expression pattern of wild-type PCSK9. Specifically, PCSK9b and PCSK9c were predominately expressed in liver and cerebellum at levels that were over 3500 times that of the tissue with the lowest expression (the heart). PCSK9b and PCSK9c were also expressed relatively highly in the lung and its associated vasculature. PCSK9b and PCSK9c were also expressed throughout the gastrointestinal tract (See FIG. 6). The PCSK9b and PCSK9c expression in the cerebellum indicates that PCSK9b and PCSK9c may function in neuronal differentiation.

The PCSK9c polynucleotides and polypeptides of the present invention, including modulators and/or fragments thereof, have uses that include detecting, prognosing, treating, preventing, and/or ameliorating the following diseases and/or disorders: autosomal dominant hypercholesterolemia; disorders associated with aberrant LDL receptor function; disorders associated with apolipoprotein B; disorders associated with autosomal recessive hypercholesterolemia; disorders associated with elevated cholesterol; disorders associated with elevated LDL; disorders associated with reduced clearance rate of LDL in the liver; disorders associated with elevated LDL apoB production; familial hypercholesterolemia; lipid metabolism disorders; elevated LDL; cholesterol depositions; tendon xanthomas; atheroma; premature arteriosclerosis, coronary heart disease; famialial defective apolipoprotein B; statin hypersensitivity; disorders associated with accelerated LDLR degradation.

The PCSK9c polynucleotides and polypeptides of the present invention, including modulators and/or fragments thereof, have uses that include detecting, prognosing, treating, preventing, and/or ameliorating the following diseases and/or disorders: neural differentiation disorders.

The PCSK9c polynucleotides and polypeptides of the present invention, including modulators and/or fragments thereof, have uses that include detecting, prognosing, treating, preventing, and/or ameliorating the following cardiovascular diseases and/or disorders: myocardio infarction, congestive heart failure, arrthymias, cardiomyopathy, atherosclerosis, arterialsclerosis, microvascular disease, embolism, thrombosis, pulmonary edema, palpitation, dyspnea, angina, hypotension, syncope, heart murmur, aberrant ECG, hypertrophic cardiomyopathy, the Marfan syndrome, sudden death, prolonged QT syndrome, congenital defects, cardiac viral infections, valvular heart disease, hypertension, among others disclosed herein, particularly in the "Cardiovascular Disorders" section and below.

Similarly, PCSK9c polynucleotides and polypeptides may be useful for ameliorating cardiovascular diseases and symptoms which result indirectly from various non-cardiovascular effects, which include, but are not limited to, the following, obesity, smoking, Down syndrome (associated with endocardial cushion defect); bony abnormalities of the upper extremities (associated with atrial septal defect in the Holt-Oram syndrome); muscular dystrophies (associated with cardiomyopathy); hemochromatosis and glycogen storage disease (associated with myocardial infiltration and restrictive cardiomyopathy); congenital deafness (associated with prolonged QT interval and serious cardiac arrhythmias); Raynaud's disease (associated with primary pulmonary hypertension and coronary vasospasm); connective tissue disorders, i.e., the Marfan syndrome, Ehlers-Danlos and Hurler syndromes, and related disorders of mucopolysaccharide metabolism (aortic dilatation, prolapsed mitral valve, a variety of arterial abnormalities); acromegaly (hypertension, accelerated coronary atherosclerosis, conduction defects, cardiomyopathy); hyperthyroidism (heart failure, atrial fibrillation); hypothyroidism (pericardial effusion, coronary artery disease); rheumatoid arthritis (pericarditis, aortic valve disease); scleroderma (cor pulmonale, myocardial fibrosis, pericarditis); systemic lupus erythematosus (valvulitis, myocarditis, pericarditis); sarcoidosis (arrhythmias, cardiomyopathy); postmenopausal effects, Chlamydial infections, polycystic ovary disease, thyroid disease, alcoholism, diet, and exfoliative dermatitis (high-output heart failure), for example.

Moreover, polynucleotides and polypeptides, including fragments and/or antagonists thereof, have uses which include, directly or indirectly, treating, preventing, diagnosing, and/or prognosing the following, non-limiting, cardiovascular infections: blood stream invasion, bacteremia, sepsis, *Streptococcus pneumoniae* infection, group a streptococci infection, group b streptococci infection, *Enterococcus* infection, nonenterococcal group D streptococci infection, nonenterococcal group C streptococci infection, nonenterococcal group G streptococci infection, *Streptoccus viridans* infection, *Staphylococcus aureus* infection, coagulase-negative staphylococci infection, gram-negative Bacilli infection, Enterobacteriaceae infection, *Psudomonas* spp. Infection, *Acinobacter* spp. Infection, *Flavobacterium meningosepticum* infection, *Aeromonas* spp. Infection, *Stenotrophomonas maltophilia* infection, gram-negative coccobacilli infection, *Haemophilus influenza* infection, *Bra-* nhamella catarrhalis infection, anaerobe infection, *Bacteriodes fragilis* infection, *Clostridium* infection, fungal infection, *Candida* spp. Infection, non-albicans *Candida* spp. Infection, *Hansenula anomala* infection, *Malassezia furfur* infection, nontuberculous *Mycobacteria* infection, *Mycobacterium avium* infection, *Mycobacterium chelonae* infection, *Mycobacterium fortuitum* infection, spirochetal infection, *Borrelia burgdorferi* infection, in addition to any other cardiovascular disease and/or disorder (e.g., non-sepsis) implicated by the causative agents listed above or elsewhere herein.

The PCSK9c polynucleotides and polypeptides of the present invention, including modulators and/or fragments thereof, have uses that include detecting, prognosing, treating, preventing, and/or ameliorating the following metabolic diseases and/or disorders: dyslipidemia, diabetic dyslipidemia, mixed dyslipidemia, hypercholesteremia, hypertriglyceridemia, type II diabetes mellitus, type I diabetes, insulin resistance, hyperlipidemia, obesity, and/or anorexia nervosa.

The present invention also encompasses therapeutic combinations of a modulator of PCSK9c with a statin for the treatment, prevention and/or amelioration of a disease or disorder referenced herein, particularly dyslipidemia. Representative statins include, but are not limited to, the following: pravastatin, lovastatin, cerivastatin, simvastatin, pitivastatin, atorvastatin or rousuvastatin.

The PCSK9c polynucleotides and polypeptides of the present invention, including modulators and/or fragments thereof, have uses that include modulating signal transduction activity, in various cells, tissues, and organisms, and particularly in liver, brain, mammalian adipose, omentum, spleen, inflammatory tissues, macrophages, neutrophils, synovial histiomonocytes, neutrophils, and epithelioid histiocytes.

The PCSK9c polynucleotides and polypeptides of the present invention, including modulators and/or fragments thereof, have uses that include detecting, prognosing, treating, preventing, and/or ameliorating the following hepatic disorders: hepatoblastoma, jaundice, hepatitis, liver metabolic diseases and conditions that are attributable to the differentiation of hepatocyte progenitor cells, cirrhosis, hepatic cysts, pyrogenic abscess, amebic abcess, hydatid cyst, cystadenocarcinoma, adenoma, focal nodular hyperplasia, hemangioma, hepatocellulae carcinoma, cholangiocarcinoma, and angiosarcoma, granulomatous liver disease, liver transplantation, hyperbilirubinemia, jaundice, parenchymal liver disease, portal hypertension, hepatobiliary disease, hepatic parenchyma, hepatic fibrosis, anemia, gallstones, cholestasis, carbon tetrachloride toxicity, beryllium toxicity, vinyl chloride toxicity, choledocholithiasis, hepatocellular necrosis, aberrant metabolism of amino acids, aberrant metabolism of carbohydrates, aberrant synthesis proteins, aberrant synthesis of glycoproteins, aberrant degradation of proteins, aberrant degradation of glycoproteins, aberrant metabolism of drugs, aberrant metabolism of hormones, aberrant degradation of drugs, aberrant degradation of drugs, aberrant regulation of lipid metabolism, aberrant regulation of cholesterol metabolism, aberrant glycogenesis, aberrant glycogenolysis, aberrant glycolysis, aberrant gluconeogenesis, hyperglycemia, glucose intolerance, hyperglycemia, decreased hepatic glucose uptake, decreased hepatic glycogen synthesis, hepatic resistance to insulin, portal-systemic glucose shunting, peripheral insulin resistance, hormonal abnormalities, increased levels of systemic glucagon, decreased levels of systemic cortisol, increased levels of systemic insulin, hypoglycemia, decreased gluconeogenesis, decreased hepatic glycogen content, hepatic resistance to glucagon, elevated levels of systemic aromatic amino acids, decreased levels of systemic branched-chain amino acids, hepatic encephalopathy, aberrant hepatic amino acid transamination, aberrant hepatic amino acid oxidative deamination, aberrant ammonia synthesis, aberrant albumin secretion, hypoalbuminemia, aberrant cytochromes b5 function, aberrant P450 function, aberrant glutathione S-acyltransferase function, aberrant cholesterol synthesis, and aberrant bile acid synthesis.

Moreover, polynucleotides and polypeptides, including fragments and/or antagonists thereof, have uses which include, directly or indirectly, treating, preventing, diagnosing, and/or prognosing the following, non-limiting, hepatic infections: liver disease caused by sepsis infection, liver disease caused by bacteremia, liver disease caused by Pneomococcal pneumonia infection, liver disease caused by Toxic shock syndrome, liver disease caused by Listeriosis, liver disease caused by Legionnaries' disease, liver disease caused by Brucellosis infection, liver disease caused by *Neisseria gonorrhoeae* infection, liver disease caused by *Yersinia* infection, liver disease caused by Salmonellosis, liver disease caused by Nocardiosis, liver disease caused by *Spirochete* infection, liver disease caused by *Treponema pallidum* infection, liver disease caused by *Brrelia burgdorferi* infection, liver disease caused by Leptospirosis, liver disease caused by *Coxiella burnetii* infection, liver disease caused by *Rickettsia richettsii* infection, liver disease caused by *Chlamydia trachomatis* infection, liver disease caused by *Chlamydia psittaci* infection, liver disease caused by hepatitis virus infection, liver disease caused by Epstein-Barr virus infection in addition to any other hepatic disease and/or disorder implicated by the causative agents listed above or elsewhere herein.

The PCSK9c polynucleotides and polypeptides, including fragments and/or antagonsists thereof, may have uses which include identification of modulators of PCSK9c function including antibodies (for detection or neutralization), naturally-occurring modulators and small molecule modulators. Antibodies to domains of the PCSK9c protein could be used as diagnostic agents of lipid metabolic disorders, including hypercholesterolemia, among others.

The expression level of PCSK9c also may be useful as a biomarker for predicting which patients may be at risk of developing hypercholesterolemia, and/or those patients which may be at risk of being overly sensitive to statin therapy.

PCSK9c polypeptides and polynucleotides have additional uses which include diagnosing diseases related to the over and/or under expression of PCSK9c by identifying mutations in the PCSK9c gene by using PCSK9c sequences as probes or by determining PCSK9c protein or mRNA expression levels. PCSK9c polypeptides may be useful for screening compounds that affect the activity of the protein. PCSK9c peptides can also be used for the generation of specific antibodies and as bait in yeast two hybrid screens to find proteins the specifically interact with PCSK9c (described elsewhere herein).

In preferred embodiments, the present invention is also directed to polynucleotides comprising, or alternatively consisting of, a sequence encoding following N-terminal PCSK9c deletion polypeptides: M1-Q523, S2-Q523, P3-Q523, W4-Q523, K5-Q523, D6-Q523, G7-Q523, G8-Q523, S9-Q523, L10-Q523, V11-Q523, E12-Q523, V13-Q523, Y14-Q523, L15-Q523, L16-Q523, D17-Q523, T18-Q523, S19-Q523, I20-Q523, Q21-Q523, S22-Q523, D23-Q523, H24-Q523, R25-Q523, E26-Q523, I27-Q523, E28-Q523, G29-Q523, R30-Q523, V31-Q523, M32-Q523, V33-Q523, T34-Q523, D35-Q523, F36-Q523, E37-Q523, N38-Q523, V39-Q523, P40-Q523, E41-Q523, E42-Q523, D43-

Q523, G44-Q523, T45-Q523, R46-Q523, F47-Q523, H48-Q523, R49-Q523, Q50-Q523, A51-Q523, S52-Q523, K53-Q523, C54-Q523, D55-Q523, S56-Q523, H57-Q523, G58-Q523, T59-Q523, H60-Q523, L61-Q523, A62-Q523, G63-Q523, V64-Q523; V65-Q523, S66-Q523, G67-Q523, R68-Q523, D69-Q523, A70-Q523, G71-Q523, V72-Q523, A732-Q523, K74-Q523, G75-Q523, A76-Q523, S77-Q523, M78-Q523, R79-Q523, S80-Q523-L81-Q523, R82-Q523, V83-Q523, L84-Q523, N85-Q523, C86-Q523, Q87-Q523, G88-Q523, K89-Q523, G90-Q523, T91-Q523, V92-Q523, S93-Q523, G94-Q523, T95-Q523, L96-Q523, I97-Q523, G98-Q523, L99-Q523, E100-Q523, F101-Q523, I102-Q523, R103-Q523, K104-Q523, S105-Q523, Q106-Q523, L107-Q523, V108-Q523, Q109-Q523, P110-Q523, V111-Q523, G112-Q523, P113-Q523, L114-Q523, V115-Q523, V116-Q523, L117-Q523, L118-Q523, P119-Q523, L120-Q523, A121-Q523, G122-Q523, G123-Q523, Y124-Q523, S125-Q523, R126-Q523, V127-Q523, L128-Q523, N129-Q523, A130-Q523, A131-Q523, C132-Q523, Q133-Q523, R134-Q523, L135-Q523, A136-Q523, R137-Q523, A138-Q523, G139-Q523, V140-Q523, V141-Q523, L142-Q523, V143-Q523, T144-Q523, A145-Q523, A146-Q523, G147-Q523, N148-Q523, F149-Q523, R150-Q523, D151-Q523, D152-Q523, A153-Q523, C154-Q523, L155-Q523, Y156-Q523, S157-Q523, P158-Q523, A159-Q523, S160-Q523, A161-Q523, P162-Q523, E163-Q523, V164-Q523, I165-Q523, T166-Q523, V167-Q523, G168-Q523, A169-Q523, T170-Q523, N171-Q523, A172-Q523, Q173-Q523, D174-Q523, Q175-Q523, P176-Q523, V177-Q523, T178-Q523, L179-Q523, G180-Q523, T181-Q523, L182-Q523, G183-Q523, T184-Q523, N185-Q523, F186-Q523, G187-Q523, R188-Q523, C189-Q523, V190-Q523, D191-Q523, L192-Q523, F193-Q523, A194-Q523, P195-Q523, G196-Q523, E197-Q523, D198-Q523, I199-Q523, I200-Q523, G201-Q523, A202-Q523, S203-Q523, S204-Q523, D205-Q523, C206-Q523, S207-Q523, T208-Q523, C209-Q523, F210-Q523, V211-Q523, S212-Q523, Q213-Q523, S214-Q523, G215-Q523, T216-Q523, S217-Q523, Q218-Q523, A219-Q523, A220-Q523, A221-Q523, H222-Q523, V223-Q523, A224-Q523, G225-Q523, I226-Q523, A227-Q523, A228-Q523, M229-Q523, M230-Q523, L231-Q523, S232-Q523, A233-Q523, E234-Q523, P235-Q523, E236-Q523, L237-Q523, T238-Q523, L239-Q523, A240-Q523, E241-Q523, L242-Q523, R243-Q523, Q244-Q523, R245-Q523, L246-Q523, I247-Q523, H248-Q523, F249-Q523, S250-Q523, A251-Q523, K252-Q523, D253-Q523, V254-Q523, I255-Q523, N256-Q523, E257-Q523, A258-Q523, W259-Q523, F260-Q523, P261-Q523, E262-Q523, D263-Q523, Q264-Q523, R265-Q523, V266-Q523, L267-Q523, T268-Q523, P269-Q523, N270-Q523, L271-Q523, V272-Q523, A273-Q523, A274-Q523, L275-Q523, P276-Q523, P277-Q523, S278-Q523, T279-Q523, H280-Q523, G281-Q523, A282-Q523, G283-Q523, W284-Q523, Q285-Q523, L286-Q523, F287-Q523, C288-Q523, R289-Q523, T290-Q523, V291-Q523, W292-Q523, S293-Q523, A294-Q523, H295-Q523, S296-Q523, G297-Q523, P298-Q523, T299-Q523, R300-Q523, M301-Q523, A302-Q523, T303-Q523, A304-Q523, I305-Q523, A306-Q523, R307-Q523, C308-Q523, A309-Q523, P310-Q523, D311-Q523, E312-Q523, E313-Q523, L314-Q523, L315-Q523, S316-Q523, C317-Q523, S318-Q523, S319-Q523, F320-Q523, S321-Q523, R322-Q523, S323-Q523, G324-Q523, K325-Q523, R326-Q523, R327-Q523, G328-Q523, E329-Q523, R330-Q523, M331-Q523, E332-Q523, A333-Q523, Q334-Q523, G335-Q523, G336-Q523, K337-Q523, L338-Q523, V339-Q523, C340-Q523, R341-Q523, A342-Q523, H343-Q523, N344-Q523, A345-Q523, F346-Q523, G347-Q523, G348-Q523, E349-Q523, G350-Q523, V351-Q523, Y352-Q523, A353-Q523, I354-Q523, A355-Q523, R356-Q523, C357-Q523, C358-Q523, L359-Q523, L360-Q523, P361-Q523, Q362-Q523, A363-Q523, N364-Q523, C365-Q523, S366-Q523, V367-Q523, H368-Q523, T369-Q523, A370-Q523, P371-Q523, P372-Q523, A373-Q523, E374-Q523, A375-Q523, S376-Q523, M377-Q523, G378-Q523, T379-Q523, R380-Q523, V381-Q523, H382-Q523, C383-Q523, H384-Q523, Q385-Q523, Q386-Q523, G387-Q523, H388-Q523, V389-Q523, L390-Q523, T391-Q523, G392-Q523, C393-Q523, S394-Q523, S395-Q523, H396-Q523, W397-Q523, E398-Q523, V399-Q523, E400-Q523, D401-Q523, L402-Q523, G403-Q523, T404-Q523, H405-Q523, K406-Q523, P407-Q523, P408-Q523, V409-Q523, L410-Q523, R411-Q523, P412-Q523, R413-Q523, G414-Q523, Q415-Q523, P416-Q523, N417-Q523, Q418-Q523, C419-Q523, V420-Q523, G421-Q523, H422-Q523, R423-Q523, E424-Q523, A425-Q523, S426-Q523, I427-Q523, H428-Q523, A429-Q523, S430-Q523, C431-Q523, C432-Q523, H433-Q523, A434-Q523, P435-Q523, G436-Q523, L437-Q523, E438-Q523, C439-Q523, K440-Q523, V441-Q523, K442-Q523, E443-Q523, H444-Q523, G445-Q523, 446-Q523, P447-Q523, A448-Q523, P449-Q523, Q450-Q523, E451-Q523, Q452-Q523, V453-Q523, T454-Q523, V455-Q523, A456-Q523, C457-Q523, E458-Q523, E459-Q523, G460-Q523, W461-Q523, T462-Q523, L463-Q523, T464-Q523, G465-Q523, C466-Q523, S467-Q523, A468-Q523, L469-Q523, P470-Q523, G471-Q523, T472-Q523, S473-Q523, H474-Q523, V475-Q523, L476-Q523, G477-Q523, A478-Q523, Y479-Q523, A480-Q523, V481-Q523, D482-Q523, N483-Q523, T484-Q523, C485-Q523, V486-Q523, V487-Q523, R488-Q523, S489-Q523, R490-Q523, D491-Q523, V492-Q523, S493-Q523, T494-Q523, T495-Q523, G496-Q523, S497-Q523, T498-Q523, S499-Q523, E500-Q523, G501-Q523, A502-Q523, V503-Q523, T504-Q523, A505-Q523, V506-Q523, A507-Q523, I508-Q523, C509-Q523, C510-Q523, R511-Q523, S512-Q523, R513-Q523, H514-Q523, L515-Q523, A516-Q523, and/or Q517-Q523 of SEQ ID NO:4. Polypeptide sequences encoded by these polynucleotides are also provided. In addition, the invention also encompasses polynucleotides encoding a polypeptide that is at least as long as any one of the aforementioned polypeptides. The present invention also encompasses the use of these N-terminal PCSK9c deletion polypeptides as immunogenic and/or antigenic epitopes as described elsewhere herein.

In preferred embodiments, the present invention is also directed to polynucleotides comprising, or alternatively consisting of, a sequence encoding the following C-terminal PCSK9c deletion polypeptides: M1-Q523, M1-L522, M1-E521, M1-Q520, M1-S519, M1-A518, M1-Q517, M1-A516, M1-L515, M1-H514, M1-R513, M1-S512, M1-R511, M1-C510, M1-C509, M1-I508, M1-A507, M1-V506, M1-A505, M1-T504, M1-V503, M1-A502, M1-G501, M1-E500, M1-S499, M1-T498, M1-S497, M1-G496, M1-T495, M1-T494, M1-S493, M1-V492, M1-D491, M1-R490, M1-S489, M1-R488, M1-V487, M1-V486, M1-C485, M1-T484, M1-N483, M1-D482, M1-V481, M1-A480, M1-Y479, M1-A478, M1-G477, M1-L476, M1-V475, M1-H474, M1-S473, M1-T472, M1-G471, M1-P470, M1-L469, M1-A468, M1-S467, M1-C466, M1-G465, M1-T464, M1-L463, M1-T462, M1-W461, M1-G460, M1-E459, M1-E458, M1-C457, M1-A456, M1-V455, M1-T454, M1-V453, M1-Q452, M1-E451, M1-Q450, M1-P449, M1-A448, M1-P447, M1-I446, M1-G445, M1-H444, M1-E443, M1-K442, M1-V441, M1-K440, M1-C439, M1-E438, M1-L437, M1-G436, M1-P435, M1-A434, M1-H433, M1-C432, M1-C431, M1-S430, M1-A429, M1-H428, M1-I427, M1-S426, M1-A425, M1-E424, M1-R423, M1-H422, M1-G421, M1-V420, M1-C419, M1-Q418, M1-N417, M1-P416, M1-Q415, M1-G414, M1-R413, M1-P412, M1-R411, M1-L410, M1-V409, M1-P408, M1-P407, M1-K406, M1-H405, M1-T404, M1-G403, M1-L402, M1-D401, M1-E400, M1-V399, M1-E398, M1-W397, M1-H396, M1-S395, M1-S394, M1-C393, M1-G392, M1-T391, M1-L390, M1-V389, M1-H388, M1-G387, M1-Q386, M1-Q385, M1-H384, M1-C383, M1-H382, M1-V381, M1-R380, M1-T379, M1-G378, M1-M377, M1-S376, M1-A375, M1-E374, M1-A373, M1-P372, M1-P371, M1-A370, M1-T369, M1-H368, M1-V367, M1-S366, M1-C365, M1-N364, M1-A363, M1-Q362, M1-P361, M1-L360, M1-L359, M1-C358, M1-C357, M1-R356, M1-A355, M1-I354, M1-A353, M1-Y352, M1-V351, M1-G350, M1-E349, M1-G348, M1-G347, M1-F346, M1-A345, M1-N344, M1-H343, M1-A342, M1-R341, M1-C340, M1-V339, M1-L338, M1-K337, M1-G336, M1-G335, M1-Q334, M1-A333, M1-E332, M1-M331, M1-R330, M1-E329, M1-G328, M1-R327, M1-R326, M1-K325, M1-G324, M1-S323, M1-R322, M1-S321, M1-F320, M1-S319, M1-S318, M1-C317, M1-S316, M1-L315, M1-L314, M1-E313, M1-E312, M1-D311, M1-P310, M1-A309, M1-C308, M1-R307, M1-A306, M1-I305, M1-A304, M1-T303, M1-A302, M1-M301, M1-R300, M1-T299, M1-P298, M1-G297, M1-S296, M1-H295, M1-A294, M1-S293, M1-W292, M1-V291, M1-T290, M1-R289, M1-C288, M1-F287, M1-L286, M1-Q285, M1-W284, M1-G283, M1-A282, M1-G281, M1-H280, M1-T279, M1-S278, M1-P277, M1-P276, M1-L275, M1-A274, M1-A273, M1-V272, M1-L271, M1-N270, M1-P269, M1-T268, M1-L267, M1-V266, M1-R265, M1-Q264, M1-D263, M1-E262, M1-P261, M1-F260, M1-W259, M1-A258, M1-E257, M1-N256, M1-I255, M1-V254, M1-D253, M1-K252, M1-A251, M1-S250, M1-F249, M1-H248, M1-I247, M1-L246, M1-R245, M1-Q244, M1-R243, M1-L242, M1-E241, M1-A240, M1-L239, M1-T238, M1-L237, M1-E236, M1-P235, M1-E234, M1-A233, M1-S232, M1-L231, M1-M230, M1-M229, M1-A228, M1-A227, M1-I226, M1-G225, M1-A224, M1-V223, M1-H222, M1-A221, M1-A220, M1-A219, M1-Q218, M1-S217, M1-T216, M1-G215, M1-S214, M1-Q213, M1-S212, M1-V211, M1-F210, M1-C209, M1-T208, M1-S207, M1-C206, M1-D205, M1-S204, M1-S203, M1-A202, M1-G201, M1-I200, M1-I199, M1-D198, M1-E197, M1-G196, M1-P195, M1-A194, M1-F193, M1-L192, M1-D191, M1-V190, M1-C189, M1-R188, M1-G187, M1-F186, M1-N185, M1-T184, M1-G183, M1-L182, M1-T181, M1-G180, M1-L179, M1-T178, M1-V177, M1-P176, M1-Q175, M1-D174, M1-Q173, M1-A172, M1-N171, M1-T170, M1-A169, M1-G168, M1-V167, M1-T166, M1-I165, M1-V164, M1-E163, M1-P162, M1-A161, M1-S160, M1-A159, M1-P158, M1-S157, M1-Y156, M1-L155, M1-C154, M1-A153, M1-D152, M1-D151, M1-R150, M1-F149, M1-N148, M1-G147, M1-A146, M1-A145, M1-T144, M1-V143, M1-L142, M1-V141, M1-V140, M1-G139, M1-A138, M1-R137, M1-A136, M1-L135, M1-R134, M1-Q133, M1-C132, M1-A131, M1-A130, M1-N129, M1-L128, M1-V127, M1-R126, M1-S125, M1-Y124, M1-G123, M1-G122, M1-A121, M1-L120, M1-P119, M1-L118, M1-L117, M1-V116, M1-V115, M1-L114, M1-P113, M1-G112, M1-V111, M1-P110, M1-Q109, M1-V108, M1-L107, M1-Q106, M1-S105, M1-K104, M1-R103, M1-I102, M1-F110, M1-E100, M1-L99, M1-G98, M1-I97, M1-L96, M1-T95, M1-G94, M1-S93, M1-V92, M1-T91, M1-G90, M1-K89, M1-G88, M1-Q87, M1-C86, M1-N85, M1-L84, M1-V83, M1-A82, M1-R82, M1-L81, M1-S80, M1-R79, M1-M78, M1-S77, M1-A76, M1-G75, M1-K74, M1-A73, M1-V72, M1-G71, M1-A70, M1-D69, M1-R68, M1-G67, M1-S66, M1-V65, M1-V64, M1-G63, M1-A62, M1-L61, M1-H60, M1-T59, M1-G58, M1-H57, M1-S56, M1-D55, M1-C54, M1-K53, M1-S52, M1-A51, M1-Q50, M1-R49, M1-H48, M1-F47, M1-R46, M1-T45, M1-G44, M1-D43, M1-E42, M1-E41, M1-P40, M1-V39, M1-N38, M1-E37, M1-F36, M1-D35, M1-T34, M1-V33, M1-M32, M1-V31, M1-R30, M1-G29, M1-E28, M1-I27, M1-E26, M1-R25, M1-H24, M1-D23, M1-S22, M1-Q21, M1-I20, M1-S19, M1-T18, M1-D17, M1-L16, M1-L15, M1-Y14, M1-V13, M1-E12, M1-V11, M1-L10, M1-S9, M1-G8, and/or M1-G7 of SEQ ID NO:4. Polypeptide sequences encoded by these polynucleotides are also provided. In addition, the invention also encompasses polynucleotides encoding a polypeptide that is at least as long as any one of the aforementioned polypeptides. The present invention also encompasses the use of these C-terminal PCSK9c deletion polypeptides as immunogenic and/or antigenic epitopes as described elsewhere herein.

Alternatively, preferred polypeptides of the present invention may comprise polypeptide sequences corresponding to, for example, internal regions of the PCSK9c polypeptide (e.g., any combination of both N- and C-terminal PCSK9c polypeptide deletions) of SEQ ID NO:4. For example, internal regions could be defined by the equation: amino acid NX to amino acid CX, wherein NX refers to any N-terminal deletion polypeptide amino acid of PCSK9c (SEQ ID NO:4), and where CX refers to any C-terminal deletion polypeptide amino acid of PCSK9c (SEQ ID NO:4). Polynucleotides encoding these polypeptides are also provided. The present invention also encompasses the use of these polypeptides as an immunogenic and/or antigenic epitope as described elsewhere herein.

The present invention also encompasses immunogenic and/or antigenic epitopes of the PCSK9c polypeptide.

Many polynucleotide sequences, such as EST sequences, are publicly available and accessible through sequence databases. Some of these sequences are related to SEQ ID NO:3 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides consisting of a nucleotide sequence described by the general formula of a-b, where a is any integer between 1 to 3742 of SEQ ID NO:3, b is an integer between 15 to 3756, where both a and b correspond to the positions of nucleotide residues shown in SEQ ID NO:3, and where b is greater than or equal to a+14.

Features of the Polypeptide Encoded by Polynucleotide No:3

The invention further relates to an N-terminal truncation of PCSK9 (SEQ ID NO:5), wherein said N-terminal truncation results in the deletion of anywhere between about 1 to about 218 amino acids from the N-terminus of SEQ ID NO:5, and wherein said N-terminal truncation results in elevated PCSK9 biological activity, including, but not limited to decreased LDLR protein levels, and/or decreased LDL uptake by LDLR. Polynucleotides encoding such PCSK9 truncations are provided as SEQ ID NO:38.

The inventors are the first to discover that N-terminal truncations of PCSK9 result in elevated levels of PCSK9 biological activity. Such truncated forms may also greatly facilitate the identification of small molecule modulators of PCSK9 as well. Experiments designed to assess whether truncation of the N-terminus of PCSK9 results in elevated biological activity have been performed. For example, truncation of the N-terminus by 15 amino acids resulted in significant increases in PCSK9 activity (data not shown), although not as significant as that observed for the PCSK9b and PCSK9c variants (see FIGS. 9A-B). Furthermore, truncation was tolerated by PCSK9 up to a truncation of about 218 amino acids, after which decreased levels of PCSK9 biological activity was observed (data not shown).

The invention further relates to an N-terminal truncation of PCSK9 (SEQ ID NO:5), wherein said N-terminal truncation results in the deletion of anywhere between about 1 to about 218 amino acids from the N-terminus of SEQ ID NO:5, including, but not limited to decreased LDLR protein levels and/or decreased LDL uptake by LDLR, and wherein said elevated PCSK9 biological activity is at least about 5%, 10%, 15%, 20%, 25%, 30%, 35%, 40%, 45%, 50%, 55%, 60%, 65%, 70%, 75%, 80%, 85%, 90%, 100%, or more than wildtype elevated PCSK9 biological activity. In this context, the term "about" shall be construed to mean anywhere between 1, 2, 3, 4, or 5 percent more or less than the cited amount. Alternatively, said elevated PCSK9 biological activity may be at least about 1×, 2×, 3×, 4×, 5×, 6×,7×, 8×, 9×, or 10× more than wildtype PCSK9 biological activity. In this context, the term "about" shall be construed to mean anywhere between 0.1×, 0.2×, 0.3×, 0.4×, 0.5×, 0.6×, 0.7×, 0.8×, or 0.9× more or less than the cited amount.

Preferably, an N-terminal deletion mutant of PCSK9 (SEQ ID NO:5) is at least about 15 amino acids, but less than about 218 amino acids, of SEQ ID NO:5. Truncated forms of PCSK9 may be created using molecular biology techniques (see Example 13), proteolytic cleavage, post-translational processing, chemical synthesis, etc., among other methods known in the art.

The coding region of PCSK9 encoding polynucleotides is represented by nucleotides 292 to 2367 of SEQ ID NO:38.

In preferred embodiments, the present invention is also directed to polynucleotides comprising, or alternatively consisting of, a sequence encoding the following N-terminal PCSK9c deletion polypeptides: M1-Q692, G2-Q692, T3-Q692, V4-Q692, S5-Q692, S6-Q692, R7-Q692, R8-Q692, S9-Q692, W10-Q692, W11-Q692, P12-Q692, L13-Q692, P14-Q692, L15-Q692, L16-Q692, L17-Q692, L18-Q692, L19-Q692, L20-Q692, L21-Q692, L22-Q692, L23-Q692, G24-Q692, P25-Q692, A26-Q692, G27-Q692, A28-Q692, R29-Q692, A30-Q692, Q31-Q692, E32-Q692, D33-Q692, E34-Q692, D35-Q692, G36-Q692, D37-Q692, Y38-Q692, E39-Q692, E40-Q692, L41-Q692, V42-Q692, L43-Q692, A44-Q692, L45-Q692, R46-Q692, S47-Q692, E48-Q692, E49-Q692, D50-Q692, G51-Q692, L52-Q692, A53-Q692, E54-Q692, A55-Q692, P56-Q692, E57-Q692, H58-Q692, G59-Q692, T60-Q692, T61-Q692, A62-Q692, T63-Q692, F64-Q692, H65-Q692, R66-Q692, C67-Q692, A68-Q692, K69-Q692, D70-Q692, P71-Q692, W72-Q692, R73-Q692, L74-Q692, P75-Q692, G76-Q692, T77-Q692, Y78-Q692, V79-Q692, V80-Q692, V81-Q692, L82-Q692, K83-Q692, E84-Q692, E85-Q692, T86-Q692, H87-Q692, L88-Q692, S89-Q692, Q90-Q692, S91-Q692, E92-Q692, R93-Q692, T94-Q692, A95-Q692, R96-Q692, R97-Q692, L98-Q692, Q99-Q692, A100-Q692, Q101-Q692, A102-Q692, A103-Q692, R104-Q692, R105-Q692, G106-Q692, Y107-Q692, L108-Q692, T109-Q692, K110-Q692, I111-Q692, L112-Q692, H113-Q692, V114-Q692, F115-Q692, H116-Q692, G117-Q692, L118-Q692, L119-Q692, P120-Q692, G121-Q692, F122-Q692, L123-Q692, V124-Q692, K125-Q692, M126-Q692, S127-Q692, G128-Q692, D129-Q692, L130-Q692, L131-Q692, E132-Q692, L133-Q692, A134-Q692, L135-Q692, K136-Q692, L137-Q692, P138-Q692, H139-Q692, V140-Q692, D141-Q692, Y142-Q692, I143-Q692, E144-Q692, E145-Q692, D146-Q692, S147-Q692, S148-Q692, V149-Q692, F150-Q692, A151-Q692, Q152-Q692, S153-Q692, I154-Q692, P155-Q692, W156-Q692, N157-Q692, L158-Q692, E159-Q692, R160-Q692, I161-Q692, T162-Q692, P163-Q692, P164-Q692, R165-Q692, Y166-Q692, R167-Q692, A168-Q692, D169-Q692, E170-Q692, Y171-Q692, Q172-Q692, P173-Q692, P174-Q692, D175-Q692, G176-Q692, G177-Q692, S178-Q692, L179-Q692, V180-Q692, E181-Q692, V182-Q692, Y183-Q692, L184-Q692, L185-Q692, D186-Q692, T187-Q692, S188-Q692, I189-Q692, Q190-Q692, S191-Q692, D192-Q692, H193-Q692, R194-Q692, E195-Q692, I196-Q692, E197-Q692, G198-Q692, R199-Q692, V200-Q692, M201-Q692, V202-Q692, T203-Q692, D204-Q692, F205-Q692, E206-Q692, N207-Q692, V208-Q692, P209-Q692, E210-Q692, E211-Q692, D212-Q692, G213-Q692, T214-Q692, R215-Q692, F216-Q692, H217-Q692, R218-Q692, Q219-Q692, A220-Q692, S221-Q692, K222-Q692, C223-Q692, D224-Q692, S225-Q692, H226-Q692, G227-Q692, T228-Q692, Q229-Q692, H229-Q692, L230-Q692, A231-Q692, G232-Q692, V233-Q692, V234-Q692, S235-Q692, G236-Q692, R237-Q692, D238-Q692, A239-Q692, G240-Q692, V241-Q692, A242-Q692, K243-Q692, G244-Q692, A245-Q692, S246-Q692, M247-Q692, R248-Q692, S249-Q692, L250-Q692, R251-Q692, V252-Q692, L253-Q692, N254-Q692, C255-Q692, Q256-Q692, G257-Q692, K258-Q692, G259-Q692, T260-Q692, V261-Q692, S262-Q692, G263-Q692, T264-Q692, L265-Q692, I266-Q692, G267-Q692, L268-Q692, E269-Q692, F270-Q692, I271-Q692, R272-Q692, K273-Q692, S274-Q692, Q275-Q692, L276-Q692, V277-Q692, Q278-Q692, P279-Q692, V280-Q692, G281-Q692, P282-Q692, L283-Q692, V284-Q692, V285-Q692, L286-Q692, L287-Q692, P288-Q692, L289-Q692, A290-Q692, G291-Q692, Q292-Q692, Y293-Q692, S294-Q692, R295-Q692, V296-Q692, L297-Q692, N298-Q692, A299-Q692, A300-Q692, C301-Q692, Q302-Q692, R303-Q692, L304-Q692, A305-Q692, R306-Q692, A307-Q692, G308-Q692, V309-Q692, V310-Q692, L311-Q692, V312-Q692, T313-Q692, A314-Q692, A315-Q692, G316-Q692, N317-Q692, F318-Q692, R319-Q692, D320-Q692, D321-Q692, A322-Q692, C323-Q692, L324-Q692, Y325-Q692, S326-Q692, P327-Q692, A328-Q692, S329-Q692, A330-Q692, P331-Q692, E332-Q692, V333-Q692, I334-Q692, T335-Q692, V336-Q692, G337-Q692, A338-Q692, T339-Q692, N340-Q692, A341-Q692, Q342-Q692, D343-Q692, Q344-Q692, P345-Q692, V346-Q692, T347-Q692, L348-Q692, G349-Q692, T350-Q692, L351-Q692, G352-Q692, T353-Q692, N354-Q692, F355-Q692, G356-Q692, R357-Q692, C358-Q692, V359-Q692, D360-Q692, L361-Q692, F362-Q692, A363-Q692, P364-Q692, G365-Q692, E366-Q692, D367-Q692, I368-Q692, I369-Q692, G370-Q692, A371-Q692, S372-Q692, S373-Q692, D374-Q692, C375-Q692, S376-Q692, T377-Q692, C378-Q692, F379-Q692, V380-Q692, S381-Q692, Q382-Q692, S383-Q692, G384-Q692, T385-Q692, S386-Q692, Q387-Q692, A388-Q692, A389-Q692, A390-Q692, H391-Q692, V392-Q692, A393-Q692, G394-Q692, I395-Q692, A396-Q692, A397-Q692, M398-Q692, M399-Q692, L400-Q692, S401-Q692, A402-Q692, E403-Q692, P404-Q692, E405-Q692, L406-Q692, T407-Q692, L408-Q692, A409-Q692, E410-Q692, L411-Q692, R412-Q692, Q413-Q692, R414-Q692, L415-Q692, I416-Q692, H417-Q692, Q692, F418-Q692, S419-Q692, A420-Q692, K421-Q692, D422-Q692, V423-Q692, I424-Q692, N425-Q692, E426-Q692, A427-Q692, W428-Q692, F429-Q692, P430-Q692, E431-Q692, D432-Q692, Q433-Q692, R434-Q692, V435-Q692, L436-Q692, T437-Q692, P438-Q692, N439-Q692, L440-Q692, V441-Q692, A442-Q692, A443-Q692, L444-Q692, P445-Q692, P446-Q692, S447-Q692, T448-Q692, H449-Q692, G450-Q692, A451-Q692, G452-Q692, W453-Q692, Q454-Q692, L455-Q692, F456-Q692, C457-Q692, R458-Q692, T459-Q692, V460-Q692, W461-Q692, S462-Q692, A463-Q692, H464-Q692, S465-Q692, G466-Q692, P467-Q692, T468-Q692, R469-Q692, M470-Q692, A471-Q692, T472-Q692, A473-Q692, V474-Q692, A475-Q692, R476-Q692, C477-Q692, A478-Q692, P479-Q692, D480-Q692, E481-Q692, E482-Q692, L483-Q692, L484-Q692, S485-Q692, C486-Q692, S487-Q692, S488-Q692, F489-Q692, S490-Q692, R491-Q692, S492-Q692, G493-Q692, K494-Q692, R495-Q692, R496-Q692, G497-Q692, E498-Q692, R499-Q692, M500-Q692, E501-Q692, A502-Q692, Q503-Q692, G504-Q692, G505-Q692, K506-Q692, L507-Q692, V508-Q692, C509-Q692, R510-Q692, A511-Q692, H512-Q692, N513-Q692, A514-Q692, F515-Q692, G516-Q692, G517-Q692, E518-Q692, G519-Q692, V520-Q692, Y521-Q692, A522-Q692, I523-Q692, A524-Q692, R525-Q692, C526-Q692, C527-Q692, L528-Q692, L529-Q692, P530-Q692, Q531-Q692, A532-Q692, N533-Q692, C534-Q692, S535-Q692, V536-Q692, H537-Q692, T538-Q692, A539-Q692, P540-Q692, P541-Q692, A542-Q692, E543-Q692, A544-Q692, S545-Q692, M546-Q692, G547-Q692, T548-Q692, R549-Q692, V550-Q692, H551-Q692, C552-Q692, H553-Q692, Q554-Q692, Q555-Q692, G556-Q692, H557-Q692, V558-Q692, L559-Q692, T560-Q692, G561-Q692, C562-Q692, S563-Q692, S564-Q692, H565-Q692, W566-Q692, E567-Q692, V568-Q692, E569-Q692, D570-Q692, L571-Q692, G572-Q692, T573-Q692, H574-Q692, K575-Q692, P576-Q692, P577-Q692, V578-Q692, L579-Q692, R580-Q692, P581-Q692, R582-Q692, G583-Q692, Q584-Q692, P585-Q692, N586-Q692, Q587-Q692, C588-Q692, V589-Q692, G590-Q692, H591-Q692, R592-Q692, E593-Q692, A594-Q692, S595-Q692, I596-Q692, H597-Q692, A598-Q692, S599-Q692, C600-Q692, C601-Q692, H602-Q692, A603-Q692, P604-Q692, G605-Q692, L606-Q692, E607-Q692, C608-Q692, K609-Q692, V610-Q692, K611-Q692, E612-Q692, H613-Q692, G614-Q692, I615-Q692, P616-Q692, A617-Q692, P618-Q692, Q619-Q692, E620-Q692, Q621-Q692, V622-Q692, T623-Q692, V624-Q692, A625-Q692, C626-Q692, E627-Q692, E628-Q692, G629-Q692, W630-Q692, T631-Q692, L632-Q692, T633-Q692, G634-Q692, C635-Q692, S636-Q692, A637-Q692, L638-Q692, P639-Q692, G640-Q692, T641-Q692, S642-Q692, H643-Q692, V644-Q692, L645-Q692, G646-Q692, A647-Q692, Y648-Q692, A649-Q692, V650-Q692, D651-Q692, N652-Q692, T653-Q692, C654-Q692, V655-Q692, V656-Q692, R657-Q692, S658-Q692, R659-Q692, D660-Q692, V661-Q692, S662-Q692, T663-Q692, T664-Q692, G665-Q692, S666-Q692, T667-Q692, S668-Q692, E669-Q692, G670-Q692, A671-Q692, V672-Q692, T673-Q692, A674-Q692, V675-Q692, A676-Q692, I677-Q692, C678-Q692, C679-Q692, R680-Q692, S681-Q692, R682-Q692, H683-Q692, L684-Q692, A685-Q692, and/or Q686-Q692 of SEQ ID NO:5. Polypeptide sequences encoded by these polynucleotides are also provided as SEQ ID NO:38. In addition, the invention also encompasses polynucleotides encoding a polypeptide that is at least as long as any one of the aforementioned polypeptides. The present invention also encompasses the use of these N-terminal PCSK9c deletion polypeptides as immunogenic and/or antigenic epitopes as described elsewhere herein.

In preferred embodiments, the present invention is also directed to polynucleotides comprising, or alternatively consisting of, a sequence encoding the following C-terminal PCSK9c deletion polypeptides: M1-Q692, M1-L691, M1-E690, M1-Q689, M1-S688, M1-A687, M1-A686, M1-A685, M1-L684, M1-H683, M1-R682, M1-S681, M1-R680, M1-C679, M1-C678, M1-I677, M1-A676, M1-V675, M1-A674, M1-T673, M1-V672, M1-A671, M1-G670, M1-E669, M1-S668, M1-T667, M1-S666, M1-G665, M1-T664, M1-T663, M1-S662, M1-V661, M1-D660, M1-R659, M1-S658, M1-R657, M1-V656, M1-V655, M1-C654, M1-T653, M1-N652, M1-D651, M1-V650, M1-A649, M1-Y648, M1-A647, M1-G646, M1-L645, M1-V644, M1-H643, M1-S642, M1-T641, M1-G640, M1-P639, M1-L638, M1-A637, M1-S636, M1-C635, M1-G634, M1-T633, M1-L632, M1-T631, M1-W630, M1-G629, M1-E628, M1-E627, M1-C626, M1-A625, M1-V624, M1-T623, M1-V622, M1-Q621, M1-E620, M1-Q619, M1-P618, M1-A617, M1-P616, M1-I615, M1-G614, M1-H613, M1-E612, M1-K611, M1-V610, M1-K609, M1-C608, M1-E607, M1-L606, M1-G605, M1-P604, M1-A603, M1-H602, M1-C601, M1-C600, M1-S599, M1-A598, M1-H597, M1-I596, M1-S595, M1-A594, M1-E593, M1-R592, M1-H591, M1-G590, M1-V589, M1-C588, M1-Q587, M1-N586, M1-P585, M1-Q584, M1-G583, M1-R582, M1-P581, M1-R580, M1-L579, M1-V578, M1-P577, M1-P576, M1-K575, M1-H574, M1-T573, M1-G572, M1-L571, M1-D570, M1-E569, M1-V568, M1-E567, M1-W566, M1-H565, M1-S564, M1-S563, M1-C562, M1-G561, M1-T560, M1-L559, M1-V558, M1-H557, M1-G556, M1-Q555, M1-Q554, M1-H553, M1-C552, M1-H551, M1-V550, M1-R549, M1-T548, M1-G547, M1-M546, M1-S545, M1-A544, M1-E543, M1-A542, M1-P541, M1-P540, M1-A539, M1-T538, M1-H537, M1-V536, M1-S535, M1-C534, M1-N533, M1-A532, M1-Q531, M1-P530, M1-L529, M1-L528, M1-C527, M1-C526, M1-R525, M1-A524, M1-I523, M1-A522, M1-Y521, M1-V520, M1-G519, M1-E518, M1-G517, M1-G516, M1-F515, M1-A514, M1-N513, M1-H512, M1-A511, M1-R510, M1-C509, M1-V508, M1-L507, M1-K506, M1-G505, M1-G504, M1-Q503, M1-A502, M1-E501, M1-M500, M1-R499, M1-E498, M1-G497, M1-R496, M1-R495, M1-K494, M1-G493, M1-S492, M1-R491, M1-S490, M1-F489, M1-S488, M1-S487, M1-C486, M1-S485, M1-L484, M1-L483, M1-E482, M1-E481, M1-D480, M1-P479, M1-A478, M1-C477, M1-R476, M1-A475, M1-V474, M1-A473, M1-T472, M1-A471, M1-M470, M1-R469, M1-T468, M1-P467, M1-G466, M1-S465, M1-H464, M1-A463, M1-S462, M1-W461, M1-V460, M1-T459, M1-R458, M1-C457, M1-F456, M1-L455, M1-Q454, M1-W453, M1-G452, M1-A451, M1-G450, M1-H449, M1-T448, M1-S447, M1-P446, M1-P445, M1-L444, M1-A443, M1-A442, M1-V441, M1-L440, M1-N439, M1-P438, M1-T437, M1-L436, M1-V435, M1-R434, M1-Q433, M1-D432, M1-E431, M1-P430, M1-F429, M1-W428, M1-A427, M1-E426, M1-N425, M1-I424, M1-V423, M1-D422, M1-K421, M1-A420, M1-S419, M1-F418, M1-H417, M1-I416, M1-L415, M1-R414, M1-Q413, M1-R412, M1-L411, M1-E410, M1-A409, M1-L408, M1-T407, M1-L406, M1-E405, M1-P404, M1-E403, M1-A402, M1-S401, M1-L400, M1-M399, M1-M398, M1-A397, M1-A396, M1-I395, M1-G394, M1-A393, M1-V392, M1-H391, M1-A390, M1-A389, M1-A388, M1-Q387, M1-S386, M1-T385, M1-G384, M1-S383, M1-Q382, M1-S381, M1-V380, M1-F379, M1-C378, M1-T377, M1-S376, M1-C375, M1-D374, M1-S373, M1-S372, M1-A371,
M1-G370, M1-I369, M1-I368, M1-D367, M1-E366,
M1-G365, M1-P364, M1-A363, M1-F362, M1-L361,
M1-D360, M1-V359, M1-C358, M1-R357, M1-G356,
M1-F355, M1-N354, M1-T353, M1-G352, M1-L351,
M1-T350, M1-G349, M1-L348, M1-T347, M1-V346,
M1-P345, M1-Q344, M1-D343, M1-Q342, M1-A341,
M1-N340, M1-T339, M1-A338, M1-G337, M1-V336,
M1-T335, M1-I334, M1-V333, M1-E332, M1-P331,
M1-A330, M1-S329, M1-A328, M1-P327, M1-S326,
M1-Y325, M1-L324, M1-C323, M1-A322, M1-D321,
M1-D320, M1-R319, M1-F318, M1-N317, M1-G316,
M1-A315, M1-A314, M1-T313, M1-V312, M1-L311,
M1-V310, M1-V309, M1-G308, M1-A307, M1-R306,
M1-A305, M1-L304, M1-R303, M1-Q302, M1-C301,
M1-A300, M1-A299, M1-N298, M1-L297, M1-V296,
M1-R295, M1-S294, M1-Y293, M1-G292, M1-G291,
M1-A290, M1-L289, M1-P288, M1-L287, M1-L286,
M1-V285, M1-V284, M1-L283, M1-P282, M1-G281,
M1-V280, M1-P279, M1-Q278, M1-V277, M1-L276,
M1-Q275, M1-S274, M1-K273, M1-R272, M1-I271,
M1-F270, M1-E269, M1-L268, M1-G267, M1-I266,
M1-L265, M1-T264, M1-G263, M1-S262, M1-V261,
M1-T260, M1-G259, M1-K258, M1-G257, M1-Q256,
M1-C255, M1-N254, M1-L253, M1-V252, M1-R251,
M1-L250, M1-S249, M1-R248, M1-M247, M1-S246,
M1-A245, M1-G244, M1-K243, M1-A242, M1-V241,
M1-G240, M1-A239, M1-D238, M1-R237, M1-G236,
M1-S235, M1-V234, M1-V233, M1-G232, M1-A231,
M1-L230, M1-H229, M1-T228, M1-G227, M1-H226,
M1-S225, M1-D224, M1-C223, M1-K222, M1-S221,
M1-A220, M1-Q219, M1-R218, M1-H217, M1-F216,
M1-R215, M1-T214, M1-G213, M1-D212, M1-E211,
M1-E210, M1-P209, M1-V208, M1-N207, M1-E206,
M1-F205, M1-D204, M1-T203, M1-V202, M1-M201,
M1-V200, M1-R199, M1-G198, M1-E197, M1-I196,
M1-E195, M1-R194, M1-H193, M1-D192, M1-S191,
M1-Q190, M1-I189, M1-S188, M1-T187, M1-D186,
M1-L185, M1-L184, M1-Y183, M1-V182, M1-E181,
M1-V180, M1-L179, M1-S178, M1-G177, M1-G176,
M1-D175, M1-P174, M1-P173, M1-Q172, M1-Y171,
M1-E170, M1-D169, M1-A168, M1-R167, M1-Y166,
M1-R165, M1-P164, M1-P163, M1-T162, M1-I161,
M1-R160, M1-E159, M1-L158, M1-N157, M1-W156,
M1-P155, M1-I154, M1-S153, M1-Q152, M1-A151,
M1-F150, M1-V149, M1-S148, M1-S147, M1-D146,
M1-E145, M1-I144, M1-I143, M1-Y142, M1-D141,
M1-V140, M1-H139, M1-P138, M1-L137, M1-K136,
M1-L135, M1-A134, M1-L133, M1-E132, M1-L131,
M1-L130, M1-D129, M1-G128, M1-S127, M1-M126,
M1-K125, M1-V124, M1-L123, M1-F122, M1-G121,
M1-P120, M1-L119, M1-L118, M1-G117, M1-H116,
M1-F115, M1-V114, M1-H113, M1-L112, M1-I111,
M1-K110, M1-I109, M1-T108, M1-L108, M1-Y107, M1-G106,
M1-R105, M1-R104, M1-A103, M1-A102, M1-Q100,
M1-A100, M-Q99, M1-L98, M1-R97, M1-R96, M1-A95,
M1-T94, M1-R93, M1-E92, M1-S91, M1-Q90, M1-S89,
M1-L88, M1-H87, M1-T86, M1-E85, M1-E84, M1-K83,
M1-L82, M1-V81, M1-V80, M1-V79, M1-Y78, M1-T77,
M1-G76, M1-P75, M1-L74, M1-R73, M1-W72, M1-P71,
M1-D70, M1-K69, M1-A68, M1-C67, M1-R66, M1-H65,
M1-F64, M1-T63, M1-A62, M1-T61, M1-T60, M1-G59,
M1-H58, M1-E57, M1-P56, M1-A55, M1-E54, M1-A53,
M1-L52, M1-G51, M1-D50, M1-E49, M1-E48, M1-S47,
M1-R46, M1-L45, M1-A44, M1-L43, M1-V42, M1-L41,
M1-E40, M1-E39, M1-Y38, M1-D37, M1-G36, M1-D35,
M1-E34, M1-D33, M1-E32, M1-Q31, M1-A30, M1-R29,
M1-A28, M1-G27, M1-A26, M1-P25, M1-G24, M1-L23,
M1-L22, M1-L21, M1-L20, M1-L19, M1-L18, M1-L17,
M1-L16, M1-L15, M1-P14, M1-L13, M1-P12, M1-W11,
M1-W10, M1-S9, M1-R8, and/or M1-R7 of SEQ ID NO:5. Polypeptide sequences encoded by these polynucleotides are also provided as SEQ ID NO:38. In addition, the invention also encompasses polynucleotides encoding a polypeptide that is at least as long as any one of the aforementioned polypeptides. The present invention also encompasses the use of these C-terminal PCSK9c deletion polypeptides as immunogenic and/or antigenic epitopes as described elsewhere herein.

TABLE I

| Gene No. | CDNA CloneID | ATCC ® Deposit No. Z and Date | Vector | NT SEQ ID. No. X | Total NT Seq of Clone | 5' NT of Start Codon of ORF | 3' NT of ORF | AA Seq ID No. Y | Total AA of ORF |
|---|---|---|---|---|---|---|---|---|---|
| 1. | PCSK9b (also referred to as PCSK9-b) | PTA-7622 May 10, 2006 | pSPORT2 | 1 | 3175 | 250 | 1194 | 2 | 315 |
| 2. | PCSK9c (also referred to as PCSK9-c) | PTA-7622 May 10, 2006 | pSPORT1 | 3 | 3756 | 881 | 2449 | 4 | 523 |

Table I summarizes the information corresponding to each "Gene No." described above. The nucleotide sequence identified as "NT SEQ ID NO:X" was assembled from partially homologous ("overlapping") sequences obtained from the "cDNA clone ID" identified in Table I and, in some cases, from additional related DNA clones. The overlapping sequences were assembled into a single contiguous sequence of high redundancy (usually several overlapping sequences at each nucleotide position), resulting in a final sequence identified as SEQ ID NO:X.

The cDNA Clone ID was deposited on the date and given the corresponding deposit number listed in "ATCC® Deposit No:Z and Date." "Vector" refers to the type of vector contained in the cDNA Clone ID.

"Total NT Seq. Of Clone" refers to the total number of nucleotides in the clone contig identified by "Gene No." The deposited clone may contain all or most of the sequence of SEQ ID NO:X. The nucleotide position of SEQ ID NO:X of the putative start codon (methionine) is identified as "5' NT of Start Codon of ORF."

The translated amino acid sequence, beginning with the methionine, is identified as "AA SEQ ID NO:Y" although other reading frames can also be easily translated using known molecular biology techniques. The polypeptides produced by these alternative open reading frames are specifically contemplated by the present invention.

The total number of amino acids within the open reading frame of SEQ ID NO:Y is identified as "Total AA of ORF".

SEQ ID NO:X (where X may be any of the polynucleotide sequences disclosed in the sequence listing) and the translated SEQ ID NO:Y (where Y may be any of the polypeptide sequences disclosed in the sequence listing) are sufficiently accurate and otherwise suitable for a variety of uses well known in the art and described further herein. For instance, SEQ ID NO:X is useful for designing nucleic acid hybridization probes that will detect nucleic acid sequences contained in SEQ ID NO:X or the cDNA contained in the deposited clone. These probes will also hybridize to nucleic acid molecules in biological samples, thereby enabling a variety of forensic and diagnostic methods of the invention. Similarly, polypeptides identified from SEQ ID NO:Y may be used, for example, to generate antibodies which bind specifically to proteins containing the polypeptides and the proteins encoded by the cDNA clones identified in Table I.

Nevertheless, DNA sequences generated by sequencing reactions can contain sequencing errors. The errors exist as misidentified nucleotides, or as insertions or deletions of nucleotides in the generated DNA sequence. The erroneously inserted or deleted nucleotides may cause frame shifts in the reading frames of the predicted amino acid sequence. In these cases, the predicted amino acid sequence diverges from the actual amino acid sequence, even though the generated DNA sequence may be greater than 99.9% identical to the actual DNA sequence (for example, one base insertion or deletion in an open reading frame of over 1000 bases).

Accordingly, for those applications requiring precision in the nucleotide sequence or the amino acid sequence, the present invention provides not only the generated nucleotide sequence identified as SEQ ID NO:X and the predicted translated amino acid sequence identified as SEQ ID NO:Y, but also a sample of plasmid DNA containing a cDNA of the invention deposited with the ATCC®, as set forth in Table I. The nucleotide sequence of each deposited clone can readily be determined by sequencing the deposited clone in accordance with known methods. The predicted amino acid sequence can then be verified from such deposits. Moreover, the amino acid sequence of the protein encoded by a particular clone can also be directly determined by peptide sequencing or by expressing the protein in a suitable host cell containing the deposited cDNA, collecting the protein, and determining its sequence.

The present invention also relates to the genes corresponding to SEQ ID NO:X, SEQ ID NO:Y, or the deposited clone. The corresponding gene can be isolated in accordance with known methods using the sequence information disclosed herein. Such methods include preparing probes or primers from the disclosed sequence and identifying or amplifying the corresponding gene from appropriate sources of genomic material.

Also provided in the present invention are species homologs, allelic variants, and/or orthologs. The skilled artisan could, using procedures well-known in the art, obtain the polynucleotide sequence corresponding to full-length genes (including, but not limited to the full-length coding region), allelic variants, splice variants, orthologs, and/or species homologues of genes corresponding to SEQ ID NO:X, SEQ ID NO:Y, or a deposited clone, relying on the sequence from the sequences disclosed herein or the clones deposited with the ATCC®. For example, allelic variants and/or species homologues may be isolated and identified by making suitable probes or primers which correspond to the 5', 3', or internal regions of the sequences provided herein and screening a suitable nucleic acid source for allelic variants and/or the desired homologue.

The polypeptides of the invention can be prepared in any suitable manner. Such polypeptides include isolated naturally occurring polypeptides, recombinantly produced polypeptides, synthetically produced polypeptides, or polypeptides produced by a combination of these methods. Means for preparing such polypeptides are well understood in the art.

The polypeptides may be in the form of the protein, or may be a part of a larger protein, such as a fusion protein (see below). It is often advantageous to include an additional amino acid sequence which contains secretory or leader sequences, pro-sequences, sequences which aid in purification, such as multiple histidine residues, or an additional sequence for stability during recombinant production.

The polypeptides of the present invention are preferably provided in an isolated form, and preferably are substantially purified. A recombinantly produced version of a polypeptide, can be substantially purified using techniques described herein or otherwise known in the art, such as, for example, by the one-step method described in Smith and Johnson, Gene 67:31-40 (1988). Polypeptides of the invention also can be purified from natural, synthetic or recombinant sources using protocols described herein or otherwise known in the art, such as, for example, antibodies of the invention raised against the full-length form of the protein.

The present invention provides a polynucleotide comprising, or alternatively consisting of, the sequence identified as SEQ ID NO:X, and/or a cDNA provided in ATCC® Deposit No. Z:. The present invention also provides a polypeptide comprising, or alternatively consisting of, the sequence identified as SEQ ID NO:Y, and/or a polypeptide encoded by the cDNA provided in ATCC® Deposit NO:Z. The present invention also provides polynucleotides encoding a polypeptide comprising, or alternatively consisting of the polypeptide sequence of SEQ ID NO:Y, and/or a polypeptide sequence encoded by the cDNA contained in ATCC® Deposit No:Z.

Preferably, the present invention is directed to a polynucleotide comprising, or alternatively consisting of, the sequence identified as SEQ ID NO:X, and/or a cDNA provided in ATCC® Deposit No.: that is less than, or equal to, a polynucleotide sequence that is 5 mega basepairs, 1 mega basepairs, 0.5 mega basepairs, 0.1 mega basepairs, 50,000 basepairs, 20,000 basepairs, or 10,000 basepairs in length.

The present invention encompasses polynucleotides with sequences complementary to those of the polynucleotides of the present invention disclosed herein. Such sequences may be complementary to the sequence disclosed as SEQ ID NO:X, the sequence contained in a deposit, and/or the nucleic acid sequence encoding the sequence disclosed as SEQ ID NO:Y.

The present invention also encompasses polynucleotides capable of hybridizing, preferably under reduced stringency conditions, more preferably under stringent conditions, and most preferably under highly stringent conditions, to polynucleotides described herein. Examples of stringency conditions are shown in Table II below: highly stringent conditions are those that are at least as stringent as, for example, conditions A-F; stringent conditions are at least as stringent as, for example, conditions G-L; and reduced stringency conditions are at least as stringent as, for example, conditions M-R.

TABLE II

| Stringency Condition | Polynucleotide Hybrid± | Hybrid Length (bp)‡ | Hybridization Temperature and Buffer† | Wash Temperature and Buffer† |
|---|---|---|---|---|
| A | DNA:DNA | >or equal to 50 | 65° C.; 1xSSC -or- 42° C.; 1xSSC, 50% formamide | 65° C.; 0.3xSSC |
| B | DNA:DNA | <50 | Tb*; 1xSSC | Tb*; 1xSSC |
| C | DNA:RNA | >or equal to 50 | 67° C.; 1xSSC -or- 45° C.; 1xSSC, 50% formamide | 67° C.; 0.3xSSC |
| D | DNA:RNA | <50 | Td*; 1xSSC | Td*; 1xSSC |
| E | RNA:RNA | >or equal to 50 | 70° C.; 1xSSC -or- 50° C.; 1xSSC, 50% formamide | 70° C.; 0.3xSSC |
| F | RNA:RNA | <50 | Tf*; 1xSSC | Tf*; 1xSSC |
| G | DNA:DNA | >or equal to 50 | 65° C.; 4xSSC -or- 45° C.; 4xSSC, 50% formamide | 65° C.; 1xSSC |
| H | DNA:DNA | <50 | Th*; 4xSSC | Th*; 4xSSC |
| I | DNA:RNA | >or equal to 50 | 67° C.; 4xSSC -or- 45° C.; 4xSSC, 50% formamide | 67° C.; 1xSSC |
| J | DNA:RNA | <50 | Tj*; 4xSSC | Tj*; 4xSSC |
| K | RNA:RNA | >or equal to 50 | 70° C.; 4xSSC -or- 40° C.; 6xSSC, 50% formamide | 67° C.; 1xSSC |
| L | RNA:RNA | <50 | Tl*; 2xSSC | Tl*; 2xSSC |
| M | DNA:DNA | >or equal to 50 | 50° C.; 4xSSC -or- 40° C. 6xSSC, 50% formamide | 50° C.; 2xSSC |
| N | DNA:DNA | <50 | Tn*; 6xSSC | Tn*; 6xSSC |
| O | DNA:RNA | >or equal to 50 | 55° C.; 4xSSC -or- 42° C.; 6xSSC, 50% formamide | 55° C.; 2xSSC |
| P | DNA:RNA | <50 | Tp*; 6xSSC | Tp*; 6xSSC |
| Q | RNA:RNA | >or equal to 50 | 60° C.; 4xSSC -or- 45° C.; 6xSSC, 50% formamide | 60° C.; 2xSSC |
| R | RNA:RNA | <50 | Tr*; 4xSSC | Tr*; 4xSSC |

‡The "hybrid length" is the anticipated length for the hybridized region(s) of the hybridizing polynucleotides. When hybridizing a polynucleotide of unknown sequence, the hybrid is assumed to be that of the hybridizing polynucleotide of the present invention. When polynucleotides of known sequence are hybridized, the hybrid length can be determined by aligning the sequences of the polynucleotides and identifying the region or regions of optimal sequence complementarity. Methods of aligning two or more polynucleotide sequences and/or determining the percent identity between two polynucleotide sequences are well known in the art (e.g., MegAlign program of the DNASTAR ® suite of programs, etc).
†SSPE (1xSSPE is 0.15M NaCl, 10 mM NaH2PO4, and 1.25 mM EDTA, pH 7.4) can be substituted for SSC (1xSSC is 0.15M NaCl and 15 mM sodium citrate) in the hybridization and wash buffers; washes are performed for 15 minutes after hybridization is complete. The hybridizations and washes may additionally include 5X Denhardt's reagent, .5-1.0% SDS, 100 µg/ml denatured, fragmented salmon sperm DNA, 0.5% sodium pyrophosphate, and up to 50% formamide.
*Tb – Tr: The hybridization temperature for hybrids anticipated to be less than 50 base paris in length should be 5-10° C. less than the melting temperature Tm of the hybrids there Tm is determined according to the following equations. For hybrids less than 18 base pairs in length, Tm(° C.) = 2(# of A + T bases) + 4(# of G + C bases). For hybrids between 18 and 49 base pairs in length, Tm(° C.) = 81.5 + 16.6(log$_{10}$[Na+]) + 0.41(% G + C) – (600/N), where N is the number of bases in the hybrid, and [Na+] is the concentration of sodium ions in the hybridization buffer ([NA+] for 1xSSC = .165M).
±The present invention encompasses the substitution of any one, or more DNA or RNA hybrid partners with either a PNA, or a modified polynucleotide. Such modified polynucleotides are known in the art and are more particularly described elsewhere herein.

Additional examples of stringency conditions for polynucleotide hybridization are provided, for example, in Sambrook, J., E. F. Fritsch, and T. Maniatis, 1989, Molecular Cloning: A Laboratory Manual, Cold Spring Harbor Laboratory Press, Cold Spring Harbor, N.Y., chapters 9 and 11, and Current Protocols in Molecular Biology, 1995, F. M., Ausubel et al., eds., John Wiley and Sons, Inc., sections 2.10 and 6.3-6.4, which are hereby incorporated by reference herein.

Preferably, such hybridizing polynucleotides have at least 70% sequence identity (more preferably, at least 80% identity; and most preferably at least 90% or 95% identity) with the polynucleotide of the present invention to which they hybridize, where sequence identity is determined by comparing the sequences of the hybridizing polynucleotides when aligned so as to maximize overlap and identity while minimizing sequence gaps. The determination of identity is well known in the art, and discussed more specifically elsewhere herein.

The invention encompasses the application of PCR methodology to the polynucleotide sequences of the present invention, the clone deposited with the ATCC®, and/or the cDNA encoding the polypeptides of the present invention. PCR techniques for the amplification of nucleic acids are described in U.S. Pat. No. 4,683,195 and Saiki et al., Science, 239:487-491 (1988). PCR, for example, may include the following steps, of denaturation of template nucleic acid (if double-stranded), annealing of primer to target, and polymerization. The nucleic acid probed or used as a template in the amplification reaction may be genomic DNA, cDNA, RNA, or a PNA. PCR may be used to amplify specific sequences from genomic DNA, specific RNA sequence, and/or cDNA transcribed from mRNA. References for the general use of PCR techniques, including specific method parameters, include Mullis et al., Cold Spring Harbor Symp. Quant. Biol., 51:263, (1987), Ehrlich (ed), PCR Technology, Stockton Press, NY, 1989; Ehrlich et al., Science, 252:1643-1650, (1991); and "PCR Protocols, A Guide to Methods and Applications", Eds., Innis et al., Academic Press, New York, (1990).

Polynucleotide and Polypeptide Variants

The present invention also encompasses variants (e.g., allelic variants, orthologs, etc.) of the polynucleotide sequence disclosed herein in SEQ ID NO:X, the complementary strand thereto, and/or the cDNA sequence contained in the deposited clone.

The present invention also encompasses variants of the polypeptide sequence, and/or fragments therein, disclosed in SEQ ID NO:Y, a polypeptide encoded by the polynucleotide sequence in SEQ ID NO:X, and/or a polypeptide encoded by a cDNA in the deposited clone.

"Variant" refers to a polynucleotide or polypeptide differing from the polynucleotide or polypeptide of the present invention, but retaining essential properties thereof. Generally, variants are overall closely similar, and, in many regions, identical to the polynucleotide or polypeptide of the present invention.

Thus, one aspect of the invention provides an isolated nucleic acid molecule comprising, or alternatively consisting of, a polynucleotide having a nucleotide sequence selected from the group consisting of: (a) a nucleotide sequence encoding a PCSK9b or PCSK9c polypeptide having an amino acid sequence as shown in the sequence listing and described in SEQ ID NO:2 or SEQ ID NO:4 or the cDNA contained in ATCC® deposit No:Z; (b) a nucleotide sequence encoding a mature PCSK9b or PCSK9c polypeptide having the amino acid sequence as shown in the sequence listing and described in SEQ ID NO:2 or SEQ ID NO:4 or the cDNA contained in ATCC® deposit No:Z; (c) a nucleotide sequence encoding a biologically active fragment of a PCSK9b or PCSK9c polypeptide having an amino acid sequence shown in the sequence listing and described in SEQ ID NO:2 or SEQ ID NO:4 or the cDNA contained in ATCC® deposit No:Z; (d) a nucleotide sequence encoding an antigenic fragment of a PCSK9b or PCSK9c polypeptide having an amino acid sequence sown in the sequence listing and described in SEQ ID NO:2 or SEQ ID NO:4 or the cDNA contained in ATCC® deposit No:Z; (e) a nucleotide sequence encoding a PCSK9b or PCSK9c polypeptide comprising the complete amino acid sequence encoded by a human cDNA plasmid contained in SEQ ID NO:2 or SEQ ID NO:4 or the cDNA contained in ATCC® deposit No:Z; (f) a nucleotide sequence encoding a mature PCSK9b or PCSK9c polypeptide having an amino acid sequence encoded by a human cDNA plasmid contained in SEQ ID NO:2 or SEQ ID NO:4 or the cDNA contained in ATCC® deposit No:Z; (g) a nucleotide sequence encoding a biologically active fragment of a PCSK9b or PCSK9c polypeptide having an amino acid sequence encoded by a human cDNA plasmid contained in SEQ ID NO:2 or SEQ ID NO:4 or the cDNA contained in ATCC® deposit No:Z; (h) a nucleotide sequence encoding an antigenic fragment of a PCSK9b or PCSK9c polypeptide having an amino acid sequence encoded by a human cDNA plasmid contained in SEQ ID NO:X or the cDNA contained in ATCC® deposit No:Z; and (i) a nucleotide sequence complimentary to any of the nucleotide sequences in (a), (b), (c), (d), (e), (f), (g), or (h), above.

The present invention is also directed to polynucleotide sequences which comprise, or alternatively consist of, a polynucleotide sequence which is at least about 80%, 85%, 90%, 91%, 92%, 93%, 93.6%, 94%, 95%, 96%, 97%, 98%, 99%, 99.1%, 99.2%, 99.3%, 99.4%, 99.5%, 99.6%, 99.7%, 99.8%, or 99.9% identical to, for example, any of the nucleotide sequences in (a), (b), (c), (d), (e), (f), (g), or (h), above. Polynucleotides encoded by these nucleic acid molecules are also encompassed by the invention. In another embodiment, the invention encompasses nucleic acid molecules which comprise, or alternatively, consist of a polynucleotide which hybridizes under stringent conditions, or alternatively, under lower stringency conditions, to a polynucleotide in (a), (b), (c), (d), (e), (f), (g), or (h), above. Polynucleotides which hybridize to the complement of these nucleic acid molecules under stringent hybridization conditions or alternatively, under lower stringency conditions, are also encompassed by the invention, as are polypeptides encoded by these polypeptides.

Another aspect of the invention provides an isolated nucleic acid molecule comprising, or alternatively, consisting of, a polynucleotide having a nucleotide sequence selected from the group consisting of: (a) a nucleotide sequence encoding a PCSK9b or PCSK9c polypeptide having an amino acid sequence as shown in the sequence listing and descried in Table I; (b) a nucleotide sequence encoding a mature PCSK9b or PCSK9c polypeptide having the amino acid sequence as shown in the sequence listing and descried in Table I; (c) a nucleotide sequence encoding a biologically active fragment of a PCSK9b or PCSK9c polypeptide having an amino acid sequence as shown in the sequence listing and descried in Table I; (d) a nucleotide sequence encoding an antigenic fragment of a PCSK9b or PCSK9c polypeptide having an amino acid sequence as shown in the sequence listing and descried in Table I; (e) a nucleotide sequence encoding a PCSK9b or PCSK9c polypeptide comprising the complete amino acid sequence encoded by a human cDNA in a cDNA plasmid contained in the ATCC® Deposit and described in Table I; (f) a nucleotide sequence encoding a mature PCSK9b or PCSK9c polypeptide having an amino acid sequence encoded by a human cDNA in a cDNA plasmid contained in the ATCC® Deposit and described in Table I: (g) a nucleotide sequence encoding a biologically active fragment of a PCSK9b or PCSK9c polypeptide having an amino acid sequence encoded by a human cDNA in a cDNA plasmid contained in the ATCC® Deposit and described in Table I; (h) a nucleotide sequence encoding an antigenic fragment of a PCSK9b or PCSK9c polypeptide having an amino acid sequence encoded by a human cDNA in a cDNA plasmid contained in the ATCC® deposit and described in Table I; and (i) a nucleotide sequence complimentary to any of the nucleotide sequences in (a), (b), (c), (d), (e), (f), (g), or (h) above.

The present invention is also directed to nucleic acid molecules which comprise, or alternatively, consist of, a nucleotide sequence which is at least about 80%, 85%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, or 99.9% identical to, for example, any of the nucleotide sequences in (a), (b), (c), (d), (e), (f), (g), or (h), above.

The present invention encompasses polypeptide sequences which comprise, or alternatively consist of, an amino acid sequence which is at least about 80%, 85%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, or 99.9% identical to, the following non-limited examples, the polypeptide sequence identified as SEQ ID NO:Y, the polypeptide sequence encoded by a cDNA provided in the deposited clone, and/or polypeptide fragments of any of the polypeptides provided herein. Polynucleotides encoded by these nucleic acid molecules are also encompassed by the invention. In another embodiment, the invention encompasses nucleic acid molecules which comprise, or alternatively, consist of a polynucleotide which hybridizes under stringent conditions, or alternatively, under lower stringency conditions, to a polynucleotide in (a), (b), (c), (d), (e), (f), (g), or (h), above. Polynucleotides which hybridize to the complement of these nucleic acid molecules under stringent hybridization conditions or alternatively, under lower stringency conditions, are also encompassed by the invention, as are polypeptides encoded by these polypeptides.

The present invention is also directed to polypeptides which comprise, or alternatively consist of, an amino acid sequence which is at least about 80%, 85%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, or 99.9% identical to; for example, the polypeptide sequence shown in SEQ ID NO:Y, a polypeptide sequence encoded by the nucleotide sequence in SEQ ID NO:X, a polypeptide sequence encoded by the cDNA in cDNA plasmid: Z, and/or polypeptide fragments of any of these polypeptides (e.g., those fragments described herein). Polynucleotides which hybridize to the complement of the nucleic acid molecules encoding these polypeptides under stringent hybridization conditions or alternatively, under lower stringency conditions, are also encompasses by the present invention, as are the polypeptides encoded by these polynucleotides.

By a nucleic acid having a nucleotide sequence at least, for example, 95% "identical" to a reference nucleotide sequence of the present invention, it is intended that the nucleotide sequence of the nucleic acid is identical to the reference sequence except that the nucleotide sequence may include up to five point mutations per each 100 nucleotides of the reference nucleotide sequence encoding the polypeptide. In other words, to obtain a nucleic acid having a nucleotide sequence at least 95% identical to a reference nucleotide sequence, up to 5% of the nucleotides in the reference sequence may be deleted or substituted with another nucleotide, or a number of nucleotides up to 5% of the total nucleotides in the reference sequence may be inserted into the reference sequence. The query sequence may be an entire sequence referenced in Table I, the ORF (open reading frame), or any fragment specified as described herein.

As a practical matter, whether any particular nucleic acid molecule or polypeptide is at least about 80%, 85%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, or 99.9% identical to a nucleotide sequence of the present invention can be determined conventionally using known computer programs. A preferred method for determining the best overall match between a query sequence (a sequence of the present invention) and a subject sequence, also referred to as a global sequence alignment, can be determined using the CLUSTALW computer program (Thompson, J. D., et al., Nucleic Acids Research, 2(22):4673-4680, (1994)), which is based on the algorithm of Higgins, D. G., et al., Computer Applications in the Biosciences (CABIOS), 8(2):189-191, (1992). In a sequence alignment the query and subject sequences are both DNA sequences. An RNA sequence can be compared by converting U's to T's. However, the CLUSTALW algorithm automatically converts U's to T's when comparing RNA sequences to DNA sequences. The result of said global sequence alignment is in percent identity. Preferred parameters used in a CLUSTALW alignment of DNA sequences to calculate percent identity via pairwise alignments are: Matrix=IUB, k-tuple=1, Number of Top Diagonals=5, Gap Penalty=3, Gap Open Penalty 10, Gap Extension Penalty=0.1, Scoring Method=Percent, Window Size=5 or the length of the subject nucleotide sequence, whichever is shorter. For multiple alignments; the following CLUSTALW parameters are preferred: Gap Opening Penalty=10; Gap Extension Parameter=0.05; Gap Separation Penalty Range=8; End Gap Separation Penalty=Off; % Identity for Alignment Delay=40%; Residue Specific Gaps:Off; Hydrophilic Residue Gap=Off; and Transition Weighting=0. The pairwise and multiple alignment parameters provided for CLUSTALW above represent the default parameters as provided with the ALIGNX® software program (VECTOR NTI® suite of programs, version 6.0).

The present invention encompasses the application of a manual correction to the percent identity results, in the instance where the subject sequence is shorter than the query sequence because of 5' or 3' deletions, not because of internal deletions. If only the local pairwise percent identity is required, no manual correction is needed. However, a manual correction may be applied to determine the global percent identity from a global polynucleotide alignment. Percent identity calculations based upon global polynucleotide alignments are often preferred since they reflect the percent identity between the polynucleotide molecules as a whole (i.e., including any polynucleotide overhangs, not just overlapping regions), as opposed to, only local matching polynucleotides. Manual corrections for global percent identity determinations are required since the CLUSTALW program does not account for 5' and 3' truncations of the subject sequence when calculating percent identity. For subject sequences truncated at the 5' or 3' ends, relative to the query sequence, the percent identity is corrected by calculating the number of bases of the query sequence that are 5' and 3' of the subject sequence, which are not matched/aligned, as a percent of the total bases of the query sequence. Whether a nucleotide is matched/aligned is determined by results of the CLUSTALW sequence alignment. This percentage is then subtracted from the percent identity, calculated by the above CLUSTALW program using the specified parameters, to arrive at a final percent identity score. This corrected score may be used for the purposes of the present invention. Only bases outside the 5' and 3' bases of the subject sequence, as displayed by the CLUSTALW alignment, which are not matched/aligned with the query sequence, are calculated for the purposes of manually adjusting the percent identity score.

For example, a 90 base subject sequence is aligned to a 100 base query sequence to determine percent identity. The deletions occur at the 5' end of the subject sequence and therefore, the CLUSTALW alignment does not show a matched/alignment of the first 10 bases at 5' end. The 10 unpaired bases represent 10% of the sequence (number of bases at the 5' and 3' ends not matched/total number of bases in the query sequence) so 10% is subtracted from the percent identity score calculated by the CLUSTALW program. If the remaining 90 bases were perfectly matched the final percent identity would be 90%. In another example, a 90 base subject sequence is compared with a 100 base query sequence. This time the deletions are internal deletions so that there are no bases on the 5' or 3' of the subject sequence which are not matched/aligned with the query. In this case the percent identity calculated by CLUSTALW is not manually corrected. Once again, only bases 5' and 3' of the subject sequence which are not matched/aligned with the query sequence are manually corrected for. No other manual corrections are required for the purposes of the present invention.

In addition to the above method of aligning two or more polynucleotide or polypeptide sequences to arrive at a percent identity value for the aligned sequences, it may be desirable in some circumstances to use a modified version of the CLUSTALW algorithm which takes into account known structural features of the sequences to be aligned, such as for example, the SWISS-PROT® designations for each sequence. The result of such a modified CLUSTALW algorithm may provide a more accurate value of the percent identity for two polynucleotide or polypeptide sequences. Support for such a modified version of CLUSTALW is provided within the CLUSTALW algorithm and would be readily appreciated to one of skill in the art of bioinformatics.

The variants may contain alterations in the coding regions, non-coding regions, or both. Especially preferred are polynucleotide variants containing alterations which produce silent substitutions, additions, or deletions, but do not alter the properties or activities of the encoded polypeptide. Nucleotide variants produced by silent substitutions due to the degeneracy of the genetic code are preferred. Moreover, variants in which 5-10, 1-5, or 1-2 amino acids are substituted, deleted, or added in any combination are also preferred. Polynucleotide variants can be produced for a variety of reasons, e.g., to optimize codon expression for a particular host (change codons in the mRNA to those preferred by a bacterial host such as E. coli).

Naturally occurring variants are called "allelic variants" and refer to one of several alternate forms of a gene occupying a given locus on a chromosome of an organism. (Genes II, Lewin, B., ed., John Wiley & Sons, New York (1985).) These allelic variants can vary at either the polynucleotide and/or polypeptide level and are included in the present invention. Alternatively, non-naturally occurring variants may be produced by mutagenesis techniques or by direct synthesis.

Using known methods of protein engineering and recombinant DNA technology, variants may be generated to improve or alter the characteristics of the polypeptides of the present invention. For instance, one or more amino acids can be deleted from the N-terminus or C-terminus of the protein without substantial loss of biological function. The authors of Ron et al., J. Biol. Chem. 268:2984-2988 (1993), reported variant KGF proteins having heparin binding activity even after deleting 3, 8, or 27 amino-terminal amino acid residues. Similarly, Interferon gamma exhibited up to ten times higher activity after deleting 8-10 amino acid residues from the carboxy terminus of this protein (Dobeli et al., J. Biotechnology 7:199-216 (1988)).

Moreover, ample evidence demonstrates that variants often retain a biological activity similar to that of the naturally occurring protein. For example, Gayle and coworkers (J. Biol. Chem. 268:22105-22111 (1993)) conducted extensive mutational analysis of human cytokine IL-1a. They used random mutagenesis to generate over 3,500 individual IL-1a mutants that averaged 2.5 amino acid changes per variant over the entire length of the molecule. Multiple mutations were examined at every possible amino acid position. The investigators found that "[m]ost of the molecule could be altered with little effect on either [binding or biological activity]." In fact, only 23 unique amino acid sequences, out of more than 3,500 nucleotide sequences examined, produced a protein that significantly differed in activity from wild-type.

Furthermore, even if deleting one or more amino acids from the N-terminus or C-terminus of a polypeptide results in modification or loss of one or more biological functions, other biological activities may still be retained. For example, the ability of a deletion variant to induce and/or to bind antibodies which recognize the protein will likely be retained when less than the majority of the residues of the protein are removed from the N-terminus or C-terminus. Whether a particular polypeptide lacking N- or C-terminal residues of a protein retains such immunogenic activities can readily be determined by routine methods described herein and otherwise known in the art.

Alternatively, such N-terminus or C-terminus deletions of a polypeptide of the present invention may, in fact, result in a significant increase in one or more of the biological activities of the polypeptide(s). For example, biological activity of many polypeptides are governed by the presence of regulatory domains at either one or both termini. Such regulatory domains effectively inhibit the biological activity of such polypeptides in lieu of an activation event (e.g., binding to a cognate ligand or receptor, phosphorylation, proteolytic processing, etc.). Thus, by eliminating the regulatory domain of a polypeptide, the polypeptide may effectively be rendered biologically active in the absence of an activation event.

Thus, the invention further includes polypeptide variants that show substantial biological activity. Such variants include deletions, insertions, inversions, repeats, and substitutions selected according to general rules known in the art so as have little effect on activity. For example, guidance concerning how to make phenotypically silent amino acid substitutions is provided in Bowie et al., Science 247:1306-1310 (1990), wherein the authors indicate that there are two main strategies for studying the tolerance of an amino acid sequence to change.

The first strategy exploits the tolerance of amino acid substitutions by natural selection during the process of evolution. By comparing amino acid sequences in different species, conserved amino acids can be identified. These conserved amino acids are likely important for protein function. In contrast, the amino acid positions where substitutions have been tolerated by natural selection indicates that these positions are not critical for protein function. Thus, positions tolerating amino acid substitution could be modified while still maintaining biological activity of the protein.

The second strategy uses genetic engineering to introduce amino acid changes at specific positions of a cloned gene to identify regions critical for protein function. For example, site directed mutagenesis or alanine-scanning mutagenesis (introduction of single alanine mutations at every residue in the molecule) can be used. (Cunningham and Wells, Science 244:1081-1085 (1989).) The resulting mutant molecules can then be tested for biological activity.

As the authors state, these two strategies have revealed that proteins are surprisingly tolerant of amino acid substitutions. The authors further indicate which amino acid changes are likely to be permissive at certain amino acid positions in the protein. For example, most buried (within the tertiary structure of the protein) amino acid residues require nonpolar side chains, whereas few features of surface side chains are generally conserved.

The invention encompasses polypeptides having a lower degree of identity but having sufficient similarity so as to perform one or more of the same functions performed by the polypeptide of the present invention. Similarity is determined by conserved amino acid substitution. Such substitutions are those that substitute a given amino acid in a polypeptide by another amino acid of like characteristics (e.g., chemical properties). According to Cunningham et al above, such conservative substitutions are likely to be phenotypically silent. Additional guidance concerning which amino acid changes are likely to be phenotypically silent are found in Bowie et al., Science 247:1306-1310 (1990).

The invention encompasses polypeptides having a lower degree of identity but having sufficient similarity so as to perform one or more of the same functions performed by the polypeptide of the present invention. Similarity is determined by conserved amino acid substitution. Such substitutions are those that substitute a given amino acid in a polypeptide by another amino acid of like characteristics (e.g., chemical properties). According to Cunningham et al above, such conservative substitutions are likely to be phenotypically silent. Additional guidance concerning which amino acid changes are likely to be phenotypically silent are found in Bowie et al., Science 247:1306-1310 (1990).

Tolerated conservative amino acid substitutions of the present invention involve replacement of the aliphatic or hydrophobic amino acids Ala, Val, Leu and Ile; replacement of the hydroxyl residues Ser and Thr; replacement of the acidic residues Asp and Glu; replacement of the amide residues Asn and Gln, replacement of the basic residues Lys, Arg, and His; replacement of the aromatic residues Phe, Tyr, and Trp, and replacement of the small-sized amino acids Ala, Ser, Thr, Met, and Gly.

In addition, the present invention also encompasses the conservative substitutions provided in Table III below.

TABLE III

| For Amino Acid | Code | Replace with any of: |
|---|---|---|
| Alanine | A | D-Ala, Gly, beta-Ala, L-Cys, D-Cys |
| Arginine | R | D-Arg, Lys, D-Lys, homo-Arg, D-homo-Arg, Met, Ile, D-Met, D-Ile, Orn, D-Orn |
| Asparagine | N | D-Asn, Asp, D-Asp, Glu, D-Glu, Gln, D-Gln |
| Aspartic Acid | D | D-Asp, D-Asn, Asn, Glu, D-Glu, Gln, D-Gln |
| Cysteine | C | D-Cys, S-Me-Cys, Met, D-Met, Thr, D-Thr |
| Glutamine | Q | D-Gln, Asn, D-Asn, Glu, D-Glu, Asp, D-Asp |
| Glutamic Acid | E | D-Glu, D-Asp, Asp, Asn, D-Asn, Gln, D-Gln |
| Glycine | G | Ala, D-Ala, Pro, D-Pro, β-Ala, Acp |
| Isoleucine | I | D-Ile, Val, D-Val, Leu, D-Leu, Met, D-Met |
| Leucine | L | D-Leu, Val, D-Val, Met, D-Met |
| Lysine | K | D-Lys, Arg, D-Arg, homo-Arg, D-homo-Arg, Met, D-Met, Ile, D-Ile, Orn, D-Orn |
| Methionine | M | D-Met, S-Me-Cys, Ile, D-Ile, Leu, D-Leu, Val, D-Val |
| Phenylalanine | F | D-Phe, Tyr, D-Thr, L-Dopa, His, D-His, Trp, D-Trp, Trans-3,4, or 5-phenylproline, cis-3,4, or 5-phenylproline |
| Proline | P | D-Pro, L-1-thioazolidine-4-carboxylic acid, D- or L-1-oxazolidine-4-carboxylic acid |
| Serine | S | D-Ser, Thr, D-Thr, allo-Thr, Met, D-Met, Met(O), D-Met(O), L-Cys, D-Cys |
| Threonine | T | D-Thr, Ser, D-Ser, allo-Thr, Met, D-Met, Met(O), D-Met(O), Val, D-Val |
| Tyrosine | Y | D-Tyr, Phe, D-Phe, L-Dopa, His, D-His |
| Valine | V | D-Val, Leu, D-Leu, Ile, D-Ile, Met, D-Met |

Aside from the uses described above, such amino acid substitutions may also increase protein or peptide stability. The invention encompasses amino acid substitutions that contain, for example, one or more non-peptide bonds (which replace the peptide bonds) in the protein or peptide sequence. Also included are substitutions that include amino acid residues other than naturally occurring L-amino acids, e.g., D-amino acids or non-naturally occurring or synthetic amino acids, e.g., β or γ amino acids.

Both identity and similarity can be readily calculated by reference to the following publications: Computational Molecular Biology, Lesk, A. M., ed., Oxford University Press, New York, 1988; Biocomputing: Informatics and Genome Projects, Smith, D. W., ed., Academic Press, New York, 1993; Informatics Computer Analysis of Sequence Data, Part 1, Griffin, A. M., and Griffin, H. G., eds., Humana Press, New Jersey, 1994; Sequence Analysis in Molecular Biology, von Heinje, G., Academic Press, 1987; and Sequence Analysis Primer, Gribskov, M. and Devereux, J., eds., M Stockton Press, New York, 1991.

In addition, the present invention also encompasses substitution of amino acids based upon the probability of an amino acid substitution resulting in conservation of function. Such probabilities are determined by aligning multiple genes with related function and assessing the relative penalty of each substitution to proper gene function. Such probabilities are often described in a matrix and are used by some algorithms (e.g., BLAST®, CLUSTALW, GAP®, etc.) in calculating percent similarity wherein similarity refers to the degree by which one amino acid may substitute for another amino acid without lose of function. An example of such a matrix is the PAM250 or BLOSUM62 matrix.

Aside from the canonical chemically conservative substitutions referenced above, the invention also encompasses substitutions which are typically not classified as conservative, but that may be chemically conservative under certain circumstances. Analysis of enzymatic catalysis for proteases, for example, has shown that certain amino acids within the active site of some enzymes may have highly perturbed pKa's due to the unique microenvironment of the active site. Such perturbed pKa's could enable some amino acids to substitute for other amino acids while conserving enzymatic structure and function. Examples of amino acids that are known to have amino acids with perturbed pKa's are the Glu-35 residue of Lysozyme, the Ile-16 residue of Chymotrypsin, the His-159 residue of Papain, etc. The conservation of function relates to either anomalous protonation or anomalous deprotonation of such amino acids relative to their canonical, non-perturbed pKa. The pKa perturbation may enable these amino acids to actively participate in general acid-base catalysis due to the unique ionization environment within the enzyme active site. Thus, substituting an amino acid capable of serving as either a general acid or general base within the microenvironment of an enzyme active site or cavity, as may be the case, in the same or similar capacity as the wild-type amino acid, would effectively serve as a conservative amino substitution.

Besides conservative amino acid substitution, variants of the present invention include, but are not limited to, the following: (i) substitutions with one or more of the non-conserved amino acid residues, where the substituted amino acid residues may or may not be one encoded by the genetic code, or (ii) substitution with one or more of amino acid residues having a substituent group, or (iii) fusion of the mature polypeptide with another compound, such as a compound to increase the stability and/or solubility of the polypeptide (for example, polyethylene glycol), or (iv) fusion of the polypeptide with additional amino acids, such as, for example, an IgG Fc fusion region peptide, or leader or secretory sequence, or a sequence facilitating purification; Such variant polypeptides are deemed to be within the scope of those skilled in the art from the teachings herein.

For example, polypeptide variants containing amino acid substitutions of charged amino acids with other charged or neutral amino acids may produce proteins with improved characteristics, such as less aggregation. Aggregation of pharmaceutical formulations both reduces activity and increases clearance due to the aggregate's immunogenic activity. (Pinckard et al., Clin. Exp. Immunol. 2:331-340 (1967); Robbins et al., Diabetes 36:838-845 (1987); Cleland et al., Crit. Rev. Therapeutic Drug Carrier Systems 10:307-377 (1993).)

Moreover, the invention further includes polypeptide variants created through the application of molecular evolution ("DNA Shuffling") methodology to the polynucleotide disclosed as SEQ ID NO:X, the sequence of the clone submitted in a deposit, and/or the cDNA encoding the polypeptide disclosed as SEQ ID NO:Y. Such DNA Shuffling technology is known in the art and more particularly described elsewhere herein (e.g., WPC, Stemmer, PNAS, 91:10747, (1994)), and in the Examples provided herein).

A further embodiment of the invention relates to a polypeptide which comprises the amino acid sequence of the present invention having an amino acid sequence which contains at least one amino acid substitution, but not more than 50 amino acid substitutions, even more preferably, not more than 40 amino acid substitutions, still more preferably, not more than 30 amino acid substitutions, and still even more preferably, not more than 20 amino acid substitutions. Of course, in order of ever-increasing preference, it is highly preferable for a peptide or polypeptide to have an amino acid sequence which comprises the amino acid sequence of the present invention, which contains at least one, but not more than 10, 9, 8, 7, 6, 5, 4, 3, 2 or 1 amino acid substitutions. In specific embodiments, the number of additions, substitutions, and/or deletions in the amino acid sequence of the present invention or fragments thereof (e.g., the mature form and/or other fragments described herein), is 1-5, 5-10, 5-25, 5-50, 10-50 or 50-150 conservative amino acid substitutions are preferable.

Polynucleotide and Polypeptide Fragments

The present invention is directed to polynucleotide fragments of the polynucleotides of the invention, in addition to polypeptides encoded therein by said polynucleotides and/or fragments.

In the present invention, a "polynucleotide fragment" refers to a short polynucleotide having a nucleic acid sequence which: is a portion of that contained in a deposited clone, or encoding the polypeptide encoded by the cDNA in a deposited clone; is a portion of that shown in SEQ ID NO:X or the complementary strand thereto, or is a portion of a polynucleotide sequence encoding the polypeptide of SEQ ID NO:Y. The nucleotide fragments of the invention are preferably at least about 15 nt, and more preferably at least about 20 nt, still more preferably at least about 30 nt, and even more preferably, at least about 40 nt, at least about 50 nt, at least about 75 nt, or at least about 150 nt in length, or at least about 875 nt in length, or at least about 837 nt in length, or at least about 903 nt in length, or at least about 915 nt in length, or at least about 930 nt in length, or at least about 945 nt in length, or at least about 1000 nt in length, or at least about 1050 nt in length, or at least about 1100 nt in length, or at least about 1150 nt in length, or at least about 1200 nt in length, or at least about 1250 nt in length, or at least about 1300 nt in length, or at least about 1350 nt in length, or at least about 1400 nt in length, or at least about 1450 nt in length, or at least about 1500 nt in length, or at least about 1554 nt in length. A fragment "at least 20 nt in length" for example, is intended to include 20 or more contiguous bases from the cDNA sequence contained in a deposited clone or the nucleotide sequence shown in SEQ ID NO:X. In this context "about" includes the particularly recited value, a value larger or smaller by several (25, 24, 23, 22, 21, 20, 19, 18, 17, 16, 15, 14, 13, 12, 11, 10, 9, 8, 7, 6, 5, 4, 3, 2, or 1) nucleotides, at either terminus, or at both termini. These nucleotide fragments have uses that include, but are not limited to, as diagnostic probes and primers as discussed herein. Of course, larger fragments (e.g., 50, 150, 500, 600, 837, 903, 1554, 2000 nucleotides) are preferred.

Moreover, representative examples of polynucleotide fragments of the invention, include, for example, fragments comprising, or alternatively consisting of, a sequence from about nucleotide number 1-50, 51-100, 101-150, 151-200, 201-250, 251-300, 301-350, 351-400, 401-450, 451-500, 501-550, 551-600, 651-700, 701-750, 751-800, 800-850, 851-900, 901-950, 951-1000, 1001-1050, 1051-1100, 1101-1150, 1151-1200, 1201-1250, 1251-1300, 1301-1350, 1351-1400, 1401-1450, 1451-1500, 1501-1550, 1551-1600, 1601-1650, 1651-1700, 1701-1750, 1751-1800, 1801-1850, 1851-1900, 1901-1950, 1951-2000, or 2001 to the end of SEQ ID NO:X, or the complementary strand thereto, or the cDNA contained in a deposited clone. In this context "about" includes the particularly recited ranges, and ranges larger or smaller by several (5, 4, 3, 2, or 1) nucleotides, at either terminus or at both termini. Preferably, these fragments encode a polypeptide which has biological activity. More preferably, these polynucleotides can be used as probes or primers as discussed herein. Also encompassed by the present invention are polynucleotides which hybridize to these nucleic acid molecules under stringent hybridization conditions or lower stringency conditions, as are the polypeptides encoded by these polynucleotides.

In the present invention, a "polypeptide fragment" refers to an amino acid sequence which is a portion of that contained in SEQ ID NO:Y or encoded by the cDNA contained in a deposited clone. Protein (polypeptide) fragments may be "freestanding" or comprised within a larger polypeptide of which the fragment forms a part or region, most preferably as a single continuous region. Representative examples of polypeptide fragments of the invention, include, for example, fragments comprising, or alternatively consisting of, from about amino acid number 1-20, 21-40, 41-60, 61-80, 81-100, 102-120, 121-140, 141-160, or 161 to the end of the coding region. Moreover, polypeptide fragments can be about 20, 30, 40, 50, 60, 70, 80, 90, 100, 110, 120, 130, 140, 150, 279, 301, 325, 350, 375, 400, 425, 450, 475, 500, or 518 amino acids in length. In this context "about" includes the particularly recited ranges or values, and ranges or values larger or smaller by several (25, 24, 23, 22, 21, 20, 19, 18, 17, 16, 15, 14, 13, 12, 11, 10, 9, 8, 7, 6, 5, 4, 3, 2, or 1) amino acids, at either extreme or at both extremes. Polynucleotides encoding these polypeptides are also encompassed by the invention.

Preferred polypeptide fragments include the full-length protein. Further preferred polypeptide fragments include the full-length protein having a continuous series of deleted residues from the amino or the carboxy terminus, or both. For example, any number of amino acids, ranging from 1-60, can be deleted from the amino terminus of the full-length polypeptide. Similarly, any number of amino acids, ranging from 1-30, can be deleted from the carboxy terminus of the full-length protein. Furthermore, any combination of the above amino and carboxy terminus deletions are preferred. Similarly, polynucleotides encoding these polypeptide fragments are also preferred.

Also preferred are polypeptide and polynucleotide fragments characterized by structural or functional domains, such as fragments that comprise alpha-helix and alpha-helix forming regions, beta-sheet and beta-sheet-forming regions, turn and turn-forming regions, coil and coil-forming regions, hydrophilic regions, hydrophobic regions, alpha amphipathic regions, beta amphipathic regions, flexible regions, surface-forming regions, substrate binding region, and high antigenic index regions. Polypeptide fragments of SEQ ID NO:Y falling within conserved domains are specifically contemplated by the present invention. Moreover, polynucleotides encoding these domains are also contemplated.

Other preferred polypeptide fragments are biologically active fragments. Biologically active fragments are those exhibiting activity similar, but not necessarily identical, to an activity of the polypeptide of the present invention. The biological activity of the fragments may include an improved desired activity, or a decreased undesirable activity. Polynucleotides encoding these polypeptide fragments are also encompassed by the invention.

In a preferred embodiment, the functional activity displayed by a polypeptide encoded by a polynucleotide fragment of the invention may be one or more biological activities typically associated with the full-length polypeptide of the invention. Illustrative of these biological activities includes the fragments ability to bind to at least one of the same antibodies which bind to the full-length protein, the fragments ability to interact with at least one of the same proteins which bind to the full-length, the fragments ability to elicit at least one of the same immune responses as the full-length protein (i.e., to cause the immune system to create antibodies specific to the same epitope, etc.), the fragments ability to bind to at least one of the same polynucleotides as the full-length protein, the fragments ability to bind to a receptor of the full-length protein, the fragments ability to bind to a ligand of the full-length protein, and the fragments ability to multimerize with the full-length protein. However, the skilled artisan would appreciate that some fragments may have biological activities which are desirable and directly inapposite to the biological activity of the full-length protein. The functional activity of polypeptides of the invention, including fragments, variants, derivatives, and analogs thereof can be determined by numerous methods available to the skilled artisan, some of which are described elsewhere herein.

The present invention encompasses polypeptides comprising, or alternatively consisting of, an epitope of the polypeptide having an amino acid sequence of SEQ ID NO:Y, or an epitope of the polypeptide sequence encoded by a polynucleotide sequence contained in ATCC® deposit No. Z or encoded by a polynucleotide that hybridizes to the complement of the sequence of SEQ ID NO:X or contained in ATCC® deposit No. Z under stringent hybridization conditions or lower stringency hybridization conditions as defined supra. The present invention further encompasses polynucleotide sequences encoding an epitope of a polypeptide sequence of the invention (such as, for example, the sequence disclosed in SEQ ID NO:1 or SEQ ID NO:3), polynucleotide sequences of the complementary strand of a polynucleotide sequence encoding an epitope of the invention, and polynucleotide sequences which hybridize to the complementary strand under stringent hybridization conditions or lower stringency hybridization conditions defined supra.

The term "epitopes" as used herein, refers to portions of a polypeptide having antigenic or immunogenic activity in an animal, preferably a mammal, and most preferably in a human. In a preferred embodiment, the present invention encompasses a polypeptide comprising an epitope, as well as the polynucleotide encoding this polypeptide. An "immunogenic epitope" as used herein, is defined as a portion of a protein that elicits an antibody response in an animal, as determined by any method known in the art, for example, by the methods for generating antibodies described infra. (See, for example, Geysen et al., Proc. Natl. Acad. Sci. USA 81:3998-4002 (1983)). The term "antigenic epitope" as used herein, is defined as a portion of a protein to which an antibody can immunospecifically bind its antigen as determined by any method well known in the art, for example, by the immunoassays described herein. Immunospecific binding excludes non-specific binding but does not necessarily exclude cross-reactivity with other antigens. Antigenic epitopes need not necessarily be immunogenic.

Fragments which function as epitopes may be produced by any conventional means. (See, e.g., Houghten, Proc. Natl. Acad. Sci. USA 82:5131-5135 (1985), further described in U.S. Pat. No. 4,631,211).

In the present invention, antigenic epitopes preferably contain a sequence of at least 4, at least 5, at least 6, at least 7, more preferably at least 8, at least 9, at least 10, at least 11, at least 12, at least 13, at least 14, at least 15, at least 20, at least 25, at least 30, at least 40, at least 50, and, most preferably, between about 15 to about 30 amino acids. Preferred polypeptides comprising immunogenic or antigenic epitopes are at least 10, 15, 20, 25, 30, 35, 40, 45, 50, 55, 60, 65, 70, 75, 80, 85, 90, 95, or 100 amino acid residues in length, or longer. Additional non-exclusive preferred antigenic epitopes include the antigenic epitopes disclosed herein, as well as portions thereof. Antigenic epitopes are useful, for example, to raise antibodies, including monoclonal antibodies, that specifically bind the epitope. Preferred antigenic epitopes include the antigenic epitopes disclosed herein, as well as any combination of two, three, four, five or more of these antigenic epitopes. Antigenic epitopes can be used as the target molecules in immunoassays. (See, for instance, Wilson et al., Cell 37:767-778 (1984); Sutcliffe et al., Science 219:660-666 (1983)).

Similarly, immunogenic epitopes can be used, for example, to induce antibodies according to methods well known in the art. (See, for instance, Sutcliffe et al., supra; Wilson et al., supra; Chow et al., Proc. Natl. Acad. Sci. USA 82:910-914; and Bittle et al., J. Gen. Virol. 66:2347-2354 (1985). Preferred immunogenic epitopes include the immunogenic epitopes disclosed herein, as well as any combination of two, three, four, five or more of these immunogenic epitopes. The polypeptides comprising one or more immunogenic epitopes may be presented for eliciting an antibody response together with a carrier protein, such as an albumin, to an animal system (such as rabbit or mouse), or, if the polypeptide is of sufficient length (at least about 25 amino acids), the polypeptide may be presented without a carrier. However, immunogenic epitopes comprising as few as 8 to 10 amino acids have been shown to be sufficient to raise antibodies capable of binding to, at the very least, linear epitopes in a denatured polypeptide (e.g., in Western blotting).

Epitope-bearing polypeptides of the present invention may be used to induce antibodies according to methods well known in the art including, but not limited to, in vivo immunization, in vitro immunization, and phage display methods. See, e.g., Sutcliffe et al., supra; Wilson et al., supra, and Bittle et al., J. Gen. Virol., 66:2347-2354 (1985). If in vivo immunization is used, animals may be immunized with free peptide; however, anti-peptide antibody titer may be boosted by coupling the peptide to a macromolecular carrier, such as keyhole limpet hemacyanin (KLH) or tetanus toxoid. For instance, peptides containing cysteine residues may be coupled to a carrier using a linker such as maleimidobenzoyl-N-hydroxysuccinimide ester (MBS), while other peptides may be coupled to carriers using a more general linking agent such as glutaraldehyde. Animals such as rabbits, rats and mice are immunized with either free or carrier-coupled peptides, for instance, by intraperitoneal and/or intradermal injection of emulsions containing about 100 µg of peptide or carrier protein and Freund's adjuvant or any other adjuvant known for stimulating an immune response. Several booster injections may be needed, for instance, at intervals of about two weeks, to provide a useful titer of anti-peptide antibody which can be detected, for example, by ELISA assay using free peptide adsorbed to a solid surface. The titer of anti-peptide antibodies in serum from an immunized animal may be increased by selection of anti-peptide antibodies, for instance, by adsorption to the peptide on a solid support and elution of the selected antibodies according to methods well known in the art.

As one of skill in the art will appreciate, and as discussed above, the polypeptides of the present invention comprising an immunogenic or antigenic epitope can be fused to other polypeptide sequences. For example, the polypeptides of the present invention may be fused with the constant domain of immunoglobulins (IgA, IgE, IgG, IgM), or portions thereof (CH1, CH2, CH3, or any combination thereof and portions thereof) resulting in chimeric polypeptides. Such fusion proteins may facilitate purification and may increase half-life in vivo. This has been shown for chimeric proteins consisting of the first two domains of the human CD4-polypeptide and various domains of the constant regions of the heavy or light chains of mammalian immunoglobulins. See, e.g., EP 394,827; Traunecker et al., Nature, 331:84-86 (1988). Enhanced delivery of an antigen across the epithelial barrier to the immune system has been demonstrated for antigens (e.g., insulin) conjugated to an FcRn binding partner such as IgG or Fc fragments (see, e.g., PCT Publications WO 96/22024 and WO 99/04813). IgG Fusion proteins that have a disulfide-linked dimeric structure due to the IgG portion disulfide bonds have also been found to be more efficient in binding and neutralizing other molecules than monomeric polypeptides or fragments thereof alone. See, e.g., Fountoulakis et al., J. Biochem., 270:3958-3964 (1995). Nucleic acids encoding the above epitopes can also be recombined with a gene of interest as an epitope tag (e.g., the hemagglutinin ("HA") tag or flag tag) to aid in detection and purification of the expressed polypeptide. For example, a system described by Janknecht et al. allows for the ready purification of non-denatured fusion proteins expressed in human cell lines (Janknecht et al., 1991, Proc. Natl. Acad. Sci. USA 88:8972-897). In this system, the gene of interest is subcloned into a vaccinia recombination plasmid such that the open reading frame of the gene is translationally fused to an amino-terminal tag consisting of six histidine residues. The tag serves as a matrix binding domain for the fusion protein. Extracts from cells infected with the recombinant vaccinia virus are loaded onto Ni2+ nitriloacetic acid-agarose column and histidine-tagged proteins can be selectively eluted with imidazole-containing buffers.

Additional fusion proteins of the invention may be generated through the techniques of gene-shuffling, motif-shuffling, exon-shuffling, and/or codon-shuffling (collectively referred to as "DNA shuffling"). DNA shuffling may be employed to modulate the activities of polypeptides of the invention, such methods can be used to generate polypeptides with altered activity; as well as agonists and antagonists of the polypeptides. See, generally, U.S. Pat. Nos. 5,605,793, 5,811, 238; 5,830,721; 5,834,252; and 5,837,458, and Patten et al., Curr. Opinion Biotechnol. 8:724-33 (1997); Harayama, Trends Biotechnol. 16(2):76-82 (1998); Hansson, et al., J. Mol. Biol. 287:265-76 (1999); and Lorenzo and Blasco, Biotechniques 24(2):308-13 (1998) (each of these patents and publications are hereby incorporated by reference in its entirety). In one embodiment, alteration of polynucleotides corresponding to SEQ ID NO:X and the polypeptides encoded by these polynucleotides may be achieved by DNA shuffling. DNA shuffling involves the assembly of two or more DNA segments by homologous or site-specific recombination to generate variation in the polynucleotide sequence. In another embodiment, polynucleotides of the invention, or the encoded polypeptides, may be altered by being subjected to random mutagenesis by error-prone PCR, random nucleotide insertion or other methods prior to recombination. In another embodiment, one or more components, motifs, sections, parts, domains, fragments, etc., of a polynucleotide encoding a polypeptide of the invention may be recombined with one or more components, motifs, sections, parts, domains, fragments, etc. of one or more heterologous molecules.

Antibodies

Further polypeptides of the invention relate to antibodies and T-cell antigen receptors (TCR) which immunospecifically bind a polypeptide, polypeptide fragment, or variant of SEQ ID NO:2, and/or an epitope, of the present invention (as determined by immunoassays well known in the art for assaying specific antibody-antigen binding). Antibodies of the invention include, but are not limited to, polyclonal, monoclonal, monovalent, bispecific, heteroconjugate, multispecific, human, humanized or chimeric antibodies, single chain antibodies, Fab fragments, F(ab') fragments, fragments produced by a Fab expression library, anti-idiotypic (anti-Id) antibodies (including, e.g., anti-Id antibodies to antibodies of the invention), and epitope-binding fragments of any of the above. The term "antibody," as used herein, refers to immunoglobulin molecules and immunologically active portions of immunoglobulin molecules, i.e., molecules that contain an antigen binding site that immunospecifically binds an antigen. The immunoglobulin molecules of the invention can be of any type (e.g., IgG, IgE, IgM, IgD, IgA and IgY), class (e.g., IgG1, IgG2, IgG3, IgG4, IgA1 and IgA2) or subclass of immunoglobulin molecule. Moreover, the term "antibody" (Ab) or "monoclonal antibody" (Mab) is meant to include intact molecules, as well as, antibody fragments (such as, for example, Fab and F(ab')2 fragments) which are capable of specifically binding to protein. Fab and F(ab')2 fragments lack the Fc fragment of intact antibody, clear more rapidly from the circulation of the animal or plant, and may have less non-specific tissue binding than an intact antibody (Wahl et al., J. Nucl. Med . . . 24:316-325 (1983)). Thus, these fragments are preferred, as well as the products of a FAB or other immunoglobulin expression library. Moreover, antibodies of the present invention include chimeric, single chain, and humanized antibodies.

Most preferably the antibodies are human antigen-binding antibody fragments of the present invention and include, but are not limited to, Fab, Fab' and F(ab')2, Fd, single-chain Fvs (scFv), single-chain antibodies, disulfide-linked Fvs (sdFv) and fragments comprising either a VL or VH domain. Antigen-binding antibody fragments, including single-chain antibodies, may comprise the variable region(s) alone or in combination with the entirety or a portion of the following: hinge region, CH1, CH2, and CH3 domains. Also included in the invention are antigen-binding fragments also comprising any combination of variable region(s) with a hinge region, CH1, CH2, and CH3 domains. The antibodies of the invention may be from any animal origin including birds and mammals. Preferably, the antibodies are human, murine (e.g., mouse and rat), donkey, ship rabbit, goat, guinea pig, camel, horse, or chicken. As used herein, "human" antibodies include antibodies having the amino acid sequence of a human immunoglobulin and include antibodies isolated from human immunoglobulin libraries or from animals transgenic for one or more human immunoglobulin and that do not express endogenous immunoglobulins, as described infra and, for example in, U.S. Pat. No. 5,939,598 by Kucherlapati et al.

The antibodies of the present invention may be monospecific, bispecific, trispecific or of greater multispecificity. Multispecific antibodies may be specific for different epitopes of a polypeptide of the present invention or may be specific for both a polypeptide of the present invention as well as for a heterologous epitope, such as a heterologous polypeptide or solid support material. See, e.g., PCT publications WO 93/17715; WO 92/08802; WO 91/00360; WO 92/05793; Tutt, et al., J. Immunol. 147:60-69 (1991); U.S. Pat. Nos. 4,474,893; 4,714,681; 4,925,648; 5,573,920; 5,601,819; Kostelny et al., J. Immunol. 148:1547-1553 (1992).

Antibodies of the present invention may be described or specified in terms of the epitope(s) or portion(s) of a polypeptide of the present invention which they recognize or specifically bind. The epitope(s) or polypeptide portion(s) may be specified as described herein, e.g., by N-terminal and C-terminal positions, by size in contiguous amino acid residues, or listed in the Tables and Figures. Antibodies which specifically bind any epitope or polypeptide of the present invention may also be excluded. Therefore, the present invention includes antibodies that specifically bind polypeptides of the present invention, and allows for the exclusion of the same.

Antibodies of the present invention may also be described or specified in terms of their cross-reactivity. Antibodies that do not bind any other analog, ortholog, or homologue of a polypeptide of the present invention are included. Antibodies that bind polypeptides with at least 95%, at least 90%, at least 85%, at least 80%, at least 75%, at least 70%, at least 65%, at least 60%, at least 55%, and at least 50% identity (as calculated using methods known in the art and described herein) to a polypeptide of the present invention are also included in the present invention. In specific embodiments, antibodies of the present invention cross-react with murine, rat and/or rabbit homologues of human proteins and the corresponding epitopes thereof. Antibodies that do not bind polypeptides with less than 95%, less than 90%, less than 85%, less than 80%, less than 75%, less than 70%, less than 65%, less than 60%, less than 55%, and less than 50% identity (as calculated using methods known in the art and described herein) to a polypeptide of the present invention are also included in the present invention. In a specific embodiment, the above-described cross-reactivity is with respect to any single specific antigenic or immunogenic polypeptide, or combination(s) of 2, 3, 4, 5, or more of the specific antigenic and/or immunogenic polypeptides disclosed herein. Further included in the present invention are antibodies which bind polypeptides encoded by polynucleotides which hybridize to a polynucleotide of the present invention under stringent hybridization conditions (as described herein). Antibodies of the present invention may also be described or specified in terms of their binding affinity to a polypeptide of the invention. Preferred binding affinities include those with a dissociation constant or Kd less than $5 \times 10^{-2}$ M, $10^{-2}$ M, $5 \times 10^{-3}$ M, $10^{-3}$ M, $5 \times 10^{-4}$ M, $10^{-4}$ M, $5 \times 10^{-5}$ M, $10^{-5}$ M, $5 \times 10^{-6}$ M, $10^{-6}$ M, $5 \times 10^{-7}$ M, $10^{-7}$ M, $5 \times 10^{-8}$ M, $10^{-8}$ M, $5 \times 10^{-9}$ M, $10^{-9}$ M, $5 \times 10^{-10}$ M, $10^{-10}$ M, $5 \times 10^{-11}$ M, $10^{-11}$ M, $5 \times 10^{-12}$ M, $10^{-12}$ M, $5 \times 10^{-13}$ M, $10^{-13}$ M, $5 \times 10^{-14}$ M, $10^{-14}$ M, $5 \times 10^{-15}$ M, or $10^{-15}$ M.

The invention also provides antibodies that competitively inhibit binding of an antibody to an epitope of the invention as determined by any method known in the art for determining competitive binding, for example, the immunoassays described herein. In preferred embodiments, the antibody competitively inhibits binding to the epitope by at least 95%, at least 90%, at least 85%, at least 80%, at least 75%, at least 70%, at least 60%, or at least 50%.

Antibodies of the present invention may act as agonists or antagonists of the polypeptides of the present invention. For example, the present invention includes antibodies which disrupt the receptor/ligand interactions with the polypeptides of the invention either partially or fully. Preferably, antibodies of the present invention bind an antigenic epitope disclosed herein, or a portion thereof. The invention features both receptor-specific antibodies and ligand-specific antibodies. The invention also features receptor-specific antibodies which do not prevent ligand binding but prevent receptor activation. Receptor activation (i.e., signaling) may be determined by techniques described herein or otherwise known in the art. For example, receptor activation can be determined by detecting the phosphorylation (e.g., tyrosine or serine/threonine) of the receptor or its substrate by immunoprecipitation followed by western blot analysis (for example, as described supra). In specific embodiments, antibodies are provided that inhibit ligand activity or receptor activity by at least 95%, at least 90%, at least 85%, at least 80%, at least 75%, at least 70%, at least 60%, or at least 50% of the activity in absence of the antibody.

The invention also features receptor-specific antibodies which both prevent ligand binding and receptor activation as well as antibodies that recognize the receptor-ligand complex, and, preferably, do not specifically recognize the unbound receptor or the unbound ligand. Likewise, included in the invention are neutralizing antibodies which bind the ligand and prevent binding of the ligand to the receptor, as well as antibodies which bind the ligand, thereby preventing receptor activation, but do not prevent the ligand from binding the receptor. Further included in the invention are antibodies which activate the receptor. These antibodies may act as receptor agonists, i.e., potentiate or activate either all or a subset of the biological activities of the ligand-mediated receptor activation, for example, by inducing dimerization of the receptor. The antibodies may be specified as agonists, antagonists or inverse agonists for biological activities comprising the specific biological activities of the peptides of the invention disclosed herein. The above antibody agonists can be made using methods known in the art. See, e.g., PCT publication WO 96/40281; U.S. Pat. No. 5,811,097; Deng et al., Blood 92(6):1981-1988 (1998); Chen et al., Cancer Res. 58(16):3668-3678 (1998); Harrop et al., J. Immunol. 161(4): 1786-1794 (1998); Zhu et al., Cancer Res. 58(15):3209-3214 (1998); Yoon et al., J. Immunol. 160(7):3170-3179 (1998); Prat et al., J. Cell. Sci. 111(Pt2):237-247 (1998); Pitard et al., J. Immunol. Methods 205(2):177-190 (1997); Liautard et al., Cytokine 9(4):233-241 (1997); Carlson et al., J. Biol. Chem. 272(17):11295-11301 (1997); Taryman et al., Neuron 14(4): 755-762 (1995); Muller et al., Structure 6(9):1153-1167 (1998); Bartunek et al., Cytokine 8(1):14-20 (1996) (which are all incorporated by reference herein in their entireties).

Antibodies of the present invention may be used, for example, but not limited to, to purify, detect, and target the polypeptides of the present invention, including both in vitro and in vivo diagnostic and therapeutic methods. For example, the antibodies have use in immunoassays for qualitatively and quantitatively measuring levels of the polypeptides of the present invention in biological samples. See, e.g., Harlow et al., Antibodies: A Laboratory Manual, (Cold Spring Harbor Laboratory Press, 2nd ed. 1988) (incorporated by reference herein in its entirety).

As discussed in more detail below, the antibodies of the present invention may be used either alone or in combination with other compositions. The antibodies may further be recombinantly fused to a heterologous polypeptide at the N- or C-terminus or chemically conjugated (including covalently and non-covalently conjugations) to polypeptides or other compositions. For example, antibodies of the present invention may be recombinantly fused or conjugated to molecules useful as labels in detection assays and effector molecules such as heterologous polypeptides, drugs, radionucleotides, or toxins. See, e.g., PCT publications WO 92/08495; WO 91/14438; WO 89/12624; U.S. Pat. No. 5,314,995; and EP 396,387.

The antibodies of the invention include derivatives that are modified, i.e., by the covalent attachment of any type of molecule to the antibody such that covalent attachment does not prevent the antibody from generating an anti-idiotypic response. For example, but not by way of limitation, the antibody derivatives include antibodies that have been modified, e.g., by glycosylation, acetylation, pegylation, phosphorylation, amidation, derivatization by known protecting/blocking groups, proteolytic cleavage, linkage to a cellular ligand or other protein, etc. Any of numerous chemical modifications may be carried out by known techniques, including, but not limited to specific chemical cleavage, acetylation, formylation, metabolic synthesis of tunicamycin, etc. Additionally, the derivative may contain one or more non-classical amino acids.

The antibodies of the present invention may be generated by any suitable method known in the art.

The antibodies of the present invention may comprise polyclonal antibodies. Methods of preparing polyclonal antibodies are known to the skilled artisan (Harlow, et al., Antibodies: A Laboratory Manual, (Cold spring Harbor Laboratory Press, $2^{nd}$ ed. (1988); and Current Protocols, Chapter 2; which are hereby incorporated herein by reference in its entirety). In a preferred method, a preparation of the PCSK9b or PCSK9c protein is prepared and purified to render it substantially free of natural contaminants. Such a preparation is then introduced into an animal in order to produce polyclonal antisera of greater specific activity. For example, a polypeptide of the invention can be administered to various host animals including, but not limited to, rabbits, mice, rats, etc. to induce the production of sera containing polyclonal antibodies specific for the antigen. The administration of the polypeptides of the present invention may entail one or more injections of an immunizing agent and, if desired, an adjuvant. Various adjuvants may be used to increase the immunological response, depending on the host species, and include but are not limited to, Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (bacille Calmette-Guerin) and *corynebacterium parvum*. Such adjuvants are also well known in the art. For the purposes of the invention, "immunizing agent" may be defined as a polypeptide of the invention, including fragments, variants, and/or derivatives thereof, in addition to fusions with heterologous polypeptides and other forms of the polypeptides described herein.

Typically, the immunizing agent and/or adjuvant will be injected in the mammal by multiple subcutaneous or intraperitoneal injections, though they may also be given intramuscularly, and/or through IV). The immunizing agent may include polypeptides of the present invention or a fusion protein or variants thereof. Depending upon the nature of the polypeptides (i.e., percent hydrophobicity, percent hydrophilicity, stability, net charge, isoelectric point etc.), it may be useful to conjugate the immunizing agent to a protein known to be immunogenic in the mammal being immunized. Such conjugation includes either chemical conjugation by derivitizing active chemical functional groups to both the polypeptide of the present invention and the immunogenic protein such that a covalent bond is formed, or through fusion-protein based methodology, or other methods known to the skilled artisan. Examples of such immunogenic proteins include, but are not limited to keyhole limpet hemocyanin, serum albumin, bovine thyroglobulin, and soybean trypsin inhibitor. Various adjuvants may be used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanin, dinitrophenol, and potentially useful human adjuvants such as BCG (bacille Calmette-Guerin) and *Corynebacterium parvum*. Additional examples of adjuvants which may be employed includes the MPL-TDM adjuvant (monophosphoryl lipid A, synthetic trehalose dicorynomycolate). The immunization; protocol may be selected by one skilled in the art without undue experimentation.

The antibodies of the present invention may comprise monoclonal antibodies. Monoclonal antibodies may be prepared using hybridoma methods, such as those described by Kohler and Milstein, Nature, 256:495 (1975) and U.S. Pat. No. 4,376,110, by Harlow, et al., Antibodies: A Laboratory Manual, (Cold spring Harbor Laboratory Press, $2^{nd}$ ed. (1988), by Hammerling, et al., Monoclonal Antibodies and T-Cell Hybridomas (Elsevier, N.Y., pp. 563-681 (1981); Köhler et al., Eur. J. Immunol. 6:511 (1976); Köhler et al., Eur. J. Immunol. 6:292 (1976), or other methods known to the artisan. Other examples of methods which may be employed for producing monoclonal antibodies includes, but are not limited to, the human B-cell hybridoma technique (Kosbor et al., 1983, Immunology Today 4:72; Cole et al., 1983, Proc. Natl. Acad. Sci. USA 80:2026-2030), and the EBV-hybridoma technique (Cole et al., 1985, Monoclonal Antibodies And Cancer Therapy, Alan R. Liss, Inc., pp. 77-96). Such antibodies may be of any immunoglobulin class including IgG, IgM, IgE, IgA, IgD and any subclass thereof. The hybridoma producing the mAb of this invention may be cultivated in vitro or in vivo. Production of high titers of mAbs in vivo makes this the presently preferred method of production.

In a hybridoma method, a mouse, a humanized mouse, a mouse with a human immune system, hamster, or other appropriate host animal, is typically immunized with an immunizing agent to elicit lymphocytes that produce or are capable of producing antibodies that will specifically bind to the immunizing agent. Alternatively, the lymphocytes may be immunized in vitro.

The immunizing agent will typically include polypeptides of the present invention or a fusion protein thereof. Preferably, the immunizing agent consists of an PCSK9b or PCSK9c polypeptide or, more preferably, with a PCSK9b or PCSK9c polypeptide-expressing cell. Such cells may be cultured in any suitable tissue culture medium; however, it is preferable to culture cells in Earle's modified Eagle's medium supplemented with 10% fetal bovine serum (inactivated at about 56 degrees C.), and supplemented with about 10 g/l of nonessential amino acids, about 1,000 U/ml of penicillin, and about 100 ug/ml of streptomycin. Generally, either peripheral blood lymphocytes ("PBLs") are used if cells of human origin are desired, or spleen cells or lymph node cells are used if non-human mammalian sources are desired. The lymphocytes are then fused with an immortalized cell line using a suitable fusing agent, such as polyethylene glycol, to form a hybridoma cell (Goding, Monoclonal Antibodies: Principles and Practice, Academic Press, (1986), pp. 59-103). Immortalized cell lines are usually transformed mammalian cells, particularly myeloma cells of rodent, bovine and human origin. Usually, rat or mouse myeloma cell lines are employed. The hybridoma cells may be cultured in a suitable culture medium that preferably contains one or more substances that inhibit the growth or survival of the unfused, immortalized cells. For example, if the parental cells lack the enzyme hypoxanthine guanine phosphoribosyl transferase (HGPRT or HPRT), the culture medium for the hybridomas typically will include hypoxanthine, aminopterin, and thymidine ("HAT medium"), which substances prevent the growth of HGPRT-deficient cells.

Preferred immortalized cell lines are those that fuse efficiently, support stable high level expression of antibody by the selected antibody-producing cells, and are sensitive to a medium such as HAT medium. More preferred immortalized cell lines are murine myeloma lines, which can be obtained, for instance, from the Salk Institute Cell Distribution Center, San Diego, Calif. and the American Type Culture Collection, Manassas, Va. More preferred are the parent myeloma cell line (SP2O) as provided by the ATCC®. As inferred throughout the specification, human myeloma and mouse-human heteromyeloma cell lines also have been described for the production of human monoclonal antibodies (Kozbor, J. Immunol., 133:3001 (1984); Brodeur et al., Monoclonal Antibody Production Techniques and Applications, Marcel Dekker, Inc., New York, (1987) pp. 51-63).

The culture medium in which the hybridoma cells are cultured can then be assayed for the presence of monoclonal antibodies directed against the polypeptides of the present invention. Preferably, the binding specificity of monoclonal antibodies produced by the hybridoma cells is determined by immunoprecipitation or by an in vitro binding assay, such as radioimmunoassay (RIA) or enzyme-linked immunoabsorbant assay (ELISA). Such techniques are known in the art and within the skill of the artisan. The binding affinity of the monoclonal antibody can, for example, be determined by the Scatchard analysis of Munson and Pollart, Anal. Biochem., 107:220 (1980).

After the desired hybridoma cells are identified, the clones may be subcloned by limiting dilution procedures and grown by standard methods (Goding, supra, and/or according to Wands et al. (Gastroenterology 80:225-232 (1981)). Suitable culture media for this purpose include, for example, Dulbecco's Modified Eagle's Medium and RPMI-1640. Alternatively, the hybridoma cells may be grown in vivo as ascites in a mammal.

The monoclonal antibodies secreted by the subclones may be isolated or purified from the culture medium or ascites fluid by conventional immunoglobulin purification procedures such as, for example, protein A-sepharose, hydroxyapatite chromatography, gel exclusion chromatography, gel electrophoresis, dialysis, or affinity chromatography.

The skilled artisan would acknowledge that a variety of methods exist in the art for the production of monoclonal antibodies and thus, the invention is not limited to their sole production in hybridomas. For example, the monoclonal antibodies may be made by recombinant DNA methods, such as those described in U.S. Pat. No. 4,816,567. In this context, the term "monoclonal antibody" refers to an antibody derived from a single eukaryotic, phage, or prokaryotic clone. The DNA encoding the monoclonal antibodies of the invention can be readily isolated and sequenced using conventional procedures (e.g., by using oligonucleotide probes that are capable of binding specifically to genes encoding the heavy and light chains of murine antibodies, or such chains from human, humanized, or other sources). The hybridoma cells of the invention serve as a preferred source of such DNA. Once isolated, the DNA may be placed into expression vectors, which are then transformed into host cells such as Simian COS cells, Chinese hamster ovary (CHO) cells, or myeloma cells that do not otherwise produce immunoglobulin protein, to obtain the synthesis of monoclonal antibodies in the recombinant host cells. The DNA also may be modified, for example, by substituting the coding sequence for human heavy and light chain constant domains in place of the homologous murine sequences (U.S. Pat. No. 4,816,567; Morrison et al, supra) or by covalently joining to the immunoglobulin coding sequence all or part of the coding sequence for a non-immunoglobulin polypeptide. Such a non-immunoglobulin polypeptide can be substituted for the constant domains of an antibody of the invention, or can be substituted for the variable domains of one antigen-combining site of an antibody of the invention to create a chimeric bivalent antibody.

The antibodies may be monovalent antibodies. Methods for preparing monovalent antibodies are well known in the art. For example, one method involves recombinant expression of immunoglobulin light chain and modified heavy chain. The heavy chain is truncated generally at any point in the Fc region so as to prevent heavy chain crosslinking. Alternatively, the relevant cysteine residues are substituted with another amino acid residue or are deleted so as to prevent crosslinking.

In vitro methods are also suitable for preparing monovalent antibodies. Digestion of antibodies to produce fragments thereof, particularly, Fab fragments, can be accomplished using routine techniques known in the art.

Monoclonal antibodies can be prepared using a wide variety of techniques known in the art including the use of hybridoma, recombinant, and phage display technologies, or a combination thereof. For example, monoclonal antibodies can be produced using hybridoma techniques including those known in the art and taught, for example, in Harlow et al., Antibodies: A Laboratory Manual, (Cold Spring Harbor Laboratory Press, 2nd ed. 1988); Hammerling, et al., in: Monoclonal Antibodies and T-Cell Hybridomas 563-681 (Elsevier, N.Y., 1981) (said references incorporated by reference in their entireties). The term "monoclonal antibody" as used herein is not limited to antibodies produced through hybridoma technology. The term "monoclonal antibody" refers to an antibody that is derived from a single clone, including any eukaryotic, prokaryotic, or phage clone, and not the method by which it is produced.

Methods for producing and screening for specific antibodies using hybridoma technology are routine and well known in the art and are discussed in detail in the Examples described herein. In a non-limiting example, mice can be immunized with a polypeptide of the invention or a cell expressing such peptide. Once an immune response is detected, e.g., antibodies specific for the antigen are detected in the mouse serum, the mouse spleen is harvested and splenocytes isolated. The splenocytes are then fused by well known techniques to any suitable myeloma cells, for example cells from cell line SP2O available from the ATCC®. Hybridomas are selected and cloned by limited dilution. The hybridoma clones are then assayed by methods known in the art for cells that secrete antibodies capable of binding a polypeptide of the invention.

Ascites fluid, which generally contains high levels of antibodies, can be generated by immunizing mice with positive hybridoma clones.

Accordingly, the present invention provides methods of generating monoclonal antibodies as well as antibodies produced by the method comprising culturing a hybridoma cell secreting an antibody of the invention wherein, preferably, the hybridoma is generated by fusing splenocytes isolated from a mouse immunized with an antigen of the invention with myeloma cells and then screening the hybridomas resulting from the fusion for hybridoma clones that secrete an antibody able to bind a polypeptide of the invention.

Antibody fragments which recognize specific epitopes may be generated by known techniques. For example, Fab and F(ab')2 fragments of the invention may be produced by proteolytic cleavage of immunoglobulin molecules, using enzymes such as papain (to produce Fab fragments) or pepsin (to produce F(ab')2 fragments). F(ab')2 fragments contain the variable region, the light chain constant region and the CH1 domain of the heavy chain.

For example, the antibodies of the present invention can also be generated using various phage display methods known in the art. In phage display methods, functional antibody domains are displayed on the surface of phage particles which carry the polynucleotide sequences encoding them. In a particular embodiment, such phage can be utilized to display antigen binding domains expressed from a repertoire or combinatorial antibody library (e.g., human or murine). Phage expressing an antigen binding domain that binds the antigen of interest can be selected or identified with antigen, e.g., using labeled antigen or antigen bound or captured to a solid surface or bead. Phage used in these methods are typically filamentous phage including fd and M13 binding domains expressed from phage with Fab, Fv or disulfide stabilized Fv antibody domains recombinantly fused to either the phage gene III or gene VIII protein. Examples of phage display methods that can be used to make the antibodies of the present invention include those disclosed in Brinkman et al., J. Immunol. Methods 182:41-50 (1995); Ames et al., J. Immunol. Methods 184:177-186 (1995); Kettleborough et al., Eur. J. Immunol. 24:952-958 (1994); Persic et al., Gene 187 9-18 (1997); Burton et al., Advances in Immunology 57:191-280 (1994); PCT application No. PCT/GB91/01134; PCT publications WO 90/02809; WO 91/10737; WO 92/01047; WO 92/18619; WO 93/11236; WO 95/15982; WO 95/20401; and U.S. Pat. Nos. 5,698,426; 5,223,409; 5,403,484; 5,580,717; 5,427,908; 5,750,753; 5,821,047; 5,571,698; 5,427,908; 5,516,637; 5,780,225; 5,658,727; 5,733,743 and 5,969,108; each of which is incorporated herein by reference in its entirety.

As described in the above references, after phage selection, the antibody coding regions from the phage can be isolated and used to generate whole antibodies, including human antibodies, or any other desired antigen binding fragment, and expressed in any desired host, including mammalian cells, insect cells, plant cells, yeast, and bacteria, e.g., as described in detail below. For example, techniques to recombinantly produce Fab, Fab' and F(ab')2 fragments can also be employed using methods known in the art such as those disclosed in PCT publication WO 92/22324; Mullinax et al., BioTechniques 12(6):864-869 (1992); and Sawai et al., AJRI 34:26-34 (1995); and Better et al., Science 240:1041-1043 (1988) (said references incorporated by reference in their entireties). Examples of techniques which can be used to produce single-chain Fvs and antibodies include those described in U.S. Pat. Nos. 4,946,778 and 5,258,498; Huston et al., Methods in Enzymology 203:46-88 (1991); Shu et al., PNAS 90:7995-7999 (1993); and Skerra et al., Science 240: 1038-1040 (1988).

For some uses, including in vivo use of antibodies in humans and in vitro detection assays, it may be preferable to use chimeric, humanized, or human antibodies. A chimeric antibody is a molecule in which different portions of the antibody are derived from different animal species, such as antibodies having a variable region derived from a murine monoclonal antibody and a human immunoglobulin constant region. Methods for producing chimeric antibodies are known in the art. See e.g., Morrison, Science 229:1202 (1985); Oi et al., BioTechniques 4:214 (1986); Gillies et al., (1989) J. Immunol. Methods 125:191-202; Cabilly et al., Taniguchi et al., EP 171496; Morrison et al., EP 173494; Neuberger et al., WO 8601533; Robinson et al., WO 8702671; Boulianne et al., Nature 312:643 (1984); Neuberger et al., Nature 314:268 (1985); U.S. Pat. Nos. 5,807, 715; 4,816,567; and 4,816,397, which are incorporated herein by reference in their entirety. Humanized antibodies are antibody molecules from non-human species antibody that binds the desired antigen having one or more complementarity determining regions (CDRs) from the non-human species and a framework regions from a human immunoglobulin molecule. Often, framework residues in the human framework regions will be substituted with the corresponding residue from the CDR donor antibody to alter, preferably improve, antigen binding. These framework substitutions are identified by methods well known in the art, e.g., by modeling of the interactions of the CDR and framework residues to identify framework residues important for antigen binding and sequence comparison to identify unusual framework residues at particular positions. (See, e.g., Queen et al., U.S. Pat. No. 5,585,089; Riechmann et al., Nature 332:323 (1988), which are incorporated herein by reference in their entireties.) Antibodies can be humanized using a variety of techniques known in the art including, for example, CDR-grafting (EP 239,400; PCT publication WO 91/09967; U.S. Pat. Nos. 5,225,539; 5,530,101; and 5,585,089), veneering or resurfacing (EP 592,106; EP 519,596; Padlan, Molecular Immunology 28(4/5):489-498 (1991); Studnicka et al., Protein Engineering 7(6):805-814 (1994); Roguska. et al., PNAS 91:969-973 (1994)), and chain shuffling (U.S. Pat. No. 5,565,332). Generally, a humanized antibody has one or more amino acid residues introduced into it from a source that is non-human. These non-human amino acid residues are often referred to as "import" residues, which are typically taken from an "import" variable domain. Humanization can be essentially performed following the methods of Winter and co-workers (Jones et al., Nature, 321:522-525 (1986); Reichmann et al., Nature, 332:323-327 (1988); Verhoeyen et al., Science, 239: 1534-1536 (1988), by substituting rodent CDRs or CDR sequences for the corresponding sequences of a human antibody. Accordingly, such "humanized" antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possible some FR residues are substituted from analogous sites in rodent antibodies.

In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin (Jones et al., Nature, 321:522-525 (1986); Riechmann et al., Nature 332:323-329 (1988)1 and Presta, Curr. Op. Struct. Biol., 2:593-596 (1992).

Completely human antibodies are particularly desirable for therapeutic treatment of human patients. Human antibodies can be made by a variety of methods known in the art including phage display methods described above using antibody libraries derived from human immunoglobulin sequences. See also, U.S. Pat. Nos. 4,444,887 and 4,716,111; and PCT publications WO 98/46645, WO 98/50433, WO 98/24893, WO 98/16654, WO 96/34096, WO 96/33735, and WO 91/10741', each of which is incorporated herein by reference in its entirety. The techniques of Cole et al., and Boerder et al., are also available for the preparation of human monoclonal antibodies (Cole et al., Monoclonal Antibodies and Cancer Therapy, Alan R. Riss, (1985); and Boerner et al., J. Immunol., 147(1):86-95, (1991)).

Human antibodies can also be produced using transgenic mice which are incapable of expressing functional endogenous immunoglobulins, but which can express human immunoglobulin genes. For example, the human heavy and light chain immunoglobulin gene complexes may be introduced randomly or by homologous recombination into mouse embryonic stem cells. Alternatively, the human variable region, constant region, and diversity region may be introduced into mouse embryonic stem cells in addition to the human heavy and light chain genes. The mouse heavy and light chain immunoglobulin genes may be rendered non-functional separately or simultaneously with the introduction of human immunoglobulin loci by homologous recombination. In particular, homozygous deletion of the JH region prevents endogenous antibody production. The modified embryonic stem cells are expanded and microinjected into blastocysts to produce chimeric mice. The chimeric mice are then bred to produce homozygous offspring which express human antibodies. The transgenic mice are immunized in the normal fashion with a selected antigen, e.g., all or a portion of a polypeptide of the invention. Monoclonal antibodies directed against the antigen can be obtained from the immunized, transgenic mice using conventional hybridoma technology. The human immunoglobulin transgenes harbored by the transgenic mice rearrange during B cell differentiation, and subsequently undergo class switching and somatic mutation. Thus, using such a technique, it is possible to produce therapeutically useful IgG, IgA, IgM and IgE antibodies. For an overview of this technology for producing human antibodies, see Lonberg and Huszar, Int. Rev. Immunol. 13:65-93 (1995). For a detailed discussion of this technology for producing human antibodies and human monoclonal antibodies and protocols for producing such antibodies, see, e.g., PCT publications WO 98/24893; WO 92/01047; WO 96/34096; WO 96/33735; European Patent No. 0 598 877; U.S. Pat. Nos. 5,413,923; 5,625,126; 5,633,425; 5,569,825; 5,661,016; 5,545,806; 5,814,318; 5,885,793; 5,916,771; and 5,939,598, which are incorporated by reference herein in their entirety. In addition, companies such as Genpharm (San Jose, Calif.), and Medarex, Inc. (Princeton, N.J.) can be engaged to provide human antibodies directed against a selected antigen using technology similar to that described above.

Similarly, human antibodies can be made by introducing human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and creation of an antibody repertoire. This approach is described, for example, in U.S. Pat. Nos. 5,545,807; 5,545,806; 5,569,825; 5,625,126; 5,633,425; 5,661,106, and in the following scientific publications: Marks et al., Biotechnol., 10:779-783 (1992); Lonberg et al., Nature 368:856-859 (1994); Fishwild et al., Nature Biotechnol., 14:845-51 (1996); Neuberger, Nature Biotechnol., 14:826 (1996); Lonberg and Huszer, Intern. Rev. Immunol., 13:65-93 (1995).

Completely human antibodies which recognize a selected epitope can be generated using a technique referred to as "guided selection." In this approach a selected non-human monoclonal antibody, e.g., a mouse antibody, is used to guide the selection of a completely human antibody recognizing the same epitope. (Jespers et al., Bio/Technology 12:899-903 (1988)).

Further, antibodies to the polypeptides of the invention can, in turn, be utilized to generate anti-idiotype antibodies that "mimic" polypeptides of the invention using techniques well known to those skilled in the art. (See, e.g., Greenspan & Bona, FASEB J. 7(5):437-444; (1989) and Nissinoff, J. Immunol. 147(8):2429-2438 (1991)). For example, antibodies which bind to and competitively inhibit polypeptide multimerization and/or binding of a polypeptide of the invention to a ligand can be used to generate anti-idiotypes that "mimic" the polypeptide multimerization and/or binding domain and, as a consequence, bind to and neutralize polypeptide and/or its ligand. Such neutralizing anti-idiotypes or Fab fragments of such anti-idiotypes can be used in therapeutic regimens to neutralize polypeptide ligand. For example, such anti-idiotypic antibodies can be used to bind a polypeptide of the invention and/or to bind its ligands/receptors, and thereby block its biological activity.

Such anti-idiotypic antibodies capable of binding to the PCSK9b or PCSK9c polypeptide can be produced in a two-step procedure. Such a method makes use of the fact that antibodies are themselves antigens, and therefore, it is possible to obtain an antibody that binds to a second antibody. In accordance with this method, protein specific antibodies are used to immunize an animal, preferably a mouse. The splenocytes of such an animal are then used to produce hybridoma cells, and the hybridoma cells are screened to identify clones that produce an antibody whose ability to bind to the protein-specific antibody can be blocked by the polypeptide. Such antibodies comprise anti-idiotypic antibodies to the protein-specific antibody and can be used to immunize an animal to induce formation of further protein-specific antibodies.

The antibodies of the present invention may be bispecific antibodies. Bispecific antibodies are monoclonal, Preferably human or humanized, antibodies that have binding specificities for at least two different antigens. In the present invention, one of the binding specificities may be directed towards a polypeptide of the present invention, the other may be for any other antigen, and preferably for a cell-surface protein, receptor, receptor subunit, tissue-specific antigen, virally derived protein, virally encoded envelope protein, bacterially derived protein, or bacterial surface protein, etc.

Methods for making bispecific antibodies are known in the art. Traditionally, the recombinant production of bispecific antibodies is based on the co-expression of two immunoglobulin heavy-chain/light-chain pairs, where the two heavy chains have different specificities (Milstein and Cuello, Nature, 305:537-539 (1983). Because of the random assortment of immunoglobulin heavy and light chains, these hybridomas (quadromas) produce a potential mixture of ten different antibody molecules, of which only one has the correct bispecific structure. The purification of the correct molecule is usually accomplished by affinity chromatography steps. Similar procedures are disclosed in WO 93/08829, published 13 May 1993, and in Traunecker et al., EMBO J.; 10:3655-3659 (1991).

Antibody variable domains with the desired binding specificities (antibody-antigen combining sites) can be fused to immunoglobulin constant domain sequences. The fusion preferably is with an immunoglobulin heavy-chain constant domain, comprising at least part of the hinge, CH2, and CH3 regions. It is preferred to have the first heavy-chain constant region (CH1) containing the site necessary for light-chain binding present in at least one of the fusions. DNAs encoding the immunoglobulin heavy-chain fusions and, if desired, the immunoglobulin light chain, are inserted into separate expression vectors, and are co-transformed into a suitable host organism. For further details of generating bispecific antibodies see, for example Suresh et al., Meth. In Enzym., 121:210 (1986).

Heteroconjugate antibodies are also contemplated by the present invention. Heteroconjugate antibodies are composed of two covalently joined antibodies. Such antibodies have, for example, been proposed to target immune system cells to unwanted cells (U.S. Pat. No. 4,676,980), and for the treatment of HIV infection (WO 91/00360; WO 92/20373; and EP03089). It is contemplated that the antibodies may be prepared in vitro using known methods in synthetic protein chemistry, including those involving crosslinking agents. For example, immunotoxins may be constructed using a disulfide exchange reaction or by forming a thioester bond. Examples of suitable reagents for this purpose include iminothiolate and methyl-4-mercaptobutyrimidate and those disclosed, for example, in U.S. Pat. No. 4,676,980.

Polynucleotides Encoding Antibodies

The invention further provides polynucleotides comprising a nucleotide sequence encoding an antibody of the invention and fragments thereof. The invention also encompasses polynucleotides that hybridize under stringent or lower stringency hybridization conditions, e.g., as defined supra, to polynucleotides that encode an antibody, preferably, that specifically binds to a polypeptide of the invention, preferably, an antibody that binds to a polypeptide having the amino acid sequence of SEQ ID NO:2 or SEQ ID NO:4.

The polynucleotides may be obtained, and the nucleotide sequence of the polynucleotides determined, by any method known in the art. For example, if the nucleotide sequence of the antibody is known, a polynucleotide encoding the antibody may be assembled from chemically synthesized oligonucleotides (e.g., as described in Kutmeier et al., BioTechniques 17:242 (1994)), which, briefly, involves the synthesis of overlapping oligonucleotides containing portions of the sequence encoding the antibody, annealing and ligating of those oligonucleotides, and then amplification of the ligated oligonucleotides by PCR.

Alternatively, a polynucleotide encoding an antibody may be generated from nucleic acid from a suitable source. If a clone containing a nucleic acid encoding a particular antibody is not available, but the sequence of the antibody molecule is known, a nucleic acid encoding the immunoglobulin may be chemically synthesized or obtained from a suitable source (e.g., an antibody cDNA library, or a cDNA library generated from, or nucleic acid, preferably poly A+ RNA, isolated from, any tissue or cells expressing the antibody, such as hybridoma cells selected to express an antibody of the invention) by PCR amplification using synthetic primers hybridizable to the 3' and 5' ends of the sequence or by cloning using an oligonucleotide probe specific for the particular gene sequence to identify, e.g., a cDNA clone from a cDNA library that encodes the antibody. Amplified nucleic acids generated by PCR may then be cloned into replicable cloning vectors using any method well known in the art.

Once the nucleotide sequence and corresponding amino acid sequence of the antibody is determined, the nucleotide sequence of the antibody may be manipulated using methods well known in the art for the manipulation of nucleotide sequences, e.g., recombinant DNA techniques, site directed mutagenesis, PCR, etc. (see, for example, the techniques described in Sambrook et al., 1990, Molecular Cloning, A Laboratory Manual, 2d Ed., Cold Spring Harbor Laboratory, Cold Spring Harbor, N.Y. and Ausubel et al., eds., 1998, Current Protocols in Molecular Biology, John Wiley & Sons, NY, which are both incorporated by reference herein in their entireties), to generate antibodies having a different amino acid sequence, for example to create amino acid substitutions, deletions, and/or insertions.

In a specific embodiment, the amino acid sequence of the heavy and/or light chain variable domains may be inspected to identify the sequences of the complementarity determining regions (CDRs) by methods that are well know in the art, e.g., by comparison to known amino acid sequences of other heavy and light chain variable regions to determine the regions of sequence hypervariability. Using routine recombinant DNA techniques, one or more of the CDRs may be inserted within framework regions, e.g., into human framework regions to humanize a non-human antibody, as described supra. The framework regions may be naturally occurring or consensus framework regions, and preferably human framework regions (see, e.g., Chothia et al., J. Mol. Biol. 278: 457-479 (1998) for a listing of human framework regions). Preferably, the polynucleotide generated by the combination of the framework regions and CDRs encodes an antibody that specifically binds a polypeptide of the invention. Preferably, as discussed supra, one or more amino acid substitutions may be made within the framework regions, and, preferably, the amino acid substitutions improve binding of the antibody to its antigen. Additionally, such methods may be used to make amino acid substitutions or deletions of one or more variable region cysteine residues participating in an intrachain disulfide bond to generate antibody molecules lacking one or more intrachain disulfide bonds. Other alterations to the polynucleotide are encompassed by the present invention and within the skill of the art.

In addition, techniques developed for the production of "chimeric antibodies" (Morrison et al., Proc. Natl. Acad. Sci. 81:851-855 (1984); Neuberger et al., Nature 312:604-608 (1984); Takeda et al., Nature 314:452-454 (1985)) by splicing genes from a mouse antibody molecule of appropriate antigen specificity together with genes from a human antibody molecule of appropriate biological activity can be used. As described supra, a chimeric antibody is a molecule in which different portions are derived from different animal species, such as those having a variable region derived from a murine mAb and a human immunoglobulin constant region, e.g., humanized antibodies.

Alternatively, techniques described for the production of single chain antibodies (U.S. Pat. No. 4,946,778; Bird, Science 242:423-42 (1988); Huston et al., Proc. Natl. Acad. Sci. USA 85:5879-5883 (1988); and Ward et al., Nature 334:544-54 (1989)) can be adapted to produce single chain antibodies. Single chain antibodies are formed by linking the heavy and light chain fragments of the Fv region via an amino acid bridge, resulting in a single chain polypeptide. Techniques for the assembly of functional Fv fragments in *E. coli* may also be used (Skerra et al., Science 242:1038-1041 (1988)).

More preferably, a clone encoding an antibody of the present invention may be obtained according to the method described in the Example section herein.

Methods of Producing Antibodies

The antibodies of the invention can be produced by any method known in the art for the synthesis of antibodies, in particular, by chemical synthesis or preferably, by recombinant expression techniques.

Recombinant expression of an antibody of the invention, or fragment, derivative or analog thereof, (e.g., a heavy or light chain of an antibody of the invention or a single chain antibody of the invention), requires construction of an expression vector containing a polynucleotide that encodes the antibody. Once a polynucleotide encoding an antibody molecule or a heavy or light chain of an antibody, or portion thereof (preferably containing the heavy or light chain variable domain), of the invention has been obtained, the vector for the production of the antibody molecule may be produced by recombinant DNA technology using techniques well known in the art. Thus, methods for preparing a protein by expressing a polynucleotide containing an antibody encoding nucleotide sequence are described herein. Methods which are well known to those skilled in the art can be used to construct expression vectors containing antibody coding sequences and appropriate transcriptional and translational control signals. These methods include, for example, in vitro recombinant DNA techniques, synthetic techniques, and in vivo genetic recombination. The invention, thus, provides replicable vectors comprising a nucleotide sequence encoding an antibody molecule of the invention, or a heavy or light chain thereof, or a heavy or light chain variable domain, operably linked to a promoter. Such vectors may include the nucleotide sequence encoding the constant region of the antibody molecule (see, e.g., PCT Publication WO 86/05807; PCT Publication WO 89/01036; and U.S. Pat. No. 5,122,464) and the variable domain of the antibody may be cloned into such a vector for expression of the entire heavy or light chain.

The expression vector is transferred to a host cell by conventional techniques and the transfected cells are then cultured by conventional techniques to produce an antibody of the invention. Thus, the invention includes host cells containing a polynucleotide encoding an antibody of the invention, or a heavy or light chain thereof, or a single chain antibody of the invention, operably linked to a heterologous promoter. In preferred embodiments for the expression of double-chained antibodies, vectors encoding both the heavy and light chains may be co-expressed in the host cell for expression of the entire immunoglobulin molecule, as detailed below.

A variety of host-expression vector systems may be utilized to express the antibody molecules of the invention. Such host-expression systems represent vehicles by which the coding sequences of interest may be produced and subsequently purified, but also represent cells which may, when transformed or transfected with the appropriate nucleotide coding sequences, express an antibody molecule of the invention in situ. These include but are not limited to microorganisms such as bacteria (e.g., *E. coli, B. subtilis*) transformed with recombinant bacteriophage DNA, plasmid DNA or cosmid DNA expression vectors containing antibody coding sequences; yeast (e.g., *Saccharomyces, Pichia*) transformed with recombinant yeast expression vectors containing antibody coding sequences; insect cell systems infected with recombinant virus expression vectors (e.g., baculovirus) containing antibody coding sequences; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing antibody coding sequences; or mammalian cell systems (e.g., COS, CHO, BHK, 293, 3T3 cells) harboring recombinant expression constructs containing promoters derived from the genome of mammalian cells (e.g., metallothionein promoter) or from mammalian viruses (e.g., the adenovirus late promoter; the vaccinia virus 7.5K promoter). Preferably, bacterial cells such as *Escherichia coli*, and more preferably, eukaryotic cells, especially for the expression of whole recombinant antibody molecule, are used for the expression of a recombinant antibody molecule. For example, mammalian cells such as Chinese hamster ovary cells (CHO), in conjunction with a vector such as the major intermediate early gene promoter element from human cytomegalovirus is an effective expression system for antibodies (Foecking et al., Gene 45:101 (1986); Cockett et al., Bio/Technology 8:2 (1990)).

In bacterial systems, a number of expression vectors may be advantageously selected depending upon the use intended for the antibody molecule being expressed. For example, when a large quantity of such a protein is to be produced, for the generation of pharmaceutical compositions of an antibody molecule, vectors which direct the expression of high levels of fusion protein products that are readily purified may be desirable. Such vectors include, but are not limited, to the *E. coli* expression vector pUR278 (Ruther et al., EMBO J. 2:1791 (1983)), in which the antibody coding sequence may be ligated individually into the vector in frame with the lac Z coding region so that a fusion protein is produced; pIN vectors (Inouye & Inouye, Nucleic Acids Res. 13:3101-3109 (1985); Van Heeke & Schuster, J. Biol. Chem. 24:5503-5509 (1989)); and the like. pGEX vectors may also be used to express foreign polypeptides as fusion proteins with glutathione S-transferase (GST). In general, such fusion proteins are soluble and can easily be purified from lysed cells by adsorption and binding to matrix glutathione-agarose beads followed by elution in the presence of free glutathione. The pGEX vectors are designed to include thrombin or factor Xa protease cleavage sites so that the cloned target gene product can be released from the GST moiety.

In an insect system, *Autographa californica* nuclear polyhedrosis virus (AcNPV) is used as a vector to express foreign genes. The virus grows in *Spodoptera frugiperda* cells. The antibody coding sequence may be cloned individually into non-essential regions (for example the polyhedrin gene) of the virus and placed under control of an AcNPV promoter (for example the polyhedrin promoter).

In mammalian host cells, a number of viral-based expression systems may be utilized. In cases where an adenovirus is used as an expression vector, the antibody coding sequence of interest may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing the antibody molecule in infected hosts. (e.g., see Logan & Shenk, Proc. Natl. Acad. Sci. USA 81:355-359 (1984)). Specific initiation signals may also be required for efficient translation of inserted antibody coding sequences. These signals include the ATG initiation codon and adjacent sequences. Furthermore, the initiation codon must be in phase with the reading frame of the desired coding sequence to ensure translation of the entire insert.

These exogenous translational control signals and initiation codons can be of a variety of origins, both natural and synthetic. The efficiency of expression may be enhanced by the inclusion of appropriate transcription enhancer elements, transcription terminators, etc. (see Bittner et al., Methods in Enzymol. 153:51-544 (1987)).

In addition, a host cell strain may be chosen which modulates the expression of the inserted sequences, or modifies and processes the gene product in the specific fashion desired. Such modifications (e.g., glycosylation) and processing (e.g., cleavage) of protein products may be important for the function of the protein. Different host cells have characteristic and specific mechanisms for the post-translational processing and modification of proteins and gene products. Appropriate cell lines or host systems can be chosen to ensure the correct modification and processing of the foreign protein expressed. To this end, eukaryotic host cells which possess the cellular machinery for proper processing of the primary transcript, glycosylation, and phosphorylation of the gene product may be used. Such mammalian host cells include but are not limited to CHO, VERY, BHK, Hela, COS, MDCK, 293, 3T3, WI38, and in particular, breast cancer cell lines such as, for example, BT483, Hs578T, HTB2, BT20 and T47D, and normal mammary gland cell line such as, for example, CRL7030 and Hs578Bst.

For long-term, high-yield production of recombinant proteins, stable expression is preferred. For example, cell lines which stably express the antibody molecule may be engineered. Rather than using expression vectors which contain viral origins of replication, host cells can be transformed with DNA controlled by appropriate expression control elements (e.g., promoter, enhancer, sequences, transcription terminators, polyadenylation sites, etc.), and a selectable marker. Following the introduction of the foreign DNA, engineered cells may be allowed to grow for 1-2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines. This method may advantageously be used to engineer cell lines which express the antibody molecule. Such engineered cell lines may be particularly useful in screening and evaluation of compounds that interact directly or indirectly with the antibody molecule.

A number of selection systems may be used, including but not limited to the herpes simplex virus thymidine kinase (Wigler et al., Cell 11:223 (1977)), hypoxanthine-guanine phosphoribosyltransferase (Szybalska & Szybalski, Proc. Natl. Acad. Sci. USA 48:202 (1992)), and adenine phosphoribosyltransferase (Lowy et al., Cell 22:817 (1980)) genes can be employed in tk–, hgprt– or aprt– cells, respectively. Also, antimetabolite resistance can be used as the basis of selection for the following genes: dhfr, which confers resistance to methotrexate (Wigler et al., Natl. Acad. Sci. USA 77:357 (1980); O'Hare et al., Proc. Natl. Acad. Sci. USA 78:1527 (1981)); gpt, which confers resistance to mycophenolic acid (Mulligan & Berg, Proc. Natl. Acad. Sci. USA 78:2072 (1981)); neo, which confers resistance to the aminoglycoside G-418 Clinical Pharmacy 12:488-505; Wu and Wu, Biotherapy 3:87-95 (1991); Tolstoshev, Ann. Rev. Pharmacol. Toxicol. 32:573-596 (1993); Mulligan, Science 260:926-932 (1993); and Morgan and Anderson, Ann. Rev. Biochem. 62:191-217 (1993); May, 1993, TIBTECH 11(5):155-215); and hygro, which confers resistance to hygromycin (Santerre et al., Gene 30:147 (1984)). Methods commonly known in the art of recombinant DNA technology may be routinely applied to select the desired recombinant clone, and such methods are described, for example, in Ausubel et al. (eds.), Current Protocols in Molecular Biology, John Wiley & Sons, NY (1993); Kriegler, Gene Transfer and Expression, A Laboratory Manual, Stockton Press, NY (1990); and in Chapters 12 and 13, Dracopoli et al. (eds), Current Protocols in Human Genetics, John Wiley & Sons, NY (1994); Colberre-Garapin et al., J. Mol. Biol. 150:1 (1981), which are incorporated by reference herein in their entireties.

The expression levels of an antibody molecule can be increased by vector amplification (for a review, see Bebbington and Hentschel, The use of vectors based on gene amplification for the expression of cloned genes in mammalian cells in DNA cloning, Vol. 3. (Academic Press, New York, 1987)). When a marker in the vector system expressing antibody is amplifiable, increase in the level of inhibitor present in culture of host cell will increase the number of copies of the marker gene. Since the amplified region is associated with the antibody gene, production of the antibody will also increase (Crouse et al., Mol. Cell. Biol. 3:257 (1983)).

The host cell may be co-transfected with two expression vectors of the invention, the first vector encoding a heavy chain derived polypeptide and the second vector encoding a light chain derived polypeptide. The two vectors may contain identical selectable markers which enable equal expression of heavy and light chain polypeptides. Alternatively, a single vector may be used which encodes, and is capable of expressing, both heavy and light chain polypeptides. In such situations, the light chain should be placed before the heavy chain to avoid an excess of toxic free heavy chain (Proudfoot, Nature 322:52 (1986); Kohler, Proc. Natl. Acad. Sci. USA 77:2197 (1980)). The coding sequences for the heavy and light chains may comprise cDNA or genomic DNA.

Once an antibody molecule of the invention has been produced by an animal, chemically synthesized, or recombinantly expressed, it may be purified by any method known in the art for purification of an immunoglobulin molecule, for example, by chromatography (e.g., ion exchange, affinity, particularly by affinity for the specific antigen after Protein A, and sizing column chromatography), centrifugation, differential solubility, or by any other standard technique for the purification of proteins. In addition, the antibodies of the present invention or fragments thereof can be fused to heterologous polypeptide sequences described herein or otherwise known in the art, to facilitate purification.

The present invention encompasses antibodies recombinantly fused or chemically conjugated (including both covalently and non-covalently conjugations) to a polypeptide (or portion thereof, preferably at least 10, 20, 30, 40, 50, 60, 70, 80, 90 or 100 amino acids of the polypeptide) of the present invention to generate fusion proteins. The fusion does not necessarily need to be direct, but may occur through linker sequences. The antibodies may be specific for antigens other than polypeptides (or portion thereof, preferably at least 10, 20, 30, 40, 50, 60, 70, 80, 90 or 100 amino acids of the polypeptide) of the present invention. For example, antibodies may be used to target the polypeptides of the present invention to particular cell types, either in vitro or in vivo, by fusing or conjugating the polypeptides of the present invention to antibodies specific for particular cell surface receptors. Antibodies fused or conjugated to the polypeptides of the present invention may also be used in in vitro immunoassays and purification methods using methods known in the art. See e.g., Harbor et al., supra, and PCT publication WO 93/21232; EP 439,095; Naramura et al., Immunol. Lett. 39:91-99 (1994); U.S. Pat. No. 5,474,981; Gillies et al., PNAS 89:1428-1432 (1992); Fell et al., J. Immunol. 146:2446-2452 (1991), which are incorporated by reference in their entireties.

The present invention further includes compositions comprising the polypeptides of the present invention fused or conjugated to antibody domains other than the variable regions. For example, the polypeptides of the present invention may be fused or conjugated to an antibody Fc region, or portion thereof. The antibody portion fused to a polypeptide of the present invention may comprise the constant region, hinge region, CH1 domain, CH2 domain, and CH3 domain or any combination of whole domains or portions thereof. The polypeptides may also be fused or conjugated to the above antibody portions to form multimers. For example, Fc portions fused to the polypeptides of the present invention can form dimers through disulfide bonding between the Fc portions. Higher multimeric forms can be made by fusing the polypeptides to portions of IgA and IgM. Methods for fusing or conjugating the polypeptides of the present invention to antibody portions are known in the art. See, e.g., U.S. Pat. Nos. 5,336,603; 5,622,929; 5,359,046; 5,349,053; 5,447,851; 5,112,946; EP 307,434; EP 367,166; PCT publications WO 96/04388; WO 91/06570; Ashkenazi et al., Proc. Natl. Acad. Sci. USA 88:10535-10539 (1991); Zheng et al., J. Immunol. 154:5590-5600 (1995); and Vil et al., Proc. Natl. Acad. Sci. USA 89:11337-11341(1992) (said references incorporated by reference in their entireties).

As discussed, supra, the polypeptides corresponding to a polypeptide, polypeptide fragment, or a variant of SEQ ID NO:2 or SEQ ID NO:4 may be fused or conjugated to the above antibody portions to increase the in vivo half life of the polypeptides or for use in immunoassays using methods known in the art. Further, the polypeptides corresponding to SEQ ID NO:2 or SEQ ID NO:4 may be fused or conjugated to the above antibody portions to facilitate purification. One reported example describes chimeric proteins consisting of the first two domains of the human CD4-polypeptide and various domains of the constant regions of the heavy or light chains of mammalian immunoglobulins. (EP 394,827; Traunecker et al., Nature 331:84-86 (1988). The polypeptides of the present invention fused or conjugated to an antibody having disulfide-linked dimeric structures (due to the IgG) may also be more efficient in binding and neutralizing other molecules, than the monomeric secreted protein or protein fragment alone. (Fountoulakis et al., J. Biochem. 270:3958-3964 (1995)). In many cases, the Fc part in a fusion protein is beneficial in therapy and diagnosis, and thus can result in, for example, improved pharmacokinetic properties. (EP A 232, 262). Alternatively, deleting the Fc part after the fusion protein has been expressed, detected, and purified, would be desired. For example, the Fc portion may hinder therapy and diagnosis if the fusion protein is used as an antigen for immunizations. In drug discovery, for example, human proteins, such as hIL-5, have been fused with Fc portions for the purpose of high-throughput screening assays to identify antagonists of hIL-5. (See, Bennett et al., J. Molecular Recognition 8:52-58 (1995); Johanson et al., J. Biol. Chem. 270: 9459-9471 (1995).

Moreover, the antibodies or fragments thereof of the present invention can be fused to marker sequences, such as a peptide to facilitate purification. In preferred embodiments, the marker amino acid sequence is a hexa-histidine peptide, such as the tag provided in a pQE vector (QIAGEN, Inc., 9259 Eton Avenue, Chatsworth, Calif., 91311), among others, many of which are commercially available. As described in Gentz et al., Proc. Natl. Acad. Sci. USA 86:821-824 (1989), for instance, hexa-histidine provides for convenient purification of the fusion protein. Other peptide tags useful for purification include, but are not limited to, the "HA" tag, which corresponds to an epitope derived from the influenza hemagglutinin protein (Wilson et al., Cell 37:767 (1984)) and the "flag" tag.

The present invention further encompasses antibodies or fragments thereof conjugated to a diagnostic or therapeutic agent. The antibodies can be used diagnostically to, for example, monitor the development or progression of a tumor as part of a clinical testing procedure to, e.g., determine the efficacy of a given treatment regimen. Detection can be facilitated by coupling the antibody to a detectable substance. Examples of detectable substances include various enzymes, prosthetic groups, fluorescent materials, luminescent materials, bioluminescent materials, radioactive materials, positron emitting metals using various positron emission tomographies, and nonradioactive paramagnetic metal ions. The detectable substance may be coupled or conjugated either directly to the antibody (or fragment thereof) or indirectly, through an intermediate (such as, for example, a linker known in the art) using techniques known in the art. See, for example, U.S. Pat. No. 4,741,900 for metal ions which can be conjugated to antibodies for use as diagnostics according to the present invention. Examples of suitable enzymes include horseradish peroxidase, alkaline phosphatase, beta-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin; and examples of suitable radioactive material include 125I, 131I, 111In or 99Tc.

Further, an antibody or fragment thereof may be conjugated to a therapeutic moiety such as a cytotoxin, e.g., a cytostatic or cytocidal agent, a therapeutic agent or a radioactive metal ion, e.g., alpha-emitters such as, for example, 213Bi. A cytotoxin or cytotoxic agent includes any agent that is detrimental to cells. Examples include paclitaxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D), 1-dehydrotestosterone, glucocorticoids, procaine, tetracaine, lidocaine, propranolol, and puromycin and analogs or homologues thereof. Therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine).

The conjugates of the invention can be used for modifying a given biological response, the therapeutic agent or drug moiety is not to be construed as limited to classical chemical therapeutic agents. For example, the drug moiety may be a protein or polypeptide possessing a desired biological activity. Such proteins may include, for example, a toxin such as abrin, ricin A, pseudomonas exotoxin, or diphtheria toxin; a protein such as tumor necrosis factor, a-interferon, β-interferon, nerve growth factor, platelet derived growth factor, tissue plasminogen activator, an apoptotic agent, e.g., TNF-alpha, TNF-beta, AIM I (See, International Publication No. WO 97/33899), AIM II (See, International Publication No. WO 97/34911), Fas Ligand (Takahashi et al., Int. Immunol., 6:1567-1574 (1994)), VEGI (See, International Publication No. WO 99/23105), a thrombotic agent or an anti-angiogenic agent, e.g., angiostatin or endostatin; or, biological response modifiers such as, for example, lymphokines, interleukin-1 ("IL-1"), interleukin-2 ("IL-2"), interleukin-6 ("IL-6"), granulocyte macrophage colony stimulating factor ("GM-CSF"), granulocyte colony stimulating factor ("G-CSF"), or other growth factors.

Antibodies may also be attached to solid supports, which are particularly useful for immunoassays or purification of the target antigen. Such solid supports include, but are not limited to, glass, cellulose, polyacrylamide, nylon, polystyrene, polyvinyl chloride or polypropylene.

Techniques for conjugating such therapeutic moiety to antibodies are well known, see, e.g., Amon et al., "Monoclonal Antibodies For Immunotargeting Of Drugs In Cancer Therapy", in Monoclonal Antibodies And Cancer Therapy, Reisfeld et al. (eds.), pp. 243-56 (Alan R. Liss, Inc. 1985); Hellstrom et al., "Antibodies For Drug Delivery", in Controlled Drug Delivery (2nd Ed.), Robinson et al. (eds.), pp. 623-53 (Marcel Dekker, Inc. 1987); Thorpe, "Antibody Carriers Of Cytotoxic Agents In Cancer Therapy: A Review", in Monoclonal Antibodies '84: Biological And Clinical Applications, Pinchera et al. (eds.), pp. 475-506 (1985); "Analysis, Results, And Future Prospective Of The Therapeutic Use Of Radiolabeled Antibody In Cancer Therapy", in Monoclonal Antibodies For Cancer Detection And Therapy, Baldwin et al. (eds.), pp. 303-16 (Academic Press 1985), and Thorpe et al., "The Preparation And Cytotoxic Properties Of Antibody-Toxin Conjugates", Immunol. Rev. 62:119-58 (1982).

Alternatively, an antibody can be conjugated to a second antibody to form an antibody heteroconjugate as described by Segal in U.S. Pat. No. 4,676,980, which is incorporated herein by reference in its entirety.

An antibody, with or without a therapeutic moiety conjugated to it, administered alone or in combination with cytotoxic factor(s) and/or cytokine(s) can be used as a therapeutic.

The present invention also encompasses the creation of synthetic antibodies directed against the polypeptides of the present invention. One example of synthetic antibodies is described in Radrizzani, M., et al., Medicina, (Aires), 59(6):753-8, (1999)). Recently, a new class of synthetic antibodies has been described and are referred to as molecularly imprinted polymers (MIPs) (Semorex, Inc.). Antibodies, peptides, and enzymes are often used as molecular recognition elements in chemical and biological sensors. However, their lack of stability and signal transduction mechanisms limits their use as sensing devices. Molecularly imprinted polymers (MIPs) are capable of mimicking the function of biological receptors but with less stability constraints. Such polymers provide high sensitivity and selectivity while maintaining excellent thermal and mechanical stability. MIPs have the ability to bind to small molecules and to target molecules such as organics and proteins' with equal or greater potency than that of natural antibodies. These "super" MIPs have higher affinities for their target and thus require lower concentrations for efficacious binding.

During synthesis, the MIPs are imprinted so as to have complementary size, shape, charge and functional groups of the selected target by using the target molecule itself (such as a polypeptide, antibody, etc.), or a substance having a very similar structure, as its "print" or "template." MIPs can be derivatized with the same reagents afforded to antibodies. For example, fluorescent 'super' MIPs can be coated onto beads or wells for use in highly sensitive separations or assays, or for use in high throughput screening of proteins.

Moreover, MIPs based upon the structure of the polypeptide(s) of the present invention may be useful in screening for compounds that bind to the polypeptide(s) of the invention. Such a MIP would serve the role of a synthetic "receptor" by minimicking the native architecture of the polypeptide. In fact, the ability of a MIP to serve the role of a synthetic receptor has already been demonstrated for the estrogen receptor (Ye, L., Yu, Y., Mosbach, K, Analyst., 126(6):760-5, (2001); Dickert, F, L., Hayden, O., Halikias, K, P, Analyst., 126(6):766-71, (2001)). A synthetic receptor may either be mimicked in its entirety (e.g., as the entire protein), or mimicked as a series of short peptides corresponding to the protein (Rachkov, A., Minoura, N, Biochim, Biophys, Acta., 1544(1-2):255-66, (2001)). Such a synthetic receptor MIPs may be employed in any one or more of the screening methods described elsewhere herein.

MIPs have also been shown to be useful in "sensing" the presence of its mimicked molecule (Cheng, Z., Wang, E., Yang, X, Biosens, Bioelectron., 16(3):179-85, (2001); Jenkins, A, L., Yin, R., Jensen, J. L, Analyst., 126(6):798-802, (2001); Jenkins, A, L., Yin, R., Jensen, J. L, Analyst., 126(6):798-802, (2001)). For example, a MIP designed using a polypeptide of the present invention may be used in assays designed to identify, and potentially quantitate, the level of said polypeptide in a sample. Such a MIP may be used as a substitute for any component described in the assays, or kits, provided herein (e.g., ELISA, etc.).

A number of methods may be employed to create MIPs to a specific receptor, ligand, polypeptide, peptide, organic molecule. Several preferred methods are described by Esteban et al in J. Anal, Chem., 370(7):795-802, (2001), which is hereby incorporated herein by reference in its entirety in addition to any references cited therein. Additional methods are known in the art and are encompassed by the present invention, such as for example, Hart, B, R., Shea, K, J. J. Am. Chem., Soc., 123(9):2072-3, (2001); and Quaglia, M., Chenon, K., Hall, A, J., De, Lorenzi, E., Sellergren, B, J. Am. Chem., Soc., 123(10):2146-54, (2001); which are hereby incorporated by reference in their entirety herein.

Uses for Antibodies Directed Against Polypeptides of the Invention

The antibodies of the present invention have various utilities. For example, such antibodies may be used in diagnostic assays to detect the presence or quantification of the polypeptides of the invention in a sample. Such a diagnostic assay may be comprised of at least two steps. The first, subjecting a sample with the antibody, wherein the sample is a tissue (e.g., human, animal, etc.), biological fluid (e.g., blood, urine, sputum, semen, amniotic fluid, saliva, etc.), biological extract (e.g., tissue or cellular homogenate, etc.), a protein microchip (e.g., See Arenkov P, et al., Anal Biochem., 278(2):123-131 (2000)), or a chromatography column, etc. And a second step involving the quantification of antibody bound to the substrate. Alternatively, the method may additionally involve a first step of attaching the antibody, either covalently, electrostatically, or reversibly, to a solid support, and a second step of subjecting the bound antibody to the sample, as defined above and elsewhere herein.

Various diagnostic assay techniques are known in the art, such as competitive binding assays, direct or indirect sandwich assays and immunoprecipitation assays conducted in either heterogeneous or homogenous phases (Zola, Monoclonal Antibodies: A Manual of Techniques, CRC Press, Inc., (1987), pp. 147-158). The antibodies used in the diagnostic assays can be labeled with a detectable moiety. The detectable moiety should be capable of producing, either directly or indirectly, a detectable signal. For example, the detectable moiety may be a radioisotope, such as 2H, 14C, 32P, or 125I, a florescent or chemiluminescent compound, such as fluorescein isothiocyanate, rhodamine, or luciferin, or an enzyme, such as alkaline phosphatase, beta-galactosidase, green fluorescent protein, or horseradish peroxidase. Any method known in the art for conjugating the antibody to the detectable moiety may be employed, including those methods described by Hunter et al., Nature, 144:945 (1962); Dafvid et al., Biochem., 13:1014 (1974); Pain et al., J. Immunol. Metho., 40:219(1981); and Nygren, J. Histochem. And Cytochem., 30:407 (1982).

Antibodies directed against the polypeptides of the present invention are useful for the affinity purification of such polypeptides from recombinant cell culture or natural sources. In this process, the antibodies against a particular polypeptide are immobilized on a suitable support, such as a SEPHADEX® resin or filter paper, using methods well known in the art. The immobilized antibody then is contacted with a sample containing the polypeptides to be purified, and thereafter the support is washed with a suitable solvent that will remove substantially all the material in the sample except for the desired polypeptides, which are bound to the immobilized antibody. Finally, the support is washed with another suitable solvent that will release the desired polypeptide from the antibody.

Immunophenotyping

The antibodies of the invention may be utilized for immunophenotyping of cell lines and biological samples. The translation product of the gene of the present invention may be useful as a cell specific marker, or more specifically as a cellular marker that is differentially expressed at various stages of differentiation and/or maturation of particular cell types. Monoclonal antibodies directed against a specific epitope, or combination of epitopes, will allow for the screening of cellular populations expressing the marker. Various techniques can be utilized using monoclonal antibodies to screen for cellular populations expressing the marker(s), and include magnetic separation using antibody-coated magnetic beads, "panning" with antibody attached to a solid matrix (i.e., plate), and flow cytometry (See, e.g., U.S. Pat. No. 5,985,660; and Morrison et al., Cell, 96:737-49 (1999)).

These techniques allow for the screening of particular populations of cells, such as might be found with hematological malignancies (i.e. minimal residual disease (MRD) in acute leukemic patients) and "non-self" cells in transplantations to prevent Graft-versus-Host Disease (GVHD). Alternatively, these techniques allow for the screening of hematopoietic stem and progenitor cells capable of undergoing proliferation and/or differentiation, as might be found in human umbilical cord blood.

Assays for Antibody Binding

The antibodies of the invention may be assayed for immunospecific binding by any method known in the art. The immunoassays which can be used include but are not limited to competitive and non-competitive assay systems using techniques such as western blots, radioimmunoassays, ELISA (enzyme linked immunosorbent assay), "sandwich" immunoassays, immunoprecipitation assays, precipitin reactions, gel diffusion precipitin reactions, immunodiffusion assays, agglutination assays, complement-fixation assays, immunoradiometric assays, fluorescent immunoassays, protein A immunoassays, to name but a few. Such assays are routine and well known in the art (see, e.g., Ausubel et al, eds, 1994, Current Protocols in Molecular Biology, Vol. 1, John Wiley & Sons, Inc., New York, which is incorporated by reference herein in its entirety). Exemplary immunoassays are described briefly below (but are not intended by way of limitation).

Immunoprecipitation protocols generally comprise lysing a population of cells in a lysis buffer such as RIPA buffer (1% NP-40 or Triton X-100, 1% sodium deoxycholate, 0.1% SDS, 0.15 M NaCl, 0.01 M sodium phosphate at pH 7.2, 1% Trasylol) supplemented with protein phosphatase and/or protease inhibitors (e.g., EDTA, PMSF, aprotinin, sodium vanadate), adding the antibody of interest to the cell lysate, incubating for a period of time (e.g., 1-4 hours) at 4° C., adding protein A and/or protein G sepharose beads to the cell lysate, incubating for about an hour or more at 4° C., washing the beads in lysis buffer and resuspending the beads in SDS/sample buffer. The ability of the antibody of interest to immunoprecipitate a particular antigen can be assessed by, e.g., western blot analysis. One of skill in the art would be knowledgeable as to the parameters that can be modified to increase the binding of the antibody to an antigen and decrease the background (e.g., pre-clearing the cell lysate with sepharose beads). For further discussion regarding immunoprecipitation protocols see, e.g., Ausubel et al, eds, 1994, Current Protocols in Molecular Biology, Vol. 1, John Wiley & Sons, Inc., New York at 10.16.1.

Western blot analysis generally comprises preparing protein samples, electrophoresis of the protein samples in a polyacrylamide gel (e.g., 8%-20% SDS-PAGE depending on the molecular weight of the antigen), transferring the protein sample from the polyacrylamide gel to a membrane such as nitrocellulose, PVDF or nylon, blocking the membrane in blocking solution (e.g., PBS with 3% BSA or non-fat milk), washing the membrane in washing buffer (e.g., PBS-Tween 20), blocking the membrane with primary antibody (the antibody of interest) diluted in blocking buffer, washing the membrane in washing buffer, blocking the membrane with a secondary antibody (which recognizes the primary antibody, e.g., an anti-human antibody) conjugated to an enzymatic substrate (e.g., horseradish peroxidase or alkaline phosphatase) or radioactive molecule (e.g., 32P or 125I) diluted in blocking buffer, washing the membrane in wash buffer, and detecting the presence of the antigen. One of skill in the art would be knowledgeable as to the parameters that can be modified to increase the signal detected and to reduce the background noise. For further discussion regarding western blot protocols see, e.g., Ausubel et al, eds, 1994, Current Protocols in Molecular Biology, Vol. 1, John Wiley & Sons, Inc., New York at 10.8.1.

ELISAs comprise preparing antigen, coating the well of a 96 well microtiter plate with the antigen, adding the antibody of interest conjugated to a detectable compound such as an enzymatic substrate (e.g., horseradish peroxidase or alkaline phosphatase) to the well and incubating for a period of time, and detecting the presence of the antigen. In ELISAs the antibody of interest does not have to be conjugated to a detectable compound; instead, a second antibody (which recognizes the antibody of interest) conjugated to a detectable compound may be added to the well. Further, instead of coating the well with the antigen, the antibody may be coated to the well. In this case, a second antibody conjugated to a detectable compound may be added following the addition of the antigen of interest to the coated well. One of skill in the art would be knowledgeable as to the parameters that can be modified to increase the signal detected as well as other variations of ELISAs known in the art. For further discussion regarding ELISAs see, e.g., Ausubel et al, eds, 1994, Current Protocols in Molecular Biology, Vol. 1, John Wiley & Sons, Inc., New York at 11.2.1.

The binding affinity of an antibody to an antigen and the off-rate of an antibody-antigen interaction can be determined by competitive binding assays. One example of a competitive binding assay is a radioimmunoassay comprising the incubation of labeled antigen (e.g., 3H or 125I) with the antibody of interest in the presence of increasing amounts of unlabeled antigen, and the detection of the antibody bound to the labeled antigen. The affinity of the antibody of interest for a particular antigen and the binding off-rates can be determined from the data by scatchard plot analysis. Competition with a second antibody can also be determined using radioimmunoassays. In this case, the antigen is incubated with antibody of interest conjugated to a labeled compound (e.g., 3H or 125I) in the presence of increasing amounts of an unlabeled second antibody.

Therapeutic Uses of Antibodies

The present invention is further directed to antibody-based therapies which involve administering antibodies of the invention to an animal, preferably a mammal, and most preferably a human, patient for treating one or more of the disclosed diseases, disorders, or conditions. Therapeutic compounds of the invention include, but are not limited to, antibodies of the invention (including fragments, analogs and derivatives thereof as described herein) and nucleic acids encoding antibodies of the invention (including fragments, analogs and derivatives thereof and anti-idiotypic antibodies as described herein). The antibodies of the invention can be used to treat, inhibit or prevent diseases, disorders or conditions associated with aberrant expression and/or activity of a polypeptide of the invention, including, but not limited to, any one or more of the diseases, disorders, or conditions described herein. The treatment and/or prevention of diseases, disorders, or conditions associated with aberrant expression and/or activity of a polypeptide of the invention includes, but is not limited to, alleviating symptoms associated with those diseases, disorders or conditions. Antibodies of the invention may be provided in pharmaceutically acceptable compositions as known in the art or as described herein.

A summary of the ways in which the antibodies of the present invention may be used therapeutically includes binding polynucleotides or polypeptides of the present invention locally or systemically in the body or by direct cytotoxicity of the antibody, e.g. as mediated by complement (CDC) or by effector cells (ADCC). Some of these approaches are described in more detail below. Armed with the teachings provided herein, one of ordinary skill in the art will know how to use the antibodies of the present invention for diagnostic, monitoring or therapeutic purposes without undue experimentation.

The antibodies of this invention may be advantageously utilized in combination with other monoclonal or chimeric antibodies, or with lymphokines or hematopoietic growth factors (such as, e.g., IL-2, IL-3 and IL-7), for example, which serve to increase the number or activity of effector cells which interact with the antibodies.

The antibodies of the invention may be administered alone or in combination with other types of treatments (e.g., radiation therapy, chemotherapy, hormonal therapy, immunotherapy and anti-tumor agents). Generally, administration of products of a species origin or species reactivity (in the case of antibodies) that is the same species as that of the patient is preferred. Thus, in a preferred embodiment, human antibodies, fragments derivatives, analogs, or nucleic acids, are administered to a human patient for therapy or prophylaxis.

It is preferred to use high affinity and/or potent in vivo inhibiting and/or neutralizing antibodies against polypeptides or polynucleotides of the present invention, fragments or regions thereof, for both immunoassays directed to and therapy of disorders related to polynucleotides or polypeptides, including fragments thereof, of the present invention. Such antibodies, fragments, or regions, will preferably have an affinity for polynucleotides or polypeptides of the invention, including fragments thereof. Preferred binding affinities include those with a dissociation constant or Kd less than $5 \times 10^{-2}$ M, $10^{-2}$ M, $5 \times 10^{-3}$ M, $10^{-3}$ M, $5 \times 10^{-4}$ M, $10^{-4}$M; $5 \times 10^{-5}$ M, $10^{-5}$ M, $5 \times 10^{-6}$ M, $10^{-6}$ M, $5 \times 10^{-7}$ M, $10^{-7}$ M, $5 \times 10^{-8}$ M, $10^{-8}$ M, $5 \times 10^{-9}$ M, $10^{-9}$ M, $5 \times 10^{-10}$ M, $10^{-10}$ M, $5 \times 10^{-11}$ M, $10^{-11}$ M, $5 \times 10^{-12}$ M, $10^{-12}$ M, $5 \times 10^{-13}$ M, $10^{-13}$ M, $5 \times 10^{-14}$ M, $10^{-14}$ M, $5 \times 10^{-15}$ M, and $10^{-15}$ M.

Antibodies directed against polypeptides of the present invention are useful for inhibiting allergic reactions in animals. For example, by administering a therapeutically acceptable dose of an antibody, or antibodies, of the present invention, or a cocktail of the present antibodies, or in combination with other antibodies of varying sources, the animal may not elicit an allergic response to antigens.

Likewise, one could envision cloning the gene encoding an antibody directed against a polypeptide of the present invention, said polypeptide having the potential to elicit an allergic and/or immune response in an organism, and transforming the organism with said antibody gene such that it is expressed (e.g., constitutively, inducibly, etc.) in the organism. Thus, the organism would effectively become resistant to an allergic response resulting from the ingestion or presence of such an immune/allergic reactive polypeptide. Moreover, such a use of the antibodies of the present invention may have particular utility in preventing and/or ameliorating autoimmune diseases and/or disorders, as such conditions are typically a result of antibodies being directed against endogenous proteins. For example, in the instance where the polypeptide of the present invention is responsible for modulating the immune response to auto-antigens, transforming the organism and/or individual with a construct comprising any of the promoters disclosed herein or otherwise known in the art, in addition, to a polynucleotide encoding the antibody directed against the polypeptide of the present invention could effective inhibit the organisms immune system from eliciting an immune response to the auto-antigen(s). Detailed descriptions of therapeutic and/or gene therapy applications of the present invention are provided elsewhere herein.

Alternatively, antibodies of the present invention could be produced in a plant (e.g., cloning the gene of the antibody directed against a polypeptide of the present invention, and transforming a plant with a suitable vector comprising said gene for constitutive expression of the antibody within the plant), and the plant subsequently ingested by an animal, thereby conferring temporary immunity to the animal for the specific antigen the antibody is directed towards (See, for example, U.S. Pat. Nos. 5,914,123 and 6,034,298).

In another embodiment, antibodies of the present invention, preferably polyclonal antibodies, more preferably monoclonal antibodies, and most preferably single-chain antibodies, can be used as a means of inhibiting gene expression of a particular gene, or genes, in a human, mammal, and/or other organism. See, for example, International Publication Number WO 00/05391, published Feb. 3, 2000, to Dow Agrosciences LLC. The application of such methods for the antibodies of the present invention are known in the art, and are more particularly described elsewhere herein.

In yet another embodiment, antibodies of the present invention may be useful for multimerizing the polypeptides of the present invention. For example, certain proteins may confer enhanced biological activity when present in a multimeric state (i.e., such enhanced activity may be due to the increased effective concentration of such proteins whereby more protein is available in a localized location).

Antibody-based Gene Therapy

In a specific embodiment, nucleic acids comprising sequences encoding antibodies or functional derivatives thereof, are administered to treat, inhibit or prevent a disease or disorder associated with aberrant expression and/or activity of a polypeptide of the invention, by way of gene therapy. Gene therapy refers to therapy performed by the administration to a subject of an expressed or expressible nucleic acid. In this embodiment of the invention, the nucleic acids produce their encoded protein that mediates a therapeutic effect.

Any of the methods for gene therapy available in the art can be used according to the present invention. Exemplary methods are described below.

For general reviews of the methods of gene therapy, see Goldspiel et al., Clinical Pharmacy 12:488-505 (1993); Wu and Wu, Biotherapy 3:87-95 (1991); Tolstoshev, Ann. Rev. Pharmacol. Toxicol. 32:573-596 (1993); Mulligan, Science 260:926-932 (1993); and Morgan and Anderson, Ann. Rev. Biochem. 62:191-217 (1993); May, TIBTECH 11(5):155-215 (1993). Methods commonly known in the art of recombinant DNA technology which can be used are described in Ausubel et al. (eds.), Current Protocols in Molecular Biology, John Wiley & Sons, NY (1993); and Kriegler, Gene Transfer and Expression, A Laboratory Manual, Stockton Press, NY (1990).

In a preferred aspect, the compound comprises nucleic acid sequences encoding an antibody, said nucleic acid sequences being part of expression vectors that express the antibody or fragments or chimeric proteins or heavy or light chains thereof in a suitable host. In particular, such nucleic acid sequences have promoters operably linked to the antibody coding region, said promoter being inducible or constitutive, and, optionally, tissue-specific. In another particular embodiment, nucleic acid molecules are used in which the antibody coding sequences and any other desired sequences are flanked by regions that promote homologous recombination at a desired site in the genome, thus providing for intrachromosomal expression of the antibody encoding nucleic acids (Koller and Smithies, Proc. Natl. Acad. Sci. USA 86:8932-8935 (1989); Zijlstra et al., Nature 342:435-438 (1989). In specific embodiments, the expressed antibody molecule is a single chain antibody; alternatively, the nucleic acid sequences include sequences encoding both the heavy and light chains, or fragments thereof, of the antibody.

Delivery of the nucleic acids into a patient may be either direct, in which case the patient is directly exposed to the nucleic acid or nucleic acid-carrying vectors, or indirect, in which case, cells are first transformed with the nucleic acids in vitro, then transplanted into the patient. These two approaches are known, respectively, as in vivo or ex vivo gene therapy.

In a specific embodiment, the nucleic acid sequences are directly administered in vivo, where it is expressed to produce the encoded product. This can be accomplished by any of numerous methods known in the art, e.g., by constructing them as part of an appropriate nucleic acid expression vector and administering it so that they become intracellular, e.g., by infection using defective or attenuated retrovirals or other viral vectors (see U.S. Pat. No. 4,980,286), or by direct injection of naked DNA, or by use of microparticle bombardment (e.g., a gene gun; Biolistic, Dupont), or coating with lipids or cell-surface receptors or transfecting agents, encapsulation in liposomes, microparticles, or microcapsules, or by administering them in linkage to a peptide which is known to enter the nucleus, by administering it in linkage to a ligand subject to receptor-mediated endocytosis (see, e.g., Wu and Wu, J. Biol. Chem. 262:4429-4432 (1987)) (which can be used to target cell types specifically expressing the receptors), etc. In another embodiment, nucleic acid-ligand complexes can be formed in which the ligand comprises a fusogenic viral peptide to disrupt endosomes, allowing the nucleic acid to avoid lysosomal degradation. In yet another embodiment, the nucleic acid can be targeted in vivo for cell specific uptake and expression, by targeting a specific receptor (see, e.g., PCT Publications WO 92/06180; WO 92/22635; WO92/20316; WO93/14188, WO 93/20221). Alternatively, the nucleic acid can be introduced intracellularly and incorporated within host cell DNA for expression, by homologous recombination (Koller and Smithies, Proc. Natl. Acad. Sci. USA 86:8932-8935 (1989); Zijlstra et al., Nature 342:435-438 (1989)).

In a specific embodiment, viral vectors that contains nucleic acid sequences encoding an antibody of the invention are used. For example, a retroviral vector can be used (see Miller et al., Meth. Enzymol. 217:581-599 (1993)). These retroviral vectors contain the components necessary for the correct packaging of the viral genome and integration into the host cell DNA. The nucleic acid sequences encoding the antibody to be used in gene therapy are cloned into one or more vectors, which facilitates delivery of the gene into a patient. More detail about retroviral vectors can be found in Boesen et al., Biotherapy 6:291-302 (1994), which describes the use of a retroviral vector to deliver the mdr1 gene to hematopoietic stem cells in order to make the stem cells more resistant to chemotherapy. Other references illustrating the use of retroviral vectors in gene therapy are: Clowes et al., J. Clin. Invest. 93:644-651 (1994); Kiem et al., Blood 83:1467-1473 (1994); Salmons and Gunzberg, Human Gene Therapy 4:129-141 (1993); and Grossman and Wilson, Curr. Opin. in Genetics and Devel. 3:110-114 (1993).

Adenoviruses are other viral vectors that can be used in gene therapy. Adenoviruses are especially attractive vehicles for delivering genes to respiratory epithelia. Adenoviruses naturally infect respiratory epithelia where they cause a mild disease. Other targets for adenovirus-based delivery systems are liver, the central nervous system, endothelial cells, and muscle. Adenoviruses have the advantage of being capable of infecting non-dividing cells. Kozarsky and Wilson, Current Opinion in Genetics and Development 3:499-503 (1993) present a review of adenovirus-based gene therapy. Bout et al., Human Gene Therapy 5:3-10 (1994) demonstrated the use of adenovirus vectors to transfer genes to the respiratory epithelia of rhesus monkeys. Other instances of the use of adenoviruses in gene therapy can be found in Rosenfeld et al., Science 252:431-434 (1991); Rosenfeld et al., Cell 68:143-155 (1992); Mastrangeli et al., J. Clin. Invest. 91:225-234 (1993); PCT Publication WO94/12649; and Wang, et al., Gene Therapy 2:775-783 (1995). In a preferred embodiment, adenovirus vectors are used.

Adeno-associated virus (AAV) has also been proposed for use in gene therapy (Walsh et al., Proc. Soc. Exp. Biol. Med. 204:289-300 (1993); U.S. Pat. No. 5,436,146).

Another approach to gene therapy involves transferring a gene to cells in tissue culture by such methods as electroporation, lipofection, calcium phosphate mediated transfection, or viral infection. Usually, the method of transfer includes the transfer of a selectable marker to the cells. The cells are then placed under selection to isolate those cells that have taken up and are expressing the transferred gene. Those cells are then delivered to a patient.

In this embodiment, the nucleic acid is introduced into a cell prior to administration in vivo of the resulting recombinant cell. Such introduction can be carried out by any method known in the art, including but not limited to transfection, electroporation, microinjection, infection with a viral or bacteriophage vector containing the nucleic acid sequences, cell fusion, chromosome-mediated gene transfer, microcell-mediated gene transfer, spheroplast fusion, etc. Numerous techniques are known in the art for the introduction of foreign genes into cells (see, e.g., Loeffler and Behr, Meth. Enzymol. 217:599-618 (1993); Cohen et al., Meth. Enzymol. 217:618-644 (1993); Cline, Pharmac. Ther. 29:69-92m (1985) and may be used in accordance with the present invention, provided that the necessary developmental and physiological functions of the recipient cells are not disrupted. The technique should provide for the stable transfer of the nucleic acid to the cell, so that the nucleic acid is expressible by the cell and preferably heritable and expressible by its cell progeny.

The resulting recombinant cells can be delivered to a patient by various methods known in the art. Recombinant blood cells (e.g., hematopoietic stem or progenitor cells) are preferably administered intravenously. The amount of cells envisioned for use depends on the desired effect, patient state, etc., and can be determined by one skilled in the art.

Cells into which a nucleic acid can be introduced for purposes of gene therapy encompass any desired, available cell type, and include but are not limited to epithelial cells, endothelial cells, keratinocytes, fibroblasts, muscle cells, hepatocytes; blood cells such as Tlymphocytes, Blymphocytes, monocytes, macrophages, neutrophils, eosinophils, megakaryocytes, granulocytes; various stem or progenitor cells, in particular hematopoietic stem or progenitor cells, e.g., as obtained from bone marrow, umbilical cord blood, peripheral blood, fetal liver, etc.

In a preferred embodiment, the cell used for gene therapy is autologous to the patient.

In an embodiment in which recombinant cells are used in gene therapy, nucleic acid sequences encoding an antibody are introduced into the cells such that they are expressible by the cells or their progeny, and the recombinant cells are then administered in vivo for therapeutic effect. In a specific embodiment, stem or progenitor cells are used. Any stem and/or progenitor cells which can be isolated and maintained in vitro can potentially be used in accordance with this embodiment of the present invention (see e.g. PCT Publication WO 94/08598; Stemple and Anderson, Cell 71:973-985 (1992); Rheinwald, Meth. Cell Bio. 21A:229 (1980); and Pittelkow and Scott, Mayo Clinic Proc. 61:771 (1986)).

In a specific embodiment, the nucleic acid to be introduced for purposes of gene therapy comprises an inducible promoter operably linked to the coding region, such that expression of the nucleic acid is controllable by controlling the presence or absence of the appropriate inducer of transcription.

Demonstration of Therapeutic or Prophylactic Activity

The compounds or pharmaceutical compositions of the invention are preferably tested in vitro, and then in vivo for the desired therapeutic or prophylactic activity, prior to use in humans. For example, in vitro assays to demonstrate the therapeutic or prophylactic utility of a compound or pharmaceutical composition include, the effect of a compound on a cell line or a patient tissue sample. The effect of the compound or composition on the cell line and/or tissue sample can be determined utilizing techniques known to those of skill in the art including, but not limited to, rosette formation assays and cell lysis assays. In accordance with the invention, in vitro assays which can be used to determine whether administration of a specific compound is indicated, include in vitro cell culture assays in which a patient tissue sample is grown in culture, and exposed to or otherwise administered a compound, and the effect of such compound upon the tissue sample is observed.

Therapeutic/Prophylactic Administration and Compositions

The invention provides methods of treatment, inhibition and prophylaxis by administration to a subject of an effective amount of a compound or pharmaceutical composition of the invention, preferably an antibody of the invention. In a preferred aspect, the compound is substantially purified (e.g., substantially free from substances that limit its effect or produce undesired side-effects). The subject is preferably an animal, including but not limited to animals such as cows, pigs, horses, chickens, cats, dogs, etc., and is preferably a mammal, and most preferably human.

Formulations and methods of administration that can be employed when the compound comprises a nucleic acid or an immunoglobulin are described above; additional appropriate formulations and routes of administration can be selected from among those described herein below.

Various delivery systems are known and can be used to administer a compound of the invention, e.g., encapsulation in liposomes, microparticles, microcapsules, recombinant cells capable of expressing the compound, receptor-mediated endocytosis (see, e.g., Wu and Wu, J. Biol. Chem. 262:4429-4432 (1987)), construction of a nucleic acid as part of a retroviral or other vector, etc. Methods of introduction include but are not limited to intradermal, intramuscular, intraperitoneal, intravenous, subcutaneous, intranasal, epidural, and oral routes. The compounds or compositions may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local. In addition, it may be desirable to introduce the pharmaceutical compounds or compositions of the invention into the central nervous system by any suitable route, including intraventricular and intrathecal injection; intraventricular injection may be facilitated by an intraventricular catheter, for example, attached to a reservoir, such as an Ommaya reservoir. Pulmonary administration can also be employed, e.g., by use of an inhaler or nebulizer, and formulation with an aerosolizing agent.

In a specific embodiment, it may be desirable to administer the pharmaceutical compounds or compositions of the invention locally to the area in need of treatment; this may be achieved by, for example, and not by way of limitation, local infusion during surgery, topical application, e.g., in conjunction with a wound dressing after surgery, by injection, by means of a catheter, by means of a suppository, or by means of an implant, said implant being of a porous, non-porous, or gelatinous material, including membranes, such as sialastic membranes, or fibers. Preferably, when administering a protein, including an antibody, of the invention, care must be taken to use materials to which the protein does not absorb.

In another embodiment, the compound or composition can be delivered in a vesicle, in particular a liposome (see Langer, Science 249:1527-1533 (1990); Treat et al., in Liposomes in the Therapy of Infectious Disease and Cancer, Lopez-Berestein and Fidler (eds.), Liss, New York, pp. 353-365 (1989); Lopez-Berestein, ibid., pp. 317-327; see generally ibid.)

In yet another embodiment, the compound or composition can be delivered in a controlled release system. In one embodiment, a pump may be used (see Langer, supra; Sefton, CRC Crit. Ref. Biomed. Eng. 14:201 (1987); Buchwald et al., Surgery 88:507 (1980); Saudek et al., N. Engl. J. Med. 321: 574 (1989)). In another embodiment, polymeric materials can be used (see Medical Applications of Controlled Release, Langer and Wise (eds.), CRC Pres., Boca Raton, Fla. (1974); Controlled Drug Bioavailability, Drug Product Design and Performance, Smolen and Ball (eds.), Wiley, New York (1984); Ranger and Peppas, J., Macromol. Sci. Rev. Macromol. Chem. 23:61 (1983); see also Levy et al., Science 228: 190 (1985); During et al., Ann. Neurol. 25:351 (1989); Howard et al., J. Neurosurg. 71:105 (1989)). In yet another embodiment, a controlled release system can be placed in proximity of the therapeutic target, i.e., the brain, thus requiring only a fraction of the systemic dose (see, e.g., Goodson, in Medical Applications of Controlled Release, supra, vol. 2, pp. 115-138 (1984)).

Other controlled release systems are discussed in the review by Langer (Science 249:1527-1533 (1990)).

In a specific embodiment where the compound of the invention is a nucleic acid encoding a protein, the nucleic acid can be administered in vivo to promote expression of its encoded protein, by constructing it as part of an appropriate nucleic acid expression vector and administering it so that it becomes intracellular, e.g., by use of a retroviral vector (see U.S. Pat. No. 4,980,286), or by direct injection, or by use of microparticle bombardment (e.g., a gene gun; Biolistic, Dupont), or coating with lipids or cell-surface receptors or transfecting agents, or by administering it in linkage to a homeobox-like peptide which is known to enter the nucleus (see e.g., Joliot et al., Proc. Natl. Acad. Sci. USA 88:1864-1868 (1991)), etc. Alternatively, a nucleic acid can be introduced intracellularly and incorporated within host cell DNA for expression, by homologous recombination.

The present invention also provides pharmaceutical compositions. Such compositions comprise a therapeutically effective amount of a compound, and a pharmaceutically acceptable carrier. In a specific embodiment, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in "Remington's Pharmaceutical Sciences" by E. W. Martin. Such compositions will contain a therapeutically effective amount of the compound, preferably in purified form, together with a suitable amount of carrier so as to provide the form for proper administration to the patient. The formulation should suit the mode of administration.

In a preferred embodiment, the composition is formulated in accordance with routine procedures as a pharmaceutical composition adapted for intravenous administration to human beings. Typically, compositions for intravenous administration are solutions in sterile isotonic aqueous buffer. Where necessary, the composition may also include a solubilizing agent and a local anesthetic such as lignocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The compounds of the invention can be formulated as neutral or salt forms. Pharmaceutically acceptable salts include those formed with anions such as those derived from hydrochloric, phosphoric, acetic, oxalic, tartaric acids, etc., and those formed with cations such as those derived from sodium, potassium, ammonium, calcium, ferric hydroxides, isopropylamine, triethylamine, 2-ethylamino ethanol, histidine, procaine, etc.

The amount of the compound of the invention which will be effective in the treatment, inhibition and prevention of a disease or disorder associated with aberrant expression and/or activity of a polypeptide of the invention can be determined by standard clinical techniques. In addition, in vitro assays may optionally be employed to help identify optimal dosage ranges. The precise dose to be employed in the formulation will also depend on the route of administration, and the seriousness of the disease or disorder, and should be decided according to the judgment of the practitioner and each patient's circumstances. Effective doses may be extrapolated from dose-response curves derived from in vitro or animal model test systems.

For antibodies, the dosage administered to a patient is typically 0.1 mg/kg to 100 mg/kg of the patient's body weight. Preferably, the dosage administered to a patient is between 0.1 mg/kg and 20 mg/kg of the patient's body weight, more preferably 1 mg/kg to 10 mg/kg of the patient's body weight. Generally, human antibodies have a longer half-life within the human body than antibodies from other species due to the immune response to the foreign polypeptides. Thus, lower dosages of human antibodies and less frequent administration is often possible. Further, the dosage and frequency of administration of antibodies of the invention may be reduced by enhancing uptake and tissue penetration (e.g., into the brain) of the antibodies by modifications such as, for example, lipidation.

The invention also provides a pharmaceutical pack or kit comprising one or more containers filled with one or more of the ingredients of the pharmaceutical compositions of the invention. Optionally associated with such container(s) can be a notice in the form prescribed by a governmental agency regulating the manufacture, use or sale of pharmaceuticals or biological products, which notice reflects approval by the agency of manufacture, use or sale for human administration.

Diagnosis and Imaging with Antibodies

Labeled antibodies, and derivatives and analogs thereof, which specifically bind to a polypeptide of interest can be used for diagnostic purposes to detect, diagnose, or monitor diseases, disorders, and/or conditions associated with the aberrant expression and/or activity of a polypeptide of the invention. The invention provides for the detection of aberrant expression of a polypeptide of interest, comprising (a) assaying the expression of the polypeptide of interest in cells or body fluid of an individual using one or more antibodies specific to the polypeptide interest; and (b) comparing the level of gene expression with a standard gene expression level, whereby an increase or decrease in the assayed polypeptide gene expression level compared to the standard expression level is indicative of aberrant expression.

The invention provides a diagnostic assay for diagnosing a disorder, comprising (a) assaying the expression of the polypeptide of interest in cells or body fluid of an individual using one or more antibodies specific to the polypeptide interest; and (b) comparing the level of gene expression with a standard gene expression level, whereby an increase or decrease in the assayed polypeptide gene expression level compared to the standard expression level is indicative of a particular disorder. With respect to cancer, the presence of a relatively high amount of transcript in biopsied tissue from an individual may indicate a predisposition for the development of the disease, or may provide a means for detecting the disease prior to the appearance of actual clinical symptoms. A more definitive diagnosis of this type may allow health professionals to employ preventative measures or aggressive treatment earlier thereby preventing the development or further progression of the cancer.

Antibodies of the invention can be used to assay protein levels in a biological sample using classical immunohistological methods known to those of skill in the art (e.g., see Jalkanen, et al., J. Cell. Biol. 101:976-985 (1985); Jalkanen, et al., J. Cell. Biol. 105:3087-3096 (1987)). Other antibody-based methods useful for detecting protein gene expression include immunoassays, such as the enzyme linked immunosorbent assay (ELISA) and the radioimmunoassay (RIA). Suitable antibody assay labels are known in the art and include enzyme labels, such as, glucose oxidase; radioisotopes, such as iodine (125I, 121I), carbon (14C), sulfur (35S), tritium (3H), indium (112In), and technetium (99Tc); luminescent labels, such as luminol; and fluorescent labels, such as fluorescein and rhodamine, and biotin.

One aspect of the invention is the detection and diagnosis of a disease or disorder associated with aberrant expression of a polypeptide of interest in an animal, preferably a mammal and most preferably a human. In one embodiment, diagnosis comprises: (a) administering (for example, parenterally, subcutaneously, or intraperitoneally) to a subject an effective amount of a labeled molecule which specifically binds to the polypeptide of interest; (b) waiting for a time interval following the administering for permitting the labeled molecule to preferentially concentrate at sites in the subject where the polypeptide is expressed (and for unbound labeled molecule to be cleared to background level); (c) determining background level; and (d) detecting the labeled molecule in the subject, such that detection of labeled molecule above the background level indicates that the subject has a particular disease or disorder associated with aberrant expression of the polypeptide of interest. Background level can be determined by various methods including, comparing the amount of labeled molecule detected to a standard value previously determined for a particular system.

It will be understood in the art that the size of the subject and the imaging system used will determine the quantity of imaging moiety needed to produce diagnostic images. In the case of a radioisotope moiety, for a human subject, the quantity of radioactivity injected will normally range from about 5 to 20 millicuries of 99 mTc. The labeled antibody or antibody fragment will then preferentially accumulate at the location of cells which contain the specific protein. In vivo tumor imaging is described in S. W. Burchiel et al., "Immunopharmacokinetics of Radiolabeled Antibodies and Their Fragments." (Chapter 13 in Tumor Imaging The Radiochemical Detection of Cancer, S. W. Burchiel and B. A. Rhodes, eds., Masson Publishing Inc. (1982).

Depending on several variables, including the type of label used and the mode of administration, the time interval following the administration for permitting the labeled molecule to preferentially concentrate at sites in the subject and for unbound labeled molecule to be cleared to background level is 6 to 48 hours or 6 to 24 hours or 6 to 12 hours. In another embodiment the time interval following administration is 5 to 20 days or 5 to 10 days.

In an embodiment, monitoring of the disease or disorder is carried out by repeating the method for diagnosing the disease or disease, for example, one month after initial diagnosis, six months after initial diagnosis, one year after initial diagnosis, etc.

Presence of the labeled molecule can be detected in the patient using methods known in the art for in vivo scanning. These methods depend upon the type of label used. Skilled artisans will be able to determine the appropriate method for detecting a particular label. Methods and devices that may be used in the diagnostic methods of the invention include, but are not limited to, computed tomography (CT), whole body scan such as position emission tomography (PET), magnetic resonance imaging (MRI), and sonography.

In a specific embodiment, the molecule is labeled with a radioisotope and is detected in the patient using a radiation responsive surgical instrument (Thurston et al., U.S. Pat. No. 5,441,050). In another embodiment, the molecule is labeled with a fluorescent compound and is detected in the patient using a fluorescence responsive scanning instrument. In another embodiment, the molecule is labeled with a positron emitting metal and is detected in the patent using positron emission-tomography. In yet another embodiment, the molecule is labeled with a paramagnetic label and is detected in a patient using magnetic resonance imaging (MRI).

Kits

The present invention provides kits that can be used in the above methods. In one embodiment, a kit comprises an antibody of the invention, preferably a purified antibody, in one or more containers. In a specific embodiment, the kits of the present invention contain a substantially isolated polypeptide comprising an epitope which is specifically immunoreactive with an antibody included in the kit. Preferably, the kits of the present invention further comprise a control antibody which does not react with the polypeptide of interest. In another specific embodiment, the kits of the present invention contain a means for detecting the binding of an antibody to a polypeptide of interest (e.g., the antibody may be conjugated to a detectable substrate such as a fluorescent compound, an enzymatic substrate, a radioactive compound or a luminescent compound, or a second antibody which recognizes the first antibody may be conjugated to a detectable substrate).

In another specific embodiment of the present invention, the kit is a diagnostic kit for use in screening serum containing antibodies specific against proliferative and/or cancerous polynucleotides and polypeptides. Such a kit may include a control antibody that does not react with the polypeptide of interest. Such a kit may include a substantially isolated polypeptide antigen comprising an epitope which is specifically immunoreactive with at least one anti-polypeptide antigen antibody. Further, such a kit includes means for detecting the binding of said antibody to the antigen (e.g., the antibody may be conjugated to a fluorescent compound such as fluorescein or rhodamine which can be detected by flow cytometry). In specific embodiments, the kit may include a recombinantly produced or chemically synthesized polypeptide antigen. The polypeptide antigen of the kit may also be attached to a solid support.

In a more specific embodiment the detecting means of the above-described kit includes a solid support to which said polypeptide antigen is attached. Such a kit may also include a non-attached reporter-labeled anti-human antibody. In this embodiment, binding of the antibody to the polypeptide antigen can be detected by binding of the said reporter-labeled antibody.

In an additional embodiment, the invention includes a diagnostic kit for use in screening serum containing antigens of the polypeptide of the invention. The diagnostic kit includes a substantially isolated antibody specifically immunoreactive with polypeptide or polynucleotide antigens, and means for detecting the binding of the polynucleotide or polypeptide antigen to the antibody. In one embodiment, the antibody is attached to a solid support. In a specific embodiment, the antibody may be a monoclonal antibody. The detecting means of the kit may include a second, labeled monoclonal antibody. Alternatively, or in addition, the detecting means may include a labeled, competing antigen.

In one diagnostic configuration, test serum is reacted with a solid phase reagent having a surface-bound antigen obtained by the methods of the present invention. After binding with specific antigen antibody to the reagent and removing unbound serum components by washing, the reagent is reacted with reporter-labeled anti-human antibody to bind reporter to the reagent in proportion to the amount of bound anti-antigen antibody on the solid support. The reagent is again washed to remove unbound labeled antibody, and the amount of reporter associated with the reagent is determined. Typically, the reporter is an enzyme which is detected by incubating the solid phase in the presence of a suitable fluorometric, luminescent or calorimetric substrate (Sigma, St. Louis, Mo.).

The solid surface reagent in the above assay is prepared by known techniques for attaching protein material to solid support material, such as polymeric beads, dip sticks, 96-well plate or filter material. These attachment methods generally include non-specific adsorption of the protein to the support or covalent attachment of the protein, typically through a free amine group, to a chemically reactive group on the solid support, such as an activated carboxyl, hydroxyl, or aldehyde group. Alternatively, streptavidin coated plates can be used in conjunction with biotinylated antigen(s).

Thus, the invention provides an assay system or kit for carrying out this diagnostic method. The kit generally includes a support with surface-bound recombinant antigens, and a reporter-labeled anti-human antibody for detecting surface-bound anti-antigen antibody.

Fusion Proteins

Any polypeptide of the present invention can be used to generate fusion proteins. For example, the polypeptide of the present invention, when fused to a second protein, can be used as an antigenic tag. Antibodies raised against the polypeptide of the present invention can be used to indirectly detect the second protein by binding to the polypeptide. Moreover, because certain proteins target cellular locations based on trafficking signals, the polypeptides of the present invention can be used as targeting molecules once fused to other proteins.

Examples of domains that can be fused to polypeptides of the present invention include not only heterologous signal sequences, but also other heterologous functional regions. The fusion does not necessarily need to be direct, but may occur through linker sequences.

Moreover, fusion proteins may also be engineered to improve characteristics of the polypeptide of the present invention. For instance, a region of additional amino acids, particularly charged amino acids, may be added to the N-terminus of the polypeptide to improve stability and persistence during purification from the host cell or subsequent handling and storage. Peptide moieties may be added to the polypeptide to facilitate purification. Such regions may be removed prior to final preparation of the polypeptide. Similarly, peptide cleavage sites can be introduced in-between such peptide moieties, which could additionally be subjected to protease activity to remove said peptide(s) from the protein of the present invention. The addition of peptide moieties, including peptide cleavage sites, to facilitate handling of polypeptides are familiar and routine techniques in the art.

Moreover, polypeptides of the present invention, including fragments, and specifically epitopes, can be combined with parts of the constant domain of immunoglobulins (IgA, IgE, IgG, IgM) or portions thereof (CH1, CH2, CH3, and any combination thereof, including both entire domains and portions thereof), resulting in chimeric polypeptides. These fusion proteins facilitate purification and show an increased half-life in vivo. One reported example describes chimeric proteins consisting of the first two domains of the human CD4-polypeptide and various domains of the constant regions of the heavy or light chains of mammalian immunoglobulins. (EP A 394,827; Traunecker et al., Nature 331:84-86 (1988).) Fusion proteins having disulfide-linked dimeric structures (due to the IgG) can also be more efficient in binding and neutralizing other molecules, than the monomeric secreted protein or protein fragment alone. (Fountoulakis et al., J. Biochem. 270:3958-3964 (1995).)

Similarly, EP-A 0 464 533 (Canadian counterpart 2,045, 869) discloses fusion proteins comprising various portions of the constant region of immunoglobulin molecules together with another human protein or part thereof. In many cases, the Fc part in a fusion protein is beneficial in therapy and diagnosis, and thus can result in, for example, improved pharmacokinetic properties. (EP-A 0 232 262.) Alternatively, deleting the Fc part after the fusion protein has been expressed, detected, and purified, would be desired. For example, the Fc portion may hinder therapy and diagnosis if the fusion protein is used as an antigen for immunizations. In drug discovery, for example, human proteins, such as hIL-5, have been fused with Fc portions for the purpose of high-throughput screening assays to identify antagonists of hIL-5. (See, D. Bennett et al., J. Molecular Recognition 8:52-58 (1995); K. Johanson et al., J. Biol. Chem. 270:9459-9471 (1995).)

Moreover, the polypeptides of the present invention can be fused to marker sequences (also referred to as "tags"). Due to the availability of antibodies specific to such "tags", purification of the fused polypeptide of the invention, and/or its identification is significantly facilitated since antibodies specific to the polypeptides of the invention are not required. Such purification may be in the form of an affinity purification whereby an anti-tag antibody or another type of affinity matrix (e.g., anti-tag antibody attached to the matrix of a flow-thru column) that binds to the epitope tag is present. In preferred embodiments, the marker amino acid sequence is a hexa-histidine peptide, such as the tag provided in a pQE vector (QIAGEN, Inc., 9259 Eton Avenue, Chatsworth, Calif., 91311), among others, many of which are commercially available. As described in Gentz et al., Proc. Natl. Acad. Sci. USA 86:821-824 (1989), for instance, hexa-histidine provides for convenient purification of the fusion protein. Another peptide tag useful for purification, the "HA" tag, corresponds to an epitope derived from the influenza hemagglutinin protein. (Wilson et al., Cell 37:767 (1984)).

The skilled artisan would acknowledge the existence of other "tags" which could be readily substituted for the tags referred to supra for purification and/or identification of polypeptides of the present invention (Jones C., et al., J Chromatogr A. 707(1):3-22 (1995)). For example, the c-myc tag and the 8F9, 3C7, 6E10, G4m B7 and 9E10 antibodies thereto (Evan et al., Molecular and Cellular Biology 5:3610-3616 (1985)); the Herpes Simplex virus glycoprotein D (gD) tag and its antibody (Paborsky et al., Protein Engineering, 3(6): 547-553 (1990), the FLAG®-peptide—i.e., the octapeptide sequence DYKDDDDK (SEQ ID NO:56), (Hopp et al., Biotech. 6:1204-1210 (1988); the KT3 epitope peptide (Martin et al., Science, 255:192-194 (1992)); a-tubulin epitope peptide (Skinner et al., J. Biol. Chem., 266:15136-15166, (1991)); the T7 gene 10 protein peptide tag (Lutz-Freyermuth et al., Proc. Natl. Sci. USA, 87:6363-6397 (1990)), the FITC epitope (Zymed, Inc.), the GFP epitope (Zymed, Inc.), and the Rhodamine epitope (Zymed, Inc.).

The present invention also encompasses the attachment of up to nine codons encoding a repeating series of up to nine arginine amino acids to the coding region of a polynucleotide of the present invention. The invention also encompasses chemically derivitizing a polypeptide of the present invention with a repeating series of up to nine arginine amino acids. Such a tag, when attached to a polypeptide, has recently been shown to serve as a universal pass, allowing compounds access to the interior of cells without additional derivitization or manipulation (Wender, P., et al., unpublished data).

Protein fusions involving polypeptides of the present invention, including fragments and/or variants thereof, can be used for the following, non-limiting examples, subcellular localization of proteins, determination of protein-protein interactions via immunoprecipitation, purification of proteins via affinity chromatography, functional and/or structural characterization of protein. The present invention also encompasses the application of hapten specific antibodies for any of the uses referenced above for epitope fusion proteins. For example, the polypeptides of the present invention could be chemically derivatized to attach hapten molecules (e.g., DNP, (Zymed, Inc.)). Due to the availability of monoclonal antibodies specific to such haptens, the protein could be readily purified using immunoprecipation, for example.

Polypeptides of the present invention, including fragments and/or variants thereof, in addition to, antibodies directed against such polypeptides, fragments, and/or variants, may be fused to any of a number of known, and yet to be determined, toxins, such as ricin, saporin (Mashiba H, et al., Ann. N.Y. Acad. Sci. 1999; 886:233-5), or HC toxin (Tonukari N J, et al., Plant Cell. 2000 February; 12(2):237-248), for example. Such fusions could be used to deliver the toxins to desired tissues for which a ligand or a protein capable of binding to the polypeptides of the invention exists.

The invention encompasses the fusion of antibodies directed against polypeptides of the present invention, including variants and fragments thereof, to said toxins for delivering the toxin to specific locations in a cell, to specific tissues, and/or to specific species. Such bifunctional antibodies are known in the art, though a review describing additional advantageous fusions, including citations for methods of production, can be found in P. J. Hudson, Curr. Opp. In. 1 mm. 11:548-557, (1999); this publication, in addition to the references cited therein, are hereby incorporated by reference in their entirety herein. In this context, the term "toxin" may be expanded to include any heterologous protein, a small molecule, radionucleotides, cytotoxic drugs, liposomes, adhesion molecules, glycoproteins, ligands, cell or tissue-specific ligands, enzymes, of bioactive agents, biological response modifiers, anti-fungal agents, hormones, steroids, vitamins, peptides, peptide analogs, anti-allergenic agents, anti-tubercular agents, anti-viral agents, antibiotics, anti-protozoan agents, chelates, radioactive particles, radioactive ions, X-ray contrast agents, monoclonal antibodies, polyclonal antibodies and genetic material. In view of the present disclosure, one skilled in the art could determine whether any particular "toxin" could be used in the compounds of the present invention. Examples of suitable "toxins" listed above are exemplary only and are not intended to limit the "toxins" that may be used in the present invention.

Thus, any of these above fusions can be engineered using the polynucleotides or the polypeptides of the present invention.

Vectors, Host Cells, and Protein Production

The present invention also relates to vectors containing the polynucleotide of the present invention, host cells, and the production of polypeptides by recombinant techniques. The vector may be, for example, a phage, plasmid, viral, or retroviral vector. Retroviral vectors may be replication competent or replication defective. In the latter case, viral propagation generally will occur only in complementing host cells.

The polynucleotides may be joined to a vector containing a selectable marker for propagation in a host. Generally, a plasmid vector is introduced in a precipitate, such as a calcium phosphate precipitate, or in a complex with a charged lipid. If the vector is a virus, it may be packaged in vitro using an appropriate packaging cell line and then transduced into host cells.

The polynucleotide insert should be operatively linked to an appropriate promoter, such as the phage lambda PL promoter, the *E. coli* lac, trp, phoA and tac promoters, the SV40 early and late promoters and promoters of retroviral LTRs, to name a few. Other suitable promoters will be known to the skilled artisan. The expression constructs will further contain sites for transcription initiation, termination, and, in the transcribed region, a ribosome binding site for translation. The coding portion of the transcripts expressed by the constructs will preferably include a translation initiating codon at the beginning and a termination codon (UAA, UGA or UAG) appropriately positioned at the end of the polypeptide to be translated.

As indicated, the expression vectors will preferably include at least one selectable marker. Such markers include dihydrofolate reductase, G418 or neomycin resistance for eukaryotic cell culture and tetracycline, kanamycin or ampicillin resistance genes for culturing in *E. coli* and other bacteria. Representative examples of appropriate hosts include, but are not limited to, bacterial cells, such as *E. coli, Streptomyces* and *Salmonella typhimurium* cells; fungal cells, such as yeast cells (e.g., *Saccharomyces cerevisiae* or *Pichia pastoris* (ATCC® Accession No. 201178)); insect cells such as *Drosophila* S2 and *Spodoptera* Sf9 cells; animal cells such as CHO, COS, 293, and Bowes melanoma cells; and plant cells. Appropriate culture mediums and conditions for the above-described host cells are known in the art.

Among vectors preferred for use in bacteria include pQE70, pQE60 and pQE-9, available from QIAGEN, Inc.; PBLUESCRIPT® vectors, Phagescript vectors, pNH8A, pNH16a, pNH18A, pNH46A, available from Stratagene Cloning Systems, Inc.; and ptrc99a, pKK223-3, pKK233-3, pDR540, pRIT5 available from Pharmacia Biotech, Inc. Among preferred eukaryotic vectors are pWLNEO, pSV2CAT, pOG44, pXT1 and pSG available from Stratagene; and pSVK3, pBPV, pMSG and pSVL available from Pharmacia. Preferred expression vectors for use in yeast systems include, but are not limited to pYES2, pYD1, pTEF1/Zeo, pYES2/GS, pPICZ, pGAPZ, pGAPZalph, pPIC9, pPIC3.5, pHIL-D2; pHIL-S1, pPIC3.5K, pPIC9K, and PAO815 (all available from Invitrogen, Carlsbad, Calif.). Other suitable vectors will be readily apparent to the skilled artisan.

Introduction of the construct into the host cell can be effected by calcium phosphate transfection, DEAE-dextran mediated transfection, cationic lipid-mediated transfection, electroporation, transduction, infection, or other methods. Such methods are described in many standard laboratory manuals, such as Davis et al., Basic Methods In Molecular Biology (1986). It is specifically contemplated that the polypeptides of the present invention may in fact be expressed by a host cell lacking a recombinant vector.

A polypeptide of this invention can be recovered and purified from recombinant cell cultures by well-known methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Most preferably, high performance liquid chromatography ("HPLC") is employed for purification.

Polypeptides of the present invention, and preferably the secreted form, can also be recovered from: products purified from natural sources, including bodily fluids, tissues and cells, whether directly isolated or cultured; products of chemical synthetic procedures; and products produced by recombinant techniques from a prokaryotic or eukaryotic host, including, for example, bacterial, yeast, higher plant, insect, and mammalian cells. Depending upon the host employed in a recombinant production procedure, the polypeptides of the present invention may be glycosylated or may be non-glycosylated. In addition, polypeptides of the invention may also include an initial modified methionine residue, in some cases as a result of host-mediated processes. Thus, it is well known in the art that the N-terminal methionine encoded by the translation initiation codon generally is removed with high efficiency from any protein after translation in all eukaryotic cells. While the N-terminal methionine on most proteins also is efficiently removed in most prokaryotes, for some proteins, this prokaryotic removal process is inefficient, depending on the nature of the amino acid to which the N-terminal methionine is covalently linked.

In one embodiment, the yeast *Pichia pastoris* is used to express the polypeptide of the present invention in a eukaryotic system. *Pichia pastoris* is a methylotrophic yeast which can metabolize methanol as its sole carbon source. A main step in the methanol metabolization pathway is the oxidation of methanol to formaldehyde using O2. This reaction is catalyzed by the enzyme alcohol oxidase. In order to metabolize methanol as its sole carbon source, *Pichia pastoris* must generate high levels of alcohol oxidase due, in part, to the relatively low affinity of alcohol oxidase for O2. Consequently, in a growth medium depending on methanol as a main carbon source, the promoter region of one of the two alcohol oxidase genes (AOX1) is highly active. In the presence of methanol, alcohol oxidase produced from the AOX1 gene comprises up to approximately 30% of the total soluble protein in *Pichia pastoris*. See, Ellis, S. B., et al., Mol. Cell. Biol. 5:1111-21 (1985); Koutz, P. J, et al., Yeast 5:167-77 (1989); Tschopp, J. F., et al., Nucl. Acids Res. 15:3859-76 (1987). Thus, a heterologous coding sequence, such as, for example, a polynucleotide of the present invention, under the transcriptional regulation of all or part of the AOX1 regulatory sequence is expressed at exceptionally high levels in *Pichia* yeast grown in the presence of methanol.

In one example, the plasmid vector pPIC9K is used to express DNA encoding a polypeptide of the invention, as set forth herein, in a *Pichea* yeast system essentially as described in "*Pichia* Protocols: Methods in Molecular Biology" D. R. Higgins and J. Cregg, eds. The Humana Press, Totowa, N.J., 1998. This expression vector allows expression and secretion of a protein of the invention by virtue of the strong AOX1 promoter linked to the *Pichia pastoris* alkaline phosphatase (PHO) secretory signal peptide (i.e., leader) located upstream of a multiple cloning site.

Many other yeast vectors could be used in place of pPIC9K, such as, pYES2, pYD1, pTEF1/Zeo, pYES2/GS, pPICZ, pGAPZ, pGAPZalpha, pPIC9, pPIC3.5, pHIL-D2, pHIL-S1, pPIC3.5K, and PAO815, as one skilled in the art would readily appreciate, as long as the proposed expression construct provides appropriately located signals for transcription, translation, secretion (if desired), and the like, including an in-frame AUG, as required.

In another embodiment, high-level expression of a heterologous coding sequence, such as, for example, a polynucleotide of the present invention, may be achieved by cloning the heterologous polynucleotide of the invention into an expression vector such as, for example, pGAPZ or pGAPZalpha, and growing the yeast culture in the absence of methanol.

In addition to encompassing host cells containing the vector constructs discussed herein, the invention also encompasses primary, secondary, and immortalized host cells of vertebrate origin, particularly mammalian origin, that have been engineered to delete or replace endogenous genetic material (e.g., coding sequence), and/or to include genetic material (e.g., heterologous polynucleotide sequences) that is operably associated with the polynucleotides of the invention, and which activates, alters, and/or amplifies endogenous polynucleotides. For example, techniques known in the art may be used to operably associate heterologous control regions (e.g., promoter and/or enhancer) and endogenous polynucleotide sequences via homologous recombination, resulting in the formation of a new transcription unit (see, e.g., U.S. Pat. No. 5,641,670, issued Jun. 24, 1997; U.S. Pat. No. 5,733,761, issued Mar. 31, 1998; International Publication No. WO 96/29411, published Sep. 26, 1996; International Publication No. WO 94/12650, published Aug. 4, 1994; Koller et al., Proc. Natl. Acad. Sci. USA 86:8932-8935 (1989); and Zijlstra et al., Nature 342:435-438 (1989), the disclosures of each of which are incorporated by reference in their entireties).

In addition, polypeptides of the invention can be chemically synthesized using techniques known in the art (e.g., see Creighton, 1983, Proteins: Structures and Molecular Principles, W.H. Freeman & Co., N.Y., and Hunkapiller et al., Nature, 310:105-111 (1984)). For example, a polypeptide corresponding to a fragment of a polypeptide sequence of the invention can be synthesized by use of a peptide synthesizer. Furthermore, if desired, nonclassical amino acids or chemical amino acid analogs can be introduced as a substitution or addition into the polypeptide sequence. Non-classical amino acids include, but are not limited to, to the D-isomers of the common amino acids, 2,4-diaminobutyric acid, a-amino isobutyric acid, 4-aminobutyric acid, Abu, 2-amino butyric acid, g-Abu, e-Ahx, 6-amino hexanoic acid, Aib, 2-amino isobutyric acid, 3-amino propionic acid, ornithine, norleucine, norvaline, hydroxyproline, sarcosine, citrulline, homocitrulline, cysteic acid, t-butylglycine, t-butylalanine, phenylglycine, cyclohexylalanine, b-alanine, fluoro-amino acids, designer amino acids such as b-methyl amino acids, Ca-methyl amino acids, Na-methyl amino acids, and amino acid analogs in general. Furthermore, the amino acid can be D (dextrorotary) or L (levorotary).

The invention encompasses polypeptides which are differentially modified during or after translation, e.g., by glycosylation, acetylation, phosphorylation, amidation, derivatization by known protecting/blocking groups, proteolytic cleavage, linkage to an antibody molecule or other cellular ligand, etc. Any of numerous chemical modifications may be carried out by known techniques, including but not limited, to specific chemical cleavage by cyanogen bromide, trypsin, chymotrypsin, papain, V8 protease, NaBH4; acetylation, formylation, oxidation, reduction; metabolic synthesis in the presence of tunicamycin; etc.

Additional post-translational modifications encompassed by the invention include, for example, e.g., N-linked or O-linked carbohydrate chains, processing of N-terminal or C-terminal ends), attachment of chemical moieties to the amino acid backbone, chemical modifications of N-linked or O-linked carbohydrate chains, and addition or deletion of an N-terminal methionine residue as a result of prokaryotic host cell expression. The polypeptides may also be modified with a detectable label, such as an enzymatic, fluorescent, isotopic or affinity label to allow for detection and isolation of the protein, the addition of epitope tagged peptide fragments (e.g., FLAG®, HA, GST, thioredoxin, maltose binding protein, etc.), attachment of affinity tags such as biotin and/or streptavidin, the covalent attachment of chemical moieties to the amino acid backbone, N- or C-terminal processing of the polypeptides ends (e.g., proteolytic processing), deletion of the N-terminal methionine residue, etc.

Also provided by the invention are chemically modified derivatives of the polypeptides of the invention which may provide additional advantages such as increased solubility, stability and circulating time of the polypeptide, or decreased immunogenicity (see U.S. Pat. No. 4,179,337). The chemical moieties for derivitization may be selected from water soluble polymers such as polyethylene glycol, ethylene glycol/propylene glycol copolymers, carboxymethylcellulose, dextran, polyvinyl alcohol and the like. The polypeptides may be modified at random positions within the molecule, or at predetermined positions within the molecule and may include one, two, three or more attached chemical moieties.

The invention further encompasses chemical derivitization of the polypeptides of the present invention, preferably where the chemical is a hydrophilic polymer residue. Exemplary hydrophilic polymers, including derivatives, may be those that include polymers in which the repeating units contain one or more hydroxy groups (polyhydroxy polymers), including, for example, poly(vinyl alcohol); polymers in which the repeating units contain one or more amino groups (polyamine polymers), including, for example, peptides, polypeptides, proteins and lipoproteins, such as albumin and natural lipoproteins; polymers in which the repeating units contain one or more carboxy groups (polycarboxy polymers), including, for example, carboxymethylcellulose, alginic acid and salts thereof, such as sodium and calcium alginate, glycosaminoglycans and salts thereof, including salts of hyaluronic acid, phosphorylated and sulfonated derivatives of carbohydrates, genetic material, such as interleukin-2 and interferon, and phosphorothioate oligomers; and polymers in which the repeating units contain one or more saccharide moieties (polysaccharide polymers), including, for example, carbohydrates.

The molecular weight of the hydrophilic polymers may vary, and is generally about 50 to about 5,000,000, with polymers having a molecular weight of about 100 to about 50,000 being preferred. The polymers may be branched or unbranched. More preferred polymers have a molecular weight of about 150 to about 10,000, with molecular weights of 200 to about 8,000 being even more preferred.

For polyethylene glycol, the preferred molecular weight is between about 1 kDa and about 100 kDa (the term "about" indicating that in preparations of polyethylene glycol, some molecules will weigh more, some less, than the stated molecular weight) for ease in handling and manufacturing. Other sizes may be used, depending on the desired therapeutic profile (e.g., the duration of sustained release desired, the effects, if any on biological activity, the ease in handling, the degree or lack of antigenicity and other known effects of the polyethylene glycol to a therapeutic protein or analog).

Additional preferred polymers which may be used to derivatize polypeptides of the invention, include, for example, poly(ethylene glycol) (PEG), poly(vinylpyrrolidine), polyoxomers, polysorbate and poly(vinyl alcohol), with PEG polymers being particularly preferred. Preferred among the PEG polymers are PEG polymers having a molecular weight of from about 100 to about 10,000. More preferably, the PEG polymers have a molecular weight of from about 200 to about 8,000, with PEG 2,000, PEG 5,000 and PEG 8,000, which have molecular weights of 2,000, 5,000 and 8,000, respectively, being even more preferred. Other suitable hydrophilic polymers, in addition to those exemplified above, will be readily apparent to one skilled in the art based on the present disclosure. Generally, the polymers used may include polymers that can be attached to the polypeptides of the invention via alkylation or acylation reactions.

The polyethylene glycol molecules (or other chemical moieties) should be attached to the protein with consideration of effects on functional or antigenic domains of the protein. There are a number of attachment methods available to those skilled in the art, e.g., EP 0 401 384, herein incorporated by reference (coupling PEG to G-CSF), see also Malik et al., Exp. Hematol. 20:1028-1035 (1992) (reporting pegylation of GM-CSF using tresyl chloride). For example, polyethylene glycol may be covalently bound through amino acid residues via a reactive group, such as, a free amino or carboxyl group. Reactive groups are those to which an activated polyethylene glycol molecule may be bound. The amino acid residues having a free amino group may include lysine residues and the N-terminal amino acid residues; those having a free carboxyl group may include aspartic acid residues glutamic acid residues and the C-terminal amino acid residue. Sulfhydryl groups may also be used as a reactive group for attaching the polyethylene glycol molecules. Preferred for therapeutic purposes is attachment at an amino group, such as attachment at the N-terminus or lysine group.

One may specifically desire proteins chemically modified at the N-terminus. Using polyethylene glycol as an illustration of the present composition, one may select from a variety of polyethylene glycol molecules (by molecular weight, branching, etc.), the proportion of polyethylene glycol molecules to protein (polypeptide) molecules in the reaction mix, the type of pegylation reaction to be performed, and the method of obtaining the selected N-terminally pegylated protein. The method of obtaining the N-terminally pegylated preparation (i.e., separating this moiety from other monopegylated moieties if necessary) may be by purification of the N-terminally pegylated material from a population of pegylated protein molecules. Selective proteins chemically modified at the N-terminus modification may be accomplished by reductive alkylation which exploits differential reactivity of different types of primary amino groups (lysine versus the N-terminus) available for derivatization in a particular protein. Under the appropriate reaction conditions, substantially selective derivatization of the protein at the N-terminus with a carbonyl group containing polymer is achieved.

As with the various polymers exemplified above, it is contemplated that the polymeric residues may contain functional groups in addition, for example, to those typically involved in linking the polymeric residues to the polypeptides of the present invention. Such functionalities include, for example, carboxyl, amine, hydroxy and thiol groups. These functional groups on the polymeric residues can be further reacted, if desired, with materials that are generally reactive with such functional groups and which can assist in targeting specific tissues in the body including, for example, diseased tissue. Exemplary materials which can be reacted with the additional functional groups include, for example, proteins, including antibodies, carbohydrates, peptides, glycopeptides, glycolipids, lectins, and nucleosides.

In addition to residues of hydrophilic polymers, the chemical used to derivatize the polypeptides of the present invention can be a saccharide residue. Exemplary saccharides which can be derived include, for example, monosaccharides or sugar alcohols, such as erythrose, threose, ribose, arabinose, xylose, lyxose, fructose, sorbitol, mannitol and sedoheptulose, with preferred monosaccharides being fructose, mannose, xylose, arabinose, mannitol and sorbitol; and disaccharides, such as lactose, sucrose, maltose and cellobiose. Other saccharides include, for example, inositol and ganglioside head groups. Other suitable saccharides, in addition to those exemplified above, will be readily apparent to one skilled in the art based on the present disclosure. Generally, saccharides which may be used for derivitization include saccharides that can be attached to the polypeptides of the invention via alkylation or acylation reactions.

Moreover, the invention also encompasses derivitization of the polypeptides of the present invention, for example, with lipids (including cationic, anionic, polymerized, charged, synthetic, saturated, unsaturated, and any combination of the above, etc.). stabilizing agents.

The invention encompasses derivitization of the polypeptides of the present invention, for example, with compounds that may serve a stabilizing function (e.g., to increase the polypeptides half-life in solution, to make the polypeptides more water soluble, to increase the polypeptides hydrophilic or hydrophobic character, etc.). Polymers useful as stabilizing materials may be of natural, semi-synthetic (modified natural) or synthetic origin. Exemplary natural polymers include naturally occurring polysaccharides, such as, for example, arabinans, fructans, fucans, galactans, galacturonans, glucans, mannans, xylans (such as, for example, inulin), levan, fucoidan, carrageenan, galatocarolose, pectic acid, pectins, including amylose, pullulan, glycogen, amylopectin, cellulose, dextran, dextrin, dextrose, glucose, polyglucose, polydextrose, pustulan, chitin, agarose, keratin, chondroitin, dermatan, hyaluronic acid, alginic acid, xanthin gum, starch and various other natural homopolymer or heteropolymers, such as those containing one or more of the following aldoses, ketoses, acids or amines: erythose, threose, ribose, arabinose, xylose, lyxose, allose, altrose, glucose, dextrose, mannose, gulose, idose, galactose, talose, erythrulose, ribulose, xylulose, psicose, fructose, sorbose, tagatose, mannitol, sorbitol, lactose, sucrose, trehalose, maltose, cellobiose, glycine, serine, threonine, cysteine, tyrosine, asparagine, glutamine, aspartic acid, glutamic acid, lysine, arginine, histidine, glucuronic acid, gluconic acid, glucaric acid, galacturonic acid, mannuronic acid, glucosamine, galactosamine, and neuraminic acid, and naturally occurring derivatives thereof. Accordingly, suitable polymers include, for example, proteins, such as albumin, polyalginates, and polylactide-coglycolide polymers. Exemplary semi-synthetic polymers include carboxymethylcellulose, hydroxymethylcellulose, hydroxypropylmethylcellulose, methylcellulose, and methoxycellulose. Exemplary synthetic polymers include polyphosphazenes, hydroxyapatites, fluoroapatite polymers, polyethylenes (such as, for example, polyethylene glycol (including for example, the class of compounds referred to as PLURONIC®, commercially available from BASF, Parsippany, N.J.), polyoxyethylene, and polyethylene terephthalate), polypropylenes (such as, for example, polypropylene glycol), polyurethanes (such as, for example, polyvinyl alcohol (PVA), polyvinyl chloride and polyvinylpyrrolidone), polyamides including nylon, polystyrene, polylactic acids, fluorinated hydrocarbon polymers, fluorinated carbon polymers (such as, for example, polytetrafluoroethylene), acrylate, methacrylate, and polymethylmethacrylate, and derivatives thereof. Methods for the preparation of derivatized polypeptides of the invention which employ polymers as stabilizing compounds will be readily apparent to one skilled in the art, in view of the present disclosure, when coupled with information known in the art, such as that described and referred to in Unger, U.S. Pat. No. 5,205,290, the disclosure of which is hereby incorporated by reference herein in its entirety.

Moreover, the invention encompasses additional modifications of the polypeptides of the present invention. Such additional modifications are known in the art, and are specifically provided, in addition to methods of derivitization, etc., in U.S. Pat. No. 6,028,066, which is hereby incorporated in its entirety herein.

The polypeptides of the invention may be in monomers or multimers (i.e., dimers, trimers, tetramers and higher multimers). Accordingly, the present invention relates to monomers and multimers of the polypeptides of the invention, their preparation, and compositions (preferably, Therapeutics) containing them. In specific embodiments, the polypeptides of the invention are monomers, dimers, trimers or tetramers. In additional embodiments, the multimers of the invention are at least dimers, at least trimers, or at least tetramers.

Multimers encompassed by the invention may be homomers or heteromers. As used herein, the term homomer, refers to a multimer containing only polypeptides corresponding to the amino acid sequence of SEQ ID NO:Y or encoded by the cDNA contained in a deposited clone (including fragments, variants, splice variants, and fusion proteins, corresponding to these polypeptides as described herein). These homomers may contain polypeptides having identical or different amino acid sequences. In a specific embodiment, a homomer of the invention is a multimer containing only polypeptides having an identical amino acid sequence. In another specific embodiment, a homomer of the invention is a multimer containing polypeptides having different amino acid sequences. In specific embodiments, the multimer of the invention is a homodimer (e.g., containing polypeptides having identical or different amino acid sequences) or a homotrimer (e.g., containing polypeptides having identical and/or different amino acid sequences). In additional embodiments, the homomeric multimer of the invention is at least a homodimer, at least a homotrimer, or at least a homotetramer.

As used herein, the term heteromer refers to a multimer containing one or more heterologous polypeptides (i.e., polypeptides of different proteins) in addition to the polypeptides of the invention. In a specific embodiment, the multimer of the invention is a heterodimer, a heterotrimer, or a heterotetramer. In additional embodiments, the heteromeric multimer of the invention is at least a heterodimer, at least a heterotrimer, or at least a heterotetramer.

Multimers of the invention may be the result of hydrophobic, hydrophilic, ionic and/or covalent associations and/or may be indirectly linked, by for example, liposome formation. Thus, in one embodiment, multimers of the invention, such as, for example, homodimers or homotrimers, are formed when polypeptides of the invention contact one another in solution. In another embodiment, heteromultimers of the invention, such as, for example, heterotrimers or heterotetramers, are formed when polypeptides of the invention contact antibodies to the polypeptides of the invention (including antibodies to the heterologous polypeptide sequence in a fusion protein of the invention) in solution. In other embodiments, multimers of the invention are formed by covalent associations with and/or between the polypeptides of the invention. Such covalent associations may involve one or more amino acid residues contained in the polypeptide sequence (e.g., that recited in the sequence listing, or contained in the polypeptide encoded by a deposited clone). In one instance, the covalent associations are cross-linking between cysteine residues located within the polypeptide sequences which interact in the native (i.e., naturally occurring) polypeptide. In another instance, the covalent associations are the consequence of chemical or recombinant manipulation. Alternatively, such covalent associations may involve one or more amino acid residues contained in the heterologous polypeptide sequence in a fusion protein of the invention.

In one example, covalent associations are between the heterologous sequence contained in a fusion protein of the invention (see, e.g., U.S. Pat. No. 5,478,925). In a specific example, the covalent associations are between the heterologous sequence contained in an Fc fusion protein of the invention (as described herein). In another specific example, covalent associations of fusion proteins of the invention are between heterologous polypeptide sequence from another protein that is capable of forming covalently associated multimers, such as for example, osteoprotegerin (see, e.g., International Publication NO: WO 98/49305, the contents of which are herein incorporated by reference in its entirety). In another embodiment, two or more polypeptides of the invention are joined through peptide linkers. Examples include those peptide linkers described in U.S. Pat. No. 5,073,627 (hereby incorporated by reference). Proteins comprising multiple polypeptides of the invention separated by peptide linkers may be produced using conventional recombinant DNA technology.

Another method for preparing multimer polypeptides of the invention involves use of polypeptides of the invention fused to a leucine zipper or isoleucine zipper polypeptide sequence. Leucine zipper and isoleucine zipper domains are polypeptides that promote multimerization of the proteins in which they are found. Leucine zippers were originally identified in several DNA-binding proteins (Landschulz et al., Science 240:1759, (1988)), and have since been found in a variety of different proteins. Among the known leucine zippers are naturally occurring peptides and derivatives thereof that dimerize or trimerize. Examples of leucine zipper domains suitable for producing soluble multimeric proteins of the invention are those described in PCT application WO 94/10308, hereby incorporated by reference. Recombinant fusion proteins comprising a polypeptide of the invention fused to a polypeptide sequence that dimerizes or trimerizes in solution are expressed in suitable host cells, and the resulting soluble multimeric fusion protein is recovered from the culture supernatant using techniques known in the art.

Trimeric polypeptides of the invention may offer the advantage of enhanced biological activity. Preferred leucine zipper moieties and isoleucine moieties are those that preferentially form trimers. One example is a leucine zipper derived from lung surfactant protein D (SPD), as described in Hoppe et al. (FEBS Letters 344:191, (1994)) and in U.S. patent application Ser. No. 08/446,922, hereby incorporated by reference. Other peptides derived from naturally occurring trimeric proteins may be employed in preparing trimeric polypeptides of the invention.

In another example, proteins of the invention are associated by interactions between FLAG® polypeptide sequence contained in fusion proteins of the invention containing FLAG® polypeptide sequence. In a further embodiment, associations proteins of the invention are associated by interactions between heterologous polypeptide sequence contained in FLAG® fusion proteins of the invention and anti-FLAG® antibody.

The multimers of the invention may be generated using chemical techniques known in the art. For example, polypeptides desired to be contained in the multimers of the invention may be chemically cross-linked using linker molecules and linker molecule length optimization techniques known in the art (see, e.g., U.S. Pat. No. 5,478,925, which is herein incorporated by reference in its entirety). Additionally, multimers of the invention may be generated using techniques known in the art to form one or more inter-molecule cross-links between the cysteine residues located within the sequence of the polypeptides desired to be contained in the multimer (see, e.g., U.S. Pat. No. 5,478,925, which is herein incorporated by reference in its entirety). Further, polypeptides of the invention may be routinely modified by the addition of cysteine or biotin to the C terminus or N-terminus of the polypeptide and techniques known in the art may be applied to generate multimers containing one or more of these modified polypeptides (see, e.g., U.S. Pat. No. 5,478,925, which is herein incorporated by reference in its entirety). Additionally, techniques known in the art may be applied to generate liposomes containing the polypeptide components desired to be contained in the multimer of the invention (see, e.g., U.S. Pat. No. 5,478,925, which is herein incorporated by reference in its entirety).

Alternatively, multimers of the invention may be generated using genetic engineering techniques known in the art. In one embodiment, polypeptides contained in multimers of the invention are produced recombinantly using fusion protein technology described herein or otherwise known in the art (see, e.g., U.S. Pat. No. 5,478,925, which is herein incorporated by reference in its entirety). In a specific embodiment, polynucleotides coding for a homodimer of the invention are generated by ligating a polynucleotide sequence encoding a polypeptide of the invention to a sequence encoding a linker polypeptide and then further to a synthetic polynucleotide encoding the translated product of the polypeptide in the reverse orientation from the original C-terminus to the N-terminus (lacking the leader sequence) (see, e.g., U.S. Pat. No. 5,478,925, which is herein incorporated by reference in its entirety). In another embodiment, recombinant techniques described herein or otherwise known in the art are applied to generate recombinant polypeptides of the invention which contain a transmembrane domain (or hydrophobic or signal peptide) and which can be incorporated by membrane reconstitution techniques into liposomes (see, e.g., U.S. Pat. No. 5,478,925, which is herein incorporated by reference in its entirety).

In addition, the polynucleotide insert of the present invention could be operatively linked to "artificial" or chimeric promoters and transcription factors. Specifically, the artificial promoter could comprise, or alternatively consist, of any combination of cis-acting DNA sequence elements that are recognized by trans-acting transcription factors. Preferably, the cis acting DNA sequence elements and trans-acting transcription factors are operable in mammals. Further, the trans-acting transcription factors of such "artificial" promoters could also be "artificial" or chimeric in design themselves and could act as activators or repressors to said "artificial" promoter.

Uses of the Polynucleotides

Each of the polynucleotides identified herein can be used in numerous ways as reagents. The following description should be considered exemplary and utilizes known techniques.

The polynucleotides of the present invention are useful for chromosome identification. There exists an ongoing need to identify new chromosome markers, since few chromosome marking reagents, based on actual sequence data (repeat polymorphisms), are presently available. Each polynucleotide of the present invention can be used as a chromosome marker.

Briefly, sequences can be mapped to chromosomes by preparing PCR primers (preferably 15-25 bp) from the sequences shown in SEQ ID NO:X. Primers can be selected using computer analysis so that primers do not span more than one predicted exon in the genomic DNA. These primers are then used for PCR screening of somatic cell hybrids containing individual human chromosomes. Only those hybrids containing the human gene corresponding to the SEQ ID NO:X will yield an amplified fragment.

Similarly, somatic hybrids provide a rapid method of PCR mapping the polynucleotides to particular chromosomes. Three or more clones can be assigned per day using a single thermal cycler. Moreover, sublocalization of the polynucleotides can be achieved with panels of specific chromosome fragments. Other gene mapping strategies that can be used include in situ hybridization, prescreening with labeled flow-sorted chromosomes, and preselection by hybridization to construct chromosome specific-cDNA libraries.

Precise chromosomal location of the polynucleotides can also be achieved using fluorescence in situ hybridization (FISH) of a metaphase chromosomal spread. This technique uses polynucleotides as short as 500 or 600 bases; however, polynucleotides 2,000-4,000 bp are preferred. For a review of this technique, see Verma et al., "Human Chromosomes: a Manual of Basic Techniques" Pergamon Press, New York (1988).

For chromosome mapping, the polynucleotides can be used individually (to mark a single chromosome or a single site on that chromosome) or in panels (for marking multiple sites and/or multiple chromosomes). Preferred polynucleotides correspond to the noncoding regions of the cDNAs because the coding sequences are more likely conserved within gene families, thus increasing the chance of cross hybridization during chromosomal mapping.

Once a polynucleotide has been mapped to a precise chromosomal location, the physical position of the polynucleotide can be used in linkage analysis. Linkage analysis establishes coinheritance between a chromosomal location and presentation of a particular disease. Disease mapping data are known in the art. Assuming 1 megabase mapping resolution and one gene per 20 kb, a cDNA precisely localized to a chromosomal region associated with the disease could be one of 50-500 potential causative genes.

Thus, once coinheritance is established, differences in the polynucleotide and the corresponding gene between affected and unaffected organisms can be examined. First, visible structural alterations in the chromosomes, such as deletions or translocations, are examined in chromosome spreads or by PCR. If no structural alterations exist, the presence of point mutations are ascertained. Mutations observed in some or all affected organisms, but not in normal organisms, indicates that the mutation may cause the disease. However, complete sequencing of the polypeptide and the corresponding gene from several normal organisms is required to distinguish the mutation from a polymorphism. If a new polymorphism is identified, this polymorphic polypeptide can be used for further linkage analysis.

Furthermore, increased or decreased expression of the gene in affected organisms as compared to unaffected organisms can be assessed using polynucleotides of the present invention. Any of these alterations (altered expression, chromosomal rearrangement, or mutation) can be used as a diagnostic or prognostic marker.

Thus, the invention also provides a diagnostic method useful during diagnosis of a disorder, involving measuring the expression level of polynucleotides of the present invention in cells or body fluid from an organism and comparing the measured gene expression level with a standard level of polynucleotide expression level, whereby an increase or decrease in the gene expression level compared to the standard is indicative of a disorder.

By "measuring the expression level of a polynucleotide of the present invention" is intended qualitatively or quantitatively measuring or estimating the level of the polypeptide of the present invention or the level of the mRNA encoding the polypeptide in a first biological sample either directly (e.g., by determining or estimating absolute protein level or mRNA level) or relatively (e.g., by comparing to the polypeptide level or mRNA level in a second biological sample). Preferably, the polypeptide level or mRNA level in the first biological sample is measured or estimated and compared to a standard polypeptide level or mRNA level, the standard being taken from a second biological sample obtained from an individual not having the disorder or being determined by averaging levels from a population of organisms not having a disorder. As will be appreciated in the art, once a standard polypeptide level or mRNA level is known, it can be used repeatedly as a standard for comparison.

By "biological sample" is intended any biological sample obtained from an organism, body fluids, cell line, tissue culture, or other source which contains the polypeptide of the present invention or mRNA. As indicated, biological samples include body fluids (such as the following non-limiting examples, sputum, amniotic fluid, urine, saliva, breast milk, secretions, interstitial fluid, blood, serum, spinal fluid, etc.) which contain the polypeptide of the present invention, and other tissue sources found to express the polypeptide of the present invention. Methods for obtaining tissue biopsies and body fluids from organisms are well known in the art. Where the biological sample is to include mRNA, a tissue biopsy is the preferred source.

The method(s) provided above may preferably be applied in a diagnostic method and/or kits in which polynucleotides and/or polypeptides are attached to a solid support. In one exemplary method, the support may be a "gene chip" or a "biological chip" as described in U.S. Pat. Nos. 5,837,832, 5,874,219, and 5,856,174. Further, such a gene chip with polynucleotides of the present invention attached may be used to identify polymorphisms between the polynucleotide sequences, with polynucleotides isolated from a test subject. The knowledge of such polymorphisms (i.e. their location, as well as, their existence) would be beneficial in identifying disease loci for many disorders, including proliferative diseases and conditions. Such a method is described in U.S. Pat. Nos. 5,858,659 and 5,856,104. The US patents referenced supra are hereby incorporated by reference in their entirety herein.

The present invention encompasses polynucleotides of the present invention that are chemically synthesized, or reproduced as peptide nucleic acids (PNA), or according to other methods known in the art. The use of PNAs would serve as the preferred form if the polynucleotides are incorporated onto a solid support, or gene chip. For the purposes of the present invention, a peptide nucleic acid (PNA) is a polyamide type of DNA analog and the monomeric units for adenine, guanine, thymine and cytosine are available commercially (Perceptive Biosystems). Certain components of DNA, such as phosphorus, phosphorus oxides, or deoxyribose derivatives, are not present in PNAs. As disclosed by P. E. Nielsen, M. Egholm, R. H. Berg and O. Buchardt, Science 254, 1497 (1991); and M. Egholm, O. Buchardt, L. Christensen, C. Behrens, S. M. Freier, D. A. Driver, R. H. Berg, S. K. Kim, B. Norden, and P. E. Nielsen, Nature 365, 666 (1993), PNAs bind specifically and tightly to complementary DNA strands and are not degraded by nucleases. In fact, PNA binds more strongly to DNA than DNA itself does. This is probably because there is no electrostatic repulsion between the two strands, and also the polyamide backbone is more flexible. Because of this, PNA/DNA duplexes bind under a wider range of stringency conditions than DNA/DNA duplexes, making it easier to perform multiplex hybridization. Smaller probes can be used than with DNA due to the stronger binding characteristics of PNA:DNA hybrids. In addition, it is more likely that single base mismatches can be determined with PNA/DNA hybridization because a single mismatch in a PNA/DNA 15-mer lowers the melting point ($T_m$) by 8°-20° C., vs. 4°-16° C. for the DNA/DNA 15-mer duplex. Also, the absence of charge groups in PNA means that hybridization can be done at low ionic strengths and reduce possible interference by salt during the analysis.

In addition to the foregoing, a polynucleotide can be used to control gene expression through triple helix formation or antisense DNA or RNA. Antisense techniques are discussed, for example, in Okano, J. Neurochem. 56: 560 (1991); "Oligodeoxynucleotides as Antisense Inhibitors of Gene Expression, CRC Press, Boca Raton, Fla. (1988). Triple helix formation is discussed in, for instance Lee et al., Nucleic Acids Research 6: 3073 (1979); Cooney et al., Science 241: 456 (1988); and Dervan et al., Science 251: 1360 (1991). Both methods rely on binding of the polynucleotide to a complementary DNA or RNA. For these techniques, preferred polynucleotides are usually oligonucleotides 20 to 40 bases in length and complementary to either the region of the gene involved in transcription (triple helix—see Lee et al., Nucl. Acids Res. 6:3073 (1979); Cooney et al., Science 241:456 (1988); and Dervan et al., Science 251:1360 (1991)) or to the mRNA itself (antisense—Okano, J. Neurochem. 56:560 (1991); Oligodeoxy-nucleotides as Antisense Inhibitors of Gene Expression, CRC Press, Boca Raton, Fla. (1988).) Triple helix formation optimally results in a shut-off of RNA transcription from DNA, while antisense RNA hybridization blocks translation of an mRNA molecule into polypeptide. Both techniques are effective in model systems, and the information disclosed herein can be used to design antisense or triple helix polynucleotides in an effort to treat or prevent disease.

The present invention encompasses the addition of a nuclear localization signal, operably linked to the 5' end, 3' end, or any location therein, to any of the oligonucleotides, antisense oligonucleotides, triple helix oligonucleotides, ribozymes, PNA oligonucleotides, and/or polynucleotides, of the present invention. See, for example, G. Cutrona, et al., Nat. Biotech., 18:300-303, (2000); which is hereby incorporated herein by reference.

Polynucleotides of the present invention are also useful in gene therapy. One goal of gene therapy is to insert a normal gene into an organism having a defective gene, in an effort to correct the genetic defect. The polynucleotides disclosed in the present invention offer a means of targeting such genetic defects in a highly accurate manner. Another goal is to insert a new gene that was not present in the host genome, thereby producing a new trait in the host cell. In one example, polynucleotide sequences of the present invention may be used to construct chimeric RNA/DNA oligonucleotides corresponding to said sequences, specifically designed to induce host cell mismatch repair mechanisms in an organism upon systemic injection, for example (Bartlett, R. J., et al., Nat. Biotech, 18:615-622 (2000), which is hereby incorporated by reference herein in its entirety). Such RNA/DNA oligonucleotides could be designed to correct genetic defects in certain host strains, and/or to introduce desired phenotypes in the host (e.g., introduction of a specific polymorphism within an endogenous gene corresponding to a polynucleotide of the present invention that may ameliorate and/or prevent a disease symptom and/or disorder, etc.). Alternatively, the polynucleotide sequence of the present invention may be used to construct duplex oligonucleotides corresponding to said sequence, specifically designed to correct genetic defects in certain host strains, and/or to introduce desired phenotypes into the host (e.g., introduction of a specific polymorphism within an endogenous gene corresponding to a polynucleotide of the present invention that may ameliorate and/or prevent a disease symptom and/or disorder, etc). Such methods of using duplex oligonucleotides are known in the art and are encompassed by the present invention (see EP1007712, which is hereby incorporated by reference herein in its entirety).

The polynucleotides are also useful for identifying organisms from minute biological samples. The United States military, for example, is considering the use of restriction fragment length polymorphism (RFLP) for identification of its personnel. In this technique, an individual's genomic DNA is digested with one or more restriction enzymes, and probed on a Southern blot to yield unique bands for identifying personnel. This method does not suffer from the current limitations of "Dog Tags" which can be lost, switched, or stolen, making positive identification difficult. The polynucleotides of the present invention can be used as additional DNA markers for RFLP.

The polynucleotides of the present invention can also be used as an alternative to RFLP, by determining the actual base-by-base DNA sequence of selected portions of an organisms genome. These sequences can be used to prepare PCR primers for amplifying and isolating such selected DNA, which can then be sequenced. Using this technique, organisms can be identified because each organism will have a unique set of DNA sequences. Once an unique ID database is established for an organism, positive identification of that organism, living or dead, can be made from extremely small tissue samples. Similarly, polynucleotides of the present invention can be used as polymorphic markers, in addition to, the identification of transformed or non-transformed cells and/or tissues.

There is also a need for reagents capable of identifying the source of a particular tissue. Such need arises, for example, when presented with tissue of unknown origin. Appropriate reagents can comprise, for example, DNA probes or primers specific to particular tissue prepared from the sequences of the present invention. Panels of such reagents can identify tissue by species and/or by organ type. In a similar fashion, these reagents can be used to screen tissue cultures for contamination. Moreover, as mentioned above, such reagents can be used to screen and/or identify transformed and non-transformed cells and/or tissues.

In the very least, the polynucleotides of the present invention can be used as molecular weight markers on Southern gels, as diagnostic probes for the presence of a specific mRNA in a particular cell type, as a probe to "subtract-out" known sequences in the process of discovering novel polynucleotides, for selecting and making oligomers for attachment to a "gene chip" or other support, to raise anti-DNA antibodies using DNA immunization techniques, and as an antigen to elicit an immune response.

Uses of the Polypeptides

Each of the polypeptides identified herein can be used in numerous ways. The following description should be considered exemplary and utilizes known techniques.

A polypeptide of the present invention can be used to assay protein levels in a biological sample using antibody-based techniques. For example, protein expression in tissues can be studied with classical immunohistological methods. (Jalkanen, M., et al., J. Cell. Biol. 101:976-985 (1985); Jalkanen, M., et al., J. Cell. Biol. 105:3087-3096 (1987).) Other antibody-based methods useful for detecting protein gene expression include immunoassays, such as the enzyme linked immunosorbent assay (ELISA) and the radioimmunoassay (RIA). Suitable antibody assay labels are known in the art and include enzyme labels, such as, glucose oxidase, and radioisotopes, such as iodine ($^{125}I$, $^{121}I$), carbon ($^{14}C$), sulfur ($^{35}S$), tritium ($^{3}H$), indium ($^{112}In$), and technetium ($^{99m}Tc$), and fluorescent labels, such as fluorescein and rhodamine, and biotin.

In addition to assaying protein levels in a biological sample, proteins can also be detected in vivo by imaging. Antibody labels or markers for in vivo imaging of protein include those detectable by X-radiography, NMR or ESR. For X-radiography, suitable labels include radioisotopes such as barium or cesium, which emit detectable radiation but are not overtly harmful to the subject. Suitable markers for NMR and ESR include those with a detectable characteristic spin, such as deuterium, which may be incorporated into the antibody by labeling of nutrients for the relevant hybridoma.

A protein-specific antibody or antibody fragment which has been labeled with an appropriate detectable imaging moiety, such as a radioisotope (for example, $^{131}I$, $^{112}In$, $^{99m}Tc$), a radio-opaque substance, or a material detectable by nuclear magnetic resonance, is introduced (for example, parenterally, subcutaneously, or intraperitoneally) into the mammal. It will be understood in the art that the size of the subject and the imaging system used will determine the quantity of imaging moiety needed to produce diagnostic images. In the case of a radioisotope moiety, for a human subject, the quantity of radioactivity injected will normally range from about 5 to 20 millicuries of $^{99m}Tc$. The labeled antibody or antibody fragment will then preferentially accumulate at the location of cells which contain the specific protein. In vivo tumor imaging is described in S. W. Burchiel et al., "Immunopharmacokinetics of Radiolabeled Antibodies and Their Fragments." (Chapter 13 in Tumor Imaging The Radiochemical Detection of Cancer, S. W. Burchiel and B. A. Rhodes, eds., Masson Publishing Inc. (1982).)

Thus, the invention provides a diagnostic method of a disorder, which involves (a) assaying the expression of a polypeptide of the present invention in cells or body fluid of an individual; and (b) comparing the level of gene expression with a standard gene expression level, whereby an increase or decrease in the assayed polypeptide gene expression level compared to the standard expression level is indicative of a disorder. With respect to cancer, the presence of a relatively high amount of transcript in biopsied tissue from an individual may indicate a predisposition for the development of the disease, or may provide a means for detecting the disease prior to the appearance of actual clinical symptoms. A more definitive diagnosis of this type may allow health professionals to employ preventative measures or aggressive treatment earlier thereby preventing the development or further progression of the cancer.

Moreover, polypeptides of the present invention can be used to treat, prevent, and/or diagnose disease. For example, patients can be administered a polypeptide of the present invention in an effort to replace absent or decreased levels of the polypeptide (e.g., insulin), to supplement absent or decreased levels of a different polypeptide (e.g., hemoglobin S for hemoglobin B, SOD, catalase, DNA repair proteins), to inhibit the activity of a polypeptide (e.g., an oncogene or tumor suppressor), to activate the activity of a polypeptide (e.g., by binding to a receptor), to reduce the activity of a membrane bound receptor by competing with it for free ligand (e.g., soluble TNF receptors used in reducing inflammation), or to bring about a desired response (e.g., blood vessel growth inhibition, enhancement of the immune response to proliferative cells or tissues).

Similarly, antibodies directed to a polypeptide of the present invention can also be used to treat, prevent, and/or diagnose disease. For example, administration of an antibody directed to a polypeptide of the present invention can bind and reduce overproduction of the polypeptide. Similarly, administration of an antibody can activate the polypeptide, such as by binding to a polypeptide bound to a membrane (receptor).

At the very least, the polypeptides of the present invention can be used as molecular weight markers on SDS-PAGE gels or on molecular sieve gel filtration columns using methods well known to those of skill in the art. Polypeptides can also be used to raise antibodies, which in turn are used to measure protein expression from a recombinant cell, as a way of assessing transformation of the host cell. Moreover, the polypeptides of the present invention can be used to test the following biological activities.

Gene Therapy Methods

Another aspect of the present invention is to gene therapy methods for treating or preventing disorders, diseases and conditions. The gene therapy methods relate to the introduction of nucleic acid (DNA, RNA and antisense DNA or RNA) sequences into an animal to achieve expression of a polypeptide of the present invention. This method requires a polynucleotide which codes for a polypeptide of the invention that operatively linked to a promoter and any other genetic elements necessary for the expression of the polypeptide by the target tissue. Such gene therapy and delivery techniques are known in the art, see, for example, WO 90/11092, which is herein incorporated by reference.

Thus, for example, cells from a patient may be engineered with a polynucleotide (DNA or RNA) comprising a promoter operably linked to a polynucleotide of the invention ex vivo, with the engineered cells then being provided to a patient to be treated with the polypeptide. Such methods are well-known in the art. For example, see Belldegrun et al., J. Natl. Cancer Inst., 85:207-216 (1993); Ferrantini et al., Cancer Research, 53:107-1112 (1993); Ferrantini et al., J. Immunology 153: 4604-4615 (1994); Kaido, T., et al., Int. J. Cancer 60: 221-229 (1995); Ogura et al., Cancer Research 50: 5102-5106 (1990); Santodonato, et al., Human Gene Therapy 7:1-10 (1996); Santodonato, et al., Gene Therapy 4:1246-1255 (1997); and Zhang, et al., Cancer Gene Therapy 3: 31-38 (1996)), which are herein incorporated by reference. In one embodiment, the cells which are engineered are arterial cells. The arterial cells may be reintroduced into the patient through direct injection to the artery, the tissues surrounding the artery, or through catheter injection.

As discussed in more detail below, the polynucleotide constructs can be delivered by any method that delivers injectable materials to the cells of an animal, such as, injection into the interstitial space of tissues (heart, muscle, skin, lung, liver, and the like). The polynucleotide constructs may be delivered in a pharmaceutically acceptable liquid or aqueous carrier.

In one embodiment, the polynucleotide of the invention is delivered as a naked polynucleotide. The term "naked" polynucleotide, DNA or RNA refers to sequences that are free from any delivery vehicle that acts to assist, promote or facilitate entry into the cell, including viral sequences, viral particles, liposome formulations, lipofectin or precipitating agents and the like. However, the polynucleotides of the invention can also be delivered in liposome formulations and lipofectin formulations and the like can be prepared by methods well known to those skilled in the art. Such methods are described, for example, in U.S. Pat. Nos. 5,593,972, 5,589, 466, and 5,580,859, which are herein incorporated by reference.

The polynucleotide vector constructs of the invention used in the gene therapy method are preferably constructs that will not integrate into the host genome nor will they contain sequences that allow for replication. Appropriate vectors include pWLNEO, pSV2CAT, pOG44, pXT1 and pSG available from Stratagene; pSVK3, pBPV, pMSG and pSVL available from Pharmacia; and pEF1/V5, pcDNA3.1, and pRc/CMV2 available from Invitrogen. Other suitable vectors will be readily apparent to the skilled artisan.

Any strong promoter known to those skilled in the art can be used for driving the expression of polynucleotide sequence of the invention. Suitable promoters include adenoviral promoters, such as the adenoviral major late promoter; or heterologous promoters, such as the cytomegalovirus (CMV) promoter; the respiratory syncytial virus (RSV) promoter; inducible promoters, such as the MMT promoter, the metallothionein promoter; heat shock promoters; the albumin promoter; the ApoAI promoter; human globin promoters; viral thymidine kinase promoters, such as the Herpes Simplex thymidine kinase promoter; retroviral LTRs; the b-actin promoter; and human growth hormone promoters. The promoter also may be the native promoter for the polynucleotides of the invention.

Unlike other gene therapy techniques, one major advantage of introducing naked nucleic acid sequences into target cells is the transitory nature of the polynucleotide synthesis in the cells. Studies have shown that non-replicating DNA sequences can be introduced into cells to provide production of the desired polypeptide for periods of up to six months.

The polynucleotide construct of the invention can be delivered to the interstitial space of tissues within the an animal, including of muscle, skin, brain, lung, liver, spleen, bone marrow, thymus, heart, lymph, blood, bone, cartilage, pancreas, kidney, gall bladder, stomach, intestine, testis, ovary, uterus, rectum, nervous system, eye, gland, and connective tissue. Interstitial space of the tissues comprises the intercellular, fluid, mucopolysaccharide matrix among the reticular fibers of organ tissues, elastic fibers in the walls of vessels or chambers, collagen fibers of fibrous tissues, or that same matrix within connective tissue ensheathing muscle cells or in the lacunae of bone. It is similarly the space occupied by the plasma of the circulation and the lymph fluid of the lymphatic channels. Delivery to the interstitial space of muscle tissue is preferred for the reasons discussed below. They may be conveniently delivered by injection into the tissues comprising these cells. They are preferably delivered to and expressed in persistent, non-dividing cells which are differentiated, although delivery and expression may be achieved in non-differentiated or less completely differentiated cells, such as, for example, stem cells of blood or skin fibroblasts. In vivo muscle cells are particularly competent in their ability to take up and express polynucleotides.

For the naked nucleic acid sequence injection, an effective dosage amount of DNA or RNA will be in the range of from about 0.05 mg/kg body weight to about 50 mg/kg body weight. Preferably the dosage will be from about 0.005 mg/kg to about 20 mg/kg and more preferably from about 0.05 mg/kg to about 5 mg/kg. Of course, as the artisan of ordinary skill will appreciate, this dosage will vary according to the tissue site of injection. The appropriate and effective dosage of nucleic acid sequence can readily be determined by those of ordinary skill in the art and may depend on the condition being treated and the route of administration.

The preferred route of administration is by the parenteral route of injection into the interstitial space of tissues. However, other parenteral routes may also be used, such as, inhalation of an aerosol formulation particularly for delivery to lungs or bronchial tissues, throat or mucous membranes of the nose. In addition, naked DNA constructs can be delivered to arteries during angioplasty by the catheter used in the procedure.

The naked polynucleotides are delivered by any method known in the art, including, but not limited to, direct needle injection at the delivery site, intravenous injection, topical administration, catheter infusion, and so-called "gene guns". These delivery methods are known in the art.

The constructs may also be delivered with delivery vehicles such as viral sequences, viral particles, liposome formulations, lipofectin, precipitating agents, etc. Such methods of delivery are known in the art.

In certain embodiments, the polynucleotide constructs of the invention are complexed in a liposome preparation. Liposomal preparations for use in the instant invention include cationic (positively charged), anionic (negatively charged) and neutral preparations. However, cationic liposomes are particularly preferred because a tight charge complex can be formed between the cationic liposome and the polyanionic nucleic acid. Cationic liposomes have been shown to mediate intracellular delivery of plasmid DNA (Felgner et al., Proc. Natl. Acad. Sci. USA, 84:7413-7416 (1987), which is herein incorporated by reference); mRNA (Malone et al., Proc. Natl. Acad. Sci. USA, 86:6077-6081 (1989), which is herein incorporated by reference); and purified transcription factors (Debs et al., J. Biol. Chem., 265:10189-10192 (1990), which is herein incorporated by reference), in functional form.

Cationic liposomes are readily available. For example, N[1-2,3-dioleyloxy)propyl]-N,N,N-triethylammonium (DOTMA) liposomes are particularly useful and are available under the trademark LIPOFECTIN®, from GIBCO BRL, Grand Island, N.Y. (See, also, Felgner et al., Proc. Natl. Acad. Sci. USA, 84:7413-7416 (1987), which is herein incorporated by reference). Other commercially available liposomes include transfectace (DDAB/DOPE) and DOTAP/DOPE (Boehringer).

Other cationic liposomes can be prepared from readily available materials using techniques well known in the art. See, e.g. PCT Publication NO: WO 90/11092 (which is herein incorporated by reference) for a description of the synthesis of DOTAP (1,2-bis(oleoyloxy)-3-(trimethylammonio)propane) liposomes. Preparation of DOTMA liposomes is explained in the literature, see, e.g., Felgner et al., Proc. Natl. Acad. Sci. USA, 84:7413-7417, which is herein incorporated by reference. Similar methods can be used to prepare liposomes from other cationic lipid materials.

Similarly, anionic and neutral liposomes are readily available, such as from Avanti Polar Lipids (Birmingham; Ala.), or can be easily prepared using readily available materials. Such materials include phosphatidyl, choline, cholesterol, phosphatidyl ethanolamine, dioleoylphosphatidyl choline (DOPC), dioleoylphosphatidyl glycerol (DOPG), dioleoylphoshatidyl ethanolamine (DOPE), among others. These materials can also be mixed with the DOTMA and DOTAP starting materials in appropriate ratios. Methods for making liposomes using these materials are well known in the art.

For example, commercially dioleoylphosphatidyl choline (DOPC), dioleoylphosphatidyl glycerol (DOPG), and dioleoylphosphatidyl ethanolamine (DOPE) can be used in various combinations to make conventional liposomes, with or without the addition of cholesterol. Thus, for example, DOPG/DOPC vesicles can be prepared by drying 50 mg each of DOPG and DOPC under a stream of nitrogen gas into a sonication vial. The sample is placed under a vacuum pump overnight and is hydrated the following day with deionized water. The sample is then sonicated for 2 hours in a capped vial, using a Heat Systems model 350 sonicator equipped with an inverted cup (bath type) probe at the maximum setting while the bath is circulated at 15EC. Alternatively, negatively charged vesicles can be prepared without sonication to produce multilamellar vesicles or by extrusion through nucleopore membranes to produce unilamellar vesicles of discrete size. Other methods are known and available to those of skill in the art.

The liposomes can comprise multilamellar vesicles (MLVs), small unilamellar vesicles (SUVs), or large unilamellar vesicles (LUVs), with SUVs being preferred. The various liposome-nucleic acid complexes are prepared using methods well known in the art. See, e.g., Straubinger et al., Methods of Immunology, 101:512-527 (1983), which is herein incorporated by reference. For example, MLVs containing nucleic acid can be prepared by depositing a thin film of phospholipid on the walls of a glass tube and subsequently hydrating with a solution of the material to be encapsulated. SUVs are prepared by extended sonication of MLVs to produce a homogeneous population of unilamellar liposomes. The material to be entrapped is added to a suspension of preformed MLVs and then sonicated. When using liposomes containing cationic lipids, the dried lipid film is resuspended in an appropriate solution such as sterile water or an isotonic buffer solution such as 10 mM Tris/NaCl, sonicated, and then the preformed liposomes are mixed directly with the DNA. The liposome and DNA form a very stable complex due to binding of the positively charged liposomes to the cationic DNA. SUVs find use with small nucleic acid fragments. LUVs are prepared by a number of methods, well known in the art. Commonly used methods include $Ca^{2+}$-EDTA chelation (Papahadjopoulos et al., Biochim. Biophys. Acta, 394:483 (1975); Wilson et al., Cell, 17:77 (1979)); ether injection (Deamer et al., Biochim. Biophys. Acta, 443:629 (1976); Ostro et al., Biochem. Biophys. Res. Commun., 76:836 (1977); Fraley et al., Proc. Natl. Acad. Sci. USA, 76:3348 (1979)); detergent dialysis (Enoch et al., Proc. Natl. Acad. Sci. USA, 76:145 (1979)); and reverse-phase evaporation (REV) (Fraley et al., J. Biol. Chem., 255:10431 (1980); Szoka et al., Proc. Natl. Acad. Sci. USA, 75:145 (1978); Schaefer-Ridder et al., Science, 215:166 (1982)), which are herein incorporated by reference.

Generally, the ratio of DNA to liposomes will be from about 10:1 to about 1:10. Preferably, the ration will be from about 5:1 to about 1:5. More preferably, the ration will be about 3:1 to about 1:3. Still more preferably, the ratio will be about 1:1.

U.S. Pat. No. 5,676,954 (which is herein incorporated by reference) reports on the injection of genetic material, complexed with cationic liposomes carriers, into mice. U.S. Pat. Nos. 4,897,355, 4,946,787, 5,049,386, 5,459,127, 5,589,466, 5,693,622, 5,580,859, 5,703,055, and international publication NO: WO 94/9469 (which are herein incorporated by reference) provide cationic lipids for use in transfecting DNA into cells and mammals. U.S. Pat. Nos. 5,589,466, 5,693,622, 5,580,859, 5,703,055, and international publication NO: WO 94/9469 (which are herein incorporated by reference) provide methods for delivering DNA-cationic lipid complexes to mammals.

In certain embodiments, cells are engineered, ex vivo or in vivo, using a retroviral particle containing RNA which comprises a sequence encoding polypeptides of the invention. Retroviruses from which the retroviral plasmid vectors may be derived include, but are not limited to, Moloney Murine Leukemia Virus, spleen necrosis virus, Rous sarcoma Virus, Harvey Sarcoma Virus, avian leukosis virus, gibbon ape leukemia virus, human immunodeficiency virus, Myeloproliferative Sarcoma Virus, and mammary tumor virus.

The retroviral plasmid vector is employed to transduce packaging cell lines to form producer, cell lines. Examples of packaging cells which may be transfected include, but are not limited to, the PE501, PA317, R-2, R-AM, PA12, T19-14X, VT-19-17-H2, RCRE, RCRIP, GP+E-86, GP+envAm12, and DAN cell lines as described in Miller, Human Gene Therapy, 1:5-14 (1990), which is incorporated herein by reference in its entirety. The vector may transduce the packaging cells through any means known in the art. Such means include, but are not limited to, electroporation, the use of liposomes, and CaPO4 precipitation. In one alternative, the retroviral plasmid vector may be encapsulated into a liposome, or coupled to a lipid, and then administered to a host.

The producer cell line generates infectious retroviral vector particles which include polynucleotide encoding polypeptides of the invention. Such retroviral vector particles then may be employed, to transduce eukaryotic cells, either in vitro or in vivo. The transduced eukaryotic cells will express polypeptides of the invention.

In certain other embodiments, cells are engineered, ex vivo or in vivo, with polynucleotides of the invention contained in an adenovirus vector. Adenovirus can be manipulated such that it encodes and expresses polypeptides of the invention, and at the same time is inactivated in terms of its ability to replicate in a normal lytic viral life cycle. Adenovirus expression is achieved without integration of the viral DNA into the host cell chromosome, thereby alleviating concerns about insertional mutagenesis. Furthermore, adenoviruses have been used as live enteric vaccines for many years with an excellent safety profile (Schwartz et al., Am. Rev. Respir. Dis., 109:233-238 (1974)). Finally, adenovirus mediated gene transfer has been demonstrated in a number of instances including transfer of alpha-1-antitrypsin and CFTR to the lungs of cotton rats (Rosenfeld et al., Science, 252:431-434 (1991); Rosenfeld et al., Cell, 68:143-155 (1992)). Furthermore, extensive studies to attempt to establish adenovirus as a causative agent in human cancer were uniformly negative (Green et al. Proc. Natl. Acad. Sci. USA, 76:6606 (1979)).

Suitable adenoviral vectors useful in the present invention are described, for example, in Kozarsky and Wilson, Curr. Opin. Genet. Devel., 3:499-503 (1993); Rosenfeld et al., Cell, 68:143-155 (1992); Engelhardt et al., Human Genet. Ther., 4:759-769 (1993); Yang et al., Nature Genet., 7:362-369 (1994); Wilson et al., Nature, 365:691-692 (1993); and U.S. Pat. No. 5,652,224, which are herein incorporated by reference. For example, the adenovirus vector Ad2 is useful and can be grown in human 293 cells. These cells contain the E1 region of adenovirus and constitutively express E1a and E1b, which complement the defective adenoviruses by providing the products of the genes deleted from the vector. In addition to Ad2, other varieties of adenovirus (e.g., Ad3, Ad5, and Ad7) are also useful in the present invention.

Preferably, the adenoviruses used in the present invention are replication deficient. Replication deficient adenoviruses require the aid of a helper virus and/or packaging cell line to form infectious particles. The resulting virus is capable of infecting cells and can express a polynucleotide of interest which is operably linked to a promoter, but cannot replicate in most cells. Replication deficient adenoviruses may be deleted in one or more of all or a portion of the following genes: E1a, E1b, E3, E4, E2a, or L1 through L5.

In certain other embodiments, the cells are engineered, ex vivo or in vivo, using an adeno-associated virus (AAV). AAVs are naturally occurring defective viruses that require helper viruses to produce infectious particles (Muzyczka, Curr. Top-ics in Microbiol. Immunol., 158:97 (1992)). It is also one of the few viruses that may integrate its DNA into non-dividing cells. Vectors containing as little as 300 base pairs of AAV can be packaged and can integrate, but space for exogenous DNA is limited to about 4.5 kb. Methods for producing and using such AAVs are known in the art. See, for example, U.S. Pat. Nos. 5,139,941, 5,173,414, 5,354,678, 5,436,146, 5,474,935, 5,478,745, and 5,589,377.

For example, an appropriate AAV vector for use in the present invention will include all the sequences necessary for DNA replication, encapsidation, and host-cell integration. The polynucleotide construct containing polynucleotides of the invention is inserted into the AAV vector using standard cloning methods, such as those found in Sambrook et al., Molecular Cloning: A Laboratory Manual, Cold Spring Harbor Press (1989). The recombinant AAV vector is then transfected into packaging cells which are infected with a helper virus, using any standard technique, including lipofection, electroporation, calcium phosphate precipitation, etc. Appropriate helper viruses include adenoviruses, cytomegaloviruses, vaccinia viruses, or herpes viruses. Once the packaging cells are transfected and infected, they will produce infectious AAV viral particles which contain the polynucleotide construct of the invention. These viral particles are then used to transduce eukaryotic cells, either ex vivo or in vivo. The transduced cells will contain the polynucleotide construct integrated into its genome, and will express the desired gene product.

Another method of gene therapy involves operably associating heterologous control regions and endogenous polynucleotide sequences (e.g. encoding the polypeptide sequence of interest) via homologous recombination (see, e.g., U.S. Pat. No. 5,641,670, issued Jun. 24, 1997; International Publication NO: WO 96/29411, published Sep. 26, 1996; International Publication NO: WO 94/12650, published Aug. 4, 1994; Koller et al., Proc. Natl. Acad. Sci. USA, 86:8932-8935 (1989); and Zijlstra et al., Nature, 342:435-438 (1989). This method involves the activation of a gene which is present in the target cells, but which is not normally expressed in the cells, or is expressed at a lower level than desired.

Polynucleotide constructs are made, using standard techniques known in the art, which contain the promoter with targeting sequences flanking the promoter. Suitable promoters are described herein. The targeting sequence is sufficiently complementary to an endogenous sequence to permit homologous recombination of the promoter-targeting sequence with the endogenous sequence. The targeting sequence will be sufficiently near the 5' end of the desired endogenous polynucleotide sequence so the promoter will be operably linked to the endogenous sequence upon homologous recombination.

The promoter and the targeting sequences can be amplified using PCR. Preferably, the amplified promoter contains distinct restriction enzyme sites on the 5' and 3' ends. Preferably, the 3' end of the first targeting sequence contains the same restriction enzyme site as the 5' end of the amplified promoter and the 5' end of the second targeting sequence contains the same restriction site as the 3' end of the amplified promoter. The amplified promoter and targeting sequences are digested and ligated together.

The promoter-targeting sequence construct is delivered to the cells, either as naked polynucleotide, or in conjunction with transfection-facilitating agents, such as liposomes, viral sequences, viral particles, whole viruses, lipofection, precipitating agents, etc., described in more detail above. The P promoter-targeting sequence can be delivered by any method, included direct needle injection, intravenous injection, topical administration, catheter infusion, particle accelerators, etc. The methods are described in more detail below.

The promoter-targeting sequence construct is taken up by cells. Homologous recombination between the construct and the endogenous sequence takes place, such that an endogenous sequence is placed under the control of the promoter. The promoter then drives the expression of the endogenous sequence.

The polynucleotides encoding polypeptides of the present invention may be administered along with other polynucleotides encoding angiogenic proteins. Angiogenic proteins include, but are not limited to, acidic and basic fibroblast growth factors, VEGF-1, VEGF-2 (VEGF-C), VEGF-3 (VEGF-B), epidermal growth factor alpha and beta, platelet-derived endothelial cell growth factor, platelet-derived growth factor, tumor necrosis factor alpha, hepatocyte growth factor, insulin like growth factor, colony stimulating factor, macrophage colony stimulating factor, granulocyte/macrophage colony stimulating factor, and nitric oxide synthase.

Preferably, the polynucleotide encoding a polypeptide of the invention contains a secretory signal sequence that facilitates secretion of the protein. Typically, the signal sequence is positioned in the coding region of the polynucleotide to be expressed towards or at the 5' end of the coding region. The signal sequence may be homologous or heterologous to the polynucleotide of interest and may be homologous or heterologous to the cells to be transfected. Additionally, the signal sequence may be chemically synthesized using methods known in the art.

Any mode of administration of any of the above-described polynucleotides constructs can be used so long as the mode results in the expression of one or more molecules in an amount sufficient to provide a therapeutic effect. This includes direct needle injection, systemic injection, catheter infusion, biolistic injectors, particle accelerators (i.e., "gene guns"), gelfoam sponge depots, other commercially available depot materials, osmotic pumps (e.g., ALZA® minipumps), oral or suppositorial solid (tablet or pill) pharmaceutical formulations, and decanting or topical applications during surgery. For example, direct injection of naked calcium phosphate-precipitated plasmid into rat liver and rat spleen or a protein-coated plasmid into the portal vein has resulted in gene expression of the foreign gene in the rat livers. (Kaneda et al., Science, 243:375 (1989)).

A preferred method of local administration is by direct injection. Preferably, a recombinant molecule of the present invention complexed with a delivery vehicle is administered by direct injection into or locally within the area of arteries. Administration of a composition locally within the area of arteries refers to injecting the composition centimeters and preferably, millimeters within arteries.

Another method of local administration is to contact a polynucleotide construct of the present invention in or around a surgical wound. For example, a patient can undergo surgery and the polynucleotide construct can be coated on the surface of tissue inside the wound or the construct can be injected into areas of tissue inside the wound.

Therapeutic compositions useful in systemic administration, include recombinant molecules of the present invention complexed to a targeted delivery vehicle of the present invention. Suitable delivery vehicles for use with systemic administration comprise liposomes comprising ligands for targeting the vehicle to a particular site.

Preferred methods of systemic administration, include intravenous injection, aerosol, oral and percutaneous (topical) delivery. Intravenous injections can be performed using methods standard in the art. Aerosol delivery can also be performed using methods standard in the art (see, for example, Stribling et al., Proc. Natl. Acad. Sci. USA, 189: 11277-11281 (1992), which is incorporated herein by reference). Oral delivery can be performed by complexing a polynucleotide construct of the present invention to a carrier capable of withstanding degradation by digestive enzymes in the gut of an animal. Examples of such carriers, include plastic capsules or tablets, such as those known in the art. Topical delivery can be performed by mixing a polynucleotide construct of the present invention with a lipophilic reagent (e.g., DMSO) that is capable of passing into the skin.

Determining an effective amount of substance to be delivered can depend upon a number of factors including, for example, the chemical structure and biological activity of the substance, the age and weight of the animal, the precise condition requiring treatment and its severity, and the route of administration. The frequency of treatments depends upon a number of factors, such as the amount of polynucleotide constructs administered per dose, as well as the health and history of the subject. The precise amount, number of doses, and timing of doses will be determined by the attending physician or veterinarian. Therapeutic compositions of the present invention can be administered to any animal, preferably to mammals and birds. Preferred mammals include humans, dogs, cats, mice, rats, rabbits sheep, cattle, horses and pigs, with humans being particularly preferred.

Biological Activities

The polynucleotides or polypeptides, or agonists or antagonists of the present invention can be used in assays to test for one or more biological activities. If these polynucleotides and polypeptides do exhibit activity in a particular assay, it is likely that these molecules may be involved in the diseases associated with the biological activity. Thus, the polynucleotides or polypeptides, or agonists or antagonists could be used to treat the associated disease.

Immune Activity

The polynucleotides or polypeptides, or agonists or antagonists of the present invention may be useful in treating, preventing, and/or diagnosing diseases, disorders, and/or conditions of the immune system, by activating or inhibiting the proliferation, differentiation, or mobilization (chemotaxis) of immune cells. Immune cells develop through a process called hematopoiesis, producing myeloid (platelets, red blood cells, neutrophils, and macrophages) and lymphoid (B and T lymphocytes) cells from pluripotent stem cells. The etiology of these immune diseases, disorders, and/or conditions may be genetic, somatic, such as cancer or some autoimmune diseases, disorders, and/or conditions, acquired (e.g., by chemotherapy or toxins), or infectious. Moreover, a polynucleotides or polypeptides, or agonists or antagonists of the present invention can be used as a marker or detector of a particular immune system disease or disorder.

A polynucleotides or polypeptides, or agonists or antagonists of the present invention may be useful in treating, preventing, and/or diagnosing diseases, disorders, and/or conditions of hematopoietic cells. A polynucleotides or polypeptides, or agonists or antagonists of the present invention could be used to increase differentiation and proliferation of hematopoietic cells, including the pluripotent stem cells, in an effort to treat or prevent those diseases, disorders, and/or conditions associated with a decrease in certain (or many) types hematopoietic cells. Examples of immunologic deficiency syndromes include, but are not limited to: blood protein diseases, disorders, and/or conditions (e.g. agammaglobulinemia, dysgammaglobulinemia), ataxia telangiectasia, common variable immunodeficiency, Digeorge Syndrome, HIV infection, HTLV-BLV infection, leukocyte adhesion deficiency syndrome, lymphopenia, phagocyte bactericidal dysfunction, severe combined immunodeficiency (SCIDs), Wiskott-Aldrich Disorder, anemia, thrombocytopenia, or hemoglobinuria.

Moreover, a polynucleotides or polypeptides, or agonists or antagonists of the present invention could also be used to modulate hemostatic (the stopping of bleeding) or thrombolytic activity (clot formation). For example, by increasing hemostatic or thrombolytic activity, a polynucleotides or polypeptides, or agonists or antagonists of the present invention could be used to treat or prevent blood coagulation diseases, disorders, and/or conditions (e.g., afibrinogenemia, factor deficiencies, arterial thrombosis, venous thrombosis, etc.), blood platelet diseases, disorders, and/or conditions (e.g. thrombocytopenia), or wounds resulting from trauma, surgery, or other causes. Alternatively, a polynucleotides or polypeptides, or agonists or antagonists of the present invention that can decrease hemostatic or thrombolytic activity could be used to inhibit or dissolve clotting. Polynucleotides or polypeptides, or agonists or antagonists of the present invention are may also be useful for the detection, prognosis, treatment, and/or prevention of heart attacks (infarction), strokes, scarring, fibrinolysis, uncontrolled bleeding, uncontrolled coagulation, uncontrolled complement fixation, and/or inflammation.

A polynucleotides or polypeptides, or agonists or antagonists of the present invention may also be useful in treating, preventing, and/or diagnosing autoimmune diseases, disorders, and/or conditions. Many autoimmune diseases, disorders, and/or conditions result from inappropriate recognition of self as foreign material by immune cells. This inappropriate recognition results in an immune response leading to the destruction of the host tissue. Therefore, the administration of a polynucleotides or polypeptides, or agonists or antagonists of the present invention that inhibits an immune response, particularly the proliferation, differentiation, or chemotaxis of T-cells, may be an effective therapy in preventing autoimmune diseases, disorders, and/or conditions.

Examples of autoimmune diseases, disorders, and/or conditions that can be treated, prevented, and/or diagnosed or detected by the present invention include, but are not limited to: Addison's Disease, hemolytic anemia, antiphospholipid syndrome, rheumatoid arthritis, dermatitis, allergic encephalomyelitis, glomerulonephritis, Goodpasture's Syndrome, Graves' Disease, Multiple Sclerosis, Myasthenia Gravis, Neuritis, Ophthalmia, Bullous Pemphigoid, Pemphigus, Polyendocrinopathies, Purpura, Reiter's Disease, Stiff-Man Syndrome, Autoimmune Thyroiditis, Systemic Lupus Erythematosus, Autoimmune Pulmonary Inflammation, Guillain-Barre Syndrome, insulin dependent diabetes mellitis, and autoimmune inflammatory eye disease.

Similarly, allergic reactions and conditions, such as asthma (particularly allergic asthma) or other respiratory problems, may also be treated, prevented, and/or diagnosed by polynucleotides or polypeptides, or agonists or antagonists of the present invention. Moreover, these molecules can be used to treat anaphylaxis, hypersensitivity to an antigenic molecule, or blood group incompatibility.

A polynucleotides or polypeptides, or agonists or antagonists of the present invention may also be used to treat, prevent, and/or diagnose organ rejection or graft-versus-host disease (GVHD). Organ rejection occurs by host immune cell destruction of the transplanted tissue through an immune response. Similarly, an immune response is also involved in GVHD, but, in this case, the foreign transplanted immune cells destroy the host tissues. The administration of a polynucleotides or polypeptides, or agonists or antagonists of the present invention that inhibits an immune response, particularly the proliferation, differentiation, or chemotaxis of T-cells, may be an effective therapy in preventing organ rejection or GVHD.

Similarly, a polynucleotides or polypeptides, or agonists or antagonists of the present invention may also be used to modulate inflammation. For example, the polypeptide or polynucleotide or agonists or antagonist may inhibit the proliferation and differentiation of cells involved in an inflammatory response. These molecules can be used to treat, prevent, and/or diagnose inflammatory conditions, both chronic and acute conditions, including chronic prostatitis, granulomatous prostatitis and malacoplakia, inflammation associated with infection (e.g., septic shock, sepsis, or systemic inflammatory response syndrome (SIRS)), ischemia-reperfusion injury, endotoxin lethality, arthritis, complement-mediated hyperacute rejection, nephritis, cytokine or chemokine induced lung injury, inflammatory bowel disease, Crohn's disease, or resulting from over production of cytokines (e.g., TNF or IL-1.)

Hyperproliferative Disorders

A polynucleotides or polypeptides, or agonists or antagonists of the invention can be used to treat, prevent, and/or diagnose hyperproliferative diseases, disorders, and/or conditions, including neoplasms. A polynucleotides or polypeptides, or agonists or antagonists of the present invention may inhibit the proliferation of the disorder through direct or indirect interactions. Alternatively, a polynucleotides or polypeptides, or agonists or antagonists of the present invention may proliferate other cells which can inhibit the hyperproliferative disorder.

For example, by increasing an immune response, particularly increasing antigenic qualities of the hyperproliferative disorder or by proliferating, differentiating, or mobilizing T-cells, hyperproliferative diseases, disorders, and/or conditions can be treated, prevented, and/or diagnosed. This immune response may be increased by either enhancing an existing immune response, or by initiating a new immune response. Alternatively, decreasing an immune response may also be a method of treating, preventing, and/or diagnosing hyperproliferative diseases, disorders, and/or conditions, such as a chemotherapeutic agent.

Examples of hyperproliferative diseases, disorders, and/or conditions that can be treated, prevented, and/or diagnosed by polynucleotides or polypeptides, or agonists or antagonists of the present invention include, but are not limited to neoplasms located in the: colon, abdomen, bone, breast, digestive system, liver, pancreas, peritoneum, endocrine glands (adrenal, parathyroid, pituitary, testicles, ovary, thymus, thyroid), eye, head and neck, nervous (central and peripheral), lymphatic system, pelvic, skin, soft tissue, spleen, thoracic, and urogenital.

Similarly, other hyperproliferative diseases, disorders, and/or conditions can also be treated, prevented, and/or diagnosed by a polynucleotides or polypeptides, or agonists or antagonists of the present invention. Examples of such hyperproliferative diseases, disorders, and/or conditions include, but are not limited to: hypergammaglobulinemia, lymphoproliferative diseases, disorders, and/or conditions, paraproteinemias, purpura, sarcoidosis, Sezary Syndrome, Waldenstron's Macroglobulinemia, Gaucher's Disease, histiocytosis, and any other hyperproliferative disease, besides neoplasia, located in an organ system listed above.

One preferred embodiment utilizes polynucleotides of the present invention to inhibit aberrant cellular division, by gene therapy using the present invention, and/or protein fusions or fragments thereof.

Thus, the present invention provides a method for treating or preventing cell proliferative diseases, disorders, and/or conditions by inserting into an abnormally proliferating cell a polynucleotide of the present invention, wherein said polynucleotide represses said expression.

Another embodiment of the present invention provides a method of treating or preventing cell-proliferative diseases, disorders, and/or conditions in individuals comprising administration of one or more active gene copies of the present invention to an abnormally proliferating cell or cells. In a preferred embodiment, polynucleotides of the present invention is a DNA construct comprising a recombinant expression vector effective in expressing a DNA sequence encoding said polynucleotides. In another preferred embodiment of the present invention, the DNA construct encoding the polynucleotides of the present invention is inserted into cells to be treated utilizing a retrovirus, or more Preferably an adenoviral vector (See G J. Nabel, et. al., PNAS 1999 96: 324-326, which is hereby incorporated by reference). In a most preferred embodiment, the viral vector is defective and will not transform non-proliferating cells, only proliferating cells. Moreover, in a preferred embodiment, the polynucleotides of the present invention inserted into proliferating cells either alone, or in combination with or fused to other polynucleotides, can then be modulated via an external stimulus (i.e. magnetic, specific small molecule, chemical, or drug administration, etc.), which acts upon the promoter upstream of said polynucleotides to induce expression of the encoded protein product. As such the beneficial therapeutic affect of the present invention may be expressly modulated (i.e. to increase, decrease, or inhibit expression of the present invention) based upon said external stimulus.

Polynucleotides of the present invention may be useful in repressing expression of oncogenic genes or antigens. By "repressing expression of the oncogenic genes" is intended the suppression of the transcription of the gene, the degradation of the gene transcript (pre-message RNA), the inhibition of splicing, the destruction of the messenger RNA, the prevention of the post-translational modifications of the protein, the destruction of the protein, or the inhibition of the normal function of the protein.

For local administration to abnormally proliferating cells, polynucleotides of the present invention may be administered by any method known to those of skill in the art including, but not limited to transfection, electroporation, microinjection of cells, or in vehicles such as liposomes, lipofectin, or as naked polynucleotides, or any other method described throughout the specification. The polynucleotide of the present invention may be delivered by known gene delivery systems such as, but not limited to, retroviral vectors (Gilboa, J. Virology 44:845 (1982); Hocke, Nature 320:275 (1986); Wilson, et al., Proc. Natl. Acad. Sci. U.S.A. 85:3014), vaccinia virus system (Chakrabarty et al., Mol. Cell. Biol. 5:3403 (1985) or other efficient DNA delivery systems (Yates et al., Nature 313:812 (1985)) known to those skilled in the art. These references are exemplary only and are hereby incorporated by reference. In order to specifically deliver or transfect cells which are abnormally proliferating and spare non-dividing cells, it is preferable to utilize a retrovirus, or adenoviral (as described in the art and elsewhere herein) delivery system known to those of skill in the art. Since host DNA replication is required for retroviral DNA to integrate and the retrovirus will be unable to self replicate due to the lack of the retrovirus genes needed for its life cycle. Utilizing such a retroviral delivery system for polynucleotides of the present invention will target said gene and constructs to abnormally proliferating cells and will spare the non-dividing normal cells.

The polynucleotides of the present invention may be delivered directly to cell proliferative disorder/disease sites in internal organs, body cavities and the like by use of imaging devices used to guide an injecting needle directly to the disease site. The polynucleotides of the present invention may also be administered to disease sites at the time of surgical intervention.

By "cell proliferative disease" is meant any human or animal disease or disorder, affecting any one or any combination of organs, cavities, or body parts, which is characterized by single or multiple local abnormal proliferations of cells, groups of cells, or tissues, whether benign or malignant.

Any amount of the polynucleotides of the present invention may be administered as long as it has a biologically inhibiting effect on the proliferation of the treated cells. Moreover, it is possible to administer more than one of the polynucleotide of the present invention simultaneously to the same site. By "biologically inhibiting" is meant partial or total growth inhibition as well as decreases in the rate of proliferation or growth of the cells. The biologically inhibitory dose may be determined by assessing the effects of the polynucleotides of the present invention on target malignant or abnormally proliferating cell growth in tissue culture, tumor growth in animals and cell cultures, or any other method known to one of ordinary skill in the art.

The present invention is further directed to antibody-based therapies which involve administering of anti-polypeptides and anti-polynucleotide antibodies to a mammalian, preferably human, patient for treating, preventing, and/or diagnosing one or more of the described diseases, disorders, and/or conditions. Methods for producing anti-polypeptides and anti-polynucleotide antibodies polyclonal and monoclonal antibodies are described in detail elsewhere herein. Such antibodies may be provided in pharmaceutically acceptable compositions as known in the art or as described herein.

A summary of the ways in which the antibodies of the present invention may be used therapeutically includes binding polynucleotides or polypeptides of the present invention locally or systemically in the body or by direct cytotoxicity of the antibody, e.g. as mediated by complement (CDC) or by effector cells (ADCC). Some of these approaches are described in more detail below. Armed with the teachings provided herein, one of ordinary skill in the art will know how to use the antibodies of the present invention for diagnostic, monitoring or therapeutic purposes without undue experimentation.

In particular, the antibodies, fragments and derivatives of the present invention are useful for treating, preventing, and/or diagnosing a subject having or developing cell proliferative and/or differentiation diseases, disorders, and/or conditions as described herein. Such treatment comprises administering a single or multiple doses of the antibody, or a fragment, derivative, or a conjugate thereof.

The antibodies of this invention may be advantageously utilized in combination with other monoclonal or chimeric antibodies, or with lymphokines or hematopoietic growth factors, for example, which serve to increase the number or activity of effector cells which interact with the antibodies.

It is preferred to use high affinity and/or potent in vivo inhibiting and/or neutralizing antibodies against polypeptides or polynucleotides of the present invention, fragments or regions thereof, for both immunoassays directed to and therapy of diseases, disorders, and/or conditions related to polynucleotides or polypeptides, including fragments thereof, of the present invention. Such antibodies, fragments, or regions, will preferably have an affinity for polynucleotides or polypeptides, including fragments thereof. Preferred binding affinities include those with a dissociation constant or Kd less than 5×10–6M, 10–6M, 5×10–7M, 10–7M, 5×10–8M, 10–8M, 5×10–9M, 10–9M, 5×10–10M, 10–10M, 5×10–11M, 10–11M, 5×10–12M, 10–12M, 5×10–13M, 10–13M, 5×10–14M, 10–14M, 5×10–15M, and 10–15M.

Moreover, polypeptides of the present invention may be useful in inhibiting the angiogenesis of proliferative cells or tissues, either alone, as a protein fusion, or in combination with other polypeptides directly or indirectly, as described elsewhere herein. In a most preferred embodiment, said anti-angiogenesis effect may be achieved indirectly, for example, through the inhibition of hematopoietic, tumor-specific cells, such as tumor-associated macrophages (See Joseph I B, et al. J Natl Cancer Inst, 90(21):1648-53 (1998), which is hereby incorporated by reference). Antibodies directed to polypeptides or polynucleotides of the present invention may also result in inhibition of angiogenesis directly, or indirectly (See Witte L, et al., Cancer Metastasis Rev. 17(2):155-61 (1998), which is hereby incorporated by reference)).

Polypeptides, including protein fusions, of the present invention, or fragments thereof may be useful in inhibiting proliferative cells or tissues through the induction of apoptosis. Said polypeptides may act either directly, or indirectly to induce apoptosis of proliferative cells and tissues, for example in the activation of a death-domain receptor, such as tumor necrosis factor (TNF) receptor-1, CD95 (Fas/APO-1), TNF-receptor-related apoptosis-mediated protein (TRAMP) and TNF-related apoptosis-inducing ligand (TRAIL) receptor-1 and -2 (See Schulze-Osthoff K, et al., Eur J Biochem 254(3):439-59 (1998), which is hereby incorporated by reference). Moreover, in another preferred embodiment of the present invention, said polypeptides may induce apoptosis through other mechanisms, such as in the activation of other proteins which will activate apoptosis, or through stimulating the expression of said proteins, either alone or in combination with small molecule drugs or adjuvants, such as apoptonin, galectins, thioredoxins, antiinflammatory proteins (See for example, Mutat. Res. 400(1-2):447-55 (1998), Med. Hypotheses. 50(5):423-33 (1998), Chem. Biol. Interact. April 24; 111-112:23-34 (1998), J Mol. Med. 76(6):402-12 (1998), Int. J. Tissue React. 20(1):3-15 (1998), which are all hereby incorporated by reference).

Polypeptides, including protein fusions to, or fragments thereof, of the present invention are useful in inhibiting the metastasis of proliferative cells or tissues. Inhibition may occur as a direct result of administering polypeptides, or antibodies directed to said polypeptides as described elsewhere herein, or indirectly, such as activating the expression of proteins known to inhibit metastasis, for example alpha 4 integrins, (See, e.g., Curr Top Microbiol Immunol 1998; 231: 125-41, which is hereby incorporated by reference). Such therapeutic affects of the present invention may be achieved either alone, or in combination with small molecule drugs or adjuvants.

In another embodiment, the invention provides a method of delivering compositions containing the polypeptides of the invention (e.g., compositions containing polypeptides or polypeptide antibodies associated with heterologous polypeptides, heterologous nucleic acids, toxins, or prodrugs) to targeted cells expressing the polypeptide of the present invention. Polypeptides or polypeptide antibodies of the invention may be associated with heterologous polypeptides, heterologous nucleic acids, toxins, or prodrugs via hydrophobic, hydrophilic, ionic and/or covalent interactions.

Polypeptides, protein fusions to, or fragments thereof, of the present invention are useful in enhancing the immunogenicity and/or antigenicity of proliferating cells or tissues, either directly, such as would occur if the polypeptides of the present invention 'vaccinated' the immune response to respond to proliferative antigens and immunogens, or indirectly, such as in activating the expression of proteins known to enhance the immune response (e.g. chemokines), to said antigens and immunogens.

Cardiovascular Disorders

Polynucleotides or polypeptides, or agonists or antagonists of the invention may be used to treat, prevent, and/or diagnose cardiovascular diseases, disorders, and/or conditions, including peripheral artery disease, such as limb ischemia.

Cardiovascular diseases, disorders, and/or conditions include cardiovascular abnormalities, such as arterio-arterial fistula, arteriovenous fistula, cerebral arteriovenous malformations, congenital heart defects, pulmonary atresia, and Scimitar Syndrome. Congenital heart defects include aortic coarctation, cor triatriatum, coronary vessel anomalies, crisscross heart, dextrocardia, patent ductus arteriosus, Ebstein's anomaly, Eisenmenger complex, hypoplastic left heart syndrome, levocardia, tetralogy of fallot, transposition of great vessels, double outlet right ventricle, tricuspid atresia, persistent truncus arteriosus, and heart septal defects, such as aortopulmonary septal defect, endocardial cushion defects, Lutembacher's Syndrome, trilogy of Fallot, ventricular heart septal defects.

Cardiovascular diseases, disorders, and/or conditions also include heart disease, such as arrhythmias, carcinoid heart disease, high cardiac output, low cardiac output, cardiac tamponade, endocarditis (including bacterial), heart aneurysm, cardiac arrest, congestive heart failure, congestive cardiomyopathy, paroxysmal dyspnea, cardiac edema, heart hypertrophy, congestive cardiomyopathy, left ventricular hypertrophy, right ventricular hypertrophy, post-infarction heart rupture, ventricular septal rupture, heart valve diseases, myocardial diseases, myocardial ischemia, pericardial effusion, pericarditis (including constrictive and tuberculous), pneumopericardium, postpericardiotomy syndrome, pulmonary heart disease, rheumatic heart disease, ventricular dysfunction, hyperemia, cardiovascular pregnancy complications, Scimitar Syndrome, cardiovascular syphilis, and cardiovascular tuberculosis.

Arrhythmias include sinus arrhythmia, atrial fibrillation, atrial flutter, bradycardia, extrasystole, Adams-Stokes Syndrome, bundle-branch block, sinoatrial block, long QT syndrome, parasystole, Lown-Ganong-Levine Syndrome, Mahaim-type pre-excitation syndrome, Wolff-Parkinson-White syndrome, sick sinus syndrome, tachycardias, and ventricular fibrillation. Tachycardias include paroxysmal tachycardia, supraventricular tachycardia, accelerated idioventricular rhythm, atrioventricular nodal reentry tachycardia, ectopic atrial tachycardia, ectopic junctional tachycardia, sinoatrial nodal reentry tachycardia, sinus tachycardia, Torsades de Pointes, and ventricular tachycardia.

Heart valve disease include aortic valve insufficiency, aortic valve stenosis, hear murmurs, aortic valve prolapse, mitral valve prolapse, tricuspid valve prolapse, mitral valve insufficiency, mitral valve stenosis, pulmonary atresia, pulmonary valve insufficiency, pulmonary valve stenosis, tricuspid atresia, tricuspid valve insufficiency, and tricuspid valve stenosis.

Myocardial diseases include alcoholic cardiomyopathy, congestive cardiomyopathy, hypertrophic cardiomyopathy, aortic subvalvular stenosis, pulmonary subvalvular stenosis, restrictive cardiomyopathy, Chagas cardiomyopathy, endocardial fibroelastosis, endomyocardial fibrosis, Kearns Syndrome, myocardial reperfusion injury, and myocarditis.

Myocardial ischemias include coronary disease, such as angina pectoris, coronary aneurysm, coronary arteriosclerosis, coronary thrombosis, coronary vasospasm, myocardial infarction and myocardial stunning.

Cardiovascular diseases also include vascular diseases such as aneurysms, angiodysplasia, angiomatosis, bacillary angiomatosis, Hippel-Lindau Disease, Klippel-Trenaunay-Weber Syndrome, Sturge-Weber Syndrome, angioneurotic edema, aortic diseases, Takayasu's Arteritis, aortitis, Leriche's Syndrome, arterial occlusive diseases, arteritis, enarteritis, polyarteritis nodosa, cerebrovascular diseases, disorders, and/or conditions, diabetic angiopathies, diabetic retinopathy, embolisms, thrombosis, erythromelalgia, hemorrhoids, hepatic veno-occlusive disease, hypertension, hypotension, ischemia, peripheral vascular diseases, phlebitis, pulmonary veno-occlusive disease, Raynaud's disease, CREST syndrome, retinal vein occlusion, Scimitar syndrome, superior vena cava syndrome, telangiectasia, atacia telangiectasia, hereditary hemorrhagic telangiectasia, varicocele, varicose veins, varicose ulcer, vasculitis, and venous insufficiency.

Aneurysms include dissecting aneurysms, false aneurysms, infected aneurysms, ruptured aneurysms, aortic aneurysms, cerebral aneurysms, coronary aneurysms, heart aneurysms, and iliac aneurysms.

Arterial occlusive diseases include arteriosclerosis, intermittent claudication, carotid stenosis, fibromuscular dysplasias, mesenteric vascular occlusion, Moyamoya disease, renal artery obstruction, retinal artery occlusion, and thromboangiitis obliterans.

Cerebrovascular diseases, disorders, and/or conditions include carotid artery diseases, cerebral amyloid angiopathy, cerebral aneurysm, cerebral anoxia, cerebral arteriosclerosis, cerebral arteriovenous malformation, cerebral artery diseases, cerebral embolism and thrombosis, carotid artery thrombosis, sinus thrombosis, Wallenberg's syndrome, cerebral hemorrhage, epidural hematoma, subdural hematoma, subaraxhnoid hemorrhage, cerebral infarction, cerebral ischemia (including transient), subclavian steal syndrome, periventricular leukomalacia, vascular headache, cluster headache, migraine, and vertebrobasilar insufficiency.

Embolisms include air embolisms, amniotic fluid embolisms, cholesterol embolisms, blue toe syndrome, fat embolisms, pulmonary embolisms, and thromoboembolisms. Thrombosis include coronary thrombosis, hepatic vein thrombosis, retinal vein occlusion, carotid artery thrombosis, sinus thrombosis, Wallenberg's syndrome, and thrombophlebitis.

Ischemia includes cerebral ischemia, ischemic colitis, compartment syndromes, anterior compartment syndrome, myocardial ischemia, reperfusion injuries, and peripheral limb ischemia. Vasculitis includes aortitis, arteritis, Behcet's Syndrome, Churg-Strauss Syndrome, mucocutaneous lymph node syndrome, thromboangiitis obliterans, hypersensitivity vasculitis, Schoenlein-Henoch purpura, allergic cutaneous vasculitis, and Wegener's granulomatosis.

Polynucleotides or polypeptides, or agonists or antagonists of the invention, are especially effective for the treatment of critical limb ischemia and coronary disease.

Polypeptides may be administered using any method known in the art, including, but not limited to, direct needle injection at the delivery site, intravenous injection, topical administration, catheter infusion, biolistic injectors, particle accelerators, gelfoam sponge depots, other commercially available depot materials, osmotic pumps, oral or suppositorial solid pharmaceutical formulations, decanting or topical applications during surgery, aerosol delivery. Such methods are known in the art. Polypeptides of the invention may be administered as part of a Therapeutic, described in more detail below. Methods of delivering polynucleotides of the invention are described in more detail herein.

Neurological Diseases

Nervous system diseases, disorders, and/or conditions, which can be treated, prevented, and/or diagnosed with the compositions of the invention (e.g., polypeptides, polynucleotides, and/or agonists or antagonists), include, but are not limited to, nervous system injuries, and diseases, disorders, and/or conditions which result in either a disconnection of axons, a diminution or degeneration of neurons, or demyelination. Nervous system lesions which may be treated, prevented, and/or diagnosed in a patient (including human and non-human mammalian patients) according to the invention, include but are not limited to, the following lesions of either the central (including spinal cord, brain) or peripheral nervous systems: (1) ischemic lesions, in which a lack of oxygen in a portion of the nervous system results in neuronal injury or death, including cerebral infarction or ischemia, or spinal cord infarction or ischemia; (2) traumatic lesions, including lesions caused by physical injury or associated with surgery, for example, lesions which sever a portion of the nervous system, or compression injuries; (3) malignant lesions, in which a portion of the nervous system is destroyed or injured by malignant tissue which is either a nervous system associated malignancy or a malignancy derived from non-nervous system tissue; (4) infectious lesions, in which a portion of the nervous system is destroyed or injured as a result of infection, for example, by an abscess or associated with infection by human immunodeficiency virus, herpes zoster, or herpes simplex virus or with Lyme disease, tuberculosis, syphilis; (5) degenerative lesions, in which a portion of the nervous system is destroyed or injured as a result of a degenerative process including but not limited to degeneration associated with Parkinson's disease, Alzheimer's disease, Huntington's chorea, or amyotrophic lateral sclerosis (ALS); (6) lesions associated with nutritional diseases, disorders, and/or conditions, in which a portion of the nervous system is destroyed or injured by a nutritional disorder or disorder of metabolism including but not limited to, vitamin B12 deficiency, folic acid deficiency, Wernicke disease, tobacco-alcohol amblyopia, Marchiafava-Bignami disease (primary degeneration of the corpus callosum), and alcoholic cerebellar degeneration; (7) neurological lesions associated with systemic diseases including, but not limited to, diabetes (diabetic neuropathy, Bell's palsy), systemic lupus erythematosus, carcinoma, or sarcoidosis; (8) lesions caused by toxic substances including alcohol, lead, or particular neurotoxins; and (9) demyelinated lesions in which a portion of the nervous system is destroyed or injured by a demyelinating disease including, but not limited to, multiple sclerosis, human immunodeficiency virus-associated myelopathy, transverse myelopathy or various etiologies, progressive multifocal leukoencephalopathy, and central pontine myelinolysis.

In a preferred embodiment, the polypeptides, polynucleotides, or agonists or antagonists of the invention are used to protect neural cells from the damaging effects of cerebral hypoxia. According to this embodiment, the compositions of the invention are used to treat, prevent, and/or diagnose neural cell injury associated with cerebral hypoxia. In one aspect of this embodiment, the polypeptides, polynucleotides, or agonists or antagonists of the invention are used to treat, prevent, and/or diagnose neural cell injury associated with cerebral ischemia. In another aspect of this embodiment, the polypeptides, polynucleotides, or agonists or antagonists of the invention are used to treat, prevent, and/or diagnose neural cell injury associated with cerebral infarction. In another aspect of this embodiment, the polypeptides, polynucleotides, or agonists or antagonists of the invention are used to treat, prevent, and/or diagnose or prevent neural cell injury associated with a stroke. In a further aspect of this embodiment, the polypeptides, polynucleotides, or agonists or antagonists of the invention are used to treat, prevent, and/or diagnose neural cell injury associated with a heart attack.

The compositions of the invention which are useful for treating or preventing a nervous system disorder may be selected by testing for biological activity in promoting the survival or differentiation of neurons. For example, and not by way of limitation, compositions of the invention which elicit any of the following effects may be useful according to the invention: (1) increased survival time of neurons in culture; (2) increased sprouting of neurons in culture or in vivo; (3) increased production of a neuron-associated molecule in culture or in vivo, e.g., choline acetyltransferase or acetylcholinesterase with respect to motor neurons; or (4) decreased symptoms of neuron dysfunction in vivo. Such effects may be measured by any method known in the art. In preferred, non-limiting embodiments, increased survival of neurons may routinely be measured using a method set forth herein or otherwise known in the art, such as, for example, the method set forth in Arakawa et al. (J. Neurosci. 10:3507-3515 (1990)); increased sprouting of neurons may be detected by methods known in the art, such as, for example, the methods set forth in Pestronk et al. (Exp. Neurol. 70:65-82 (1980)) or Brown et al. (Ann. Rev. Neurosci. 4:17-42 (1981)); increased production of neuron-associated molecules may be measured by bioassay, enzymatic assay, antibody binding, Northern blot assay, etc., using techniques known in the art and depending on the molecule to be measured; and motor neuron dysfunction may be measured by assessing the physical manifestation of motor neuron disorder, e.g., weakness, motor neuron conduction velocity, or functional disability.

In specific embodiments, motor neuron diseases, disorders, and/or conditions that may be treated, prevented, and/or diagnosed according to the invention include, but are not limited to, diseases, disorders, and/or conditions such as infarction, infection, exposure to toxin, trauma, surgical damage, degenerative disease or malignancy that may affect motor neurons as well as other components of the nervous system, as well as diseases, disorders, and/or conditions that selectively affect neurons such as amyotrophic lateral sclerosis, and including, but not limited to, progressive spinal muscular atrophy, progressive bulbar palsy, primary lateral sclerosis, infantile and juvenile muscular atrophy, progressive bulbar paralysis of childhood (Fazio-Londe syndrome), poliomyelitis and the post polio syndrome, and Hereditary Motorsensory Neuropathy (Charcot-Marie-Tooth Disease).

Infectious Disease

A polypeptide or polynucleotide and/or agonist or antagonist of the present invention can be used to treat, prevent, and/or diagnose infectious agents. For example, by increasing the immune response, particularly increasing the proliferation and differentiation of B and/or T cells, infectious diseases may be treated, prevented, and/or diagnosed. The immune response may be increased by either enhancing an existing immune response, or by initiating a new immune response. Alternatively, polypeptide or polynucleotide and/or agonist or antagonist of the present invention may also directly inhibit the infectious agent, without necessarily eliciting an immune response.

Viruses are one example of an infectious agent that can cause disease or symptoms that can be treated, prevented, and/or diagnosed by a polynucleotide or polypeptide and/or agonist or antagonist of the present invention. Examples of viruses, include, but are not limited to Examples of viruses, include, but are not limited to the following DNA and RNA viruses and viral families: Arbovirus, Adenoviridae, Arenaviridae, Arterivirus, Birnaviridae, Bunyaviridae, Caliciviridae, Circoviridae, Coronaviridae, Dengue, EBV, HIV, Flaviviridae, Hepadnaviridae (Hepatitis), Herpesviridae (such as, Cytomegalovirus, Herpes Simplex, Herpes Zoster), Mononegavirus (e.g., Paramyxoviridae, Morbillivirus, Rhabdoviridae), Orthomyxoviridae (e.g., Influenza A, Influenza B, and parainfluenza), Papiloma virus, Papovaviridae, Parvoviridae, Picornaviridae, Poxyiridae (such as Smallpox or Vaccinia), Reoviridae (e.g., Rotavirus), Retroviridae (HTLV-I, HTLV-II, Lentivirus), and Togaviridae (e.g., Rubivirus). Viruses falling within these families can cause a variety of diseases or symptoms, including, but not limited to: arthritis, bronchiolitis, respiratory syncytial virus, encephalitis, eye infections (e.g., conjunctivitis, keratitis), chronic fatigue syndrome, hepatitis (A, B, C, E, Chronic Active, Delta), Japanese B encephalitis, Junin, Chikungunya, Rift Valley fever, yellow fever, meningitis, opportunistic infections (e.g., AIDS), pneumonia, Burkitt's Lymphoma, chickenpox, hemorrhagic fever, Measles, Mumps, Parainfluenza, Rabies, the common cold, Polio, leukemia, Rubella, sexually transmitted diseases, skin diseases (e.g., Kaposi's, warts), and viremia. polynucleotides or polypeptides, or agonists or antagonists of the invention, can be used to treat, prevent, and/or diagnose any of these symptoms or diseases. In specific embodiments, polynucleotides, polypeptides, or agonists or antagonists of the invention are used to treat, prevent, and/or diagnose: meningitis, Dengue, EBV, and/or hepatitis (e.g., hepatitis B). In an additional specific embodiment polynucleotides, polypeptides, or agonists or antagonists of the invention are used to treat patients nonresponsive to one or more other commercially available hepatitis vaccines. In a further specific embodiment polynucleotides, polypeptides, or agonists or antagonists of the invention are used to treat, prevent, and/or diagnose AIDS.

Similarly, bacterial or fungal agents that can cause disease or symptoms and that can be treated, prevented, and/or diagnosed by a polynucleotide or polypeptide and/or agonist or antagonist of the present invention include, but not limited to, include, but not limited to, the following Gram-Negative and Gram-positive bacteria and bacterial families and fungi: Actinomycetales (e.g., *Corynebacterium, Mycobacterium, Norcardia*), *Cryptococcus neoformans*, Aspergillosis, Bacillaceae (e.g., Anthrax, *Clostridium*), Bacteroidaceae, Blastomycosis, *Bordetella, Borrelia* (e.g., *Borrelia burgdorferi*), Brucellosis, Candidiasis, *Campylobacter, Coccidioidomycosis, Cryptococcosis, Dermatocycoses, E. coli* (e.g., Enterotoxigenic *E. coli* and Enterohemorrhagic *E. coli*), Enterobacteriaceae (*Klebsiella, Salmonella* (e.g., *Salmonella typhi*, and *Salmonella paratyphi*), *Serratia, Yersinia*), *Erysipelothrix, Helicobacter, Legionellosis, Leptospirosis, Listeria, Mycoplasmatales, Mycobacterium leprae, Vibrio cholerae*, Neisseriaceae (e.g., *Acinetobacter, Gonorrhea,*

*Menigococcal*), *Meisseria meningitidis*, Pasteurellacea Infections (e.g., *Actinobacillus, Heamophilus* (e.g., *Heamophilus influenza* type B), *Pasteurella*), *Pseudomonas*, Rickettsiaceae, Chlamydiaceae, Syphilis, *Shigella* spp., Staphylococcal, Meningiococcal, Pneumococcal and Streptococcal (e.g., *Streptococcus pneumoniae* and Group B *Streptococcus*). These bacterial or fungal families can cause the following diseases or symptoms, including, but not limited to: bacteremia, endocarditis, eye infections (conjunctivitis, tuberculosis, uveitis), gingivitis, opportunistic infections (e.g., AIDS related infections), paronychia, prosthesis-related infections, Reiter's Disease, respiratory tract infections, such as Whooping Cough or Empyema, sepsis, Lyme Disease, Cat-Scratch Disease, Dysentery, Paratyphoid Fever, food poisoning, Typhoid, pneumonia, Gonorrhea, meningitis (e.g., mengitis types A and B), Chlamydia, Syphilis, Diphtheria, Leprosy, Paratuberculosis, Tuberculosis, Lupus, Botulism, gangrene, tetanus, impetigo, Rheumatic Fever, Scarlet Fever, sexually transmitted diseases, skin diseases (e.g., cellulitis, dermatocycoses), toxemia, urinary tract infections, wound infections. Polynucleotides or polypeptides, agonists or antagonists of the invention, can be used to treat, prevent, and/or diagnose any of these symptoms or diseases. In specific embodiments, polynucleotides, polypeptides, agonists or antagonists of the invention are used to treat, prevent, and/or diagnose: tetanus, Diptheria, botulism, and/or meningitis type B.

Moreover, parasitic agents causing disease or symptoms that can be treated, prevented, and/or diagnosed by a polynucleotide or polypeptide and/or agonist or antagonist of the present invention include, but not limited to, the following families or class: Amebiasis, Babesiosis, Coccidiosis, Cryptosporidiosis, Dientamoebiasis, Dourine, Ectoparasitic, Giardiasis, Helminthiasis, Leishmaniasis, Theileriasis, Toxoplasmosis, Trypanosomiasis, and Trichomonas and Sporozoans (e.g., *Plasmodium virax, Plasmodium falciparium, Plasmodium malariae* and *Plasmodium ovale*). These parasites can cause a variety of diseases or symptoms, including, but not limited to: Scabies, Trombiculiasis, eye infections, intestinal disease (e.g., dysentery, giardiasis), liver disease, lung disease, opportunistic infections (e.g., AIDS related), malaria, pregnancy complications, and toxoplasmosis. polynucleotides or polypeptides, or agonists or antagonists of the invention, can be used to treat, prevent, and/or diagnose any of these symptoms or diseases. In specific embodiments, polynucleotides, polypeptides, or agonists or antagonists of the invention are used to treat, prevent, and/or diagnose malaria.

Preferably, treatment or prevention using a polypeptide or polynucleotide and/or agonist or antagonist of the present invention could either be by administering an effective amount of a polypeptide to the patient, or by removing cells from the patient, supplying the cells with a polynucleotide of the present invention, and returning the engineered cells to the patient (ex vivo therapy). Moreover, the polypeptide or polynucleotide of the present invention can be used as an antigen in a vaccine to raise an immune response against infectious disease.

Regeneration

A polynucleotide or polypeptide and/or agonist or antagonist of the present invention can be used to differentiate, proliferate, and attract cells, leading to the regeneration of tissues. (See, Science 276:59-87 (1997).) The regeneration of tissues could be used to repair, replace, or protect tissue damaged by congenital defects, trauma (wounds, burns, incisions, or ulcers), age, disease (e.g. osteoporosis, osteocarthritis, periodontal disease, liver failure), surgery, including cosmetic plastic surgery, fibrosis, reperfusion injury, or systemic cytokine damage.

Tissues that could be regenerated using the present invention include organs (e.g., pancreas, liver, intestine, kidney, skin, endothelium), muscle (smooth, skeletal or cardiac), vasculature (including vascular and lymphatics), nervous, hematopoietic, and skeletal (bone, cartilage, tendon, and ligament) tissue. Preferably, regeneration occurs without or decreased scarring. Regeneration also may include angiogenesis.

Moreover, a polynucleotide or polypeptide and/or agonist or antagonist of the present invention may increase regeneration of tissues difficult to heal. For example, increased tendon/ligament regeneration would quicken recovery time after damage. A polynucleotide or polypeptide and/or agonist or antagonist of the present invention could also be used prophylactically in an effort to avoid damage. Specific diseases that could be treated, prevented, and/or diagnosed include of tendinitis, carpal tunnel syndrome, and other tendon or ligament defects. A further example of tissue regeneration of non-healing wounds includes pressure ulcers, ulcers associated with vascular insufficiency, surgical, and traumatic wounds.

Similarly, nerve and brain tissue could also be regenerated by using a polynucleotide or polypeptide and/or agonist or antagonist of the present invention to proliferate and differentiate nerve cells. Diseases that could be treated, prevented, and/or diagnosed using this method include central and peripheral nervous system diseases, neuropathies, or mechanical and traumatic diseases, disorders, and/or conditions (e.g., spinal cord disorders, head trauma, cerebrovascular disease, and stoke). Specifically, diseases associated with peripheral nerve injuries, peripheral neuropathy (e.g., resulting from chemotherapy or other medical therapies), localized neuropathies, and central nervous system diseases (e.g., Alzheimer's disease, Parkinson's disease, Huntington's disease, amyotrophic lateral sclerosis, and Shy-Drager syndrome), could all be treated, prevented, and/or diagnosed using the polynucleotide or polypeptide and/or agonist or antagonist of the present invention.

Binding Activity

A polypeptide of the present invention may be used to screen for molecules that bind to the polypeptide or for molecules to which the polypeptide binds. The binding of the polypeptide and the molecule may activate (agonist), increase, inhibit (antagonist), or decrease activity of the polypeptide or the molecule bound. Examples of such molecules include antibodies, oligonucleotides, proteins (e.g., receptors), or small molecules.

Preferably, the molecule is closely related to the natural ligand of the polypeptide, e.g., a fragment of the ligand, or a natural substrate, a ligand, a structural or functional mimetic. (See, Coligan et al., Current Protocols in Immunology 1(2): Chapter 5 (1991).) Similarly, the molecule can be closely related to the natural receptor to which the polypeptide binds, or at least, a fragment of the receptor capable of being bound by the polypeptide (e.g., active site). In either case, the molecule can be rationally designed using known techniques.

Preferably, the screening for these molecules involves producing appropriate cells which express the polypeptide, either as a secreted protein or on the cell membrane. Preferred cells include cells from mammals, yeast, *Drosophila*, or *E. coli*. Cells expressing the polypeptide (or cell membrane containing the expressed polypeptide) are then preferably contacted with a test compound potentially containing the molecule to observe binding, stimulation, or inhibition of activity of either the polypeptide or the molecule.

The assay may simply test binding of a candidate compound to the polypeptide, wherein binding is detected by a label, or in an assay involving competition with a labeled competitor. Further, the assay may test whether the candidate compound results in a signal generated by binding to the polypeptide.

Alternatively, the assay can be carried out using cell-free preparations, polypeptide/molecule affixed to a solid support, chemical libraries, or natural product mixtures. The assay may also simply comprise the steps of mixing a candidate compound with a solution containing a polypeptide, measuring polypeptide/molecule activity or binding, and comparing the polypeptide/molecule activity or binding to a standard.

Preferably, an ELISA assay can measure polypeptide level or activity in a sample (e.g., biological sample) using a monoclonal or polyclonal antibody. The antibody can measure polypeptide level or activity by either binding, directly or indirectly, to the polypeptide or by competing with the polypeptide for a substrate.

Additionally, the receptor to which a polypeptide of the invention binds can be identified by numerous methods known to those of skill in the art, for example, ligand panning and FACS® sorting (Coligan, et al., Current Protocols in Immun., 1(2), Chapter 5, (1991)). For example, expression cloning is employed wherein polyadenylated RNA is prepared from a cell responsive to the polypeptides, for example, NIH3T3 cells which are known to contain multiple receptors for the FGF family proteins, and SC-3 cells, and a cDNA library created from this RNA is divided into pools and used to transfect COS cells or other cells that are not responsive to the polypeptides. Transfected cells which are grown on glass slides are exposed to the polypeptide of the present invention, after they have been labeled. The polypeptides can be labeled by a variety of means including iodination or inclusion of a recognition site for a site-specific protein kinase.

Following fixation and incubation, the slides are subjected to auto-radiographic analysis. Positive pools are identified and sub-pools are prepared and re-transfected using an iterative sub-pooling and re-screening process, eventually yielding a single clones that encodes the putative receptor.

As an alternative approach for receptor identification, the labeled polypeptides can be photoaffinity linked with cell membrane or extract preparations that express the receptor molecule. Cross-linked material is resolved by PAGE analysis and exposed to X-ray film. The labeled complex containing the receptors of the polypeptides can be excised, resolved into peptide fragments, and subjected to protein microsequencing. The amino acid sequence obtained from microsequencing would be used to design a set of degenerate oligonucleotide probes to screen a cDNA library to identify the genes encoding the putative receptors.

Moreover, the techniques of gene-shuffling, motif-shuffling, exon-shuffling, and/or codon-shuffling (collectively referred to as "DNA shuffling") may be employed to modulate the activities of polypeptides of the invention thereby effectively generating agonists and antagonists of polypeptides of the invention. See generally, U.S. Pat. Nos. 5,605,793, 5,811,238, 5,830,721, 5,834,252, and 5,837,458, and Patten, P. A., et al., Curr. Opinion Biotechnol. 8:724-33 (1997); Harayama, S. Trends Biotechnol. 16(2):76-82 (1998); Hansson, L. O., et al., J. Mol. Biol. 287:265-76 (1999); and Lorenzo, M. M. and Blasco, R. Biotechniques 24(2):308-13 (1998) (each of these patents and publications are hereby incorporated by reference). In one embodiment, alteration of polynucleotides and corresponding polypeptides of the invention may be achieved by DNA shuffling. DNA shuffling involves the assembly of two or more DNA segments into a desired polynucleotide sequence of the invention molecule by homologous, or site-specific, recombination. In another embodiment, polynucleotides and corresponding polypeptides of the invention may be altered by being subjected to random mutagenesis by error-prone PCR, random nucleotide insertion or other methods prior to recombination. In another embodiment, one or more components, motifs, sections, parts, domains, fragments, etc., of the polypeptides of the invention may be recombined with one or more components, motifs, sections, parts, domains, fragments, etc. of one or more heterologous molecules. In preferred embodiments, the heterologous molecules are family members. In further preferred embodiments, the heterologous molecule is a growth factor such as, for example, platelet-derived growth factor (PDGF), insulin-like growth factor (IGF-I), transforming growth factor (TGF)-alpha, epidermal growth factor (EGF), fibroblast growth factor (FGF), TGF-beta, bone morphogenetic protein (BMP)-2, BMP-4, BMP-5, BMP-6, BMP-7, activins A and B, decapentaplegic (dpp), 60A, OP-2, dorsalin, growth differentiation factors (GDFs), nodal, MIS, inhibin-alpha, TGF-beta1, TGF-beta2, TGF-beta3, TGF-beta5, and glial-derived neurotrophic factor (GDNF).

Other preferred fragments are biologically active fragments of the polypeptides of the invention. Biologically active fragments are those exhibiting activity similar, but not necessarily identical, to an activity of the polypeptide. The biological activity of the fragments may include an improved desired activity, or a decreased undesirable activity.

Additionally, this invention provides a method of screening compounds to identify those which modulate the action of the polypeptide of the present invention. An example of such an assay comprises combining a mammalian fibroblast cell, a the polypeptide of the present invention, the compound to be screened and 3[H] thymidine under cell culture conditions where the fibroblast cell would normally proliferate. A control assay may be performed in the absence of the compound to be screened and compared to the amount of fibroblast proliferation in the presence of the compound to determine if the compound stimulates proliferation by determining the uptake of 3[H] thymidine in each case. The amount of fibroblast cell proliferation is measured by liquid scintillation chromatography which measures the incorporation of 3[H] thymidine. Both agonist and antagonist compounds may be identified by this procedure.

In another method, a mammalian cell or membrane preparation expressing a receptor for a polypeptide of the present invention is incubated with a labeled polypeptide of the present invention in the presence of the compound. The ability of the compound to enhance or block this interaction could then be measured. Alternatively, the response of a known second messenger system following interaction of a compound to be screened and the receptor is measured and the ability of the compound to bind to the receptor and elicit a second messenger response is measured to determine if the compound is a potential agonist or antagonist. Such second messenger systems include but are not limited to, cAMP guanylate cyclase, ion channels or phosphoinositide hydrolysis.

All of these above assays can be used as diagnostic or prognostic markers. The molecules discovered using these assays can be used to treat, prevent, and/or diagnose disease or to bring about a particular result in a patient (e.g., blood vessel growth) by activating or inhibiting the polypeptide/ molecule. Moreover, the assays can discover agents which may inhibit or enhance the production of the polypeptides of the invention from suitably manipulated cells or tissues. Therefore, the invention includes a method of identifying compounds which bind to the polypeptides of the invention comprising the steps of: (a) incubating a candidate binding compound with the polypeptide; and (b) determining if binding has occurred. Moreover, the invention includes a method of identifying agonists/antagonists comprising the steps of: (a) incubating a candidate compound with the polypeptide, (b) assaying a biological activity, and (c) determining if a biological activity of the polypeptide has been altered.

Also, one could identify molecules bind a polypeptide of the invention experimentally by using the beta-pleated sheet regions contained in the polypeptide sequence of the protein. Accordingly, specific embodiments of the invention are directed to polynucleotides encoding polypeptides which comprise, or alternatively consist of, the amino acid sequence of each beta pleated sheet regions in a disclosed polypeptide sequence. Additional embodiments of the invention are directed to polynucleotides encoding polypeptides which comprise, or alternatively consist of, any combination or all of contained in the polypeptide sequences of the invention. Additional preferred embodiments of the invention are directed to polypeptides which comprise, or alternatively consist of, the amino acid sequence of each of the beta pleated sheet regions in one of the polypeptide sequences of the invention. Additional embodiments of the invention are directed to polypeptides which comprise, or alternatively consist of, any combination or all of the beta pleated sheet regions in one of the polypeptide sequences of the invention.

Drug Screening

Further contemplated is the use of the polypeptides of the present invention, or the polynucleotides encoding these polypeptides, to screen for molecules which modify the activities of the polypeptides of the present invention. Such a method would include contacting the polypeptide of the present invention with a selected compound(s) suspected of having antagonist or agonist activity, and assaying the activity of these polypeptides following binding.

This invention is particularly useful for screening therapeutic compounds by using the polypeptides of the present invention, or binding fragments thereof, in any of a variety of drug screening techniques. The polypeptide or fragment employed in such a test may be affixed to a solid support, expressed on a cell surface, free in solution, or located intracellularly. One method of drug screening utilizes eukaryotic or prokaryotic host cells which are stably transformed with recombinant nucleic acids expressing the polypeptide or fragment. Drugs are screened against such transformed cells in competitive binding assays. One may measure, for example, the formulation of complexes between the agent being tested and a polypeptide of the present invention.

Thus, the present invention provides methods of screening for drugs or any other agents which affect activities mediated by the polypeptides of the present invention. These methods comprise contacting such an agent with a polypeptide of the present invention or a fragment thereof and assaying for the presence of a complex between the agent and the polypeptide or a fragment thereof, by methods well known in the art. In such a competitive binding assay, the agents to screen are typically labeled. Following incubation, free agent is separated from that present in bound form, and the amount of free or uncomplexed label is a measure of the ability of a particular agent to bind to the polypeptides of the present invention.

Another technique for drug screening provides high throughput screening for compounds having suitable binding affinity to the polypeptides of the present invention, and is described in great detail in European Patent Application 84/03564, published on Sep. 13, 1984, which is incorporated herein by reference herein. Briefly stated, large numbers of different small peptide test compounds are synthesized on a solid substrate, such as plastic pins or some other surface. The peptide test compounds are reacted with polypeptides of the present invention and washed. Bound polypeptides are then detected by methods well known in the art. Purified polypeptides are coated directly onto plates for use in the aforementioned drug screening techniques. In addition, non-neutralizing antibodies may be used to capture the peptide and immobilize it on the solid support.

This invention also contemplates the use of competitive drug screening assays in which neutralizing antibodies capable of binding polypeptides of the present invention specifically compete with a test compound for binding to the polypeptides or fragments thereof. In this manner, the antibodies are used to detect the presence of any peptide which shares one or more antigenic epitopes with a polypeptide of the invention.

The human PCSK9b or PCSK9c polypeptides and/or peptides of the present invention, or immunogenic fragments or oligopeptides thereof, can be used for screening therapeutic drugs or compounds in a variety of drug screening techniques. The fragment employed in such a screening assay may be free in solution, affixed to a solid support, borne on a cell surface, or located intracellularly. The reduction or abolition of activity of the formation of binding complexes between the ion channel protein and the agent being tested can be measured. Thus, the present invention provides a method for screening or assessing a plurality of compounds for their specific binding affinity with a PCSK9b or PCSK9c polypeptide, or a bindable peptide fragment, of this invention, comprising providing a plurality of compounds, combining the PCSK9b or PCSK9c polypeptide, or a bindable peptide fragment, with each of a plurality of compounds for a time sufficient to allow binding under suitable conditions and detecting binding of the PCSK9b or PCSK9c polypeptide or peptide to each of the plurality of test compounds, thereby identifying the compounds that specifically bind to the PCSK9b or PCSK9c polypeptide or peptide.

Methods of identifying compounds that modulate the activity of the novel human PCSK9b or PCSK9c polypeptides and/or peptides are provided by the present invention and comprise combining a potential or candidate compound or drug modulator of calpain biological activity with an PCSK9b or PCSK9c polypeptide or peptide, for example, the PCSK9b or PCSK9c amino acid sequence as set forth in SEQ ID NO:2 or SEQ ID NO:4, and measuring an effect of the candidate compound or drug modulator on the biological activity of the PCSK9b or PCSK9c polypeptide or peptide. Such measurable effects include, for example, physical binding interaction; the ability to cleave a suitable calpain substrate; effects on native and cloned PCSK9b or PCSK9c-expressing cell line; and effects of modulators or other calpain-mediated physiological measures.

Another method of identifying compounds that modulate the biological activity of the novel PCSK9b or PCSK9c polypeptides of the present invention comprises combining a potential or candidate compound or drug modulator of a calpain biological activity with a host cell that expresses the PCSK9b or PCSK9c polypeptide and measuring an effect of the candidate compound or drug modulator on the biological activity of the PCSK9b or PCSK9c polypeptide. The host cell can also be capable of being induced to express the PCSK9b or PCSK9c polypeptide, e.g., via inducible expression. Physiological effects of a given modulator candidate on the PCSK9b or PCSK9c polypeptide can also be measured. Thus, cellular assays for particular calpain modulators may be either direct measurement or quantification of the physical biological activity of the PCSK9b or PCSK9c polypeptide, or they may be measurement or quantification of a physiological effect. Such methods preferably employ a PCSK9b or PCSK9c polypeptide as described herein, or an overexpressed recombinant PCSK9b or PCSK9c polypeptide in suitable host cells containing an expression vector as described herein, wherein the PCSK9b or PCSK9c polypeptide is expressed, overexpressed, or undergoes upregulated expression.

Another aspect of the present invention embraces a method of screening for a compound that is capable of modulating the biological activity of a PCSK9b or PCSK9c polypeptide, comprising providing a host cell containing an expression vector harboring a nucleic acid sequence encoding a PCSK9b or PCSK9c polypeptide, or a functional peptide or portion thereof (e.g., SEQ ID NO:2 or SEQ ID NO:4); determining the biological activity of the expressed PCSK9b or PCSK9c polypeptide in the absence of a modulator compound; contacting the cell with the modulator compound and determining the biological activity of the expressed PCSK9b or PCSK9c polypeptide in the presence of the modulator compound. In such a method, a difference between the activity of the PCSK9b or PCSK9c polypeptide in the presence of the modulator compound and in the absence of the modulator compound indicates a modulating effect of the compound.

Essentially any chemical compound can be employed as a potential modulator or ligand in the assays according to the present invention. Compounds tested as calpain modulators can be any small chemical compound, or biological entity (e.g., protein, sugar, nucleic acid, lipid). Test compounds will typically be small chemical molecules and peptides. Generally, the compounds used as potential modulators can be dissolved in aqueous or organic (e.g., DMSO-based) solutions. The assays are designed to screen large chemical libraries by automating the assay steps and providing compounds from any convenient source. Assays are typically run in parallel, for example, in microtiter formats on microtiter plates in robotic assays. There are many suppliers of chemical compounds, including Sigma (St. Louis, Mo.), Aldrich (St. Louis, Mo.), Sigma-Aldrich (St. Louis, Mo.), Fluka Chemika-Biochemica Analytika (Buchs, Switzerland), for example. Also, compounds may be synthesized by methods known in the art.

High throughput screening methodologies are particularly envisioned for the detection of modulators of the novel PCSK9b or PCSK9c polynucleotides and polypeptides described herein. Such high throughput screening methods typically involve providing a combinatorial chemical or peptide library containing a large number of potential therapeutic compounds (e.g., ligand or modulator compounds). Such combinatorial chemical libraries or ligand libraries are then screened in one or more assays to identify those library members (e.g., particular chemical species or subclasses) that display a desired characteristic activity. The compounds so identified can serve as conventional lead compounds, or can themselves be used as potential or actual therapeutics.

A combinatorial chemical library is a collection of diverse chemical compounds generated either by chemical synthesis or biological synthesis, by combining a number of chemical building blocks (i.e., reagents such as amino acids). As an example, a linear combinatorial library, e.g., a polypeptide or peptide library, is formed by combining a set of chemical building blocks in every possible way for a given compound length (i.e., the number of amino acids in a polypeptide or peptide compound). Millions of chemical compounds can be synthesized through such combinatorial mixing of chemical building blocks.

The preparation and screening of combinatorial chemical libraries is well known to those having skill in the pertinent art. Combinatorial libraries include, without limitation, peptide libraries (e.g. U.S. Pat. No. 5,010,175; Furka, 1991, *Int. J. Pept. Prot. Res.*, 37:487-493; and Houghton et al., 1991, *Nature*, 354:84-88). Other chemistries for generating chemical diversity libraries can also be used. Nonlimiting examples of chemical diversity library chemistries include, peptides (PCT Publication No. WO 91/019735), encoded peptides (PCT Publication No. WO 93/20242), random bio-oligomers (PCT Publication No. WO 92/00091), benzodiazepines (U.S. Pat. No. 5,288,514), diversomers such as hydantoins, benzodiazepines and dipeptides (Hobbs et al., 1993, *Proc. Natl. Acad. Sci. USA,* 90:6909-6913), vinylogous polypeptides (Hagihara et al., 1992, *J. Amer. Chem. Soc.,* 114:6568), non-peptidal peptidomimetics with glucose scaffolding (Hirschmann et al., 1992, *J. Amer. Chem. Soc.,* 114:9217-9218), analogous organic synthesis of small compound libraries (Chen et al., 1994, *J. Amer. Chem. Soc.,* 116:2661), oligocarbamates (Cho et al., 1993, *Science,* 261:1303), and/or peptidyl phosphonates (Campbell et al., 1994, *J. Org. Chem.,* 59:658), nucleic acid libraries (see Ausubel, Berger and Sambrook, all supra), peptide nucleic acid libraries (U.S. Pat. No. 5,539,083), antibody libraries (e.g., Vaughn et al., 1996, *Nature Biotechnology,* 14(3):309-314) and PCT/US96/10287), carbohydrate libraries (e.g., Liang et al., 1996, *Science,* 274-1520-1522) and U.S. Pat. No. 5,593,853), small organic molecule libraries (e.g., benzodiazepines, Baum C&EN, Jan. 18, 1993, page 33; and U.S. Pat. No. 5,288,514; isoprenoids, U.S. Pat. No. 5,569,588; thiazolidinones and metathiazanones, U.S. Pat. No. 5,549,974; pyrrolidines, U.S. Pat. Nos. 5,525,735 and 5,519,134; morpholino compounds, U.S. Pat. No. 5,506,337; and the like).

Devices for the preparation of combinatorial libraries are commercially available (e.g., 357 MPS, 390 MPS, Advanced Chem Tech, Louisville Ky.; Symphony, Rainin, Woburn, Mass.; 433A Applied Biosystems, Foster City, Calif.; 9050 Plus, Millipore, Bedford, Mass.). In addition, a large number of combinatorial libraries are commercially available (e.g., ComGenex, Princeton, N.J.; Asinex, Moscow, Russia; Tripos, Inc., St. Louis, Mo.; ChemStar, Ltd., Moscow, Russia; 3D Pharmaceuticals, Exton, Pa.; Martek Biosciences, Columbia, Md., and the like).

In one embodiment, the invention provides solid phase based in vitro assays in a high throughput format, where the cell or tissue expressing an ion channel is attached to a solid phase substrate. In such high throughput assays, it is possible to screen up to several thousand different modulators or ligands in a single day. In particular, each well of a microtiter plate can be used to perform a separate assay against a selected potential modulator, or, if concentration or incubation time effects are to be observed, every 5-10 wells can test a single modulator. Thus, a single standard microtiter plate can assay about 96 modulators. If 1536 well plates are used, then a single plate can easily assay from about 100 to about 1500 different compounds. It is possible to assay several different plates per day; thus, for example, assay screens for up to about 6,000-20,000 different compounds are possible using the described integrated systems.

In another of its aspects, the present invention encompasses screening and small molecule (e.g., drug) detection assays which involve the detection or identification of small molecules that can bind to a given protein, i.e., a PCSK9b or PCSK9c polypeptide or peptide. Particularly preferred are assays suitable for high throughput screening methodologies.

In such binding-based detection, identification, or screening assays, a functional assay is not typically required. All that is needed is a target protein, preferably substantially purified, and a library or panel of compounds (e.g., ligands, drugs, small molecules) or biological entities to be screened or assayed for binding to the protein target. Preferably, most small molecules that bind to the target protein will modulate activity in some manner, due to preferential, higher affinity binding to functional areas or sites on the protein.

An example of such an assay is the fluorescence based thermal shift assay (3-Dimensional Pharmaceuticals, Inc., 3DP, Exton, Pa.) as described in U.S. Pat. Nos. 6,020,141 and 6,036,920 to Pantoliano et al.; see also, J. Zimmerman, 2000, Gen. Eng. News, 20(8)). The assay allows the detection of small molecules (e.g., drugs, ligands) that bind to expressed, and preferably purified, ion channel polypeptide based on affinity of binding determinations by analyzing thermal unfolding curves of protein-drug or ligand complexes. The drugs or binding molecules determined by this technique can be further assayed, if desired, by methods, such as those described herein, to determine if the molecules affect or modulate function or activity of the target protein.

To purify a PCSK9b or PCSK9c polypeptide or peptide to measure a biological binding or ligand binding activity, the source may be a whole cell lysate that can be prepared by successive freeze-thaw cycles (e.g., one to three) in the presence of standard protease inhibitors. The PCSK9b or PCSK9c polypeptide may be partially or completely purified by standard protein purification methods, e.g., affinity chromatography using specific antibody described infra, or by ligands specific for an epitope tag engineered into the recombinant PCSK9b or PCSK9c polypeptide molecule, also as described herein. Binding activity can then be measured as described.

Compounds which are identified according to the methods provided herein, and which modulate or regulate the biological activity or physiology of the PCSK9b or PCSK9c polypeptides according to the present invention are a preferred embodiment of this invention. It is contemplated that such modulatory compounds may be employed in treatment and therapeutic methods for treating a condition that is mediated by the novel PCSK9b or PCSK9c polypeptides by administering to an individual in need of such treatment a therapeutically effective amount of the compound identified by the methods described herein.

In addition, the present invention provides methods for treating an individual in need of such treatment for a disease, disorder, or condition that is mediated by the PCSK9b or PCSK9c polypeptides of the invention, comprising administering to the individual a therapeutically effective amount of the PCSK9b or PCSK9c-modulating compound identified by a method provided herein.

Antisense and Ribozyme

Antagonists

In specific embodiments, antagonists according to the present invention are nucleic acids corresponding to the sequences contained in SEQ ID NO:X, or the complementary strand thereof, and/or to nucleotide sequences contained a deposited clone. In one embodiment, antisense sequence is generated internally by the organism, in another embodiment, the antisense sequence is separately administered (see, for example, O'Connor, Neurochem., 56:560 (1991). Oligodeoxynucleotides as Antisense Inhibitors of Gene Expression, CRC Press, Boca Raton, Fla. (1988). Antisense technology can be used to control gene expression through antisense DNA or RNA, or through triple-helix formation. Antisense techniques are discussed for example, in Okano, Neurochem., 56:560 (1991); Oligodeoxynucleotides as Antisense Inhibitors of Gene Expression, CRC Press, Boca Raton, Fla. (1988). Triple helix formation is discussed in, for instance, Lee et al., Nucleic Acids Research, 6:3073 (1979); Cooney et al., Science, 241:456 (1988); and Dervan et al., Science, 251:1300 (1991). The methods are based on binding of a polynucleotide to a complementary DNA or RNA.

For example, the use of c-myc and c-myb antisense RNA constructs to inhibit the growth of the non-lymphocytic leukemia cell line HL-60 and other cell lines was previously described. (Wickstrom et al. (1988); Anfossi et al. (1989)). These experiments were performed in vitro by incubating cells with the oligoribonucleotide. A similar procedure for in vivo use is described in WO 91/15580. Briefly, a pair of oligonucleotides for a given antisense RNA is produced as follows: A sequence complimentary to the first 15 bases of the open reading frame is flanked by an EcoR1 site on the 5 end and a HindIII site on the 3 end. Next, the pair of oligonucleotides is heated at 90° C. for one minute and then annealed in 2× ligation buffer (20 mM TRIS HCl pH 7.5, 10 mM MgCl2, 10 mM dithiothreitol (DTT) and 0.2 mM ATP) and then ligated to the EcoR1/Hind III site of the retroviral vector PMV7 (WO 91/15580).

For example, the 5' coding portion of a polynucleotide that encodes the mature polypeptide of the present invention may be used to design an antisense RNA oligonucleotide of from about 10 to 40 base pairs in length. A DNA oligonucleotide is designed to be complementary to a region of the gene involved in transcription thereby preventing transcription and the production of the receptor. The antisense RNA oligonucleotide hybridizes to the mRNA in vivo and blocks translation of the mRNA molecule into receptor polypeptide.

In one embodiment, the antisense nucleic acid of the invention is produced intracellularly by transcription from an exogenous sequence. For example, a vector or a portion thereof, is transcribed, producing an antisense nucleic acid (RNA) of the invention. Such a vector would contain a sequence encoding the antisense nucleic acid of the invention. Such a vector can remain episomal or become chromosomally integrated, as long as it can be transcribed to produce the desired antisense RNA. Such vectors can be constructed by recombinant DNA technology methods standard in the art. Vectors can be plasmid, viral, or others known in the art, used for replication and expression in vertebrate cells. Expression of the sequence encoding a polypeptide of the invention, or fragments thereof, can be by any promoter known in the art to act in vertebrate, preferably human cells. Such promoters can be inducible or constitutive. Such promoters include, but are not limited to, the SV40 early promoter region (Bernoist and Chambon, Nature, 29:304-310 (1981), the promoter contained in the 3' long terminal repeat of Rous sarcoma virus (Yamamoto et al., Cell, 22:787-797 (1980), the herpes thymidine promoter (Wagner et al., Proc. Natl. Acad. Sci. U.S.A., 78:1441-1445 (1981), the regulatory sequences of the metallothionein gene (Brinster et al., Nature, 296:39-42 (1982)), etc.

The antisense nucleic acids of the invention comprise a sequence complementary to at least a portion of an RNA transcript of a gene of interest. However, absolute complementarity, although preferred, is not required. A sequence "complementary to at least a portion of an RNA" referred to herein, means a sequence having sufficient complementarity to be able to hybridize with the RNA, forming a stable duplex;

in the case of double stranded antisense nucleic acids of the invention, a single strand of the duplex DNA may thus be tested, or triplex formation may be assayed. The ability to hybridize will depend on both the degree of complementarity and the length of the antisense nucleic acid Generally, the larger the hybridizing nucleic acid, the more base mismatches with a RNA sequence of the invention it may contain and still form a stable duplex (or triplex as the case may be). One skilled in the art can ascertain a tolerable degree of mismatch by use of standard procedures to determine the melting point of the hybridized complex.

Oligonucleotides that are complementary to the 5' end of the message, e.g., the 5' untranslated sequence up to and including the AUG initiation codon, should work most efficiently at inhibiting translation. However, sequences complementary to the 3' untranslated sequences of mRNAs have been shown to be effective at inhibiting translation of mRNAs as well. See generally, Wagner, R., Nature, 372:333-335 (1994). Thus, oligonucleotides complementary to either the 5'- or 3'-non-translated, non-coding regions of a polynucleotide sequence of the invention could be used in an antisense approach to inhibit translation of endogenous mRNA. Oligonucleotides complementary to the 5' untranslated region of the mRNA should include the complement of the AUG start codon. Antisense oligonucleotides complementary to mRNA coding regions are less efficient inhibitors of translation but could be used in accordance with the invention. Whether designed to hybridize to the 5'-, 3'- or coding region of mRNA, antisense nucleic acids should be at least six nucleotides in length, and are preferably oligonucleotides ranging from 6 to about 50 nucleotides in length. In specific aspects the oligonucleotide is at least 10 nucleotides, at least 17 nucleotides, at least 25 nucleotides or at least 50 nucleotides.

Antisense oligonucleotides may be single or double stranded. Double stranded RNA's may be designed based upon the teachings of Paddison et al., Proc. Nat. Acad. Sci., 99:1443-1448 (2002); and International Publication Nos. WO 01/29058, and WO 99/32619; which are hereby incorporated herein by reference.

SiRNA reagents are specifically contemplated by the present invention. Such reagents are useful for inhibiting expression of the polynucleotides of the present invention and may have therapeutic efficacy. Several methods are known in the art for the therapeutic treatment of disorders by the administration of siRNA reagents. One such method is described by Tiscornia et al (PNAS, 100(4):1844-1848 (2003)); WO0409769, filed Jul. 18$^{th}$, 2003; and Reich S J et al., Mol. Vis. 2003 May 30; 9:210-6, which are incorporated by reference herein in its entirety.

The polynucleotides of the invention can be DNA or RNA or chimeric mixtures or derivatives or modified versions thereof, single-stranded or double-stranded. The oligonucleotide can be modified at the base moiety, sugar moiety, or phosphate backbone, for example, to improve stability of the molecule, hybridization, etc. The oligonucleotide may include other appended groups such as peptides (e.g., for targeting host cell receptors in vivo), or agents facilitating transport across the cell membrane (see, e.g., Letsinger et al., Proc. Natl. Acad. Sci. U.S.A. 86:6553-6556 (1989); Lemaitre et al., Proc. Natl. Acad. Sci., 84:648-652 (1987); PCT Publication NO: WO88/09810, published Dec. 15, 1988) or the blood-brain barrier (see, e.g., PCT Publication NO: WO89/10134, published Apr. 25, 1988), hybridization-triggered cleavage agents. (See, e.g., Krol et al., BioTechniques, 6:958-976 (1988)) or intercalating agents. (See, e.g., Zon, Pharm. Res., 5:539-549 (1988)). To this end, the oligonucleotide may be conjugated to another molecule, e.g., a peptide, hybridization triggered cross-linking agent, transport agent, hybridization-triggered cleavage agent, etc.

The antisense oligonucleotide may comprise at least one modified base moiety which is selected from the group including, but not limited to, 5-fluorouracil, 5-bromouracil, 5-chlorouracil, 5-iodouracil, hypoxanthine, xanthine, 4-acetylcytosine, 5-(carboxyhydroxylmethyl)uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl)uracil, (acp3)w, and 2,6-diaminopurine.

The antisense oligonucleotide may also comprise at least one modified sugar moiety selected from the group including, but not limited to, arabinose, 2-fluoroarabinose, xylulose, and hexose.

In yet another embodiment, the antisense oligonucleotide comprises at least one modified phosphate backbone selected from the group including, but not limited to, a phosphorothioate, a phosphorodithioate, a phosphoramidothioate, a phosphoramidate, a phosphordiamidate, a methylphosphonate, an alkyl phosphotriester, and a formacetal or analog thereof.

In yet another embodiment, the antisense oligonucleotide is an a-anomeric oligonucleotide. An a-anomeric oligonucleotide forms specific double-stranded hybrids with complementary RNA in which, contrary to the usual b-units, the strands run parallel to each other (Gautier et al., Nucl. Acids Res., 15:6625-6641 (1987)). The oligonucleotide is a 2-O-methylribonucleotide (Inoue et al., Nucl. Acids Res., 15:6131-6148 (1987)), or a chimeric RNA-DNA analogue (Inoue et al., FEBS Lett. 215:327-330 (1987)).

Polynucleotides of the invention may be synthesized by standard methods known in the art, e.g. by use of an automated DNA synthesizer (such as are commercially available from Biosearch, Applied Biosystems, etc.). As examples, phosphorothioate oligonucleotides may be synthesized by the method of Stein et al. (Nucl. Acids Res., 16:3209 (1988)), methylphosphonate oligonucleotides can be prepared by use of controlled pore glass polymer supports (Sarin et al., Proc. Natl. Acad. Sci. U.S.A., 85:7448-7451 (1988)), etc.

While antisense nucleotides complementary to the coding region sequence of the invention could be used, those complementary to the transcribed untranslated region are most preferred.

Potential antagonists according to the invention also include catalytic RNA, or a ribozyme (See, e.g., PCT International Publication WO 90/11364, published Oct. 4, 1990; Sarver et al, Science, 247:1222-1225 (1990). While ribozymes that cleave mRNA at site specific recognition sequences can be used to destroy mRNAs corresponding to the polynucleotides of the invention, the use of hammerhead ribozymes is preferred. Hammerhead ribozymes cleave mRNAs at locations dictated by flanking regions that form complementary base pairs with the target mRNA. The sole requirement is that the target mRNA have the following sequence of two bases: 5'-UG-3'. The construction and production of hammerhead ribozymes is well known in the art and is described more fully in Haseloff and Gerlach, Nature, 334:585-591 (1988). There are numerous potential hammerhead ribozyme cleavage sites within each nucleotide sequence disclosed in the sequence listing. Preferably, the ribozyme is engineered so that the cleavage recognition site is located near the 5' end of the mRNA corresponding to the polynucleotides of the invention; i.e., to increase efficiency and minimize the intracellular accumulation of non-functional mRNA transcripts.

As in the antisense approach, the ribozymes of the invention can be composed of modified oligonucleotides (e.g. for improved stability, targeting, etc.) and should be delivered to cells which express the polynucleotides of the invention in vivo. DNA constructs encoding the ribozyme may be introduced into the cell in the same manner as described above for the introduction of antisense encoding DNA. A preferred method of delivery involves using a DNA construct "encoding" the ribozyme under the control of a strong constitutive promoter, such as, for example, pol III or pol II promoter, so that transfected cells will produce sufficient quantities of the ribozyme to destroy endogenous messages and inhibit translation. Since ribozymes unlike antisense molecules, are catalytic, a lower intracellular concentration is required for efficiency.

Antagonist/agonist compounds may be employed to inhibit the cell growth and proliferation effects of the polypeptides of the present invention on neoplastic cells and tissues, i.e. stimulation of angiogenesis of tumors, and, therefore, retard or prevent abnormal cellular growth and proliferation, for example, in tumor formation or growth.

The antagonist/agonist may also be employed to prevent hyper-vascular diseases, and prevent the proliferation of epithelial lens cells after extracapsular cataract surgery. Prevention of the mitogenic activity of the polypeptides of the present invention may also be desirous in cases such as restenosis after balloon angioplasty.

The antagonist/agonist may also be employed to prevent the growth of scar tissue during wound healing.

The antagonist/agonist may also be employed to treat, prevent, and/or diagnose the diseases described herein.

Thus, the invention provides a method of treating or preventing diseases, disorders, and/or conditions, including but not limited to the diseases, disorders, and/or conditions listed throughout this application, associated with overexpression of a polynucleotide of the present invention by administering to a patient (a) an antisense molecule directed to the polynucleotide of the present invention, and/or (b) a ribozyme directed to the polynucleotide of the present invention.

Biotic Associations

A polynucleotide or polypeptide and/or agonist or antagonist of the present invention may increase the organisms ability, either directly or indirectly, to initiate and/or maintain biotic associations with other organisms. Such associations may be symbiotic, nonsymbiotic, endosymbiotic, macrosymbiotic, and/or microsymbiotic in nature. In general, a polynucleotide or polypeptide and/or agonist or antagonist of the present invention may increase the organisms ability to form biotic associations with any member of the fungal, bacterial, lichen, mycorrhizal, cyanobacterial, dinoflaggellate, and/or algal, kingdom, phylums, families, classes, genuses, and/or species.

The mechanism by which a polynucleotide or polypeptide and/or agonist or antagonist of the present invention may increase the host organisms ability, either directly or indirectly, to initiate and/or maintain biotic associations is variable, though may include, modulating osmolarity to desirable levels for the symbiont, modulating pH to desirable levels for the symbiont, modulating secretions of organic acids, modulating the secretion of specific proteins, phenolic compounds, nutrients, or the increased expression of a protein required for host-biotic organisms interactions (e.g., a receptor, ligand, etc.). Additional mechanisms are known in the art and are encompassed by the invention (see, for example, "Microbial Signalling and Communication", eds., R. England, G. Hobbs, N. Bainton, and D. McL. Roberts, Cambridge University Press, Cambridge, (1999); which is hereby incorporated herein by reference).

In an alternative embodiment, a polynucleotide or polypeptide and/or agonist or antagonist of the present invention may decrease the host organisms ability to form biotic associations with another organism, either directly or indirectly. The mechanism by which a polynucleotide or polypeptide and/or agonist or antagonist of the present invention may decrease the host organisms ability, either directly or indirectly, to initiate and/or maintain biotic associations with another organism is variable, though may include, modulating osmolarity to undesirable levels, modulating pH to undesirable levels, modulating secretions of organic acids, modulating the secretion of specific proteins, phenolic compounds, nutrients, or the decreased expression of a protein required for host-biotic organisms interactions (e.g., a receptor, ligand, etc.). Additional mechanisms are known in the art and are encompassed by the invention (see, for example, "Microbial Signalling and Communication", eds., R. England, G. Hobbs, N. Bainton, and D. McL. Roberts, Cambridge University Press, Cambridge, (1999); which is hereby incorporated herein by reference).

The hosts ability to maintain biotic associations with a particular pathogen has significant implications for the overall health and fitness of the host. For example, human hosts have symbiosis with enteric bacteria in their gastrointestinal tracts, particularly in the small and large intestine. In fact, bacteria counts in feces of the distal colon often approach $10^{12}$ per milliliter of feces. Examples of bowel flora in the gastrointestinal tract are members of the Enterobacteriaceae, *Bacteriodes*, in addition to a-hemolytic streptococci, *E. coli, Bifobacteria, Anaerobic cocci, Eubacteria, Costridia, lactobacilli*, and yeasts. Such bacteria, among other things, assist the host in the assimilation of nutrients by breaking down food stuffs not typically broken down by the hosts digestive system, particularly in the hosts bowel. Therefore, increasing the hosts ability to maintain such a biotic association would help assure proper nutrition for the host.

Aberrations in the enteric bacterial population of mammals, particularly humans, has been associated with the following disorders: diarrhea, ileus, chronic inflammatory disease, bowel obstruction, duodenal diverticula, biliary calculous disease, and malnutrition. A polynucleotide or polypeptide and/or agonist or antagonist of the present invention are useful for treating, detecting, diagnosing, prognosing, and/or ameliorating, either directly or indirectly, and of the above mentioned diseases and/or disorders associated with aberrant enteric flora population.

The composition of the intestinal flora, for example, is based upon a variety of factors, which include, but are not limited to, the age, race, diet, malnutrition, gastric acidity, bile salt excretion, gut motility, and immune mechanisms. As a result, the polynucleotides and polypeptides, including agonists, antagonists, and fragments thereof, may modulate the ability of a host to form biotic associations by affecting, directly or indirectly, at least one or more of these factors.

Although the predominate intestinal flora comprises anaerobic organisms, an underlying percentage represents aerobes (e.g., *E. coli*). This is significant as such aerobes rapidly become the predominate organisms in intraabdominal infections—effectively becoming opportunistic early in infection pathogenesis. As a result, there is an intrinsic need to control aerobe populations, particularly for immune compromised individuals.

In a preferred embodiment, a polynucleotides and polypeptides, including agonists, antagonists, and fragments thereof, are useful for inhibiting biotic associations with specific enteric symbiont organisms in an effort to control the population of such organisms.

Biotic associations occur not only in the gastrointestinal tract, but also on an in the integument. As opposed to the gastrointestinal flora, the cutaneous flora is comprised almost equally with aerobic and anaerobic organisms. Examples of cutaneous flora are members of the gram-positive cocci (e.g., *S. aureus*, coagulase-negative staphylococci, micrococcus, *M. sedentarius*), gram-positive bacilli (e.g., *Corynebacterium* species, *C. minutissimum, Brevibacterium* species, *Propoionibacterium* species, *P. acnes*), gram-negative bacilli (e.g., *Acinebacter* species), and fungi (*Pityrosporum orbiculare*). The relatively low number of flora associated with the integument is based upon the inability of many organisms to adhere to the skin. The organisms referenced above have acquired this unique ability. Therefore, the polynucleotides and polypeptides of the present invention may have uses which include modulating the population of the cutaneous flora, either directly or indirectly.

Aberrations in the cutaneous flora are associated with a number of significant diseases and/or disorders, which include, but are not limited to the following: impetigo, eethyma, blistering distal dactulitis, pustules, folliculitis, cutaneous abscesses, pitted keratolysis, trichomycosis axcillaris, dermatophytosis complex, axillary odor, erthyrasma, cheesy foot odor, acne, tinea versicolor, seborrheic dermititis, and *Pityrosporum folliculitis*, to name a few. A polynucleotide or polypeptide and/or agonist or antagonist of the present invention are useful for treating, detecting, diagnosing, prognosing, and/or ameliorating, either directly or indirectly, and of the above mentioned diseases and/or disorders associated with aberrant cutaneous flora population.

Additional biotic associations, including diseases and disorders associated with the aberrant growth of such associations, are known in the art and are encompassed by the invention. See, for example, "Infectious Disease", Second Edition, Eds., S. L., Gorbach, J. G., Bartlett, and N. R., Blacklow, W.B. Saunders Company, Philadelphia, (1998); which is hereby incorporated herein by reference).

Pheromones

In another embodiment, a polynucleotide or polypeptide and/or agonist or antagonist of the present invention may increase the organisms ability to synthesize and/or release a pheromone. Such a pheromone may, for example, alter the organisms behavior and/or metabolism.

A polynucleotide or polypeptide and/or agonist or antagonist of the present invention may modulate the biosynthesis and/or release of pheromones, the organisms ability to respond to pheromones (e.g., behaviorally, and/or metabolically), and/or the organisms ability to detect pheromones. Preferably, any of the pheromones, and/or volatiles released from the organism, or induced, by a polynucleotide or polypeptide and/or agonist or antagonist of the invention have behavioral effects the organism.

Other Activities

The polypeptide of the present invention, as a result of the ability to stimulate vascular endothelial cell growth, may be employed in treatment for stimulating re-vascularization of ischemic tissues due to various disease conditions such as thrombosis, arteriosclerosis, and other cardiovascular conditions. These polypeptide may also be employed to stimulate angiogenesis and limb regeneration, as discussed above.

The polypeptide may also be employed for treating wounds due to injuries, burns, post-operative tissue repair, and ulcers since they are mitogenic to various cells of different origins, such as fibroblast cells and skeletal muscle cells, and therefore, facilitate the repair or replacement of damaged or diseased tissue.

The polypeptide of the present invention may also be employed stimulate neuronal growth and to treat, prevent, and/or diagnose neuronal damage which occurs in certain neuronal disorders or neuro-degenerative conditions such as Alzheimer's disease, Parkinson's disease, and AIDS-related complex. The polypeptide of the invention may have the ability to stimulate chondrocyte growth, therefore, they may be employed to enhance bone and periodontal regeneration and aid in tissue transplants or bone grafts.

The polypeptides of the present invention may be employed to stimulate growth and differentiation of hematopoietic cells and bone marrow cells when used in combination with other cytokines.

The polypeptide of the invention may also be employed to maintain organs before transplantation or for supporting cell culture of primary tissues.

The polypeptide of the present invention may also be employed for inducing tissue of mesodermal origin to differentiate in early embryos.

The polypeptide or polynucleotides and/or agonist or antagonists of the present invention may also increase or decrease the differentiation or proliferation of embryonic stem cells, besides, as discussed above, hematopoietic lineage.

The polypeptide or polynucleotides and/or agonist or antagonists of the present invention may also be used to modulate mammalian characteristics, such as body height, weight, hair color, eye color, skin, percentage of adipose tissue, pigmentation, size, and shape (e.g., cosmetic surgery). Similarly, polypeptides or polynucleotides and/or agonist or antagonists of the present invention may be used to modulate mammalian metabolism affecting catabolism, anabolism, processing, utilization, and storage of energy.

Polypeptide or polynucleotides and/or agonist or antagonists of the present invention may be used to change a mammal's mental state or physical state by influencing biorhythms, caricadic rhythms, depression (including depressive diseases, disorders, and/or conditions), tendency for violence, tolerance for pain, reproductive capabilities (preferably by Activin or Inhibin-like activity), hormonal or endocrine levels, appetite, libido, memory, stress, or other cognitive qualities.

Polypeptide or polynucleotides and/or agonist or antagonists of the present invention may also be used to prepare individuals for extraterrestrial travel, low gravity environments, prolonged exposure to extraterrestrial radiation levels, low oxygen levels, reduction of metabolic activity, exposure to extraterrestrial pathogens, etc. Such a use may be administered either prior to an extraterrestrial event, during an extraterrestrial event, or both. Moreover, such a use may result in a number of beneficial changes in the recipient, such as, for example, any one of the following, non-limiting, effects: an increased level of hematopoietic cells, particularly red blood cells which would aid the recipient in coping with low oxygen levels; an increased level of B-cells, T-cells, antigen presenting cells, and/or macrophages, which would aid the recipient in coping with exposure to extraterrestrial pathogens, for example; a temporary (i.e., reversible) inhibition of hematopoietic cell production which would aid the recipient in coping with exposure to extraterrestrial radiation levels; increase and/or stability of bone mass which would aid the recipient in coping with low gravity environments; and/or decreased metabolism which would effectively facilitate the recipients ability to prolong their extraterrestrial travel by any one of the following, non-limiting means: (i) aid the recipient by decreasing their basal daily energy requirements; (ii) effectively lower the level of oxidative and/or metabolic stress in recipient (i.e., to enable recipient to cope with increased extraterresial radiation levels by decreasing the level of internal oxiclative/metabolic damage acquired during normal basal energy requirements; and/or (iii) enabling recipient to subsist at a lower metabolic temperature (i.e., cryogenic, and/or sub-cryogenic environment).

Polypeptide or polynucleotides and/or agonist or antagonists of the present invention may also be used to increase the efficacy of a pharmaceutical composition, either directly or indirectly. Such a use may be administered in simultaneous conjunction with said pharmaceutical, or separately through either the same or different route of administration (e.g., intravenous for the polynucleotide or polypeptide of the present invention, and orally for the pharmaceutical, among others described herein.).

Polypeptide or polynucleotides and/or agonist or antagonists of the present invention may also be used as a food additive or preservative, such as to increase or decrease storage capabilities, fat content, lipid, protein, carbohydrate, vitamins, minerals, cofactors or other nutritional components.

Also preferred is a method of treatment of an individual in need of an increased level of a protein activity, which method comprises administering to such an individual a pharmaceutical composition comprising an amount of an isolated polypeptide, polynucleotide, or antibody of the claimed invention effective to increase the level of said protein activity in said individual.

Having generally described the invention, the same will be more readily understood by reference to the following examples, which are provided by way of illustration and are not intended as limiting.

It will be clear that the invention may be practiced otherwise than as particularly described in the foregoing description and examples. Numerous modifications and variations of the present invention are possible in light of the above teachings and, therefore, are within the scope of the appended claims.

The entire disclosure of each document cited (including patents, patent applications, journal articles, abstracts, laboratory manuals, books, GENBANK® Accession numbers, SWISS-PROT® Accession numbers, or other disclosures) in the Background of the Invention, Detailed Description, Brief Description of the Figures, and Examples is hereby incorporated herein by reference in their entirety. Further, the hard copy of the Sequence Listing submitted herewith, in addition to its corresponding Computer Readable Form, are incorporated herein by reference in their entireties.

REFERENCES

Lusis, A J. Atherosclerosis. Nature. 407, 233-241 (2000).

Fredrickson, D S., Levy, R I. & Lees, R S, N. Eng. J Med. 276, 273-281 (1967).

Austin, M A., King, M C., Bawol, R D., Hulley, S B. & Friedman, G D. Am. J Epidemiol. 125, 308-318 (1987).

Perusse, L. Arteriosclerosis. 9, 308-318 (1989).

Rice, T., Vogler, G P., Laskarzewski, P M., Perry, T S. & Rao, D C. Hum. Biol. 63, 419-439 (1991).

Khachadurian, A K., Am. J Med. 37, 402-407, (1964).

Morganroth, J., Levy, R I., McMahon, A E. & Gotto, A M Jr. J Pediatr. 85, 639-643 (1974).

Goldstein, J L. & Brown, M S.; Johns Hopkins Med. J 143, 8-16 (1978).

Brown, M S. & Goldstein, J L. Proc. Natl. Acad. Sci. USA. 96, 11041-11048 (1999).

Varret, M. et al. Am. J. Hum. Genet. 64, 1378-1387 (1999).

Innerarity, T L. et al. Proc. Natl. Acad. Sci. USA. 84, 6919-6923 (1987).

Hunt, S C. et al. Arterioscler. Thromb. Vasc. Biol. 20, 1089-1093 (2000).

Horton J. D., Cohen J. C., Hobbs H. H. 2007. Molecular biology of PCSK9: its role in LDL metabolism. Trends in Biochem. Sci. 332(2): 71-77.

Berge, K. E., Ose L, Leren, T. P. 2006. Missense mutations in the PCSK9 gene are associated with hypocholesterolemia and possibly increased response to statin therapy. Arteriscl. Thromb. Vasc. Biol. 26(5): 1094-1100.

Zhao Z, Tuakli-Wosornu, Y, Lagace T. A., Kinch L., Grishin N. V., Horton J. D., Cohen J. C., Hobbs H. H. 2006. Molecular characterization of loss-of-function mutations in PCSK and identification of a compound heterozygote. Amer. J. Human Gen. 79: 514-523.

Sun X.-M, Eden E. r., Tosi I., Neuwirth C. K., Wile D., Naoumova R. P., Soutar A. K. 2005. Evidence for effect of mutant PCSK9 on apolipoprotein B secretion as the cause of unusually severe dominant hypercholesterolemia. Hum Mol. Gen. 14(9). 1161-1169.

Maxwell K. N., Breslow J. L. 2004. Adenoviral-mediated expression of Pcsk9 in mice results in a low-density lipoprotein receptor knockout phenotype. Proc. Nat. Amer. Sci. 101: 7100-7105.

Benjannet S, Rhainds, D., Essalmani R., Mayne J., Wickham L., Jin W., Asselin M.-C., Hamelin J., Varret M., Allard D., Trillard M., Abifadel M., Tebon A., Attie A. D. Rader D. J., Boileau C., Brissette L., Chretien M., Prat A., Seidah N. G. 2004. NARC-1/PCSK9 and its natural mutants. J. Bio. Chem. 279: 48865-48875.

EXAMPLES

Example 1

Method of Cloning the Novel Human PCSK9b Polynucleotide of the Present Invention Using the sequence AK124635.1, a sense 80-mer oligo with biotin on the 5' end was designed with the following sequence:

```
                                                         (SEQ ID NO:7)
5'bGGCGCTTTCACCAGTGGCTGGGATGTGCTCTGTAGTTTCTGTGTGTT

AACTATAAGGTTGACTTTATGCTCATTCCCTCC-3'
```

One microliter (200 picograms) of the biotinylated oligo was added to six microliters (six micrograms) of a anti-sense single-stranded covalently closed circular brain cDNA library and seven microliters of 100% formamide in a 0.2 ml PCR tube. The mixture was heated in a thermal cycler to 95° C. for 2 minutes. Fourteen microliters of 2× hybridization buffer (50% formamide, 1.5M NaCl, 0.04M NaPO$_4$ pH7.2, 5 mM EDTA, 0.2% SDS) were added to the heated probe/cDNA library mixture and incubated at 42° C. for 24 hours. Hybrids between the biotinylated oligo and the circular cDNA were isolated by diluting the hybridization mixture to 228 microliters in a solution containing 1M NaCl, 10 mM Tris-HCl pH7.5, 1 mM EDTA, pH8.0 and adding 125 microliters of streptavidin magnetic beads. This solution was incubated at 42° C. for 60 minutes mixing every 5 minutes to resuspend the beads. The beads were separated from the solution with a magnet and washed three times in 200 microliters of 0.1×SSPE, 0.1% SDS at 45° C.

The single stranded cDNAs were released from the biotinylated oligo/streptavidin magnetic bead complex by adding 50 microliters of 0.1N NaOH and incubating at room temperature for 10 minutes. Six microliters of 3M Sodium Acetate were added along with 20 micrograms of glycogen and the solution was ethanol precipitated with 120 microliters of 100% ethanol. The DNA was resuspended in 12 microliters of TE (10 mM Tris-HCl pH8.0, 1 mM EDTA pH8.0).

The single stranded cDNA was converted into double strands in a thermal cycler by mixing 5 microliters of the captured DNA with 1.5 microliters 10 micromolar gene specific sense repair primer with the following sequence: 5'-CTAGGCCTCCCTTTCCTTGT-3' (SEQ ID NO:13), and 1.5 microliters of 10×PCR buffer. The mixture was heated to 95° C. for 20 seconds, then ramped down to 59° C. At this time 15 microliters of a repair mix, that was preheated to 70° C., was added (repair mix contains 0.5 microliters of 10 mM dNTPs (2.5 mM each), 1.5 microliters of 10×PCR buffer, 12.75 microliters of water, and 0.25 microliters or 1.25 U of Taq polymerase). The solution was ramped back to 73° C. and incubated for 23 minutes. The repaired DNA was ethanol precipitated and resuspended in 10 microliters of TE. Two microliters were electroporated into E. coli DH12S cells and resulting colonies were screened by PCR, using a primer pair designed from the sequence AK124635.1, to identify the proper cDNAs.

Oligos used to identify the cDNA by PCR:

```
PCSK9-int3s 5'-CTAGGCCTCCCTTTCCTTGT-3' (SEQ ID NO:8)

PCSK9-int3a 5'-TTCCAAGGTGACATTTGTGG-3' (SEQ ID NO:9)
```

95 colonies were screened, and one cDNA clone was positive by PCR. The full-length sequence was obtained.

The full-length nucleotide sequence and the encoded polypeptide for PCSK9b are shown in FIGS. 1A-C.

Analysis of this sequence indicated it was a variant of proprotein convertase subtilisin/kexin type 9 (PCSK9).

Example 2

Method of Cloning the Novel Human PCSK9c Polynucleotide of the Present Invention A method nearly identical to the method described in Example 1 was utilized to clone the variant PCSK9c with the exceptions that follow. From the sequence NM_174936.2, an anti-sense 80-mer oligo with biotin on the 5' end was designed with the following sequence:

```
                                                        (SEQ ID NO:14)
5'bTGGCAGGCGGCGTTGAGGACGCGGCTGTACCCACCCGCCAGGGGCAG

CAGCACCACCAGTGGCCCCACAGGCTGGACCA -3'.
``` and was hybridized to sense single-stranded covalently closed circular brain/testis cDNA library as described above. Following release from the biotinylated oligo/streptavidin magnetic bead complex, the cDNA was precipitated as described above. The single stranded cDNA was converted into double strands as described above except that the following gene specific anti-sense repair primer was used: 5'-GAGTAGAGGCAGGCATCGTC-3' (SEQ ID NO:17). Screening colonies to identify proper cDNAs was performed with the following PCR primers:

```
PCSK9-ex6s
5'-GCCTGGAGTTTATTCGGAAA-3'      (SEQ ID NO:15)

PCSK9-ex6a
5'-GAGTAGAGGCAGGCATCGTC-3'      (SEQ ID NO:16)
```

95 colonies were screened, and one cDNA clone was positive by PCR. The full-length sequence of the cDNA was obtained. This clone was also found to represent a variant of proprotein convertase subtilisin/kexin type 9 (PCSK9).

The full-length nucleotide sequence and the encoded polypeptide for PCSK9c are shown in FIGS. 1A-D.

Example 3

Method of Assessing the Expression Profile of the Novel PCSK9b and PCSK9c Polypeptides of the Present Invention Using Expanded mRNA Tissue and Cell Sources Total RNA from tissues was isolated using the TRIZOL® protocol (Invitrogen) and quantified by determining its absorbance at 260 nM. An assessment of the 18 s and 28 s ribosomal RNA bands was made by denaturing gel electrophoresis to determine RNA integrity.

The specific sequence to be measured was aligned with related genes found in GENBANK® to identity regions of significant sequence divergence to maximize primer and probe specificity. Gene-specific primers and probes were designed using the ABI primer express software to amplify small amplicons (150 base pairs or less) to maximize the likelihood that the primers function at 100% efficiency. All primer/probe sequences were searched against Public Genbank databases to ensure target specificity. Primer and probe sequences were designed to hybridize to regions shared by both PCSK9b and PCSK9c, in addition to wild type PCSK9. Primers and probes were obtained from ABI.

For PCSK9b and PCSK9c, the primer probe sequences were as follows:

```
Forward Primer
5'-CCTGCGCGTGCTCAACT-3'           (SEQ ID NO:10)

Reverse Primer
5'-CCGAATAAACTCCAGGCCTATG-3'      (SEQ ID NO:11)

TAQMAN ® Probe
5'-CCGCTAACCGTGCCCTTCCCTTG-3'     (SEQ ID NO:12)
```

DNA Contamination

To access the level of contaminating genomic DNA in the RNA, the RNA was divided into 2 aliquots and one half was treated with Rnase-free Dnase (Invitrogen). Samples from both the Dnase-treated and non-treated were then subjected to reverse transcription reactions with (RT+) and without (RT−) the presence of reverse transcriptase. TAQMAN® assays were carried out with gene-specific primers (see above) and the contribution of genomic DNA to the signal detected was evaluated by comparing the threshold cycles obtained with the RT+/RT− non-Dnase treated RNA to that on the RT+/RT− Dnase treated RNA. The amount of signal contributed by genomic DNA in the Dnased RT− RNA must be less that 10% of that obtained with Dnased RT+ RNA. If not the RNA was not used in actual experiments.

Reverse Transcription Reaction and Sequence Detection 100 ng of Dnase-treated total RNA was annealed to 2.5 µM of the respective gene-specific reverse primer in the presence of 5.5 mM Magnesium Chloride by heating the sample to 72° C. for 2 min and then cooling to 55° C. for 30 min. 1.25 U/µl of MuLv reverse transcriptase and 500 µM of each dNTP was added to the reaction and the tube was incubated at 37° C. for 30 min. The sample was then heated to 90° C. for 5 min to denature enzyme.

Quantitative sequence detection was carried out on an ABI PRISM® 7700 by adding to the reverse transcribed reaction 2.5 µM forward and reverse primers, 2.0 µM of the TAQMAN® probe, 500 µM of each dNTP, buffer and 5 U AMPLI-TAQ GOLD®. The PCR reaction was then held at 94° C. for 12 min, followed by 40 cycles of 94° C. for 15 sec and 60° C. for 30 sec.

Data Handling

The threshold cycle (Ct) of the lowest expressing tissue (the highest Ct value) was used as the baseline of expression and all other tissues were expressed as the relative abundance to that tissue by calculating the difference in Ct value between the baseline and the other tissues and using it as the exponent in $2^{(\Delta Ct)}$ The expanded expression profile of the PCSK9b and PCSK9c polypeptides is provided in FIG. 6, and described elsewhere herein. Table IV identifies the analyzed tissues.

TABLE IV

| Number | Tissue |
| --- | --- |
| 1 | adipose_mesenteric_ileum |
| 2 | blood_vessel_cerebral |
| 3 | blood_vessel_pulmonary |
| 4 | blood_vessel_renal |
| 5 | brain_amygdala |
| 6 | brain_cerebellum |
| 7 | brain_cortex_cingulate_anterior |
| 8 | brain_cortex_cingulate_posterior |
| 9 | brain_cortex_frontal_medial |
| 10 | brain_cortex_temporal |
| 11 | brain_dorsal_raphe_nucleus |
| 12 | brain_hippocampus |
| 13 | brain_hypothalamus_anterior |
| 14 | brain_hypothalamus_posterior |
| 15 | brain_locus_coeruleus |
| 16 | brain_medulla_oblongata |
| 17 | brain_nucleus_accumbens |
| 18 | brain_substantia_nigra |
| 19 | breast |
| 20 | caecum |
| 21 | colon |
| 22 | duodenum |
| 23 | heart_left_atria |
| 24 | heart_left_ventricle |
| 25 | ileum |
| 26 | jejunum |
| 27 | kidney_cortex |
| 28 | kidney_medulla |
| 29 | kidney_pelvis |
| 30 | liver_parenchyma |
| 31 | lung_bronchus_primary |
| 32 | lung_bronchus_tertiary |
| 33 | lung_parenchyma |
| 34 | lymph_gland_tonsil |
| 35 | muscle_skeletal |
| 36 | oesophagus |
| 37 | pancreas |
| 38 | rectum |
| 39 | spinal_cord |
| 40 | stomach_antrum |
| 41 | stomach_body |
| 42 | stomach_pyloric_canal |
| 43 | testis |

Example 4

Method of Characterizing the PCSK9b or PCSK9c Polypeptides of the Present Invention Expression analysis of PCSK9b and PCSK9c polynucleotides and polypeptides using both quantitative PCR and Western blots, in addition to the affect of PCSK9b and PCSK9c on LDL update by the LDLR, was assessed according to the methods outlined herein. Briefly: B1

Materials and Methods

Gene cloning. PCSK9 variant b was cloned from a human brain cDNA library, and variant c was clone from a brain/testis cDNA library. Each variant product was inserted in two expression vectors CD3 MYCHIS and pEF-DESTS1 tagged with His and V5 or Myc epitopes at the C-terminus (#3114 for PCSK9 variant b-pCD3 MYCHIS, 3115 for PCSK9 variant c-pEF-DESTS1, #3116 for PCSK9 variant c-pCD3 MYCHIS, #3117 for PCSK9 variant c-pEF-DESTS1). Wild type PCSK9 and PCSK9 mutant D374 were cloned by PCR product insertion in pcDNA3 vector.

Cell culture. All cells lines including HepG2, Chinese hamster ovary cells (CHO), and HEK293, were derived from American Type Cell Culture (Manassa, Va.). Both HepG2 and HEK293 cells were grown in DMEM medium (Invitrogen Gibco, Carlsbad, Calif.) supplemented with 10% heat inactivated fetal bovine serum (FBS, Gibco), 1 mM sodium pyruvate (Gibco), 2 mM Glutamax (Gibco), 100 ug/ml streptomycin sulfate and 100 U/ml penicillin (Gibco). CHO cells were grown with the F12 medium with Glutamax (Gibco) supplemented with 10% fetal bovine serum.

DiI-LDL uptake assay. 15,000 cells per well were plated in the 96-well poly D lysine-coated plate with the above 10% FBS growth medium and grown in 37° C. incubator overnight. On day two, the medium was changed to 5% lipoprotein deficient serum (LPDS) growth medium supplemented with 50 µM sodium mevalonate, and 100 ng/ml of an HMG CoA reductase inhibitor. On day three, aliquots of fluorescent-labeled LDL (DiI-LDL) (source: Biomedical Technologies, Stoughton, Mass.) were added into the medium at a concentration of 10 ug/ml and continued to incubate for two more hours. Formaldehyde was added to the cells at a concentration of 4% together with Hoechst dye at 10 ug/ml. After 20 minute incubation at room temperature, cells were washed with PBS three times and read on LJL Biosystems (Molecular Device, Sunnyvale, Calif.) for DNA content at the excitation wavelength of 360 nm, and emission wavelength of 460 nm. Cells were then lysed by NaOH (0.001 N) and SDS (0.001%). DiI-LDL uptake was measured on LJL at the excitation wavelength of 540 nm, and emission wavelength of 580 nm. The DiI-LDL uptake data were normalized to DNA content by taking the ratio of DiI-LDL reading to Hoechst dye reading.

mRNA quantification. Total RNA isolation from cells was performed by the 6100 Nucleotide Acid PrepStation (ABI, Foster City, Calif.). Cells were lysed by the Nucleic Acid Lysis Solution (ABI) following the manufacturer's instruction. Lysed cells were loaded to the instrument for RNA extraction based on the protocol suggested by the manufacturer. RNA quantity was measured by the SPECTRAMAX® Plus (Molecular Device, Sunnyvale, Calif.).

Quantitative RT-PCR: cDNA was prepared by using iScript cDNA synthesis reagents (Biorad, Hercules, and CA) following manufacturer instructions. Quantitative PCR was performed using iTaq SYBR® Green Supermix with ROX reagents (Bio-Rad) on an ABI PRISM® 7900HT Sequence Detection System. Primer sequences for the assays were: wild type PCSK9, forward TGTCTTTGCCCAGAGCATCC (SEQ ID NO:30), reverse TATTCATCCGCCCGGTACC (SEQ ID NO:31); variant b, forward AGATGTCATCAAT-GAGGCCT (SEQ ID NO:32), reverse AGCTGCCAACCT-GCAAAAAC (SEQ ID NO:33); variant b/c, forward CTCT-GAGGTTGTGACTCGTGTGA (SEQ ID NO:34), reverse AGCGTTCTCCACTCCACAAGA (SEQ ID NO:35); LDLR, forward GAGAATGATCTGCAGCACCCA (SEQ ID NO:36), reverse TGCTGATGACGGTGTCATAGG (SEQ ID NO:37). Gene expression levels were normalized to GAPDH mRNA.

Western blot analysis. Cells were plated in DMEM supplemented with 10% FBS on 6-well plates. On day two, 4 ug/well of plasmid DNA were transfected by Lipofectamine 2000 (Invitrogen) following manufacturer's suggestion. After 24 hr, the medium was switched to DMEM media with 5% LPDS, 50 uM sodium mevalonate, and 100 ng/ml of BMS-423526. After an additional 24 hr, the medium was removed and the cells were lysed with the buffer containing 0.1% Triton X-100, 150 mM NaCl, 10 mM Tris-HCl (pH 7.4) plus Complete Protease Inhibitor Cocktail (Roche). Protein concentration was assayed with BioRad protein assay (Bio-Rad). 10 ug of proteins from lysate or 15 ul from a total of 2 ml conditioned medium were loaded on 4-15% Tris-HCl gels (Invitrogen). After protein transfer, membranes were incubated with anti-hPCSK9 primary antibody or anti-LDLR primary antibody, followed by IRdye 800 labeled anti-mouse IgG for PCSK9 or IRdye 680 labeled anti-rabbit IgG for LDLR. Protein bands were subsequently detected using the ODYSSEY® Infrared Imaging System (Li-Cor, Lincoln, Nebr.) according to manufacturer's instruction.

Results

Figure 8A:
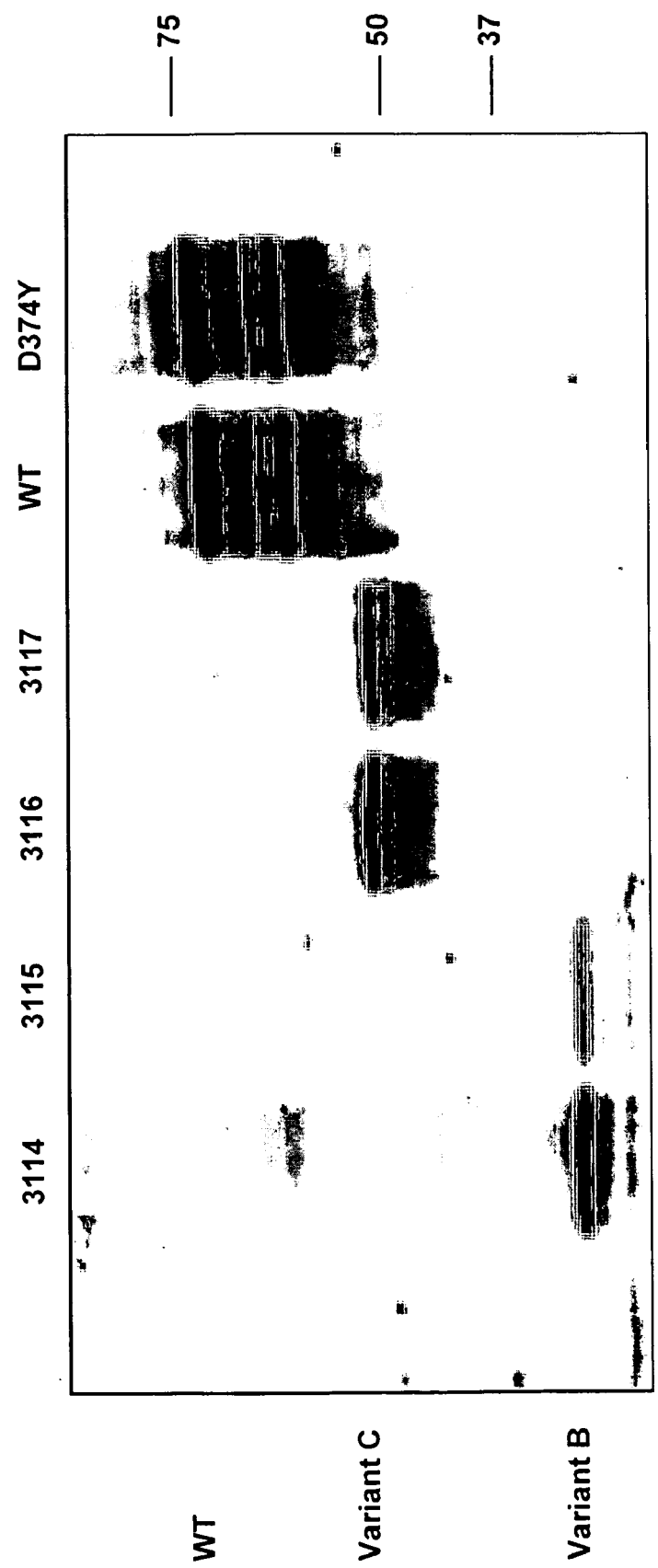
Figure 8B:
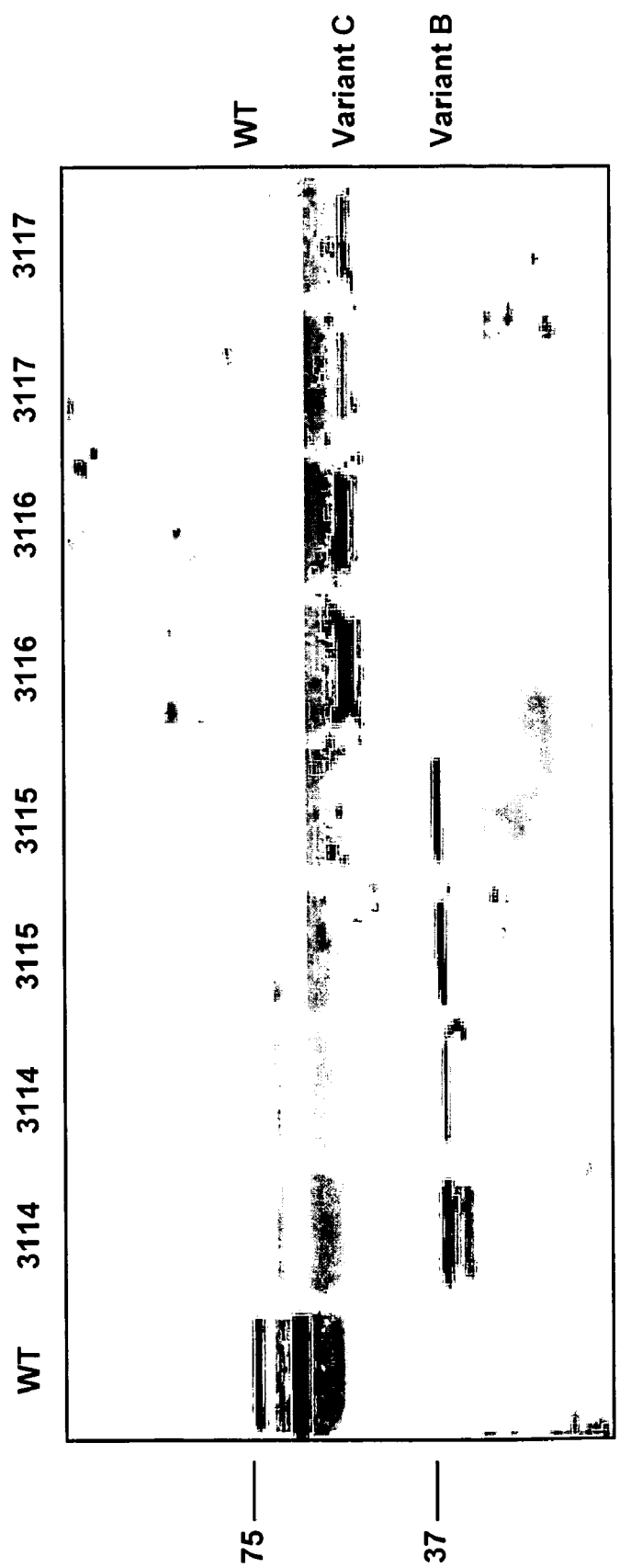

Overexpression of PCSK9 variants in cells. PCSK9 variant b and c were transfected into HEK and CHO as well as HepG2 cells. Both variants were expressed in these cells with mRNA levels comparable to that of wild type (full length) PCSK9 and the gain-of-function mutant D374Y-PCSK9 (FIG. 7A). As expected, LDLR mRNA levels were not affected by expression of the PCSK9 mRNAs in these cells (FIG. 7B), consistent with previous studies using known PCSK9 variants and mutants (Maxwell K. N., Breslow J. L., Proc. Nat. Amer. Sci., 101:7100-7105 (2004); Benjannet S., et al., J. Bio. Chem. 279:48865-48875 (2004)). Western blot results using PCSK9 antibody demonstrated that both variant b and variant c were also expressed as protein in the transfected cells. Variant b was expressed as an approximately 33-kDa protein and variant c was expressed as an approximately 57-kDa protein (FIG. 8A). The apparent molecular weights of the variant proteins as judged by SDS-PAGE mobility corresponded to their predicted molecular weight from sequence analysis. Compared with wild type PCSK9 protein, the protein expression levels of the two variants were lower yet readily detectable by antibody.

In the conditioned media of the cell culture, both PCSK9-b and -c protein expression were observed by Western blot (FIG. 8B), indicating that these two variants may be secreted by the cells.

PCSK9 variants exhibit functional activity in DiI-LDL uptake assay. DiI-LDL uptake is a standardized functional assay for LDLR receptor, while PCSK9 activity reduces LDLR. Therefore DiI-LDL uptake by cells can be used as a functional assay for PCSK9 activity. Transient expression of PCSK9 variant c decreased the uptake of DiI-LDL in HepG2 cells, compared to vector control, indicating that variant c is competent to express PCSK9 functional activity on LDLR (FIG. 9A). In this assay, variant c showed greater activity than wild-type PCSK9. Variant b showed greater activity than wildtype PCSK9, but was less than the PCSK9b variant. Based on sequence deduction and the molecular weights seen in Western blots, variant PCSK9c appears to form a nearly complete PCSK9 protein (compared to wild type), while variant PCSK9c lacks part of the C-terminal domain, consistent with the activity assay findings.

Figure 9B:
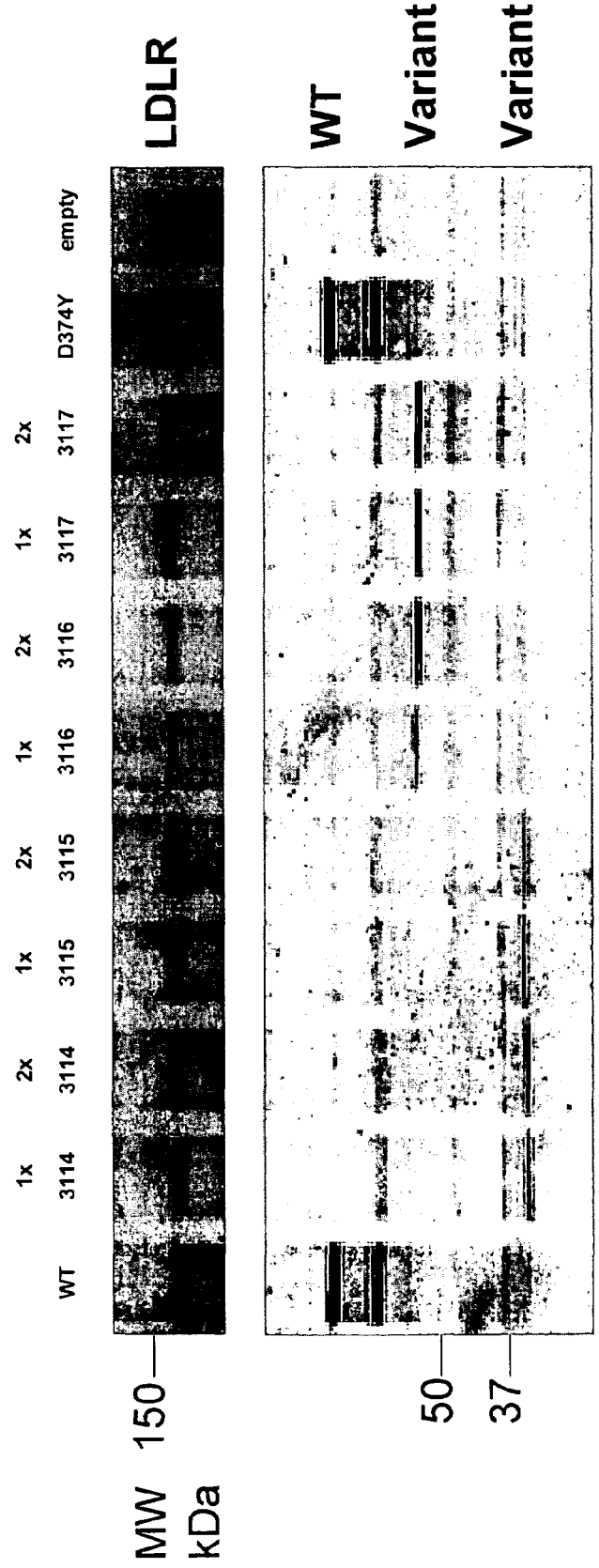

Consistent with the DiI-LDL uptake assay, expression of PCSK9 variant c decreased LDLR protein level in CHO cells assayed by Western blot, while expression of variant b did not appear to affect LDLR protein level under these conditions (FIG. 9B).

Conclusions

The two PCSK9 variants, b and c, were examined in a series of experiments to detect expression and function These two variants differ from the wild type PCSK9 by the lack of the signal peptide and prodomain as well as 22 amino acid in the N-terminus of the catalytic domain. In variant b, a portion of the C-terminal domain is also absent.

Both variants were expressed at the mRNA level in basal (sterol suppressed) HepG2 cells, with mRNA approximately 1% of the wild-type PCSK9 mRNA level in the presence of medium containing 10% fetal bovine serum (data not shown). Media containing 10% fetal bovine serum (FBS) is known to suppress sterol-sensitive genes, including PCSK9. However, under conditions including 5% lipoprotein-deficient serum (LPDS) in the medium, which is known to induce sterol-sensitive genes including PCSK9, the PCSK9c variant mRNA was highly induced, with levels reaching approximately 10% of the wild-type PCSK9 mRNA level (data not shown). Transient expression of the two variants using standard plasmid expression vectors in mammalian cell lines resulted in the PCSK9b variant being expressed as a 33 kDa protein, and the PCSK9c variant being expressed as a 57 kDa protein. Both of the PCSK9 variant proteins were detectable in conditioned medium as well as in cell lysates, indicating that both of them may also be secreted from cells. Based on the DiI-LDL uptake assay and western blot data, transient expression of variant c decreased LDLR levels in cells, while variant b exhibited lesser effects.

These data suggest that the novel PCSK9 variants, especially variant c, are not only expressed but are functionally competent and exhibit PCSK9 activity by interacting with the LDLR and decreasing LDLR levels, the main function identified for wild-type PCSK9 to date. The data support a biological role for the novel variants in modulating the LDLR and suggest they are useful in biotechnology and discovery applications involving PCSK9 expression, function, and screening.

Example 5

Method of Measuring the Proteinase Activity of the PCSK9b or PCSK9c Polypeptides of the Present Invention A number of assays known in the art may be utilized to demonstrate the proteinase activity of the PCSK9b and PCSK9c polypeptides of the present invention. Specifically, the method outlined in Naureckiene et al. (Arch. Biochem. Biophys., 420:55-67 (2003); which is hereby incorporated by reference in its entirety herein) may be utilized. Briefly:

Expression of PCSK9b and PCSK9c

*Escherichia coli* BL21 (DE3) cells may be transformed with prN1(ΔSP; ΔC@Q453)/6×His. Transformants are grown in LB medium (supplemented to 100 µg/ml with carbenicillin) at 30° C. to an $OD_{600}$ of 0.6. Expression is induced with 0.1 mM IPTG and the culture grown for an additional 3.5 h. Cells are harvested by centrifugation 30 min. at 14,000 g, and stored at −80 C.

Purification of PCSK9b and PCSK9c

Procedures may be performed at 4° C. Cells from 2 L of culture are resuspended in 25 ml lysis buffer (50 mM Tris-HCl, pH 8.0; 150 mM NaCl; 10% glycerol; and 1 M NDSB) in the presence or absence of an EDTA-free proteinase inhibitor cocktail (Roche). After cell lysis by sonication, the cell debris is removed by centrifugation (30 min, 14,000 g). The supernatant containing soluble proteins is loaded onto a pre-equilibrated 1 ml Ni-nitrilotriacetic acid (NTA) Agarose column (Qiagen). The column is washed with 20 ml lysis buffer containing 20 mM imidazole to remove weakly bound contaminating proteins. The purified protein is eluted with 5 ml lysis buffer containing 200 mM imidazole. Eluted protein is dialyzed overnight against 1 L Buffer A: 50 mM Tris-HCl, pH 8.0, 50 mM NaCl, and 10% glycerol. Dialyzed protein is loaded onto a 1 ml MONO Q® column (Amersham Biosciences) equilibrated with the same buffer. The column is washed with 10 ml of the same buffer and proteins are eluted with 12 ml NaCl gradient (0.05-1.0 M) in the same buffer. One milliliter fractions are collected and analyzed for purity on SDS-PAGE. Fractions containing purified protein are pooled and dialyzed against 1000 ml storage buffer (50 mM Tris-HCl, pH 8.0, 50 mM NaCl, and 10% glycerol), aliquoted, and stored at −80 C. In parallel, a purification from cells transformed with empty vector pET21a is performed to generate material for use as a negative control in enzymatic assays.

Proteinase Activity Assay

Subtilisin-, furin-, and TPP-specific fluorogenic substrates may be purchased from Bachem. Custom-made proteinase substrates can be synthesized by New England Peptide, Inc. Sequences of peptide substrates are as follows:

| Peptide | Sequence | |
|---|---|---|
| A | Dnp-FAQSIPK-AMC | (SEQ ID NO:18) |
| B | Dnp-DSLVFAK-AMC | (SEQ ID NO:19) |
| C | Dnp-FANAIPK-AMC | (SEQ ID NO:20) |

Proteolytic activity may be assayed at 37° C. using 100 µM substrate and 0.12 µM enzyme in various buffers, including 50 mM Tris-HCL, pH 7.5 to pH 11, 1 mM to 20 mM CaCl2, and 0.5% TX-100 at 37° C. Protein derived from an empty vector transformation is included as a negative control for enzymatic activity. Continuous and end-point fluorimetric measurements may be performed on spectrophotometer ($\lambda_{ex}$=350 nm, $\lambda_{em}$=450 nm).

Example 6

Method of Screening for Compounds that Interact with the PCSK9b or PCSK9c Polypeptide The following assays are designed to identify compounds that bind to the PCSK9b or PCSK9c polypeptide, bind to other cellular proteins that interact with the PCSK9b or PCSK9c polypeptide, and to compounds that interfere with the interaction of the PCSK9b or PCSK9c polypeptide with other cellular proteins.

Such compounds can include, but are not limited to, other cellular proteins. Specifically, such compounds can include, but are not limited to, peptides, such as, for example, soluble peptides, including, but not limited to Ig-tailed fusion peptides, comprising extracellular portions of PCSK9b or PCSK9c polypeptide transmembrane receptors, and members of random peptide libraries (see, e.g., Lam, K. S. et al., 1991, Nature 354:82-84; Houghton, R. et al., 1991, Nature 354:84-86), made of D- and/or L-configuration amino acids, phosphopeptides (including, but not limited to, members of random or partially degenerate phosphopeptide libraries; see, e.g., Songyang, Z., et al., 1993, Cell 72:767-778), antibodies (including, but not limited to, polyclonal, monoclonal, humanized, anti-idiotypic, chimeric or single chain antibodies, and FAb, F(ab').sub.2 and FAb expression library fragments, and epitope-binding fragments thereof), and small organic or inorganic molecules.

Compounds identified via assays such as those described herein can be useful, for example, in elaborating the biological function of the PCSK9b or PCSK9c polypeptide, and for ameliorating symptoms of tumor progression, for example. In instances, for example, whereby a tumor progression state or disorder results from a lower overall level of PCSK9b or PCSK9c expression, PCSK9b or PCSK9c polypeptide, and/or PCSK9b or PCSK9c polypeptide activity in a cell involved in the tumor progression state or disorder, compounds that interact with the PCSK9b or PCSK9c polypeptide can include ones which accentuate or amplify the activity of the bound PCSK9b or PCSK9c polypeptide. Such compounds would bring about an effective increase in the level of PCSK9b or PCSK9c polypeptide activity, thus ameliorating symptoms of the tumor progression disorder or state. In instances whereby mutations within the PCSK9b or PCSK9c polypeptide cause aberrant PCSK9b or PCSK9c polypeptides to be made which have a deleterious effect that leads to tumor progression, compounds that bind PCSK9b or PCSK9c polypeptide can be identified that inhibit the activity of the bound PCSK9b or PCSK9c polypeptide. Assays for testing the effectiveness of such compounds are known in the art and discussed, elsewhere herein.

Example 7

Method of Identifying Compounds that Interfere with PCSK9b or PCSK9c Polypeptide/Cellular Product Interaction The PCSK9b or PCSK9c polypeptide of the invention can, in vivo, interact with one or more cellular or extracellular macromolecules, such as proteins. Such macromolecules include, but are not limited to, polypeptides, particularly PCSK9 ligands, and those products identified via screening methods described, elsewhere herein. For the purposes of this discussion, such cellular and extracellular macromolecules are referred to herein as "binding partner(s)". For the purpose of the present invention, "binding partner" may also encompass polypeptides, small molecule compounds, polysaccarides, lipids, and any other molecule or molecule type referenced herein. Compounds that disrupt such interactions can be useful in regulating the activity of the PCSK9b or PCSK9c polypeptide, especially mutant PCSK9b or PCSK9c polypeptide. Such compounds can include, but are not limited to molecules such as antibodies, peptides, and the like described in elsewhere herein.

The basic principle of the assay systems used to identify compounds that interfere with the interaction between the PCSK9b or PCSK9c polypeptide and its cellular or extracellular binding partner or partners involves preparing a reaction mixture containing the PCSK9b or PCSK9c polypeptide, and the binding partner under conditions and for a time sufficient to allow the two products to interact and bind, thus forming a complex. In order to test a compound for inhibitory activity, the reaction mixture is prepared in the presence and absence of the test compound. The test compound can be initially included in the reaction mixture, or can be added at a time subsequent to the addition of PCSK9b or PCSK9c polypeptide and its cellular or extracellular binding partner. Control reaction mixtures are incubated without the test compound or with a placebo. The formation of any complexes between the PCSK9b or PCSK9c polypeptide and the cellular or extracellular binding partner is then detected. The formation of a complex in the control reaction, but not in the reaction mixture containing the test compound, indicates that the compound interferes with the interaction of the PCSK9b or PCSK9c polypeptide and the interactive binding partner. Additionally, complex formation within reaction mixtures containing the test compound and normal PCSK9b or PCSK9c polypeptide can also be compared to complex formation within reaction mixtures containing the test compound and mutant PCSK9b or PCSK9c polypeptide. This comparison can be important in those cases wherein it is desirable to identify compounds that disrupt interactions of mutant but not normal PCSK9b or PCSK9c polypeptide.

The assay for compounds that interfere with the interaction of the PCSK9b or PCSK9c polypeptide and binding partners can be conducted in a heterogeneous or homogeneous format. Heterogeneous assays involve anchoring either the PCSK9b or PCSK9c polypeptide or the binding partner onto a solid phase and detecting complexes anchored on the solid phase at the end of the reaction. In homogeneous assays, the entire reaction is carried out in a liquid phase. In either approach, the order of addition of reactants can be varied to obtain different information about the compounds being tested. For example, test compounds that interfere with the interaction between the PCSK9b or PCSK9c polypeptide and the binding partners, e.g., by competition, can be identified by conducting the reaction in the presence of the test substance; i.e., by adding the test substance to the reaction mixture prior to or simultaneously with the PCSK9b or PCSK9c polypeptide and interactive cellular or extracellular binding partner. Alternatively, test compounds that disrupt preformed complexes, e.g. compounds with higher binding constants that displace one of the components from the complex, can be tested by adding the test compound to the reaction mixture after complexes have been formed. The various formats are described briefly below.

In a heterogeneous assay system, either the PCSK9b or PCSK9c polypeptide or the interactive cellular or extracellular binding partner, is anchored onto a solid surface, while the non-anchored species is labeled, either directly or indirectly. In practice, microtitre plates are conveniently utilized. The anchored species can be immobilized by non-covalent or covalent attachments. Non-covalent attachment can be accomplished simply by coating the solid surface with a solution of the PCSK9b or PCSK9c polypeptide or binding partner and drying. Alternatively, an immobilized antibody specific for the species to be anchored can be used to anchor the species to the solid surface. The surfaces can be prepared in advance and stored.

In order to conduct the assay, the partner of the immobilized species is exposed to the coated surface with or without the test compound. After the reaction is complete, unreacted components are removed (e.g., by washing) and any complexes formed will remain immobilized on the solid surface. The detection of complexes anchored on the solid surface can be accomplished in a number of ways. Where the non-immobilized species is pre-labeled, the detection of label immobilized on the surface indicates that complexes were formed. Where the non-immobilized species is not pre-labeled, an indirect label can be used to detect complexes anchored on the surface; e.g., using a labeled antibody specific for the initially non-immobilized species (the antibody, in turn, can be directly labeled or indirectly labeled with a labeled anti-Ig antibody). Depending upon the order of addition of reaction components, test compounds which inhibit complex formation or which disrupt preformed complexes can be detected.

Alternatively, the reaction can be conducted in a liquid phase in the presence or absence of the test compound, the reaction products separated from unreacted components, and complexes detected; e.g., using an immobilized antibody specific for one of the binding components to anchor any complexes formed in solution, and a labeled antibody specific for the other partner to detect anchored complexes. Again, depending upon the order of addition of reactants to the liquid phase, test compounds which inhibit complex or which disrupt preformed complexes can be identified.

In an alternate embodiment of the invention, a homogeneous assay can be used. In this approach, a preformed complex of the PCSK9b or PCSK9c polypeptide and the interactive cellular or extracellular binding partner product is prepared in which either the PCSK9b or PCSK9c polypeptide or their binding partners are labeled, but the signal generated by the label is quenched due to complex formation (see, e.g., U.S. Pat. No. 4,109,496 by Rubenstein which utilizes this approach for immunoassays). The addition of a test substance that competes with and displaces one of the species from the preformed complex will result in the generation of a signal above background. In this way, test substances which disrupt PCSK9b or PCSK9c polypeptide-cellular or extracellular binding partner interaction can be identified.

In a particular embodiment, the PCSK9b or PCSK9c polypeptide can be prepared for immobilization using recombinant DNA techniques known in the art. For example, the PCSK9b or PCSK9c polypeptide coding region can be fused to a glutathione-S-transferase (GST) gene using a fusion vector such as pGEX-5X-1, in such a manner that its binding activity is maintained in the resulting fusion product. The interactive cellular or extracellular product can be purified and used to raise a monoclonal antibody, using methods routinely practiced in the art and described above. This antibody can be labeled with the radioactive isotope .sup.125I, for example, by methods routinely practiced in the art. In a heterogeneous assay, e.g., the GST-PCSK9b or PCSK9c polypeptide fusion product can be anchored to glutathione-agarose beads. The interactive cellular or extracellular binding partner product can then be added in the presence or absence of the test compound in a manner that allows interaction and binding to occur. At the end of the reaction period, unbound material can be washed away, and the labeled monoclonal antibody can be added to the system and allowed to bind to the complexed components. The interaction between the PCSK9b or PCSK9c polypeptide and the interactive cellular or extracellular binding partner can be detected by measuring the amount of radioactivity that remains associated with the glutathione-agarose beads. A successful inhibition of the interaction by the test compound will result in a decrease in measured radioactivity.

Alternatively, the GST-PCSK9b or PCSK9c polypeptide fusion product and the interactive cellular or extracellular binding partner product can be mixed together in liquid in the absence of the solid glutathione-agarose beads. The test compound can be added either during or after the binding partners are allowed to interact. This mixture can then be added to the glutathione-agarose beads and unbound material is washed away. Again the extent of inhibition of the binding partner interaction can be detected by adding the labeled antibody and measuring the radioactivity associated with the beads.

In another embodiment of the invention, these same techniques can be employed using peptide fragments that correspond to the binding domains of the PCSK9b or PCSK9c polypeptide product and the interactive cellular or extracellular binding partner (in case where the binding partner is a product), in place of one or both of the full length products.

Any number of methods routinely practiced in the art can be used to identify and isolate the protein's binding site. These methods include, but are not limited to, mutagenesis of one of the genes encoding one of the products and screening for disruption of binding in a co-immunoprecipitation assay. Compensating mutations in the gene encoding the second species in the complex can be selected. Sequence analysis of the genes encoding the respective products will reveal the mutations that correspond to the region of the product involved in interactive binding. Alternatively, one product can be anchored to a solid surface using methods described in this Section above, and allowed to interact with and bind to its labeled binding partner, which has been treated with a proteolytic enzyme, such as trypsin. After washing, a short, labeled peptide comprising the binding domain can remain associated with the solid material, which can be isolated and identified by amino acid sequencing. Also, once the gene coding for the cellular or extracellular binding partner product is obtained, short gene segments can be engineered to express peptide fragments of the product, which can then be tested for binding activity and purified or synthesized.

Example 8

Isolation of a Specific Clone from the Deposited Sample

The deposited material in the sample assigned the ATCC® Deposit Number cited in Table I for any given cDNA clone also may contain one or more additional plasmids, each comprising a cDNA clone different from that given clone. Thus, deposits sharing the same ATCC® Deposit Number contain at least a plasmid for each cDNA clone identified in Table I. Typically, each ATCC® deposit sample cited in Table I comprises a mixture of approximately equal amounts (by weight) of about 1-10 plasmid DNAs, each containing a different cDNA clone and/or partial cDNA clone; but such a deposit sample may include plasmids for more or less than 2 cDNA clones.

Two approaches can be used to isolate a particular clone from the deposited sample of plasmid DNA(s) cited for that clone in Table I. First, a plasmid is directly isolated by screening the clones using a polynucleotide probe corresponding to SEQ ID NO:1.

Particularly, a specific polynucleotide with 30-40 nucleotides is synthesized using an Applied Biosystems DNA synthesizer according to the sequence reported. The oligonucleotide is labeled, for instance, with 32P-(-ATP using T4 polynucleotide kinase and purified according to routine methods. (E.g., Maniatis et al., Molecular Cloning: A Laboratory Manual, Cold Spring Harbor Press, Cold Spring, N.Y. (1982).) The plasmid mixture is transformed into a suitable host, as indicated above (such as XL-1 Blue (Stratagene)) using techniques known to those of skill in the art, such as those provided by the vector supplier or in related publications or patents cited above. The transformants are plated on 1.5% agar plates (containing the appropriate selection agent, e.g., ampicillin) to a density of about 150 transformants (colonies) per plate. These plates are screened using Nylon membranes according to routine methods for bacterial colony screening (e.g., Sambrook et al., Molecular Cloning: A Laboratory Manual, 2nd Edit., (1989), Cold Spring Harbor Laboratory Press, pages 1.93 to 1.104), or other techniques known to those of skill in the art.

Alternatively, two primers of 17-20 nucleotides derived from both ends of the SEQ ID NO:1 or SEQ ID NO:3 (i.e., within the region of SEQ ID NO:1 or SEQ ID NO:3 bounded by the 5' NT and the 3' NT of the clone defined in Table I) are synthesized and used to amplify the desired cDNA using the deposited cDNA plasmid as a template. The polymerase chain reaction is carried out under routine conditions, for instance, in 25 ul of reaction mixture with 0.5 ug of the above cDNA template. A convenient reaction mixture is 1.5-5 mM MgCl2, 0.01% (w/v) gelatin, 20 uM each of dATP, dCTP, dGTP, dTTP, 25 pmol of each primer and 0.25 Unit of Taq polymerase. Thirty five cycles of PCR (denaturation at 94 degree C. for 1 min; annealing at 55 degree C. for 1 min; elongation at 72 degree C. for 1 min) are performed with a Perkin-Elmer Cetus automated thermal cycler. The amplified product is analyzed by agarose gel electrophoresis and the DNA band with expected molecular weight is excised and purified. The PCR product is verified to be the selected sequence by subcloning and sequencing the DNA product.

The polynucleotide(s) of the present invention, the polynucleotide encoding the polypeptide of the present invention, or the polypeptide encoded by the deposited clone may represent partial, or incomplete versions of the complete coding region (i.e., full-length gene). Several methods are known in the art for the identification of the 5' or 3' non-coding and/or coding portions of a gene which may not be present in the deposited clone. The methods that follow are exemplary and should not be construed as limiting the scope of the invention. These methods include but are not limited to, filter probing, clone enrichment using specific probes, and protocols similar or identical to 5' and 3' "RACE" protocols that are well known in the art. For instance, a method similar to 5' RACE is available for generating the missing 5' end of a desired full-length transcript. (Fromont-Racine et al., Nucleic Acids Res. 21(7):1683-1684 (1993)).

Briefly, a specific RNA oligonucleotide is ligated to the 5' ends of a population of RNA presumably containing full-length gene RNA transcripts. A primer set containing a primer specific to the ligated RNA oligonucleotide and a primer specific to a known sequence of the gene of interest is used to PCR amplify the 5' portion of the desired full-length gene. This amplified product may then be sequenced and used to generate the full-length gene.

This above method starts with total RNA isolated from the desired source, although poly-A+ RNA can be used. The RNA preparation can then be treated with phosphatase if necessary to eliminate 5' phosphate groups on degraded or damaged RNA that may interfere with the later RNA ligase step. The phosphatase should then be inactivated and the RNA treated with tobacco acid pyrophosphatase in order to remove the cap structure present at the 5' ends of messenger RNAs. This reaction leaves a 5' phosphate group at the 5' end of the cap cleaved RNA which can then be ligated to an RNA oligonucleotide using T4 RNA ligase.

This modified RNA preparation is used as a template for first strand cDNA synthesis using a gene specific oligonucleotide. The first strand synthesis reaction is used as a template for PCR amplification of the desired 5' end using a primer specific to the ligated RNA oligonucleotide and a primer specific to the known sequence of the gene of interest. The resultant product is then sequenced and analyzed to confirm that the 5' end sequence belongs to the desired gene. Moreover, it may be advantageous to optimize the RACE protocol to increase the probability of isolating additional 5' or 3' coding or non-coding sequences. Various methods of optimizing a RACE protocol are known in the art, though a detailed description summarizing these methods can be found in B. C. Schaefer, Anal. Biochem., 227:255-273, (1995).

An alternative method for carrying out 5' or 3' RACE for the identification of coding or non-coding sequences is provided by Frohman, M. A., et al., Proc. Nat'l. Acad. Sci. USA, 85:8998-9002 (1988). Briefly, a cDNA clone missing either the 5' or 3' end can be reconstructed to include the absent base pairs extending to the translational start or stop codon, respectively. In some cases, cDNAs are missing the start of translation, therefor. The following briefly describes a modification of this original 5' RACE procedure. Poly A+ total RNAs reverse transcribed with SUPERSCRIPT® II (Gibco/BRL) and an antisense or I complementary primer specific to the cDNA sequence. The primer is removed from the reaction with a MICROCON® Concentrator (Amicon). The first-strand cDNA is then tailed with dATP and terminal deoxynucleotide transferase (Gibco/BRL). Thus, an anchor sequence is produced which is needed for PCR amplification. The second strand is synthesized from the dA-tail in PCR buffer, Taq DNA polymerase (Perkin-Elmer Cetus), an oligo-dT primer containing three adjacent restriction sites (XhoIJ SalI and ClaI) at the 5' end and a primer containing just these restriction sites. This double-stranded cDNA is PCR amplified for 40 cycles with the same primers as well as a nested cDNA-specific antisense primer. The PCR products are size-separated on an ethidium bromide-agarose gel and the region of gel containing cDNA products the predicted size of missing protein-coding DNA is removed. cDNA is purified from the agarose with the Magic PCR Prep kit (Promega), restriction digested with XhoI or SalI, and ligated to a plasmid such as PBLUESCRIPT® SKII (Stratagene) at XhoI and EcoRV sites: This DNA is transformed into bacteria and the plasmid clones sequenced to identify the correct protein-coding inserts. Correct 5' ends are confirmed by comparing this sequence with the putatively identified homologue and overlap with the partial cDNA clone. Similar methods known in the art and/or commercial kits are used to amplify and recover 3' ends.

Several quality-controlled kits are commercially available for purchase. Similar reagents and methods to those above are supplied in kit form from Gibco/BRL for both 5' and 3' RACE for recovery of full length genes. A second kit is available from Clontech which is a modification of a related technique, SLIC (single-stranded ligation to single-stranded cDNA), developed by Dumas et al., Nucleic Acids Res., 19:5227-32 (1991). The major differences in procedure are that the RNA is alkaline hydrolyzed after reverse transcription and RNA ligase is used to join a restriction site-containing anchor primer to the first-strand cDNA. This obviates the necessity for the dA-tailing reaction which results in a polyT stretch that is difficult to sequence past.

An alternative to generating 5' or 3' cDNA from RNA is to use cDNA library double-stranded DNA. An asymmetric PCR-amplified antisense cDNA strand is synthesized with an antisense cDNA-specific primer and a plasmid-anchored primer. These primers are removed and a symmetric PCR reaction is performed with a nested cDNA-specific antisense primer and the plasmid-anchored primer.

RNA Ligase Protocol for Generating the 5' or 3' End Sequences to Obtain Full Length Genes Once a gene of interest is identified, several methods are available for the identification of the 5' or 3' portions of the gene which may not be present in the original cDNA plasmid. These methods include, but are not limited to, filter probing, clone enrichment using specific probes and protocols similar and identical to 5' and 3'RACE. While the full-length gene may be present in the library and can be identified by probing, a useful method for generating the 5' or 3' end is to use the existing sequence information from the original cDNA to generate the missing information. A method similar to 5'RACE is available for generating the missing 5' end of a desired full-length gene. (This method was published by Fromont-Racine et al., Nucleic Acids Res., 21(7): 1683-1684 (1993)). Briefly, a specific RNA oligonucleotide is ligated to the 5' ends of a population of RNA presumably 30 containing full-length gene RNA transcript and a primer set containing a primer specific to the ligated RNA oligonucleotide and a primer specific to a known sequence of the gene of interest, is used to PCR amplify the 5' portion of the desired full length gene which may then be sequenced and used to generate the full length gene. This method starts with total RNA isolated from the desired source, poly A RNA may be used but is not a prerequisite for this procedure. The RNA preparation may then be treated with phosphatase if necessary to eliminate 5' phosphate groups on degraded or damaged RNA which may interfere with the later RNA ligase step. The phosphatase if used is then inactivated and the RNA is treated with tobacco acid pyrophosphatase in order to remove the cap structure present at the 5' ends of messenger RNAs. This reaction leaves a 5' phosphate group at the 5' end of the cap cleaved RNA which can then be ligated to an RNA oligonucleotide using T4 RNA ligase. This modified RNA preparation can then be used as a template for first strand cDNA synthesis using a gene specific oligonucleotide. The first strand synthesis reaction can then be used as a template for PCR amplification of the desired 5' end using a primer specific to the ligated RNA oligonucleotide and a primer specific to the known sequence of the apoptosis related of interest. The resultant product is then sequenced and analyzed to confirm that the 5' end sequence belongs to the relevant apoptosis related.

Example 9

Bacterial Expression of a Polypeptide

A polynucleotide encoding a polypeptide of the present invention is amplified using PCR oligonucleotide primers corresponding to the 5' and 3' ends of the DNA sequence, as outlined herein, to synthesize insertion fragments. The primers used to amplify the cDNA insert should preferably contain restriction sites, such as BamHI and XbaI, at the 5' end of the primers in order to clone the amplified product into the expression vector. For example, BamHI and XbaI correspond to the restriction enzyme sites on the bacterial expression vector pQE-9. (Qiagen, Inc., Chatsworth, Calif.). This plasmid vector encodes antibiotic resistance (Ampr), a bacterial origin of replication (ori), an IPTG-regulatable promoter/operator (P/O), a ribosome binding site (RBS), a 6-histidine tag (6-His), and restriction enzyme cloning sites.

The pQE-9 vector is digested with BamHI and XbaI and the amplified fragment is ligated into the pQE-9 vector maintaining the reading frame initiated at the bacterial RBS. The ligation mixture is then used to transform the E. coli strain M15/rep4 (Qiagen, Inc.) which contains multiple copies of the plasmid pREP4, that expresses the lacI repressor and also confers kanamycin resistance (Kanr). Transformants are identified by their ability to grow on LB plates and ampicillin/kanamycin resistant colonies are selected. Plasmid DNA is isolated and confirmed by restriction analysis.

Clones containing the desired constructs are grown overnight (O/N) in liquid culture in LB media supplemented with both Amp (100 ug/ml) and Kan (25 ug/ml). The O/N culture is used to inoculate a large culture at a ratio of 1:100 to 1:250. The cells are grown to an optical density 600 (O.D. 600) of between 0.4 and 0.6. IPTG (Isopropyl-B-D-thiogalactopyranoside) is then added to a final concentration of 1 mM. IPTG induces by inactivating the lacI repressor, clearing the P/O leading to increased gene expression.

Cells are grown for an extra 3 to 4 hours. Cells are then harvested by centrifugation (20 mins at 6000×g). The cell pellet is solubilized in the chaotropic agent 6 Molar Guanidine HCl by stirring for 3-4 hours at 4 degree C. The cell debris is removed by centrifugation, and the supernatant containing the polypeptide is loaded onto a nickel-nitrilo-triacetic acid ("Ni-NTA") affinity resin column (available from QIAGEN, Inc., supra). Proteins with a 6×His tag bind to the Ni-NTA resin with high affinity and can be purified in a simple one-step procedure (for details see: The QIAexpressionist (1995) QIAGEN, Inc., supra).

Briefly, the supernatant is loaded onto the column in 6 M guanidine-HCl, pH 8, the column is first washed with 10 volumes of 6 M guanidine-HCl, pH 8, then washed with 10 volumes of 6 M guanidine-HCl pH 6, and finally the polypeptide is eluted with 6 M guanidine-HCl, pH 5.

The purified protein is then renatured by dialyzing it against phosphate-buffered saline (PBS) or 50 mM Na-acetate, pH 6 buffer plus 200 mM NaCl. Alternatively, the protein can be successfully refolded while immobilized on the Ni-NTA column. The recommended conditions are as follows: renature using a linear 6M-1M urea gradient in 500 mM NaCl, 20% glycerol, 20 mM Tris/HCl pH 7.4, containing protease inhibitors. The renaturation should be performed over a period of 1.5 hours or more. After renaturation the proteins are eluted by the addition of 250 mM imidazole. Imidazole is removed by a final dialyzing step against PBS or 50 mM sodium acetate pH 6 buffer plus 200 mM NaCl. The purified protein is stored at 4 degree C. or frozen at −80 degree C.

Example 10

Purification of a Polypeptide from an Inclusion Body

The following alternative method can be used to purify a polypeptide expressed in E coli when it is present in the form of inclusion bodies. Unless otherwise specified, all of the following steps are conducted at 4-10 degree C.

Upon completion of the production phase of the E. coli fermentation, the cell culture is cooled to 4-10 degree C. and the cells harvested by continuous centrifugation at 15,000 rpm (Heraeus Sepatech). On the basis of the expected yield of protein per unit weight of cell paste and the amount of purified protein required, an appropriate amount of cell paste, by weight, is suspended in a buffer solution containing 100 mM Tris, 50 mM EDTA, pH 7.4. The cells are dispersed to a homogeneous suspension using a high shear mixer.

The cells are then lysed by passing the solution through a microfluidizer (Microfluidics, Corp. or APV Gaulin, Inc.) twice at 4000-6000 psi. The homogenate is then mixed with NaCl solution to a final concentration of 0.5 M NaCl, followed by centrifugation at 7000×g for 15 min. The resultant pellet is washed again using 0.5M NaCl, 100 mM Tris, 50 mM EDTA, pH 7.4.

The resulting washed inclusion bodies are solubilized with 1.5 M guanidine hydrochloride (GuHCl) for 2-4 hours. After 7000×g centrifugation for 15 min., the pellet is discarded and the polypeptide containing supernatant is incubated at 4 degree C. overnight to allow further GuHCl extraction.

Following high speed centrifugation (30,000×g) to remove insoluble particles, the GuHCl solubilized protein is refolded by quickly mixing the GuHCl extract with 20 volumes of buffer containing 50 mM sodium, pH 4.5, 150 mM NaCl, 2 mM EDTA by vigorous stirring. The refolded diluted protein solution is kept at 4 degree C. without mixing for 12 hours prior to further purification steps.

To clarify the refolded polypeptide solution, a previously prepared tangential filtration unit equipped with 0.16 um membrane filter with appropriate surface area (e.g., Filtron), equilibrated with 40 mM sodium acetate, pH 6.0 is employed. The filtered sample is loaded onto a cation exchange resin (e.g., POROS® HS-50, Perceptive Biosystems). The column is washed with 40 mM sodium acetate, pH 6.0 and eluted with 250 mM, 500 mM, 1000 mM, and 1500 mM NaCl in the same buffer, in a stepwise manner. The absorbance at 280 nm of the effluent is continuously monitored. Fractions are collected and further analyzed by SDS-PAGE.

Fractions containing the polypeptide are then pooled and mixed with 4 volumes of water. The diluted sample is then loaded onto a previously prepared set of tandem columns of strong anion (POROS® HQ-50, Perceptive Biosystems) and weak anion (POROS® CM-20, Perceptive Biosystems) exchange resins. The columns are equilibrated with 40 mM sodium acetate, pH 6.0. Both columns are washed with 40 mM sodium acetate, pH 6.0, 200 mM NaCl. The CM-20 column is then eluted using a 10 column volume linear gradient ranging from 0.2 M NaCl, 50 mM sodium acetate, pH 6.0 to 1.0 M NaCl, 50 mM sodium acetate, pH 6.5. Fractions are collected under constant A280 monitoring of the effluent. Fractions containing the polypeptide (determined, for instance, by 16% SDS-PAGE) are then pooled.

The resultant polypeptide should exhibit greater than 95% purity after the above refolding and purification steps. No major contaminant bands should be observed from Coomassie blue stained 16% SDS-PAGE gel when 5 ug of purified protein is loaded. The purified protein can also be tested for endotoxin/LPS contamination, and typically the LPS content is less than 0.1 ng/ml according to LAL assays.

Example 11

Cloning and Expression of a Polypeptide in a Baculovirus Expression System

In this example, the plasmid shuttle vector pAc373 is used to insert a polynucleotide into a baculovirus to express a polypeptide. A typical baculovirus expression vector contains the strong polyhedrin promoter of the *Autographa californica* nuclear polyhedrosis virus (AcMNPV) followed by convenient restriction sites, which may include, for example BamHI, Xba I and Asp718. The polyadenylation site of the simian virus 40 ("SV40") is often used for efficient polyadenylation. For easy selection of recombinant virus, the plasmid contains the beta-galactosidase gene from *E. coli* under control of a weak *Drosophila* promoter in the same orientation, followed by the polyadenylation signal of the polyhedrin gene. The inserted genes are flanked on both sides by viral sequences for cell-mediated homologous recombination with wild-type viral DNA to generate a viable virus that express the cloned polynucleotide.

Many other baculovirus vectors can be used in place of the vector above, such as pVL941 and pAcIM1, as one skilled in the art would readily appreciate, as long as the construct provides appropriately located signals for transcription, translation, secretion and the like, including a signal peptide and an in-frame AUG as required. Such vectors are described, for instance, in Luckow et al., Virology 170:31-39 (1989).

A polynucleotide encoding a polypeptide of the present invention is amplified using PCR oligonucleotide primers corresponding to the 5' and 3' ends of the DNA sequence, as outlined in herein, to synthesize insertion fragments. The primers used to amplify the cDNA insert should preferably contain restriction sites at the 5' end of the primers in order to clone the amplified product into the expression vector. Specifically, the cDNA sequence contained in the deposited clone, including the AUG initiation codon and the naturally associated leader sequence identified elsewhere herein (if applicable), is amplified using the PCR protocol described herein. If the naturally occurring signal sequence is used to produce the protein, the vector used does not need a second signal peptide. Alternatively, the vector can be modified to include a baculovirus leader sequence, using the standard methods described in Summers et al., "A Manual of Methods for Baculovirus Vectors and Insect Cell Culture Procedures" Texas Agricultural Experimental Station Bulletin No. 1555 (1987).

The amplified fragment is isolated from a 1% agarose gel using a commercially available kit (GENECLEAN®, BIO 101 Inc., La Jolla, Calif.). The fragment then is digested with appropriate restriction enzymes and again purified on a 1% agarose gel.

The plasmid is digested with the corresponding restriction enzymes and optionally, can be dephosphorylated using calf intestinal phosphatase, using routine procedures known in the art. The DNA is then isolated from a 1% agarose gel using a commercially available kit (GENECLEAN®, BIO 101 Inc., La Jolla, Calif.).

The fragment and the dephosphorylated plasmid are ligated together with T4 DNA ligase. *E. coli* HB101 or other suitable *E. coli* hosts such as XL-1 Blue (Stratagene Cloning Systems, La Jolla, Calif.) cells are transformed with the ligation mixture and spread on culture plates. Bacteria containing the plasmid are identified by digesting DNA from individual colonies and analyzing the digestion product by gel electrophoresis. The sequence of the cloned fragment is confirmed by DNA sequencing.

Five ug of a plasmid containing the polynucleotide is co-transformed with 1.0 ug of a commercially available linearized baculovirus DNA ("BACULOGOLD® baculovirus DNA", Pharmingen, San Diego, Calif.), using the lipofection method described by Felgner et al., Proc. Natl. Acad. Sci. USA 84:7413-7417 (1987). One ug of BACULOGOLD® virus DNA and 5 ug of the plasmid are mixed in a sterile well of a microtiter plate containing 50 ul of serum-free Grace's medium (Life Technologies Inc., Gaithersburg, Md.). Afterwards, 10 ul LIPOFECTIN® plus 90 ul Grace's medium are added, mixed and incubated for 15 minutes at room temperature. Then the transfection mixture is added drop-wise to Sf9 insect cells (ATCC® CRL 1711) seeded in a 35 mm tissue culture plate with 1 ml Grace's medium without serum. The plate is then incubated for 5 hours at 27 degrees C. The transfection solution is then removed from the plate and 1 ml of Grace's insect medium supplemented with 10% fetal calf serum is added. Cultivation is then continued at 27 degrees C. for four days.

After four days the supernatant is collected and a plaque assay is performed, as described by Summers and Smith, supra. An agarose gel with "Blue Gal" (Life Technologies Inc., Gaithersburg) is used to allow easy identification and isolation of gal-expressing clones, which produce blue-stained plaques. (A detailed description of a "plaque assay" of this type can also be found in the user's guide for insect cell culture and baculovirology distributed by Life Technologies Inc., Gaithersburg, page 9-10.) After appropriate incubation, blue stained plaques are picked with the tip of a micropipettor (e.g., Eppendorf). The agar containing the recombinant viruses is then resuspended in a microcentrifuge tube containing 200 ul of Grace's medium and the suspension containing the recombinant baculovirus is used to infect Sf9 cells seeded in 35 mm dishes. Four days later the supernatants of these culture dishes are harvested and then they are stored at 4 degree C.

To verify the expression of the polypeptide, Sf9 cells are grown in Grace's medium supplemented with 10% heat-inactivated FBS. The cells are infected with the recombinant baculovirus containing the polynucleotide at a multiplicity of infection ("MOI") of about 2. If radiolabeled proteins are desired, 6 hours later the medium is removed and is replaced with SF900 II medium minus methionine and cysteine (available from Life Technologies Inc., Rockville, Md.). After 42 hours, 5 uCi of 35S-methionine and 5 uCi 35S-cysteine (available from Amersham) are added. The cells are further incubated for 16 hours and then are harvested by centrifugation. The proteins in the supernatant as well as the intracellular proteins are analyzed by SDS-PAGE followed by autoradiography (if radiolabeled).

Microsequencing of the amino acid sequence of the amino terminus of purified protein may be used to determine the amino terminal sequence of the produced protein.

Example 12

Expression of a Polypeptide in Mammalian Cells

The polypeptide of the present invention can be expressed in a mammalian cell. A typical mammalian expression vector contains a promoter element, which mediates the initiation of transcription of mRNA, a protein coding sequence, and signals required for the termination of transcription and polyadenylation of the transcript. Additional elements include enhancers, Kozak sequences and intervening sequences flanked by donor and acceptor sites for RNA splicing. Highly efficient transcription is achieved with the early and late promoters from SV40, the long terminal repeats (LTRs) from Retroviruses, e.g., RSV, HTLVI, HIVI and the early promoter of the cytomegalovirus (CMV). However, cellular elements can also be used (e.g., the human actin promoter).

Suitable expression vectors for use in practicing the present invention include, for example, vectors such as pSVL and pMSG (Pharmacia, Uppsala, Sweden), pRSVcat (ATCC® 37152), pSV2dhfr (ATCC® 37146), pBC12MI (ATCC® 67109), pCMVSport 2.0, and pCMVSport 3.0. Mammalian host cells that could be used include, human Hela, 293, H9 and Jurkat cells, mouse NIH3T3 and C127 cells, Cos 1, Cos 7 and CV1, quail QC1-3 cells, mouse L cells and Chinese hamster ovary (CHO) cells.

Alternatively, the polypeptide can be expressed in stable cell lines containing the polynucleotide integrated into a chromosome. The co-transformation with a selectable marker such as dhfr, gpt, neomycin, hygromycin allows the identification and isolation of the transformed cells.

The transformed gene can also be amplified to express large amounts of the encoded protein. The DHFR (dihydrofolate reductase) marker is useful in developing cell lines that carry several hundred or even several thousand copies of the gene of interest. (See, e.g., Alt, F. W., et al., J. Biol. Chem. 253:1357-1370 (1978); Hamlin, J. L. and Ma, C., Biochem. et Biophys. Acta, 1097:107-143 (1990); Page, M. J. and Sydenham, M. A., Biotechnology 9:64-68 (1991).) Another useful selection marker is the enzyme glutamine synthase (GS) (Murphy et al., Biochem J. 227:277-279 (1991); Bebbington et al., Bio/Technology 10:169-175 (1992). Using these markers, the mammalian cells are grown in selective medium and the cells with the highest resistance are selected. These cell lines contain the amplified gene(s) integrated into a chromosome. Chinese hamster ovary (CHO) and NSO cells are often used for the production of proteins.

A polynucleotide of the present invention is amplified according to the protocol outlined in herein. If the naturally occurring signal sequence is used to produce the protein, the vector does not need a second signal peptide. Alternatively, if the naturally occurring signal sequence is not used, the vector can be modified to include a heterologous signal sequence. (See, e.g., WO 96/34891.) The amplified fragment is isolated from a 1% agarose gel using a commercially available kit (GENECLEAN®, BIO 101 Inc., La Jolla, Calif.). The fragment then is digested with appropriate restriction enzymes and again purified on a 1% agarose gel.

The amplified fragment is then digested with the same restriction enzyme and purified on a 1% agarose gel. The isolated fragment and the dephosphorylated vector are then ligated with T4 DNA ligase. E. coli HB101 or XL-1 Blue cells are then transformed and bacteria are identified that contain the fragment inserted into plasmid pC6 using, for instance, restriction enzyme analysis.

Chinese hamster ovary cells lacking an active DHFR gene is used for transformation. Five μg of an expression plasmid is cotransformed with 0.5 ug of the plasmid pSVneo using LIPOFECTIN® (Felgner et al., supra). The plasmid pSV2-neo contains a dominant selectable marker, the neo gene from Tn5 encoding an enzyme that confers resistance to a group of antibiotics including G418. The cells are seeded in alpha minus MEM supplemented with 1 mg/ml G418. After 2 days, the cells are trypsinized and seeded in hybridoma cloning plates (Greiner, Germany) in alpha minus MEM supplemented with 10, 25, or 50 ng/ml of methotrexate plus 1 mg/ml G418. After about 10-14 days single clones are trypsinized and then seeded in 6-well petri dishes or 10 ml flasks using different concentrations of methotrexate (50 nM, 100 nM, 200 nM, 400 nM, 800 nM). Clones growing at the highest concentrations of methotrexate are then transferred to new 6-well plates containing even higher concentrations of methotrexate (1 uM, 2 uM, 5 uM, 10 mM, 20 mM). The same procedure is repeated until clones are obtained which grow at a concentration of 100-200 uM. Expression of the desired gene product is analyzed, for instance, by SDS-PAGE and Western blot or by reversed phase HPLC analysis.

Example 13

Method of Creating N- and C-Terminal Deletion Mutants Corresponding to PCSK9, PCSK9b or PCSK9c Polypeptides of the Present Invention As described elsewhere herein, the present invention encompasses the creation of N- and C-terminal deletion mutants, in addition to any combination of N- and C-terminal deletions thereof, corresponding to the PCSK9, PCSK9b or PCSK9c polypeptide of the present invention. A number of methods are available to one skilled in the art for creating such mutants. Such methods may include a combination of PCR amplification and gene cloning methodology. Although one of skill in the art of molecular biology, through the use of the teachings provided or referenced herein, and/or otherwise known in the art as standard methods, could readily create each deletion mutant of the present invention, exemplary methods are described below.

Briefly, using the isolated cDNA clone encoding the full-length PCSK9b or PCSK9c polypeptide sequence (as described herein, for example), appropriate primers of about 15-25 nucleotides derived from the desired 5' and 3' positions of SEQ ID NO:1 or SEQ ID NO:3 or SEQ ID NO:38 may be designed to PCR amplify, and subsequently clone, the intended N- and/or C-terminal deletion mutant. Such primers could comprise, for example, an initiation and stop codon for the 5' and 3' primer, respectively. Such primers may also comprise restriction sites to facilitate cloning of the deletion mutant post amplification. Moreover, the primers may comprise additional sequences, such as, for example, flag-tag sequences, kozac sequences, or other sequences discussed and/or referenced herein.

For example, in the case of the PCSK9b L16 to R315 N-terminal deletion mutant, the following primers could be used to amplify a cDNA fragment corresponding to this deletion mutant:

```
5' Primer                                       (SEQ ID NO:22)
5'-GCAGCA GCGGCCGC CTAGACACCAGCATACAGAGTGACC-3'
         NotI 3' Primer                                       (SEQ ID NO:23)
5'-GCAGCA GTCGAC TCTGGGGCGCAGCGGGCGATGGCTG-3'
         SalI
```

For example, in the case of the PCSK9b M1 to P284 C-terminal deletion mutant, the following primers could be used to amplify a cDNA fragment corresponding to this deletion mutant:

```
5' Primer                                       (SEQ ID NO:24)
5'-GCAGCA GCGGCCGC ATGTCGCCTTGGAAAGACGGAGGCA-3'
         NotI 3' Primer                                       (SEQ ID NO:25)
5'-GCAGCA GTCGAC AGGGCCTGCCCCATGGGTGCTGGGG-3'
         SalI
```

For example, in the case of the PCSK9c L16 to Q523 N-terminal deletion mutant, the following primers could be used to amplify a cDNA fragment corresponding to this deletion mutant:

```
5' Primer                                       (SEQ ID NO:26)
5'-GCAGCA GCGGCCGC CTAGACACCAGCATACAGAGTGACC-3'
         NotI 3' Primer                                       (SEQ ID NO:27)
5'-GCAGCA GTCGAC CTGGAGCTCCTGGGAGGCCTGCGCC-3'
         SalI
```

For example, in the case of the PCSK9c M1 to A306 C-terminal deletion mutant, the following primers could be used to amplify a cDNA fragment corresponding to this deletion mutant:

```
5' Primer                                       (SEQ ID NO:28)
5'-GCAGCA GCGGCCGC ATGTCGCCTTGGAAAGACGGAGGCA-3'
         NotI 3' Primer                                       (SEQ ID NO:29)
5'-GCAGCA GTCGAC GGCGATGGCTGTGGCCATCCGTGTA-3'
         SalI
```

For example, in the case of the PCSK9 L16 to Q692 N-terminal deletion mutant, the following primers could be used to amplify a cDNA fragment corresponding to this deletion mutant:

```
5' Primer                                       (SEQ ID NO: 39)
5'-GCAGCA GCGGCCGC CTGCTGCTGCTGCTGCTGCTGCTCC -3'
         NotI 3' Primer                                       (SEQ ID NO: 40)
5'- GCAGCA GTCGAC CTGGAGCTCCTGGGAGGCCTGCGCC -3'
          SalI
```

Representative PCR amplification conditions are provided below, although the skilled artisan would appreciate that other conditions may be required for efficient amplification. A 100 ul PCR reaction mixture may be prepared using 10 ng of the template DNA (cDNA clone of PCSK9b or PCSK9c), 200 uM 4dNTPs, 1 uM primers, 0.25 U Taq DNA polymerase (PE), and standard Taq DNA polymerase buffer. Typical PCR cycling condition are as follows:

| 20-25 cycles: | 45 sec, 93 degrees |
| --- | --- |
|  | 2 min, 50 degrees |
|  | 2 min, 72 degrees |
| 1 cycle: | 10 min, 72 degrees |

After the final extension step of PCR, 5 U Klenow Fragment may be added and incubated for 15 min at 30 degrees.

Upon digestion of the fragment with the NotI and SalI restriction enzymes, the fragment could be cloned into an appropriate expression and/or cloning vector which has been similarly digested (e.g., pSport1, among others). The skilled artisan would appreciate that other plasmids could be equally substituted, and may be desirable in certain circumstances. The digested fragment and vector are then ligated using a DNA ligase, and then used to transform competent E. coli cells using methods provided herein and/or otherwise known in the art.

The 5' primer sequence for amplifying any additional N-terminal deletion mutants may be determined by reference to the following formula: $(S+(X*3))$ to $((S+(X*3))+25)$, wherein 'S' is equal to the nucleotide position of the initiating start codon of PCSK9b (SEQ ID NO:1) or PCSK9c (SEQ ID NO:3) or PCSK9 (SEQ ID NO:38), and 'X' is equal to the most N-terminal amino acid of the intended N-terminal deletion mutant. The first term will provide the start 5' nucleotide position of the 5' primer, while the second term will provide the end 3' nucleotide position of the 5' primer corresponding to sense strand of SEQ ID NO:1 or SEQ ID NO:3 or SEQ ID NO:38. Once the corresponding nucleotide positions of the primer are determined, the final nucleotide sequence may be created by the addition of applicable restriction site sequences to the 5' end of the sequence, for example. As referenced herein, the addition of other sequences to the 5' primer may be desired in certain circumstances (e.g., kozac sequences, etc.).

The 3' primer sequence for amplifying any additional N-terminal deletion mutants may be determined by reference to the following formula: $(S+(X*3))$ to $((S+(X*3))-25)$, wherein 'S' is equal to the nucleotide position of the initiating start codon of PCSK9b (SEQ ID NO:1) or PCSK9c (SEQ ID NO:3) or PCSK9 (SEQ ID NO:38), and 'X' is equal to the most C-terminal amino acid of the intended N-terminal deletion mutant. The first term will provide the start 5' nucleotide position of the 3' primer, while the second term will provide the end 3' nucleotide position of the 3' primer corresponding to the anti-sense strand of SEQ ID NO:1 or SEQ ID NO:3 or SEQ ID NO:38. Once the corresponding nucleotide positions of the primer are determined, the final nucleotide sequence may be created by the addition of applicable restriction site sequences to the 5' end of the sequence, for example. As referenced herein, the addition of other sequences to the 3' primer may be desired in certain circumstances (e.g., stop codon sequences, etc.). The skilled artisan would appreciate that modifications of the above nucleotide positions may be necessary for optimizing PCR amplification.

The same general formulas provided above may be used in identifying the 5' and 3' primer sequences for amplifying any C-terminal deletion mutant of the present invention. Moreover, the same general formulas provided above may be used in identifying the 5' and 3' primer sequences for amplifying any combination of N-terminal and C-terminal deletion mutant of the present invention. The skilled artisan would appreciate that modifications of the above nucleotide positions may be necessary for optimizing PCR amplification.

Example 14

Protein Fusions

The polypeptides of the present invention are preferably fused to other proteins. These fusion proteins can be used for a variety of applications. For example, fusion of the present polypeptides to His-tag, HA-tag, protein A, IgG domains, and maltose binding protein facilitates purification. (as described herein; see also EP A 394,827; Traunecker, et al., Nature 331:84-86 (1988).) Similarly, fusion to IgG-1, IgG-3, and albumin increases the half-life time in vivo. Nuclear localization signals fused to the polypeptides of the present invention can target the protein to a specific subcellular localization, while covalent heterodimer or homodimers can increase or decrease the activity of a fusion protein. Fusion proteins can also create chimeric molecules having more than one function. Finally, fusion proteins can increase solubility and/or stability of the fused protein compared to the non-fused protein. All of the types of fusion proteins described above can be made by modifying the following protocol, which outlines the fusion of a polypeptide to an IgG molecule.

Briefly, the human Fc portion of the IgG molecule can be PCR amplified, using primers that span the 5' and 3' ends of the sequence described below. These primers also should have convenient restriction enzyme sites that will facilitate cloning into an expression vector, preferably a mammalian expression vector. Note that the polynucleotide is cloned without a stop codon, otherwise a fusion protein will not be produced.

The naturally occurring signal sequence may be used to produce the protein (if applicable). Alternatively, if the naturally occurring signal sequence is not used, the vector can be modified to include a heterologous signal sequence. (See, e.g., WO 96/34891 and/or U.S. Pat. No. 6,066,781, supra.)

```
Human IgG Fc region                   (SEQ ID NO: 21)
GGGATCCGGAGCCCAAATCTTCTGACAAAACTCACACATGCCCACCGTGC

CCAGCACCTGAATTCGAGGGTGCACCGTCAGTCTTCCTCTTCCCCCCAAA

ACCCAAGGACACCCTCATGATCTCCCGGACTCCTGAGGTCACATGCGTGG

TGGTGGACGTAAGCCACGAAGACCCTGAGGTCAAGTTCAACTGGTACGTG

GACGGCGTGGAGGTGCATAATGCCAAGACAAAGCCGCGGGAGGAGCAGTA

CAACAGCACGTACCGTGTGGTCAGCGTCCTCACCGTCCTGCACCAGGACT

GGCTGAATGGCAAGGAGTACAAGTGCAAGGTCTCCAACAAAGCCCTCCCA

ACCCCCATCGAGAAAACCATCTCCAAAGCCAAAGGGCAGCCCCGAGAACC

ACAGGTGTACACCCTGCCCCCATCCCGGGATGAGCTGACCAAGAACCAGG

TCAGCCTGACCTGCCTGGTCAAAGGCTTCTATCCAAGCGACATCGCCGTG

GAGTGGGAGAGCAATGGGCAGCCGGAGAACAACTACAAGACCACGCCTCC

CGTGCTGGACTCCGACGGCTCCTTCTTCCTCTACAGCAAGCTCACCGTGG

ACAAGAGCAGGTGGCAGCAGGGGAACGTCTTCTCATGCTCCGTGATGCAT
```

-continued
```
GAGGCTCTGCACAACCACTACACGCAGAAGAGCCTCTCCCTGTCTCCGGG

TAAATGAGTGCGACGGCCGCGACTCTAGAGGAT
```

Example 15

Production of an Antibody from a Polypeptide

The antibodies of the present invention can be prepared by a variety of methods. (See, Current Protocols, Chapter 2.) As one example of such methods, cells expressing a polypeptide of the present invention are administered to an animal to induce the production of sera containing polyclonal antibodies. In a preferred method, a preparation of the protein is prepared and purified to render it substantially free of natural contaminants. Such a preparation is then introduced into an animal in order to produce polyclonal antisera of greater specific activity.

In the most preferred method, the antibodies of the present invention are monoclonal antibodies (or protein binding fragments thereof). Such monoclonal antibodies can be prepared using hybridoma technology. (Köhler et al., Nature 256:495 (1975); Köhler et al., Eur. J. Immunol. 6:511 (1976); Köhler et al., Eur. J. Immunol. 6:292 (1976); Hammerling et al., in: Monoclonal Antibodies and T-Cell Hybridomas, Elsevier, N.Y., pp. 563-681 (1981).) In general, such procedures involve immunizing an animal (preferably a mouse) with polypeptide or, more preferably, with a polypeptide-expressing cell. Such cells may be cultured in any suitable tissue culture medium; however, it is preferable to culture cells in Earle's modified Eagle's medium supplemented with 10% fetal bovine serum (inactivated at about 56 degrees C.), and supplemented with about 10 g/l of nonessential amino acids, about 1,000 U/ml of penicillin, and about 100 ug/ml of streptomycin.

The splenocytes of such mice are extracted and fused with a suitable myeloma cell line. Any suitable myeloma cell line may be employed in accordance with the present invention; however, it is preferable to employ the parent myeloma cell line (SP2O), available from the ATCC®. After fusion, the resulting hybridoma cells are selectively maintained in HAT medium, and then cloned by limiting dilution as described by Wands et al. (Gastroenterology 80:225-232 (1981).) The hybridoma cells obtained through such a selection are then assayed to identify clones which secrete antibodies capable of binding the polypeptide.

Alternatively, additional antibodies capable of binding to the polypeptide can be produced in a two-step procedure using anti-idiotypic antibodies. Such a method makes use of the fact that antibodies are themselves antigens, and therefore, it is possible to obtain an antibody that binds to a second antibody. In accordance with this method, protein specific antibodies are used to immunize an animal, preferably a mouse. The splenocytes of such an animal are then used to produce hybridoma cells, and the hybridoma cells are screened to identify clones that produce an antibody whose ability to bind to the protein-specific antibody can be blocked by the polypeptide. Such antibodies comprise anti-idiotypic antibodies to the protein-specific antibody and can be used to immunize an animal to induce formation of further protein-specific antibodies.

It will be appreciated that Fab and F(ab')2 and other fragments of the antibodies of the present invention may be used according to the methods disclosed herein. Such fragments are typically produced by proteolytic cleavage, using enzymes such as papain (to produce Fab fragments) or pepsin (to produce F(ab')2 fragments). Alternatively, protein-binding fragments can be produced through the application of recombinant DNA technology or through synthetic chemistry.

For in vivo use of antibodies in humans, it may be preferable to use "humanized" chimeric monoclonal antibodies. Such antibodies can be produced using genetic constructs derived from hybridoma cells producing the monoclonal antibodies described above. Methods for producing chimeric antibodies are known in the art. (See, for review, Morrison, Science 229:1202 (1985); Oi et al., BioTechniques 4:214 (1986); Cabilly et al., U.S. Pat. No. 4,816,567; Taniguchi et al., EP 171496; Morrison et al., EP 173494; Neuberger et al., WO 8601533; Robinson et al., WO 8702671; Boulianne et al., Nature 312:643 (1984); Neuberger et al., Nature 314:268 (1985).)

Moreover, in another preferred method, the antibodies directed against the polypeptides of the present invention may be produced in plants. Specific methods are disclosed in U.S. Pat. Nos. 5,959,177, and 6,080,560, which are hereby incorporated in their entirety herein. The methods not only describe methods of expressing antibodies, but also the means of assembling foreign multimeric proteins in plants (i.e., antibodies, etc,), and the subsequent secretion of such antibodies from the plant.

Example 16

Regulation of Protein Expression Via Controlled Aggregation in the Endoplasmic Reticulum As described more particularly herein, proteins regulate diverse cellular processes in higher organisms, ranging from rapid metabolic changes to growth and differentiation. Increased production of specific proteins could be used to prevent certain diseases and/or disease states. Thus, the ability to modulate the expression of specific proteins in an organism would provide significant benefits.

Numerous methods have been developed to date for introducing foreign genes, either under the control of an inducible, constitutively active, or endogenous promoter, into organisms. Of particular interest are the inducible promoters (see, M. Gossen, et al., Proc. Natl. Acad. Sci. USA., 89:5547 (1992); Y. Wang, et al., Proc. Natl. Acad. Sci. USA, 91:8180 (1994), D. No., et al., Proc. Natl. Acad. Sci. USA, 93:3346 (1996); and V. M. Rivera, et al., Nature Med, 2:1028 (1996); in addition to additional examples disclosed elsewhere herein). In one example, the gene for erthropoietin (Epo) was transferred into mice and primates under the control of a small molecule inducer for expression (e.g., tetracycline or rapamycin) (see, D. Bohl, et al., Blood, 92:1512, (1998); K. G. Rendahl, et al., Nat. Biotech, 16:757, (1998); V. M. Rivera, et al., Proc. Natl. Acad. Sci. USA, 96:8657 (1999); and X. Ye et al., Science, 283:88 (1999). Although such systems enable efficient induction of the gene of interest in the organism upon addition of the inducing agent (i.e., tetracycline, rapamycin, etc.), the levels of expression tend to peak at 24 hours and trail off to background levels after 4 to 14 days. Thus, controlled transient expression is virtually impossible using these systems, though such control would be desirable.

A new alternative method of controlling gene expression levels of a protein from a transgene (i.e., includes stable and transient transformants) has recently been elucidated (V. M. Rivera., et al., Science, 287:826-830 (2000)). This method does not control gene expression at the level of the mRNA like the aforementioned systems. Rather, the system controls the level of protein in an active secreted form. In the absence of the inducing agent, the protein aggregates in the ER and is not secreted. However, addition of the inducing agent results in dis-aggregation of the protein and the subsequent secretion from the ER. Such a system affords low basal secretion, rapid, high level secretion in the presence of the inducing agent, and rapid cessation of secretion upon removal of the inducing agent. In fact, protein secretion reached a maximum level within 30 minutes of induction, and a rapid cessation of secretion within 1 hour of removing the inducing agent. The method is also applicable for controlling the level of production for membrane proteins.

Detailed methods are presented in V. M. Rivera., et al., Science, 287:826-830, (2000)), briefly:

Fusion protein constructs are created using polynucleotide sequences of the present invention with one or more copies (preferably at least 2, 3, 4, or more) of a conditional aggregation domain (CAD) a domain that interacts with itself in a ligand-reversible manner (i.e., in the presence of an inducing agent) using molecular biology methods known in the art and discussed elsewhere herein. The CAD domain may be the mutant domain isolated from the human FKBP12 (Phe$^{36}$ to Met) protein (as disclosed in V. M. Rivera., et al., Science, 287:826-830, (2000), or alternatively other proteins having domains with similar ligand-reversible, self-aggregation properties. As a principle of design the fusion protein vector would contain a furin cleavage sequence operably linked between the polynucleotides of the present invention and the CAD domains. Such a cleavage site would enable the proteolytic cleavage of the CAD domains from the polypeptide of the present invention subsequent to secretion from the ER and upon entry into the trans-Golgi (J. B. Denault, et al., FEBS Lett., 379:113, (1996)). Alternatively, the skilled artisan would recognize that any proteolytic cleavage sequence could be substituted for the furin sequence provided the substituted sequence is cleavable either endogenously (e.g., the furin sequence) or exogenously (e.g., post secretion, post purification, post production, etc.). The preferred sequence of each feature of the fusion protein construct, from the 5' to 3' direction with each feature being operably linked to the other, would be a promoter, signal sequence, "X" number of (CAD)x domains, the furin sequence (or other proteolytic sequence), and the coding sequence of the polypeptide of the present invention. The artisan would appreciate that the promotor and signal sequence, independent from the other, could be either the endogenous promotor or signal sequence of a polypeptide of the present invention, or alternatively, could be a heterologous signal sequence and promotor.

The specific methods described herein for controlling protein secretion levels through controlled ER aggregation are not meant to be limiting are would be generally applicable to any of the polynucleotides and polypeptides of the present invention, including variants, homologues, orthologs, and fragments therein.

Example 17

Alteration of Protein Glycosylation Sites to Enhance Characteristics of Polypeptides of the Invention Many eukaryotic cell surface and proteins are post-translationally processed to incorporate N-linked and O-linked carbohydrates (Kornfeld and Kornfeld (1985) Annu. Rev. Biochem. 54:631-64; Rademacher et al., (1988) Annu. Rev. Biochem. 57:785-838). Protein glycosylation is thought to serve a variety of functions including: augmentation of protein folding, inhibition of protein aggregation, regulation of intracellular trafficking to organelles, increasing resistance to proteolysis, modulation of protein antigenicity, and mediation of intercellular adhesion (Fieldler and Simons (1995) Cell, 81:309-312; Helenius (1994) Mol. Biol. Of the Cell 5:253-265; Olden et al., (1978) Cell, 13:461-473; Caton et al., (1982) Cell, 37:417-427; Alexamnder and Elder (1984), Science, 226:1328-1330; and Flack et al., (1994), J. Biol. Chem., 269:14015-14020). In higher organisms, the nature and extent of glycosylation can markedly affect the circulating half-life and bio-availability of proteins by mechanisms involving receptor mediated uptake and clearance (Ashwell and Morrell, (1974), Adv. Enzymol., 41:99-128; Ashwell and Harford (1982), Ann. Rev. Biochem., 51:531-54). Receptor systems have been identified that are thought to play a major role in the clearance of serum proteins through recognition of various carbohydrate structures on the glycoproteins (Stockert (1995), Physiol. Rev., 75:591-609; Kery et al., (1992), Arch. Biochem. Biophys., 298:49-55). Thus, production strategies resulting in incomplete attachment of terminal sialic acid residues might provide a means of shortening the bioavailability and half-life of glycoproteins. Conversely, expression strategies resulting in saturation of terminal sialic acid attachment sites might lengthen protein bioavailability and half-life.

In the development of recombinant glycoproteins for use as pharmaceutical products, for example, it has been speculated that the pharmacodynamics of recombinant proteins can be modulated by the addition or deletion of glycosylation sites from a glycoproteins primary structure (Berman and Lasky (1985a) Trends in Biotechnol., 3:51-53). However, studies have reported that the deletion of N-linked glycosylation sites often impairs intracellular transport and results in the intracellular accumulation of glycosylation site variants (Machamer and Rose (1988), J. Biol. Chem., 263:5955-5960; Gallagher et al., (1992), J. Virology., 66:7136-7145; Collier et al., (1993), Biochem., 32:7818-7823; Claffey et al., (1995) Biochemica et Biophysica Acta, 1246:1-9; Dube et al., (1988), J. Biol. Chem. 263:17516-17521). While glycosylation site variants of proteins can be expressed intracellularly, it has proved difficult to recover useful quantities from growth conditioned cell culture medium.

Moreover, it is unclear to what extent a glycosylation site in one species will be recognized by another species glycosylation machinery. Due to the importance of glycosylation in protein metabolism, particularly the secretion and/or expression of the protein, whether a glycosylation signal is recognized may profoundly determine a proteins ability to be expressed, either endogenously or recombinately, in another organism (i.e., expressing a human protein in *E. coli*, yeast, or viral organisms; or an *E. coli*, yeast, or viral protein in human, etc.). Thus, it may be desirable to add, delete, or modify a glycosylation site, and possibly add a glycosylation site of one species to a protein of another species to improve the proteins functional, bioprocess purification, and/or structural characteristics (e.g., a polypeptide of the present invention)

A number of methods may be employed to identify the location of glycosylation sites within a protein. One preferred method is to run the translated protein sequence through the PROSITE computer program (Swiss Institute of Bioinformatics). Once identified, the sites could be systematically deleted, or impaired, at the level of the DNA using mutagenesis methodology known in the art and available to the skilled artisan, Preferably using PCR-directed mutagenesis (See Maniatis, Molecular Cloning: A Laboratory Manual, Cold Spring Harbor Press, Cold Spring, N.Y. (1982)). Similarly, glycosylation sites could be added, or modified at the level of the DNA using similar methods, preferably PCR methods (See, Maniatis, supra). The results of modifying the glycosylation sites for a particular protein (e.g., solubility, secretion potential, activity, aggregation, proteolytic resistance, etc.) could then be analyzed using methods know in the art.

The skilled artisan would acknowledge the existence of other computer algorithms capable of predicting the location of glycosylation sites within a protein. For example, the Motif computer program (Genetics Computer Group suite of programs) provides this function, as well.

Example 18

Method of Enhancing the Biological Activity/Functional Characteristics of Invention Through Molecular Evolution Although many of the most biologically active proteins known are highly effective for their specified function in an organism, they often possess characteristics that make them undesirable for transgenic, therapeutic, and/or industrial applications. Among these traits, a short physiological half-life is the most prominent problem, and is present either at the level of the protein, or the level of the proteins mRNA. The ability to extend the half-life, for example, would be particularly important for a proteins use in gene therapy, transgenic animal production, the bioprocess production and purification of the protein, and use of the protein as a chemical modulator among others. Therefore, there is a need to identify novel variants of isolated proteins possessing characteristics which enhance their application as a therapeutic for treating diseases of animal origin, in addition to the proteins applicability to common industrial and pharmaceutical applications.

Thus, one aspect of the present invention relates to the ability to enhance specific characteristics of invention through directed molecular evolution. Such an enhancement may, in a non-limiting example, benefit the inventions utility as an essential component in a kit, the inventions physical attributes such as its solubility, structure, or codon optimization, the inventions specific biological activity, including any associated enzymatic activity, the proteins enzyme kinetics, the proteins Ki, Kcat, Km, Vmax, Kd, protein-protein activity, protein-DNA binding activity, antagonist/inhibitory activity (including direct or indirect interaction), agonist activity (including direct or indirect interaction), the proteins antigenicity (e.g., where it would be desirable to either increase or decrease the antigenic potential of the protein), the immunogenicity of the protein, the ability of the protein to form dimers, trimers, or multimers with either itself or other proteins, the antigenic efficacy of the invention, including its subsequent use a preventative treatment for disease or disease states, or as an effector for targeting diseased genes. Moreover, the ability to enhance specific characteristics of a protein may also be applicable to changing the characterized activity of an enzyme to an activity completely unrelated to its initially characterized activity. Other desirable enhancements of the invention would be specific to each individual protein, and would thus be well known in the art and contemplated by the present invention.

Directed evolution is comprised of several steps. The first step is to establish a library of variants for the gene or protein of interest. The most important step is to then select for those variants that entail the activity you wish to identify. The design of the screen is essential since your screen should be selective enough to eliminate non-useful variants, but not so stringent as to eliminate all variants. The last step is then to repeat the above steps using the best variant from the previous screen. Each successive cycle, can then be tailored as necessary, such as increasing the stringency of the screen, for example.

Over the years, there have been a number of methods developed to introduce mutations into macromolecules. Some of these methods include, random mutagenesis, "error-prone" PCR, chemical mutagenesis, site-directed mutagenesis, and other methods well known in the art (for a comprehensive listing of current mutagenesis methods, see Maniatis, Molecular Cloning: A Laboratory Manual, Cold Spring Harbor Press, Cold Spring, N.Y. (1982)). Typically, such methods have been used, for example, as tools for identifying the core functional region(s) of a protein or the function of specific domains of a protein (if a multi-domain protein). However, such methods have more recently been applied to the identification of macromolecule variants with specific or enhanced characteristics.

Random mutagenesis has been the most widely recognized method to date. Typically, this has been carried out either through the use of "error-prone" PCR (as described in Moore, J., et al, Nature Biotechnology 14:458, (1996), or through the application of randomized synthetic oligonucleotides corresponding to specific regions of interest (as described by Derbyshire, K. M. et al, Gene, 46:145-152, (1986), and Hill, D E, et al, Methods Enzymol., 55:559-568, (1987). Both approaches have limits to the level of mutagenesis that can be obtained. However, either approach enables the investigator to effectively control the rate of mutagenesis. This is particularly important considering the fact that mutations beneficial to the activity of the enzyme are fairly rare. In fact, using too high a level of mutagenesis may counter or inhibit the desired benefit of a useful mutation.

While both of the aforementioned methods are effective for creating randomized pools of macromolecule variants, a third method, termed "DNA Shuffling", or "sexual PCR" (WPC, Stemmer, PNAS, 91:10747, (1994)) has recently been elucidated. DNA shuffling has also been referred to as "directed molecular evolution", "exon-shuffling", "directed enzyme evolution", "in vitro evolution", and "artificial evolution". Such reference terms are known in the art and are encompassed by the invention. This new, preferred, method apparently overcomes the limitations of the previous methods in that it not only propagates positive traits, but simultaneously eliminates negative traits in the resulting progeny.

DNA shuffling accomplishes this task by combining the principal of in vitro recombination, along with the method of "error-prone" PCR. In effect, you begin with a randomly digested pool of small fragments of your gene, created by Dnase I digestion, and then introduce said random fragments into an "error-prone" PCR assembly reaction. During the PCR reaction, the randomly sized DNA fragments not only hybridize to their cognate strand, but also may hybridize to other DNA fragments corresponding to different regions of the polynucleotide of interest—regions not typically accessible via hybridization of the entire polynucleotide. Moreover, since the PCR assembly reaction utilizes "error-prone" PCR reaction conditions, random mutations are introduced during the DNA synthesis step of the PCR reaction for all of the fragments further diversifying the potential hybridization sites during the annealing step of the reaction.

A variety of reaction conditions could be utilized to carry-out the DNA shuffling reaction. However, specific reaction conditions for DNA shuffling are provided, for example, in PNAS, 91:10747, (1994). Briefly:

Prepare the DNA substrate to be subjected to the DNA shuffling reaction. Preparation may be in the form of simply purifying the DNA from contaminating cellular material, chemicals, buffers, oligonucleotide primers, deoxynucleotides, RNAs, etc., and may entail the use of DNA purification kits as those provided by Qiagen, Inc., or by the Promega, Corp., for example.

Once the DNA substrate has been purified, it would be subjected to Dnase I digestion. About 2-4 ug of the DNA substrate(s) would be digested with 0.0015 units of Dnase I (Sigma) per ul in 100 ul of 50 mM Tris-HCL, pH 7.4/1 mM MgCl2 for 10-20 min. at room temperature. The resulting fragments of 10-50 bp could then be purified by running them through a 2% low-melting point agarose gel by electrophoresis onto DE81 ion-exchange paper (Whatmann) or could be purified using MICROCON® concentrators (Amicon) of the appropriate molecular weight cutoff, or could use oligonucleotide purification columns (Qiagen), in addition to other methods known in the art. If using DE81 ion-exchange paper, the 10-50 bp fragments could be eluted from said paper using 1M NaCl, followed by ethanol precipitation.

The resulting purified fragments would then be subjected to a PCR assembly reaction by re-suspension in a PCR mixture containing: 2 mM of each dNTP, 2.2 mM MgCl2, 50 mM KCl, 10 mM Tris·HCL, pH 9.0, and 0.1% Triton X-100, at a final fragment concentration of 10-30 ng/ul. No primers are added at this point. Taq DNA polymerase (Promega) would be used at 2.5 units per 100 ul of reaction mixture. A PCR program of 94 C for 60 s; 94 C for 30s, 50-55 C for 30 s, and 72 C for 30s using 30-45 cycles, followed by 72 C for 5 min using an MJ RESEARCH® (Cambridge, Mass.) PTC-150 thermocycler. After the assembly reaction is completed, a 1:40 dilution of the resulting primerless product would then be introduced into a PCR mixture (using the same buffer mixture used for the assembly reaction) containing 0.8 um of each primer and subjecting this mixture to 15 cycles of PCR (using 94 C for 30 s, 50 C for 30 s, and 72 C for 30 s). The referred primers would be primers corresponding to the nucleic acid sequences of the polynucleotide(s) utilized in the shuffling reaction. Said primers could consist of modified nucleic acid base pairs using methods known in the art and referred to else where herein, or could contain additional sequences (i.e., for adding restriction sites, mutating specific base-pairs, etc.).

The resulting shuffled, assembled, and amplified product can be purified using methods well known in the art (e.g., Qiagen PCR purification kits) and then subsequently cloned using appropriate restriction enzymes.

Although a number of variations of DNA shuffling have been published to date, such variations would be obvious to the skilled artisan and are encompassed by the invention. The DNA shuffling method can also be tailored to the desired level of mutagenesis using the methods described by Zhao, et al. (Nucl Acid Res., 25(6):1307-1308, (1997).

As described above, once the randomized pool has been created, it can then be subjected to a specific screen to identify the variant possessing the desired characteristic(s). Once the variant has been identified, DNA corresponding to the variant could then be used as the DNA substrate for initiating another round of DNA shuffling. This cycle of shuffling, selecting the optimized variant of interest, and then re-shuffling, can be repeated until the ultimate variant is obtained. Examples of model screens applied to identify variants created using DNA shuffling technology may be found in the following publications: J. C., Moore, et al., J. Mol. Biol., 272:336-347, (1997), F. R., Cross, et al., Mol. Cell. Biol., 18:2923-2931, (1998), and A. Crameri., et al., Nat. Biotech., 15:436-438, (1997).

DNA shuffling has several advantages. First, it makes use of beneficial mutations. When combined with screening, DNA shuffling allows the discovery of the best mutational combinations and does not assume that the best combination contains all the mutations in a population. Secondly, recombination occurs simultaneously with point mutagenesis. An effect of forcing DNA polymerase to synthesize full-length genes from the small fragment DNA pool is a background mutagenesis rate. In combination with a stringent selection method, enzymatic activity has been evolved up to 16000 fold increase over the wild-type form of the enzyme. In essence, the background mutagenesis yielded the genetic variability on which recombination acted to enhance the activity.

A third feature of recombination is that it can be used to remove deleterious mutations. As discussed above, during the process of the randomization, for every one beneficial mutation, there may be at least one or more neutral or inhibitory mutations. Such mutations can be removed by including in the assembly reaction an excess of the wild-type random-size fragments, in addition to the random-size fragments of the selected mutant from the previous selection. During the next selection, some of the most active variants of the polynucleotide/polypeptide/enzyme, should have lost the inhibitory mutations.

Finally, recombination enables parallel processing. This represents a significant advantage since there are likely multiple characteristics that would make a protein more desirable (e.g. solubility, activity, etc.). Since it is increasingly difficult to screen for more than one desirable trait at a time, other methods of molecular evolution tend to be inhibitory. However, using recombination, it would be possible to combine the randomized fragments of the best representative variants for the various traits, and then select for multiple properties at once.

DNA shuffling can also be applied to the polynucleotides and polypeptides of the present invention to decrease their immunogenicity in a specified host. For example, a particular variant of the present invention may be created and isolated using DNA shuffling technology. Such a variant may have all of the desired characteristics, though may be highly immunogenic in a host due to its novel intrinsic structure. Specifically, the desired characteristic may cause the polypeptide to have a non-native structure which could no longer be recognized as a "self" molecule, but rather as a "foreign", and thus activate a host immune response directed against the novel variant. Such a limitation can be overcome, for example, by including a copy of the gene sequence for a xenobiotic ortholog of the native protein in with the gene sequence of the novel variant gene in one or more cycles of DNA shuffling. The molar ratio of the ortholog and novel variant DNAs could be varied accordingly. Ideally, the resulting hybrid variant identified would contain at least some of the coding sequence which enabled the xenobiotic protein to evade the host immune system, and additionally, the coding sequence of the original novel variant that provided the desired characteristics.

Likewise, the invention encompasses the application of DNA shuffling technology to the evolution of polynucleotides and polypeptides of the invention, wherein one or more cycles of DNA shuffling include, in addition to the gene template DNA, oligonucleotides coding for known allelic sequences, optimized codon sequences, known variant sequences, known polynucleotide polymorphism sequences, known ortholog sequences, known homologue sequences, additional homologous sequences, additional non-homologous sequences, sequences from another species, and any number and combination of the above.

In addition to the described methods above, there are a number of related methods that may also be applicable, or desirable in certain cases. Representative among these are the methods discussed in PCT applications WO 98/31700, and WO 98/32845, which are hereby incorporated by reference. Furthermore, related methods can also be applied to the polynucleotide sequences of the present invention in order to evolve invention for creating ideal variants for use in gene therapy, protein engineering, evolution of whole cells containing the variant, or in the evolution of entire enzyme pathways containing polynucleotides of the invention as described in PCT applications WO 98/13485, WO 98/13487, WO 98/27230, WO 98/31837, and Crameri, A., et al., Nat. Biotech., 15:436-438, (1997), respectively.

Additional methods of applying "DNA Shuffling" technology to the polynucleotides and polypeptides of the present invention, including their proposed applications, may be found in U.S. Pat. No. 5,605,793; PCT Application No. WO 95/22625; PCT Application No. WO 97/20078; PCT Application No. WO 97/35966; and PCT Application No. WO 98/42832; PCT Application No. WO 00/09727 specifically provides methods for applying DNA shuffling to the identification of herbicide selective crops which could be applied to the polynucleotides and polypeptides of the present invention; additionally, PCT Application No. WO 00/12680 provides methods and compositions for generating, modifying, adapting, and optimizing polynucleotide sequences that confer detectable phenotypic properties on plant species; each of the above are hereby incorporated in their entirety herein for all purposes.

Example 19

Method of Determining Alterations in a Gene Corresponding to a Polynucleotide

RNA isolated from entire families or individual patients presenting with a phenotype of interest (such as a disease) is be isolated. cDNA is then generated from these RNA samples using protocols known in the art. (See, Sambrook.) The cDNA is then used as a template for PCR, employing primers surrounding regions of interest in SEQ ID NO:1. Suggested PCR conditions consist of 35 cycles at 95 degrees C. for 30 seconds; 60-120 seconds at 52-58 degrees C.; and 60-120 seconds at 70 degrees C., using buffer solutions described in Sidransky et al., Science 252:706 (1991).

PCR products are then sequenced using primers labeled at their 5' end with T4 polynucleotide kinase, employing SequiTherm Polymerase. (Epicentre Technologies). The intron-exon borders of selected exons is also determined and genomic PCR products analyzed to confirm the results. PCR products harboring suspected mutations is then cloned and sequenced to validate the results of the direct sequencing.

PCR products are cloned into T-tailed vectors as described in Holton et al., Nucleic Acids Research, 19:1156 (1991) and sequenced with T7 polymerase (United States Biochemical). Affected individuals are identified by mutations not present in unaffected individuals.

Genomic rearrangements are also observed as a method of determining alterations in a gene corresponding to a polynucleotide. Genomic clones isolated according to the methods described herein are nick-translated with digoxigenindeoxy-uridine 5'-triphosphate (Boehringer Manheim), and FISH performed as described in Johnson et al., Methods Cell Biol. 35:73-99 (1991). Hybridization with the labeled probe is carried out using a vast excess of human cot-1 DNA for specific hybridization to the corresponding genomic locus.

Chromosomes are counterstained with 4,6-diamino-2-phenylidole and propidium iodide, producing a combination of C- and R-bands. Aligned images for precise mapping are obtained using a triple-band filter set (Chroma Technology, Brattleboro, Vt.) in combination with a cooled charge-coupled device camera (Photometrics, Tucson, Ariz.) and variable excitation wavelength filters. (Johnson et al., Genet. Anal. Tech. Appl., 8:75 (1991).) Image collection, analysis and chromosomal fractional length measurements are performed using the ISEE® Graphical Program System. (Inovision Corporation, Durham, N.C.) Chromosome alterations of the genomic region hybridized by the probe are identified as insertions, deletions, and translocations. These alterations are used as a diagnostic marker for an associated disease.

Example 20

Method of Detecting Abnormal Levels of a Polypeptide in a Biological Sample

A polypeptide of the present invention can be detected in a biological sample, and if an increased or decreased level of the polypeptide is detected, this polypeptide is a marker for a particular phenotype. Methods of detection are numerous, and thus, it is understood that one skilled in the art can modify the following assay to fit their particular needs.

For example, antibody-sandwich ELISAs are used to detect polypeptides in a sample, preferably a biological sample. Wells of a microtiter plate are coated with specific antibodies, at a final concentration of 0.2 to 10 ug/ml. The antibodies are either monoclonal or polyclonal and are produced by the method described elsewhere herein. The wells are blocked so that non-specific binding of the polypeptide to the well is reduced.

The coated wells are then incubated for >2 hours at RT with a sample containing the polypeptide. Preferably, serial dilutions of the sample should be used to validate results. The plates are then washed three times with deionized or distilled water to remove unbounded polypeptide.

Next, 50 ul of specific antibody-alkaline phosphatase conjugate, at a concentration of 25-400 ng, is added and incubated for 2 hours at room temperature. The plates are again washed three times with deionized or distilled water to remove unbounded conjugate.

Add 75 ul of 4-methylumbelliferyl phosphate (MUP) or p-nitrophenyl phosphate (NPP) substrate solution to each well and incubate 1 hour at room temperature. Measure the reaction by a microtiter plate reader. Prepare a standard curve, using serial dilutions of a control sample, and plot polypeptide concentration on the X-axis (log scale) and fluorescence or absorbance of the Y-axis (linear scale). Interpolate the concentration of the polypeptide in the sample using the standard curve.

Example 21

Method of Isolating Antibody Fragments Directed Against PCSK9b or PCSK9c from a Library of scFvs Naturally occurring V-genes isolated from human PBLs are constructed into a library of antibody fragments which contain reactivities against PCSK9b or PCSK9c to which the donor may or may not have been exposed (see e.g., U.S. Pat. No. 5,885,793 incorporated herein by reference in its entirety).

Rescue of the Library. A library of scFvs is constructed from the RNA of human PBLs as described in PCT publication WO 92/01047. To rescue phage displaying antibody fragments, approximately 10$^9$ E. coli harboring the phagemid are used to inoculate 50 ml of 2×TY containing 1% glucose and 100 pg/ml of ampicillin (2×TY-AMP-GLU) and grown to an O.D. of 0.8 with shaking. Five ml of this culture is used to inoculate 50 ml of 2×TY-AMP-GLU, 2×10$^8$ TU of delta gene 3 helper (M13 delta gene III, see PCT publication WO 92/01047) are added and the culture incubated at 37° C. for 45 minutes without shaking and then at 37° C. for 45 minutes with shaking. The culture is centrifuged at 4000 r.p.m. for 10 min. and the pellet resuspended in 2 liters of 2×TY containing 100 ug/ml ampicillin and 50 ug/ml kanamycin and grown overnight. Phage are prepared as described in PCT publication WO 92/01047.

M13 delta gene III is prepared as follows: M13 delta gene III helper phage does not encode gene III protein, hence the phage(mid) displaying antibody fragments have a greater avidity of binding to antigen. Infectious M13 delta gene III particles are made by growing the helper phage in cells harboring a pUC19 derivative supplying the wild type gene III protein during phage morphogenesis. The culture is incubated for 1 hour at 37° C. without shaking and then for a further hour at 37° C. with shaking. Cells are spun down (IEC-Centra 8,400 r.p.m. for 10 min), resuspended in 300 ml 2×TY broth containing 100 ug ampicillin/ml and 25 ug kanamycin/ml (2×TY-AMP-KAN) and grown overnight, shaking at 37° C. Phage particles are purified and concentrated from the culture medium by two PEG-precipitations (Sambrook et al., 1990), resuspended in 2 ml PBS and passed through a 0.45 μm filter (Minisart NML; Sartorius) to give a final concentration of approximately 10$^{13}$ transducing units/ml (ampicillin-resistant clones).

Panning of the Library. Immunotubes (Nunc) are coated overnight in PBS with 4 ml of either 100 μg/ml or 10 μg/ml of a polypeptide of the present invention. Tubes are blocked with 2% Marvel-PBS for 2 hours at 37° C. and then washed 3 times in PBS. Approximately 10$^{13}$ TU of phage is applied to the tube and incubated for 30 minutes at room temperature tumbling on an over and under turntable and then left to stand for another 1.5 hours. Tubes are washed 10 times with PBS 0.1% Tween-20 and 10 times with PBS. Phage are eluted by adding 1 ml of 100 mM triethylamine and rotating 15 minutes on an under and over turntable after which the solution is immediately neutralized with 0.5 ml of 1.0M Tris-HCl, pH 7.4. Phage are then used to infect 10 ml of mid-log E. coli TG1 by incubating eluted phage with bacteria for 30 minutes at 37° C. The E. coli are then plated on TYE plates containing 1% glucose and 100 μg/ml ampicillin. The resulting bacterial library is then rescued with delta gene 3 helper phage as described above to prepare phage for a subsequent round of selection. This process is then repeated for a total of 4 rounds of affinity purification with tube-washing increased to 20 times with PBS, 0.1% Tween-20 and 20 times with PBS for rounds 3 and 4.

Characterization of Binders. Eluted phage from the 3rd and 4th rounds of selection are used to infect E. coli HB 2151 and soluble scFv is produced (Marks, et al., 1991) from single colonies for assay. ELISAs are performed with microtitre plates coated with either 10 pg/ml of the polypeptide of the present invention in 50 mM bicarbonate pH 9.6. Clones positive in ELISA are further characterized by PCR fingerprinting (see, e.g., PCT publication WO 92/01047) and then by sequencing. These ELISA positive clones may also be further characterized by techniques known in the art, such as, for example, epitope mapping, binding affinity, receptor signal transduction, ability to block or competitively inhibit antibody/antigen binding, and competitive agonistic or antagonistic activity.

Moreover, in another preferred method, the antibodies directed against the polypeptides of the present invention may be produced in plants. Specific methods are disclosed in U.S. Pat. Nos. 5,959,177, and 6,080,560, which are hereby incorporated in their entirety herein. The methods not only describe methods of expressing antibodies, but also the means of assembling foreign multimeric proteins in plants (i.e., antibodies, etc,), and the subsequent secretion of such antibodies from the plant.

What is claimed is:

1. An isolated nucleic acid molecule comprising a polynucleotide sequence selected from the group consisting of:
   (a) an isolated polynucleotide encoding a polypeptide comprising amino acids 1 to 315 of SEQ ID NO:2; and
   (b) an isolated polynucleotide encoding a polypeptide comprising amino acids 2 to 315 of SEQ ID NO:2.

2. The isolated nucleic acid molecule of claim 1, wherein said polynucleotide is (a).

3. The isolated nucleic acid molecule of claim 2, wherein said polynucleotide comprises nucleotides 250 to 1194 of SEQ ID NO:1.

4. The isolated nucleic acid molecule of claim 1, wherein said polynucleotide is (b).

5. The isolated nucleic acid molecule of claim 4, wherein said polynucleotide comprises nucleotides 253 to 1194 of SEQ ID NO:1.

6. A recombinant vector comprising the isolated nucleic acid molecule of claim 1.

7. An isolated recombinant host cell comprising the vector of claim 6.

8. A method of making an isolated polypeptide comprising:
(a) culturing the isolated recombinant host cell of claim 7 under conditions such that said polypeptide is expressed; and
(b) recovering said polypeptide.

9. The isolated nucleic acid molecule of claim 1 wherein said nucleic acid sequence further comprises a heterologous nucleic acid sequence.

10. The isolated nucleic acid molecule of claim 9 wherein said heterologous nucleic acid sequence encodes a heterologous polypeptide and wherein said heterologous polypeptide is the Fc domain of immunoglobulin.

11. An isolated nucleic acid molecule comprising the cDNA clone contained in plasmid PCSK9-b in ATCC Deposit No. PTA-7622.

12. An isolated polynucleotide comprising the complementary sequence of (a) or (b) of claim 1.

13. An isolated polynucleotide consisting of a polynucleotide sequence encoding amino acids 10 to 256 of SEQ ID NO:2, wherein said polynucleotide encodes a polypeptide that is capable of lowering the level of LDL uptake in mammalian cells in which said polypeptide is recombinately expressed.

14. The isolated polynucleotide of claim 13, wherein said polynucleotide consists of nucleotides 277 to 1017 of SEQ ID NO:1.

15. An isolated polynucleotide comprising a polynucleotide sequence encoding amino acids 1 to 279 of SEQ ID NO:2, wherein said polynucleotide encodes a polypeptide that is capable of lowering the level of LDL uptake in mammalian cells in which said polypeptide is recombinately expressed.

16. The isolated polynucleotide of claim 15, wherein said polynucleotide comprises nucleotides 250 to 1086 of SEQ ID NO:1.

17. An isolated polynucleotide comprising a polynucleotide sequence encoding amino acids 37 to 315 of SEQ ID NO:2, wherein said polynucleotide encodes a polypeptide that is capable of lowering the level of LDL uptake in mammalian cells in which said polypeptide is recombinately expressed.

18. The isolated polynucleotide of claim 17, wherein said polynucleotide comprises nucleotides 358 to 1194 of SEQ ID NO:1.

19. An isolated polynucleotide comprising a polynucleotide sequence encoding amino acids 2 to 284 of SEQ ID NO:2, wherein said polynucleotide encodes a polypeptide that is capable of lowering the level of LDL uptake in mammalian cells in which said polypeptide is recombinately expressed.

20. The isolated polynucleotide of claim 19, wherein said polynucleotide comprises nucleotides 253 to 1101 of SEQ ID NO:1.

21. An isolated polynucleotide comprising a polynucleotide sequence encoding amino acids 16 to 315 of SEQ ID NO:2, wherein said polynucleotide encodes a polypeptide that is capable of lowering the level of LDL uptake in mammalian cells in which said polypeptide is recombinately expressed.

22. The isolated polynucleotide of claim 21, wherein said polynucleotide comprises nucleotides 295 to 1194 of SEQ ID NO:1.

* * * * *

UNITED STATES PATENT AND TRADEMARK OFFICE
CERTIFICATE OF CORRECTION

| | |
|---|---|
| PATENT NO. | : 7,572,618 B2 |
| APPLICATION NO. | : 11/824461 |
| DATED | : August 11, 2009 |
| INVENTOR(S) | : Gabriel A. Mintier et al. |

It is certified that error appears in the above-identified patent and that said Letters Patent is hereby corrected as shown below:

Title Page; item (56);
Column 2 (Other Publications)

Line 8, "30571" should read -- 30572 --.

Signed and Sealed this

Fifteenth Day of December, 2009

David J. Kappos
*Director of the United States Patent and Trademark Office*

```
                        SEQUENCE LISTING

<160> NUMBER OF SEQ ID NOS: 40

<210> SEQ ID NO 1
<211> LENGTH: 3175
<212> TYPE: DNA
<213> ORGANISM: Homo sapiens
<220> FEATURE:
<221> NAME/KEY: CDS
<222> LOCATION: (250)..(1194)

<400> SEQUENCE: 1
gatgacttgg gtccttcttg gcagtagcat tgccagctga tggccttgga cagttacctg      60
ccctctctag gcctcccttt ccttgtctat gaaatacatt atagaatagg atgtagtgtg     120
tgaggatttt ttggaggtta aacgagtgaa tatatttaag gcgctttcac cagtgcctgg     180
gatgtgctct gtagtttctg tgtgttaact ataaggttga ctttatgctc attccctcct     240 ctcccacaa atg tcg cct tgg aaa gac gga ggc agc ctg gtg gag gtg tat    291
           Met Ser Pro Trp Lys Asp Gly Gly Ser Leu Val Glu Val Tyr
             1               5                  10 ctc cta gac acc agc ata cag agt gac cac cgg gaa atc gag ggc agg       339
Leu Leu Asp Thr Ser Ile Gln Ser Asp His Arg Glu Ile Glu Gly Arg
 15                  20                  25                  30 gtc atg gtc acc gac ttc gag aat gtg ccc gag gag gac ggg acc cgc       387
Val Met Val Thr Asp Phe Glu Asn Val Pro Glu Glu Asp Gly Thr Arg
                 35                  40                  45 ttc cac aga cag gcc agc aag tgt gac agt cat ggc acc cac ctg gca       435
Phe His Arg Gln Ala Ser Lys Cys Asp Ser His Gly Thr His Leu Ala
             50                  55                  60 gga gtg gtc agc ggc cgg gat gcc ggc gtg gcc aag ggt gcc agc atg       483
Gly Val Val Ser Gly Arg Asp Ala Gly Val Ala Lys Gly Ala Ser Met
         65                  70                  75 cgc agc ctg cgc gtg ctc aac tgc caa ggg aag ggc acg gtt agc ggc       531
Arg Ser Leu Arg Val Leu Asn Cys Gln Gly Lys Gly Thr Val Ser Gly
     80                  85                  90 acc ctc ata ggc ctg gag ttt att cgg aaa agc cag ctg gtc cag cct       579
Thr Leu Ile Gly Leu Glu Phe Ile Arg Lys Ser Gln Leu Val Gln Pro
 95                 100                 105                 110 gtg ggg cca ctg gtg gtg ctg ctg ccc ctg gcg ggt ggg tac agc cgc       627
Val Gly Pro Leu Val Val Leu Leu Pro Leu Ala Gly Gly Tyr Ser Arg
                115                 120                 125 gtc ctc aac gcc gcc tgc cag cgc ctg gcg agg gct ggg gtc gtg ctg       675
Val Leu Asn Ala Ala Cys Gln Arg Leu Ala Arg Ala Gly Val Val Leu
            130                 135                 140 gtc acc gct gcc ggc aac ttc cgg gac gat gcc tgc ctc tac tcc cca       723
Val Thr Ala Ala Gly Asn Phe Arg Asp Asp Ala Cys Leu Tyr Ser Pro
        145                 150                 155 gcc tca gct ccc gag gtc atc aca gtt ggg gcc acc aat gcc cag gac       771
Ala Ser Ala Pro Glu Val Ile Thr Val Gly Ala Thr Asn Ala Gln Asp
    160                 165                 170 cag ccg gtg acc ctg ggg act ttg ggg acc aac ttt ggc cgc tgt gtg       819
Gln Pro Val Thr Leu Gly Thr Leu Gly Thr Asn Phe Gly Arg Cys Val
175                 180                 185                 190 gac ctc ttt gcc cca ggg gag gac atc att ggt gcc tcc agc gac tgc       867
```

```
Asp Leu Phe Ala Pro Gly Glu Asp Ile Ile Gly Ala Ser Ser Asp Cys
            195                 200                 205 agc acc tgc ttt gtg tca cag agt ggg aca tca cag gct gct gcc cac      915
Ser Thr Cys Phe Val Ser Gln Ser Gly Thr Ser Gln Ala Ala Ala His
        210                 215                 220 gtg gct ggc att gca gcc atg atg ctg tct gcc gag ccg gag ctc acc      963
Val Ala Gly Ile Ala Ala Met Met Leu Ser Ala Glu Pro Glu Leu Thr
            225                 230                 235 ctg gcc gag ttg agg cag aga ctg atc cac ttc tct gcc aaa gat gtc     1011
Leu Ala Glu Leu Arg Gln Arg Leu Ile His Phe Ser Ala Lys Asp Val
        240                 245                 250 atc aat gag gcc tgg ttc cct gag gac cag cgg gta ctg acc ccc aac     1059
Ile Asn Glu Ala Trp Phe Pro Glu Asp Gln Arg Val Leu Thr Pro Asn
255                 260                 265                 270 ctg gtg gcc gcc ctg ccc ccc agc acc cat ggg gca ggc cct ttt tgc     1107
Leu Val Ala Ala Leu Pro Pro Ser Thr His Gly Ala Gly Pro Phe Cys
                275                 280                 285 agg ttg gca gct gtt ttg cag gac tgt gtg gtc agc aca ctc ggg gcc     1155
Arg Leu Ala Ala Val Leu Gln Asp Cys Val Val Ser Thr Leu Gly Ala
            290                 295                 300 tac acg gat ggc cac agc cat cgc ccg ctg cgc ccc aga tgaggagctg      1204
Tyr Thr Asp Gly His Ser His Arg Pro Leu Arg Pro Arg
            305                 310                 315 ctgagctgct ccagtttctc caggagtggg aagcggcggg gcgagcgcat ggaggcccaa   1264
ggggcaagc  tggtctgccg ggcccacaac gctttgggg  gtgagggtgt ctacgccatt   1324
gccaggtgct gcctgctacc ccaggccaac tgcagcgtcc acacagctcc accagctgag   1384
gccagcatgg ggacccgtgt ccactgccac caacagggcc acgtcctcac aggctgcagc   1444
tcccactggg aggtggagga ccttggcacc cacaagccgc ctgtgctgag gccacgaggt   1504
cagcccaacc agtgcgtggg ccacagggag gccagcatcc acgcttcctg ctgccatgcc   1564
ccaggtctgg aatgcaaagt caaggagcat ggaatcccgg cccctcagga gcaggtgacc   1624
gtggcctgcg aggagggctg gaccctgact ggctgcagtg ccctccctgg gacctcccac   1684
gtcctggggg cctacgccgt agacaacacg tgtgtagtca ggagccggga cgtcagcact   1744
acaggcagca ccagcgaaga ggccgtgaca gccgttgcca tctgctgccg gagccggcac   1804
ctggcgcagg cctcccagga gctccagtga cagcccatc  ccaggatggg tgtctgggga   1864
gggtcaaggg ctggggctga gctttaaaat ggttccgact tgtccctctc tcagccctcc   1924
atggcctggc acgaggggat ggggatgctt ccgccttcc  ggggctgctg gcctggccct   1984
tgagtggggc agcctccttg cctggaactc actcactctg ggtgcctcct ccccaggtgg   2044
aggtgccagg aagctccctc cctcactgtg gggcatttca ccattcaaac aggtcgagct   2104
gtgctcgggt gctgccagct gctcccaatg tgccgatgtc cgtgggcaga atgactttta   2164
ttgagctctt gttccgtgcc aggcattcaa tcctcaggtc tccaccaagg aggcaggatt   2224
cttcccatgg atagggagg  gggcggtagg ggctgcaggg acaaacatcg ttgggggtg    2284
agtgtgaaag gtgctgatgg ccctcatctc cagctaactg tggagaagcc ctgggggct    2344
ccctgattaa tggaggctta gctttctgga tggcatctag ccagaggctg agacaggtg    2404
tgccctggt  ggtcacaggc tgtgccttgg tttcctgagc cacctttact ctgctctatg   2464
ccaggctgtg ctagcaacac ccaaaggtgg cctgcgggga ccatcacct  aggactgact   2524
cggcagtgtg cagtggtgca tgcactgtct cagccaaccc gctccactac ccggcagggt   2584
acacattcgc  cccctactt cacagaggaa gaaacctgga accagagggg gcgtgcctgc   2644
```

```
caagctcaca cagcaggaac tgagccagaa acgcagattg ggctggctct gaagccaagc    2704
ctcttcttac ttcacccggc tgggctcctc attttttacgg gtaacagtga ggctgggaag    2764
gggaacacag accaggaagc tcggtgagtg atggcagaac gatgcctgca ggcatggaac    2824
tttttccgtt atcacccagg cctgattcac tggcctggcg gagatgcttc taaggcatgg    2884
tcggggagaa gggccaacaa ctgtccctcc ttgagcacca gccccaccca agcaagcaga    2944
catttatctt tgggtctgt cctctctgtt gccttttttac agccaacttt tctagacctg    3004
ttttgctttt gtaacttgaa gatatttatt ctgggttttg tagcattttt attaatatgg    3064
tgacttttta aaataaaaac aaacaaacgt tgtcctaaaa aaaaaaaaaa aaaaaaaaa    3124 aaaaaaaaaa aaaaaaaaaa aaaaaaaaaa aaaaaaaaaa aaaaaaaaaa a             3175
```

<210> SEQ ID NO 2
<211> LENGTH: 315
<212> TYPE: PRT
<213> ORGANISM: Homo sapiens

<400> SEQUENCE: 2

```
Met Ser Pro Trp Lys Asp Gly Gly Ser Leu Val Glu Val Tyr Leu Leu
1               5                   10                  15

Asp Thr Ser Ile Gln Ser Asp His Arg Glu Ile Glu Gly Arg Val Met
            20                  25                  30

Val Thr Asp Phe Glu Asn Val Pro Glu Glu Asp Gly Thr Arg Phe His
        35                  40                  45

Arg Gln Ala Ser Lys Cys Asp Ser His Gly Thr His Leu Ala Gly Val
    50                  55                  60

Val Ser Gly Arg Asp Ala Gly Val Ala Lys Gly Ala Ser Met Arg Ser
65                  70                  75                  80

Leu Arg Val Leu Asn Cys Gln Gly Lys Gly Thr Val Ser Gly Thr Leu
                85                  90                  95

Ile Gly Leu Glu Phe Ile Arg Lys Ser Gln Leu Val Gln Pro Val Gly
            100                 105                 110

Pro Leu Val Val Leu Leu Pro Leu Ala Gly Gly Tyr Ser Arg Val Leu
        115                 120                 125

Asn Ala Ala Cys Gln Arg Leu Ala Arg Ala Gly Val Val Leu Val Thr
    130                 135                 140

Ala Ala Gly Asn Phe Arg Asp Asp Ala Cys Leu Tyr Ser Pro Ala Ser
145                 150                 155                 160

Ala Pro Glu Val Ile Thr Val Gly Ala Thr Asn Ala Gln Asp Gln Pro
                165                 170                 175

Val Thr Leu Gly Thr Leu Gly Thr Asn Phe Gly Arg Cys Val Asp Leu
            180                 185                 190

Phe Ala Pro Gly Glu Asp Ile Ile Gly Ala Ser Ser Asp Cys Ser Thr
        195                 200                 205

Cys Phe Val Ser Gln Ser Gly Thr Ser Gln Ala Ala His Val Ala
    210                 215                 220

Gly Ile Ala Ala Met Met Leu Ser Ala Glu Pro Glu Leu Thr Leu Ala
225                 230                 235                 240

Glu Leu Arg Gln Arg Leu Ile His Phe Ser Ala Lys Asp Val Ile Asn
                245                 250                 255

Glu Ala Trp Phe Pro Glu Asp Gln Arg Val Leu Thr Pro Asn Leu Val
            260                 265                 270

Ala Ala Leu Pro Pro Ser Thr His Gly Ala Gly Pro Phe Cys Arg Leu
        275                 280                 285
```

```
Ala Ala Val Leu Gln Asp Cys Val Val Ser Thr Leu Gly Ala Tyr Thr
    290                 295                 300

Asp Gly His Ser His Arg Pro Leu Arg Pro Arg
305                 310                 315

<210> SEQ ID NO 3
<211> LENGTH: 3756
<212> TYPE: DNA
<213> ORGANISM: Homo sapiens
<220> FEATURE:
<221> NAME/KEY: CDS
<222> LOCATION: (881)..(2449)

<400> SEQUENCE: 3
tgctagcagc aacctgcctg aagtcttcct ttggcctggc tgagagtttc tgagacctgc      60
gctggagcgg aggtgcttcc ttccttgctt cctttcttcc tctctcccct ctccatccag     120
caggctggac ctgcctggca tctgtgagct ctccctactt tctcctatac cctaaccttt     180
gtcctgcatg ggcgactccc ccagtgagtc tcttgcagct tttaccccag tgcctgcttc     240
ttggagaatc caaactgatc cagttaggga tgataaagtg tagggtaggc gctcggtgac     300
tgttttctct gaggttgtga ctcgtgtgag gcagaagcag tccccgtgag ccctcctggt     360
atcttgtgga gtggagaacg cttggacctg gagccaggag gcccagacat acatcctgtc     420
cgagctgcag cttcctgtct ctaaaatgag ccggccagcg caggtggcca gacatcactg     480
ttattctcct ttgagtcttt aaatcttgtt gtctttcttg cagactcggt gagctgtgaa     540
aggctataat aggggcttta ttttacactt tgatactatt ttttgaacat tcatatattt     600
gttagatatt gatattcata tgaaggagca ggatgacttg ggtccttctt ggcagtagca     660
ttgccagctg atggccttgg acagttacct gccctctcta ggcctccctt tccttgtcta     720
tgaaatacat tatagaatag gatgtagtgt gtgaggattt tttggaggtt aaacgagtga     780
atatatttaa ggcgctttca ccagtgcctg ggatgtgctc tgtagtttct gtgtgttaac     840
tataaggttg actttatgct cattccctcc tctcccacaa atg tcg cct tgg aaa      895
                                            Met Ser Pro Trp Lys
                                              1               5 gac gga ggc agc ctg gtg gag gtg tat ctc cta gac acc agc ata cag      943
Asp Gly Gly Ser Leu Val Glu Val Tyr Leu Leu Asp Thr Ser Ile Gln
             10                  15                  20 agt gac cac cgg gaa atc gag ggc agg gtc atg gtc acc gac ttc gag      991
Ser Asp His Arg Glu Ile Glu Gly Arg Val Met Val Thr Asp Phe Glu
         25                  30                  35 aat gtg ccc gag gag gac ggg acc cgc ttc cac aga cag gcc agc aag     1039
Asn Val Pro Glu Glu Asp Gly Thr Arg Phe His Arg Gln Ala Ser Lys
     40                  45                  50 tgt gac agt cat ggc acc cac ctg gca ggg gtg gtc agc ggc cgg gat     1087
Cys Asp Ser His Gly Thr His Leu Ala Gly Val Val Ser Gly Arg Asp
 55                  60                  65 gcc ggc gtg gcc aag ggt gcc agc atg cgc agc ctg cgc gtg ctc aac     1135
Ala Gly Val Ala Lys Gly Ala Ser Met Arg Ser Leu Arg Val Leu Asn
 70                  75                  80                  85 tgc caa ggg aag ggc acg gtt agc ggc acc ctc ata ggc ctg gag ttt     1183
Cys Gln Gly Lys Gly Thr Val Ser Gly Thr Leu Ile Gly Leu Glu Phe
             90                  95                 100 att cgg aaa agc cag ctg gtc cag cct gtg ggg cca ctg gtg gtg ctg     1231
Ile Arg Lys Ser Gln Leu Val Gln Pro Val Gly Pro Leu Val Val Leu
            105                 110                 115 ctg ccc ctg gcg ggt ggg tac agc cgc gtc ctc aac gcc gcc tgc cag     1279
```

```
                Leu Pro Leu Ala Gly Gly Tyr Ser Arg Val Leu Asn Ala Ala Cys Gln
                    120                 125                 130 cgc ctg gcg agg gct ggg gtc gtg ctg gtc acc gct gcc ggc aac ttc              1327
Arg Leu Ala Arg Ala Gly Val Val Leu Val Thr Ala Ala Gly Asn Phe
    135                 140                 145 cgg gac gat gcc tgc ctc tac tcc cca gcc tca gct ccc gag gtc atc              1375
Arg Asp Asp Ala Cys Leu Tyr Ser Pro Ala Ser Ala Pro Glu Val Ile
150                 155                 160                 165 aca gtt ggg gcc acc aat gcc cag gac cag ccg gtg acc ctg ggg act              1423
Thr Val Gly Ala Thr Asn Ala Gln Asp Gln Pro Val Thr Leu Gly Thr
                170                 175                 180 ttg ggg acc aac ttt ggc cgc tgt gtg gac ctc ttt gcc cca ggg gag              1471
Leu Gly Thr Asn Phe Gly Arg Cys Val Asp Leu Phe Ala Pro Gly Glu
            185                 190                 195 gac atc att ggt gcc tcc agc gac tgc agc acc tgc ttt gtg tca cag              1519
Asp Ile Ile Gly Ala Ser Ser Asp Cys Ser Thr Cys Phe Val Ser Gln
        200                 205                 210 agt ggg aca tca cag gct gct gcc cac gtg gct ggc att gca gcc atg              1567
Ser Gly Thr Ser Gln Ala Ala Ala His Val Ala Gly Ile Ala Ala Met
    215                 220                 225 atg ctg tct gcc gag ccg gag ctc acc ctg gcc gag ttg agg cag aga              1615
Met Leu Ser Ala Glu Pro Glu Leu Thr Leu Ala Glu Leu Arg Gln Arg
230                 235                 240                 245 ctg atc cac ttc tct gcc aaa gat gtc atc aat gag gcc tgg ttc cct              1663
Leu Ile His Phe Ser Ala Lys Asp Val Ile Asn Glu Ala Trp Phe Pro
                250                 255                 260 gag gac cag cgg gta ctg acc ccc aac ctg gtg gcc gcc ctg ccc ccc              1711
Glu Asp Gln Arg Val Leu Thr Pro Asn Leu Val Ala Ala Leu Pro Pro
            265                 270                 275 agc acc cat ggg gca ggt tgg cag ctg ttt tgc agg act gtg tgg tca              1759
Ser Thr His Gly Ala Gly Trp Gln Leu Phe Cys Arg Thr Val Trp Ser
        280                 285                 290 gca cac tcg ggg cct aca cgg atg gcc aca gcc atc gcc cgc tgc gcc              1807
Ala His Ser Gly Pro Thr Arg Met Ala Thr Ala Ile Ala Arg Cys Ala
    295                 300                 305 cca gat gag gag ctg ctg agc tgc tcc agt ttc tcc agg agt ggg aag              1855
Pro Asp Glu Glu Leu Leu Ser Cys Ser Ser Phe Ser Arg Ser Gly Lys
310                 315                 320                 325 cgg cgg ggc gag cgc atg gag gcc caa ggg ggc aag ctg gtc tgc cgg              1903
Arg Arg Gly Glu Arg Met Glu Ala Gln Gly Gly Lys Leu Val Cys Arg
                330                 335                 340 gcc cac aac gct ttt ggg ggt gag ggt gtc tac gcc att gcc agg tgc              1951
Ala His Asn Ala Phe Gly Gly Glu Gly Val Tyr Ala Ile Ala Arg Cys
            345                 350                 355 tgc ctg cta ccc cag gcc aac tgc agc gtc cac aca gct cca cca gct              1999
Cys Leu Leu Pro Gln Ala Asn Cys Ser Val His Thr Ala Pro Pro Ala
        360                 365                 370 gag gcc agc atg ggg acc cgt gtc cac tgc cac caa cag ggc cac gtc              2047
Glu Ala Ser Met Gly Thr Arg Val His Cys His Gln Gln Gly His Val
    375                 380                 385 ctc aca ggc tgc agc tcc cac tgg gag gtg gag gac ctt ggc acc cac              2095
Leu Thr Gly Cys Ser Ser His Trp Glu Val Glu Asp Leu Gly Thr His
390                 395                 400                 405 aag ccg cct gtg ctg agg cca cga ggt cag ccc aac cag tgc gtg ggc              2143
Lys Pro Pro Val Leu Arg Pro Arg Gly Gln Pro Asn Gln Cys Val Gly
                410                 415                 420 cac agg gag gcc agc atc cac gct tcc tgc tgc cat gcc cca ggt ctg              2191
His Arg Glu Ala Ser Ile His Ala Ser Cys Cys His Ala Pro Gly Leu
            425                 430                 435
```

```
gaa tgc aaa gtc aag gag cat gga atc ccg gcc cct cag gag cag gtg     2239
Glu Cys Lys Val Lys Glu His Gly Ile Pro Ala Pro Gln Glu Gln Val
    440             445                 450 acc gtg gcc tgc gag gag ggc tgg acc ctg act ggc tgc agt gcc ctc     2287
Thr Val Ala Cys Glu Glu Gly Trp Thr Leu Thr Gly Cys Ser Ala Leu
455             460                 465 cct ggg acc tcc cac gtc ctg ggg gcc tac gcc gta gac aac acg tgt     2335
Pro Gly Thr Ser His Val Leu Gly Ala Tyr Ala Val Asp Asn Thr Cys
470             475                 480                 485 gta gtc agg agc cgg gac gtc agc act aca ggc agc acc agc gaa ggg     2383
Val Val Arg Ser Arg Asp Val Ser Thr Thr Gly Ser Thr Ser Glu Gly
                490                 495                 500 gcc gtg aca gcc gtt gcc atc tgc tgc cgg agc cgg cac ctg gcg cag     2431
Ala Val Thr Ala Val Ala Ile Cys Cys Arg Ser Arg His Leu Ala Gln
            505                 510                 515 gcc tcc cag gag ctc cag tgacagcccc atcccaggat gggtgtctgg            2479
Ala Ser Gln Glu Leu Gln
            520
```
ggagggtcaa gggctggggc tgagctttaa aatggttccg acttgtccct ctctcagccc   2539
tccatggcct ggcacgaggg gatggggatg cttccgcctt ccggggctg ctggcctggc    2599
ccttgagtgg ggcagcctcc ttgcctggaa ctcactcact ctgggtgcct cctccccagg   2659
tggaggtgcc aggaagctcc ctccctcact gtggggcatt tcaccattca aacaggtcga   2719
gctgtgctcg ggtgctgcca gctgctccca atgtgccgat gtccgtgggc agaatgactt   2779
ttattgagct cttgttccgt gccaggcatt caatcctcag gtctccacca aggaggcagg   2839
attcttccca tggataggg aggggcggt aggggctgca gggacaaaca tcgttggggg    2899
gtgagtgtga aaggtgctga tggccctcat ctccagctaa ctgtggagaa gccccctgggg 2959
gctccctgat taatggaggc ttagctttct ggatggcatc tagccagagg ctggagacag   3019
gtgcgcccct ggtggtcaca ggctgtgcct tggtttcctg agccaccttt actctgctct   3079
atgccaggct gtgctagcaa cacccaaagg tggcctgcgg ggagccatca cctaggactg   3139
actcggcagt gtgcagtggt gcatgcactg tctcagccaa cccgctccac tacccggcag   3199
ggtacacatt cgcaccccta cttcacagag gaagaaacct ggaaccagag ggggcgtgcc   3259
tgccaagctc acacagcagg aactgagcca gaaacgcaga ttgggctggc tctgaagcca   3319
agcctcttct tacttcaccc ggctgggctc ctcatttta cggtaacag tgaggctggg    3379
aaggggaaca cagaccagga agctcggtga gtgatggcag aacgatgcct gcaggcatgg   3439
aacttttcc gttatcaccc aggcctgatt cactggcctg gcggagatgc ttctaaggca   3499
tggtcggggg agagggccaa caactgtccc tccttgagca ccagcccac ccaagcaagc    3559
agacattat cttttgggtc tgtcctctct gttgcctttt tacagccaac ttttctagac    3619
ctgttttgct tttgtaactt gaagatattt attctgggtt tgtagcatt tttattaata    3679
tggtgacttt ttaaaataaa aacaaacaaa cgttgtccta aaaaaaaaa aaaaaaaaa     3739
aaaaaaaaa aaaaaaa                                                  3756

```
<210> SEQ ID NO 4
<211> LENGTH: 523
<212> TYPE: PRT
<213> ORGANISM: Homo sapiens

<400> SEQUENCE: 4

Met Ser Pro Trp Lys Asp Gly Gly Ser Leu Val Glu Val Tyr Leu Leu
1               5                   10                  15
```

```
Asp Thr Ser Ile Gln Ser Asp His Arg Glu Ile Glu Gly Arg Val Met
             20                  25                  30

Val Thr Asp Phe Glu Asn Val Pro Glu Glu Asp Gly Thr Arg Phe His
         35                  40                  45

Arg Gln Ala Ser Lys Cys Asp Ser His Gly Thr His Leu Ala Gly Val
     50                  55                  60

Val Ser Gly Arg Asp Ala Gly Val Ala Lys Gly Ala Ser Met Arg Ser
 65                  70                  75                  80

Leu Arg Val Leu Asn Cys Gln Gly Lys Gly Thr Val Ser Gly Thr Leu
                 85                  90                  95

Ile Gly Leu Glu Phe Ile Arg Lys Ser Gln Leu Val Gln Pro Val Gly
            100                 105                 110

Pro Leu Val Val Leu Leu Pro Leu Ala Gly Gly Tyr Ser Arg Val Leu
            115                 120                 125

Asn Ala Ala Cys Gln Arg Leu Ala Arg Ala Gly Val Val Leu Val Thr
130                 135                 140

Ala Ala Gly Asn Phe Arg Asp Asp Ala Cys Leu Tyr Ser Pro Ala Ser
145                 150                 155                 160

Ala Pro Glu Val Ile Thr Val Gly Ala Thr Asn Ala Gln Asp Gln Pro
                165                 170                 175

Val Thr Leu Gly Thr Leu Gly Thr Asn Phe Gly Arg Cys Val Asp Leu
            180                 185                 190

Phe Ala Pro Gly Glu Asp Ile Ile Gly Ala Ser Ser Asp Cys Ser Thr
            195                 200                 205

Cys Phe Val Ser Gln Ser Gly Thr Ser Gln Ala Ala Ala His Val Ala
            210                 215                 220

Gly Ile Ala Ala Met Met Leu Ser Ala Glu Pro Glu Leu Thr Leu Ala
225                 230                 235                 240

Glu Leu Arg Gln Arg Leu Ile His Phe Ser Ala Lys Asp Val Ile Asn
                245                 250                 255

Glu Ala Trp Phe Pro Glu Asp Gln Arg Val Leu Thr Pro Asn Leu Val
            260                 265                 270

Ala Ala Leu Pro Pro Ser Thr His Gly Ala Gly Trp Gln Leu Phe Cys
            275                 280                 285

Arg Thr Val Trp Ser Ala His Ser Gly Pro Thr Arg Met Ala Thr Ala
            290                 295                 300

Ile Ala Arg Cys Ala Pro Asp Glu Leu Leu Ser Cys Ser Ser Phe
305                 310                 315                 320

Ser Arg Ser Gly Lys Arg Arg Gly Glu Arg Met Glu Ala Gln Gly Gly
                325                 330                 335

Lys Leu Val Cys Arg Ala His Asn Ala Phe Gly Gly Glu Gly Val Tyr
            340                 345                 350

Ala Ile Ala Arg Cys Cys Leu Leu Pro Gln Ala Asn Cys Ser Val His
            355                 360                 365

Thr Ala Pro Pro Ala Glu Ala Ser Met Gly Thr Arg Val His Cys His
        370                 375                 380

Gln Gln Gly His Val Leu Thr Gly Cys Ser Ser His Trp Glu Val Glu
385                 390                 395                 400

Asp Leu Gly Thr His Lys Pro Pro Val Leu Arg Pro Arg Gly Gln Pro
                405                 410                 415

Asn Gln Cys Val Gly His Arg Glu Ala Ser Ile His Ala Ser Cys Cys
            420                 425                 430

His Ala Pro Gly Leu Glu Cys Lys Val Lys Glu His Gly Ile Pro Ala
```

-continued

```
                435                 440                 445
Pro Gln Glu Gln Val Thr Val Ala Cys Glu Gly Trp Thr Leu Thr
        450                 455                 460
Gly Cys Ser Ala Leu Pro Gly Thr Ser His Val Leu Gly Ala Tyr Ala
465                 470                 475                 480
Val Asp Asn Thr Cys Val Val Arg Ser Arg Asp Val Ser Thr Thr Gly
                485                 490                 495
Ser Thr Ser Glu Gly Ala Val Thr Ala Val Ala Ile Cys Cys Arg Ser
                500                 505                 510
Arg His Leu Ala Gln Ala Ser Gln Glu Leu Gln
            515                 520

<210> SEQ ID NO 5
<211> LENGTH: 692
<212> TYPE: PRT
<213> ORGANISM: Homo sapiens

<400> SEQUENCE: 5

Met Gly Thr Val Ser Ser Arg Arg Ser Trp Trp Pro Leu Pro Leu Leu
1               5                   10                  15
Leu Leu Leu Leu Leu Leu Gly Pro Ala Gly Ala Arg Ala Gln Glu
            20                  25                  30
Asp Glu Asp Gly Asp Tyr Glu Glu Leu Val Leu Ala Leu Arg Ser Glu
        35                  40                  45
Glu Asp Gly Leu Ala Glu Ala Pro Glu His Gly Thr Thr Ala Thr Phe
    50                  55                  60
His Arg Cys Ala Lys Asp Pro Trp Arg Leu Pro Gly Thr Tyr Val Val
65                  70                  75                  80
Val Leu Lys Glu Glu Thr His Leu Ser Gln Ser Glu Arg Thr Ala Arg
                85                  90                  95
Arg Leu Gln Ala Gln Ala Ala Arg Arg Gly Tyr Leu Thr Lys Ile Leu
            100                 105                 110
His Val Phe His Gly Leu Leu Pro Gly Phe Leu Val Lys Met Ser Gly
        115                 120                 125
Asp Leu Leu Glu Leu Ala Leu Lys Leu Pro His Val Asp Tyr Ile Glu
    130                 135                 140
Glu Asp Ser Ser Val Phe Ala Gln Ser Ile Pro Trp Asn Leu Glu Arg
145                 150                 155                 160
Ile Thr Pro Pro Arg Tyr Arg Ala Asp Glu Tyr Gln Pro Pro Asp Gly
                165                 170                 175
Gly Ser Leu Val Glu Val Tyr Leu Leu Asp Thr Ser Ile Gln Ser Asp
            180                 185                 190
His Arg Glu Ile Glu Gly Arg Val Met Val Thr Asp Phe Glu Asn Val
        195                 200                 205
Pro Glu Glu Asp Gly Thr Arg Phe His Arg Gln Ala Ser Lys Cys Asp
    210                 215                 220
Ser His Gly Thr His Leu Ala Gly Val Val Ser Gly Arg Asp Ala Gly
225                 230                 235                 240
Val Ala Lys Gly Ala Ser Met Arg Ser Leu Arg Val Leu Asn Cys Gln
                245                 250                 255
Gly Lys Gly Thr Val Ser Gly Thr Leu Ile Gly Leu Glu Phe Ile Arg
            260                 265                 270
Lys Ser Gln Leu Val Gln Pro Val Gly Pro Leu Val Val Leu Leu Pro
        275                 280                 285
```

```
                    -continued

Leu Ala Gly Gly Tyr Ser Arg Val Leu Asn Ala Ala Cys Gln Arg Leu
    290                 295                 300

Ala Arg Ala Gly Val Val Leu Val Thr Ala Ala Gly Asn Phe Arg Asp
305                 310                 315                 320

Asp Ala Cys Leu Tyr Ser Pro Ala Ser Ala Pro Glu Val Ile Thr Val
                325                 330                 335

Gly Ala Thr Asn Ala Gln Asp Gln Pro Val Thr Leu Gly Thr Leu Gly
            340                 345                 350

Thr Asn Phe Gly Arg Cys Val Asp Leu Phe Ala Pro Gly Glu Asp Ile
        355                 360                 365

Ile Gly Ala Ser Ser Asp Cys Ser Thr Cys Phe Val Ser Gln Ser Gly
    370                 375                 380

Thr Ser Gln Ala Ala His Val Ala Gly Ile Ala Ala Met Met Leu
385                 390                 395                 400

Ser Ala Glu Pro Glu Leu Thr Leu Ala Glu Leu Arg Gln Arg Leu Ile
                405                 410                 415

His Phe Ser Ala Lys Asp Val Ile Asn Glu Ala Trp Phe Pro Glu Asp
            420                 425                 430

Gln Arg Val Leu Thr Pro Asn Leu Val Ala Ala Leu Pro Pro Ser Thr
        435                 440                 445

His Gly Ala Gly Trp Gln Leu Phe Cys Arg Thr Val Trp Ser Ala His
    450                 455                 460

Ser Gly Pro Thr Arg Met Ala Thr Ala Val Ala Arg Cys Ala Pro Asp
465                 470                 475                 480

Glu Leu Leu Ser Cys Ser Ser Phe Ser Arg Ser Gly Lys Arg Arg
                485                 490                 495

Gly Glu Arg Met Glu Ala Gln Gly Gly Lys Leu Val Cys Arg Ala His
            500                 505                 510

Asn Ala Phe Gly Gly Glu Gly Val Tyr Ala Ile Ala Arg Cys Cys Leu
        515                 520                 525

Leu Pro Gln Ala Asn Cys Ser Val His Thr Ala Pro Pro Ala Glu Ala
    530                 535                 540

Ser Met Gly Thr Arg Val His Cys His Gln Gly His Val Leu Thr
545                 550                 555                 560

Gly Cys Ser Ser His Trp Glu Val Glu Asp Leu Gly Thr His Lys Pro
                565                 570                 575

Pro Val Leu Arg Pro Arg Gly Gln Pro Asn Gln Cys Val Gly His Arg
            580                 585                 590

Glu Ala Ser Ile His Ala Ser Cys Cys His Ala Pro Gly Leu Glu Cys
        595                 600                 605

Lys Val Lys Glu His Gly Ile Pro Ala Pro Gln Glu Gln Val Thr Val
    610                 615                 620

Ala Cys Glu Glu Gly Trp Thr Leu Thr Gly Cys Ser Ala Leu Pro Gly
625                 630                 635                 640

Thr Ser His Val Leu Gly Ala Tyr Ala Val Asp Asn Thr Cys Val Val
                645                 650                 655

Arg Ser Arg Asp Val Ser Thr Thr Gly Ser Thr Ser Glu Gly Ala Val
            660                 665                 670

Thr Ala Val Ala Ile Cys Cys Arg Ser Arg His Leu Ala Gln Ala Ser
        675                 680                 685

Gln Glu Leu Gln
    690
```

```
<210> SEQ ID NO 6
<211> LENGTH: 196
<212> TYPE: PRT
<213> ORGANISM: Homo sapiens

<400> SEQUENCE: 6

Met Ser Pro Trp Lys Asp Gly Gly Ser Leu Val Glu Val Tyr Leu Leu
1               5                   10                  15

Asp Thr Ser Ile Gln Ser Asp His Arg Glu Ile Glu Gly Arg Val Met
            20                  25                  30

Val Thr Asp Phe Glu Asn Val Pro Glu Glu Asp Gly Thr Arg Phe His
        35                  40                  45

Arg Gln Ala Ser Lys Cys Asp Ser His Gly Thr His Leu Ala Gly Val
    50                  55                  60

Val Ser Gly Arg Asp Ala Gly Val Ala Lys Gly Ala Ser Met Arg Ser
65                  70                  75                  80

Leu Arg Val Leu Asn Cys Gln Gly Lys Gly Thr Val Ser Gly Thr Leu
                85                  90                  95

Ile Gly Leu Glu Phe Ile Arg Lys Ser Gln Leu Val Gln Pro Val Gly
            100                 105                 110

Pro Leu Val Val Leu Pro Leu Ala Gly Gly Tyr Ser Arg Val Leu
        115                 120                 125

Asn Ala Ala Cys Gln Arg Leu Ala Arg Ala Gly Val Val Leu Val Thr
    130                 135                 140

Ala Ala Gly Asn Phe Arg Asp Asp Ala Cys Leu Tyr Ser Pro Ala Ser
145                 150                 155                 160

Ala Pro Glu Gly Arg Thr Ser Leu Val Pro Pro Ala Thr Ala Ala Pro
                165                 170                 175

Ala Leu Cys His Arg Val Gly His His Arg Leu Leu Pro Thr Trp Leu
            180                 185                 190

Ala Leu Gln Pro
        195

<210> SEQ ID NO 7
<211> LENGTH: 80
<212> TYPE: DNA
<213> ORGANISM: Homo sapiens

<400> SEQUENCE: 7
ggcgctttca ccagtggctg ggatgtgctc tgtagtttct gtgtgttaac tataaggttg     60
actttatgct cattccctcc                                                80

<210> SEQ ID NO 8
<211> LENGTH: 20
<212> TYPE: DNA
<213> ORGANISM: Homo sapiens

<400> SEQUENCE: 8
ctaggcctcc ctttccttgt                                                20

<210> SEQ ID NO 9
<211> LENGTH: 20
<212> TYPE: DNA
<213> ORGANISM: Homo sapiens

<400> SEQUENCE: 9
ttccaaggtg acatttgtgg                                                20
```

```
<210> SEQ ID NO 10
<211> LENGTH: 17
<212> TYPE: DNA
<213> ORGANISM: Homo sapiens

<400> SEQUENCE: 10
cctgcgcgtg ctcaact                                                    17

<210> SEQ ID NO 11
<211> LENGTH: 22
<212> TYPE: DNA
<213> ORGANISM: Homo sapiens

<400> SEQUENCE: 11
ccgaataaac tccaggccta tg                                              22

<210> SEQ ID NO 12
<211> LENGTH: 23
<212> TYPE: DNA
<213> ORGANISM: Homo sapiens

<400> SEQUENCE: 12
ccgctaaccg tgcccttccc ttg                                             23

<210> SEQ ID NO 13
<211> LENGTH: 20
<212> TYPE: DNA
<213> ORGANISM: Homo sapiens

<400> SEQUENCE: 13
ctaggcctcc ctttccttgt                                                 20

<210> SEQ ID NO 14
<211> LENGTH: 79
<212> TYPE: DNA
<213> ORGANISM: Homo sapiens

<400> SEQUENCE: 14
tggcaggcgg cgttgaggac gcggctgtac ccacccgcca ggggcagcag caccaccagt     60
ggccccacag gctggacca                                                  79

<210> SEQ ID NO 15
<211> LENGTH: 20
<212> TYPE: DNA
<213> ORGANISM: Homo sapiens

<400> SEQUENCE: 15
gcctggagtt tattcggaaa                                                 20

<210> SEQ ID NO 16
<211> LENGTH: 20
<212> TYPE: DNA
<213> ORGANISM: Homo sapiens

<400> SEQUENCE: 16
gagtagaggc aggcatcgtc                                                 20

<210> SEQ ID NO 17
<211> LENGTH: 20
<212> TYPE: DNA
<213> ORGANISM: Homo sapiens

<400> SEQUENCE: 17
```

```
gagtagaggc aggcatcgtc                                                   20
```

<210> SEQ ID NO 18
<211> LENGTH: 7
<212> TYPE: PRT
<213> ORGANISM: Artificial
<220> FEATURE:
<223> OTHER INFORMATION: Synthesized Polypeptide.

<400> SEQUENCE: 18

Phe Ala Gln Ser Ile Pro Lys
1               5

<210> SEQ ID NO 19
<211> LENGTH: 7
<212> TYPE: PRT
<213> ORGANISM: Artificial
<220> FEATURE:
<223> OTHER INFORMATION: Synthesized Polypeptide.

<400> SEQUENCE: 19

Asp Ser Leu Val Phe Ala Lys
1               5

<210> SEQ ID NO 20
<211> LENGTH: 7
<212> TYPE: PRT
<213> ORGANISM: Artificial
<220> FEATURE:
<223> OTHER INFORMATION: Synthesized Polypeptide.

<400> SEQUENCE: 20

Phe Ala Asn Ala Ile Pro Lys
1               5

<210> SEQ ID NO 21
<211> LENGTH: 733
<212> TYPE: DNA
<213> ORGANISM: Homo sapiens

<400> SEQUENCE: 21

```
gggatccgga gcccaaatct tctgacaaaa ctcacacatg cccaccgtgc ccagcacctg     60
aattcgaggg tgcaccgtca gtcttcctct tccccccaaa acccaaggac accctcatga    120
tctcccggac tcctgaggtc acatgcgtgg tggtggacgt aagccacgaa gaccctgagg    180
tcaagttcaa ctggtacgtg gacggcgtgg aggtgcataa tgccaagaca aagccgcggg    240
aggagcagta caacagcacg taccgtgtgg tcagcgtcct caccgtcctg caccaggact    300
ggctgaatgg caaggagtac aagtgcaagg tctccaacaa agcccctccc acccccatcg    360
agaaaaccat ctccaaagcc aaagggcagc ccgagaacca caggtgtac accctgcccc    420
catcccggga tgagctgacc aagaaccagg tcagcctgac ctgcctggtc aaaggcttct    480
atccaagcga catcgccgtg gagtgggaga gcaatgggca gccggagaac aactacaaga    540
ccacgcctcc cgtgctggac tccgacggct ccttcttcct ctacagcaag ctcaccgtgg    600
acaagagcag gtggcagcag gggaacgtct tctcatgctc cgtgatgcat gaggctctgc    660
acaaccacta cacgcagaag agcctctccc tgtctccggg taaatgagtg cgacggccgc    720
gactctagag gat                                                       733
```

<210> SEQ ID NO 22
<211> LENGTH: 39
<212> TYPE: DNA

<210> SEQ ID NO 22
<211> LENGTH: 39
<212> TYPE: DNA
<213> ORGANISM: Homo sapiens

<400> SEQUENCE: 22
gcagcagcgg ccgcctagac accagcatac agagtgacc              39

<210> SEQ ID NO 23
<211> LENGTH: 37
<212> TYPE: DNA
<213> ORGANISM: Homo sapiens

<400> SEQUENCE: 23
gcagcagtcg actctggggc gcagcgggcg atggctg                37

<210> SEQ ID NO 24
<211> LENGTH: 39
<212> TYPE: DNA
<213> ORGANISM: Homo sapiens

<400> SEQUENCE: 24
gcagcagcgg ccgcatgtcg ccttggaaag acggaggca              39

<210> SEQ ID NO 25
<211> LENGTH: 37
<212> TYPE: DNA
<213> ORGANISM: Homo sapiens

<400> SEQUENCE: 25
gcagcagtcg acagggcctg ccccatgggt gctgggg                37

<210> SEQ ID NO 26
<211> LENGTH: 39
<212> TYPE: DNA
<213> ORGANISM: Homo sapiens

<400> SEQUENCE: 26
gcagcagcgg ccgcctagac accagcatac agagtgacc              39

<210> SEQ ID NO 27
<211> LENGTH: 25
<212> TYPE: DNA
<213> ORGANISM: Homo sapiens

<400> SEQUENCE: 27
ctggagctcc tgggaggcct gcgcc                            25

<210> SEQ ID NO 28
<211> LENGTH: 39
<212> TYPE: DNA
<213> ORGANISM: Homo sapiens

<400> SEQUENCE: 28
gcagcagcgg ccgcatgtcg ccttggaaag acggaggca              39

<210> SEQ ID NO 29
<211> LENGTH: 37
<212> TYPE: DNA
<213> ORGANISM: Homo sapiens

<400> SEQUENCE: 29
gcagcagtcg acggcgatgg ctgtggccat ccgtgta                37

<210> SEQ ID NO 30
<211> LENGTH: 20

```
<212> TYPE: DNA
<213> ORGANISM: Homo sapiens

<400> SEQUENCE: 30
tgtctttgcc cagagcatcc                                              20

<210> SEQ ID NO 31
<211> LENGTH: 19
<212> TYPE: DNA
<213> ORGANISM: Homo sapiens

<400> SEQUENCE: 31
tattcatccg cccggtacc                                               19

<210> SEQ ID NO 32
<211> LENGTH: 20
<212> TYPE: DNA
<213> ORGANISM: Homo sapiens

<400> SEQUENCE: 32
agatgtcatc aatgaggcct                                              20

<210> SEQ ID NO 33
<211> LENGTH: 20
<212> TYPE: DNA
<213> ORGANISM: Homo sapiens

<400> SEQUENCE: 33
agctgccaac ctgcaaaaac                                              20

<210> SEQ ID NO 34
<211> LENGTH: 23
<212> TYPE: DNA
<213> ORGANISM: Homo sapiens

<400> SEQUENCE: 34
ctctgaggtt gtgactcgtg tga                                          23

<210> SEQ ID NO 35
<211> LENGTH: 21
<212> TYPE: DNA
<213> ORGANISM: Homo sapiens

<400> SEQUENCE: 35
agcgttctcc actccacaag a                                            21

<210> SEQ ID NO 36
<211> LENGTH: 21
<212> TYPE: DNA
<213> ORGANISM: Homo sapiens

<400> SEQUENCE: 36
gagaatgatc tgcagcaccc a                                            21

<210> SEQ ID NO 37
<211> LENGTH: 21
<212> TYPE: DNA
<213> ORGANISM: Homo sapiens

<400> SEQUENCE: 37
tgctgatgac ggtgtcatag g                                            21

<210> SEQ ID NO 38
```

```
<211> LENGTH: 3636
<212> TYPE: DNA
<213> ORGANISM: Homo sapiens

<400> SEQUENCE: 38
cagcgacgtc gaggcgctca tggttgcagg cgggcgccgc cgttcagttc agggtctgag      60
cctggaggag tgagccaggc agtgagactg gctcgggcgg gccgggacgc gtcgttgcag     120
cagcggctcc cagctcccag ccaggattcc gcgcgcccct tcacgcgccc tgctcctgaa     180
cttcagctcc tgcacagtcc tccccaccgc aaggctcaag gcgccgccgg cgtggaccgc     240
gcacggcctc taggtctcct cgccaggaca gcaacctctc ccctggccct catgggcacc     300
gtcagctcca ggcggtcctg gtggccgctg ccactgctgc tgctgctgct gctgctcctg     360
ggtcccgcgg gcgcccgtgc gcaggaggac gaggacggcg actacgagga gctggtgcta     420
gccttgcgtt ccgaggagga cggcctggcc gaagcacccg agcacggaac cacagccacc     480
ttccaccgct gcgccaagga tccgtggagg ttgcctggca cctacgtggt ggtgctgaag     540
gaggagaccc acctctcgca gtcagagcgc actgcccgcc gcctgcaggc ccaggctgcc     600
cgccggggat acctcaccaa gatcctgcat gtcttccatg gccttcttcc tggcttcctg     660
gtgaagatga gtggcgacct gctggagctg gccttgaagt tgccccatgt cgactacatc     720
gaggaggact cctctgtctt tgcccagagc atcccgtgga acctggagcg gattacccct     780
ccacggtacc gggcggatga ataccagccc cccgacggag gcagcctggt ggaggtgtat     840
ctcctagaca ccagcataca gagtgaccac cgggaaatcg agggcagggt catggtcacc     900
gacttcgaga atgtgcccga ggaggacggg acccgcttcc acagacaggc cagcaagtgt     960
gacagtcatg gcacccacct ggcaggggtg gtcagcggcc gggatgccgg cgtggccaag    1020
ggtgccagca tgcgcagcct gcgcgtgctc aactgccaag ggaagggcac ggttagcggc    1080
accctcatag gcctggagtt tattcggaaa agccagctgg tccagcctgt ggggccactg    1140
gtggtgctgc tgcccctggc gggtgggtac agccgcgtcc tcaacgccgc ctgccagcgc    1200
ctggcgaggg ctggggtcgt gctggtcacc gctgccggca acttccggga cgatgcctgc    1260
ctctactccc cagcctcagc tcccgaggtc atcacagttg gggccaccaa tgcccaagac    1320
cagccggtga ccctggggac tttggggacc aactttggcc gctgtgtgga cctctttgcc    1380
ccaggggagg acatcattgg tgcctccagc gactgcagca cctgctttgt gtcacagagt    1440
gggacatcac aggctgctgc ccacgtggct ggcattgcag ccatgatgct gtctgccgag    1500
ccggagctca cctggccga gttgaggcag agactgatcc acttctctgc caaagatgtc    1560
atcaatgagg cctggttccc tgaggaccag cgggtactga ccccaacct ggtggccgcc    1620 ctgccccca gcacccatgg ggcaggttgg cagctgtttt gcaggactgt atggtcagca    1680
cactcggggc ctacacggat ggccacagcc gtcgcccgct gcgccccaga tgaggagctg    1740
ctgagctgct ccagtttctc caggagtggg aagcggcggg gcgagcgcat ggaggcccaa    1800
gggggcaagc tggtctgccg ggcccacaac gcttttgggg gtgagggtgt ctacgccatt    1860
gccaggtgct gcctgctacc ccaggccaac tgcagcgtcc acacagctcc accagctgag    1920
gccagcatgg ggacccgtgt ccactgccac caacagggcc acgtcctcac aggctgcagc    1980
tcccactggg aggtggagga ccttggcacc cacaagccgc ctgtgctgag gccacgaggt    2040
cagcccaacc agtgcgtggg ccacagggag gccagcatcc acgcttcctg ctgccatgcc    2100
ccaggtctgg aatgcaaagt caaggagcat ggaatcccgg cccctcagga gcaggtgacc    2160
gtggcctgcg aggagggctg gaccctgact ggctgcagtg ccctcccgg gacctcccac    2220
```

-continued

```
gtcctggggg cctacgccgt agacaacacg tgtgtagtca ggagccggga cgtcagcact    2280
acaggcagca ccagcgaagg ggccgtgaca gccgttgcca tctgctgccg gagccggcac    2340
ctggcgcagg cctcccagga gctccagtga cagccccatc ccaggatggg tgtctgggga    2400
gggtcaaggg ctggggctga gctttaaaat ggttccgact tgtccctctc tcagccctcc    2460
atggcctggc acgaggggat ggggatgctt ccgcctttcc ggggctgctg gcctggccct    2520
tgagtggggc agcctccttg cctggaactc actcactctg ggtgcctcct ccccaggtgg    2580
aggtgccagg aagctccctc cctcactgtg gggcatttca ccattcaaac aggtcgagct    2640
gtgctcgggt gctgccagct gctcccaatg tgccgatgtc cgtgggcaga atgactttta    2700
ttgagctctt gttccgtgcc aggcattcaa tcctcaggtc tccaccaagg aggcaggatt    2760
cttcccatgg ataggggagg gggcggtagg ggctgcaggg acaaacatcg ttgggggtg     2820 agtgtgaaag gtgctgatgg ccctcatctc cagctaactg tggagaagcc cctgggggct    2880
ccctgattaa tggaggctta gctttctgga tggcatctag ccagaggctg gagacaggtg    2940
cgcccctggt ggtcacaggc tgtgccttgg tttcctgagc caccttract ctgctctatg    3000
ccaggctgtg ctagcaacac ccaaaggtgg cctgcgggga gccatcacct aggactgact    3060
cggcagtgtg cagtggtgca tgcactgtct cagccaaccc gctccactac ccggcagggt    3120
acacattcgc accctactt cacagaggaa gaaacctgga accagagggg gcgtgcctgc     3180
caagctcaca cagcaggaac tgagccagaa acgcagattg ggctggctct gaagccaagc    3240
ctcttcttac ttcacccggc tgggctcctc attttttacgg gtaacagtga ggctgggaag   3300
gggaacacag accaggaagc tcggtgagtg atggcagaac gatgcctgca ggcatggaac    3360
tttttccgtt atcacccagg cctgattcac tggcctggcg gagatgcttc taaggcatgg    3420
tcgggggaga gggccaacaa ctgtccctcc ttgagcacca gccccaccca agcaagcaga    3480
catttatctt ttgggtctgt cctctctgtt gccttttac agccaacttt tctagacctg     3540
ttttgctttt gtaacttgaa gatattatt ctgggttttg tagcatttt attaatatgg      3600 tgactttta aaataaaaac aaacaaacgt tgtcct                                3636
```

<210> SEQ ID NO 39
<211> LENGTH: 39
<212> TYPE: DNA
<213> ORGANISM: Homo sapiens

<400> SEQUENCE: 39

```
gcagcagcgg ccgcctgctg ctgctgctgc tgctgctcc                              39
```

<210> SEQ ID NO 40
<211> LENGTH: 37
<212> TYPE: DNA
<213> ORGANISM: Homo sapiens

<400> SEQUENCE: 40

```
gcagcagtcg acctggagct cctgggaggc ctgcgcc                                37
```